(12) United States Patent
Dar et al.

(10) Patent No.: US 10,519,113 B2
(45) Date of Patent: Dec. 31, 2019

(54) KINASE INHIBITOR COMPOUNDS, COMPOSITIONS, AND METHODS OF TREATING CANCER

(71) Applicant: ICAHN SCHOOL OF MEDICINE AT MOUNT SINAI, New York, NY (US)

(72) Inventors: Arvin C. Dar, New York, NY (US); Ross L. Cagan, New York, NY (US); Alex P. Scopton, New York, NY (US); Masahiro Sonoshita, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 16/325,218

(22) PCT Filed: Aug. 17, 2017

(86) PCT No.: PCT/US2017/047383
§ 371 (c)(1),
(2) Date: Feb. 13, 2019

(87) PCT Pub. No.: WO2018/035346
PCT Pub. Date: Feb. 22, 2018

(65) Prior Publication Data
US 2019/0202789 A1    Jul. 4, 2019

Related U.S. Application Data

(60) Provisional application No. 62/376,138, filed on Aug. 17, 2016.

(51) Int. Cl.
*C07D 213/81* (2006.01)
*A61P 35/00* (2006.01)
(52) U.S. Cl.
CPC ............ *C07D 213/81* (2013.01); *A61P 35/00* (2018.01)

(58) Field of Classification Search
CPC .................................................... C07D 213/81
USPC .......................................................... 546/298
See application file for complete search history.

(56) References Cited

U.S. PATENT DOCUMENTS

| 2007/0020704 A1 | 1/2007 | Wilhelm et al. |
| 2015/0191467 A1 | 7/2015 | Shiau et al. |
| 2015/0197511 A1 | 7/2015 | Zhang et al. |

FOREIGN PATENT DOCUMENTS

| WO | 2004/014870 A1 | 2/2004 |
| WO | 2005/009961 A2 | 2/2005 |
| WO | 2011/046991 A2 | 4/2011 |
| WO | 2015/051149 A1 | 4/2015 |

OTHER PUBLICATIONS

International Search Report and Written Opinion for corresponding PCT/US2017/047383 (dated Nov. 3, 2017).
International Preliminary Report on Patentability for corresponding PCT/US2017/047383 (dated Feb. 28, 2019).

*Primary Examiner* — Taofiq A Solola
(74) *Attorney, Agent, or Firm* — Pepper Hamilton LLP

(57) ABSTRACT

The present invention relates to a compound having the structure of formula (I) or a stereoisomer, pharmaceutically acceptable salt, oxide, or solvate thereof, where X, Y, Z, R, $R^1$, $R^2$, $R^3$, $R^4$, $R^5$, and $R^6$ are as described herein. The present invention also relates to compositions containing the compound having the structure of formula (I), and a method of treating cancer in a subject.

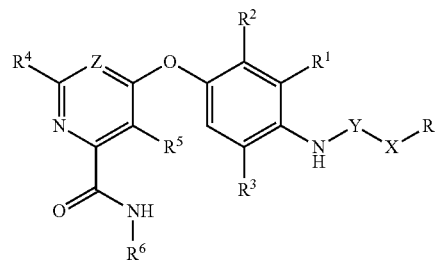

17 Claims, 72 Drawing Sheets

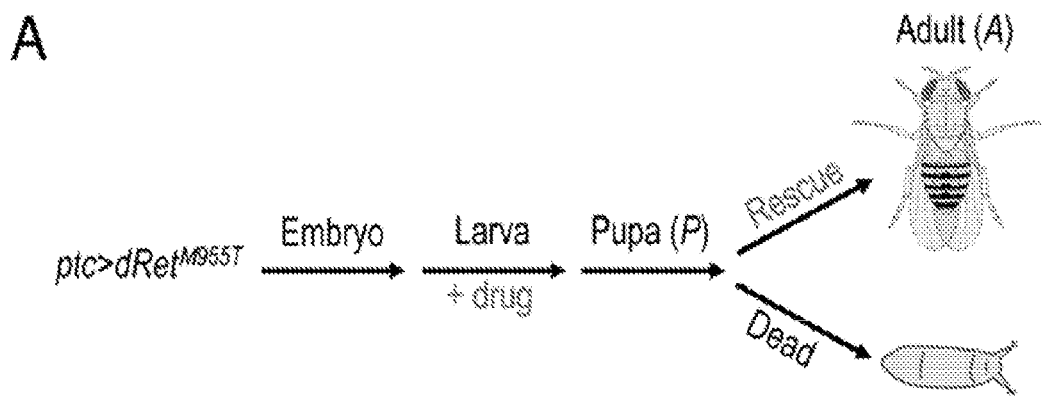
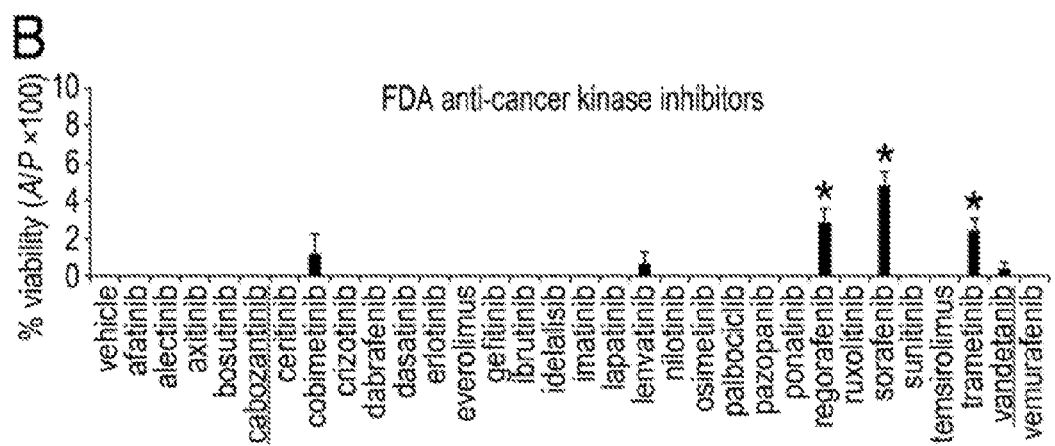
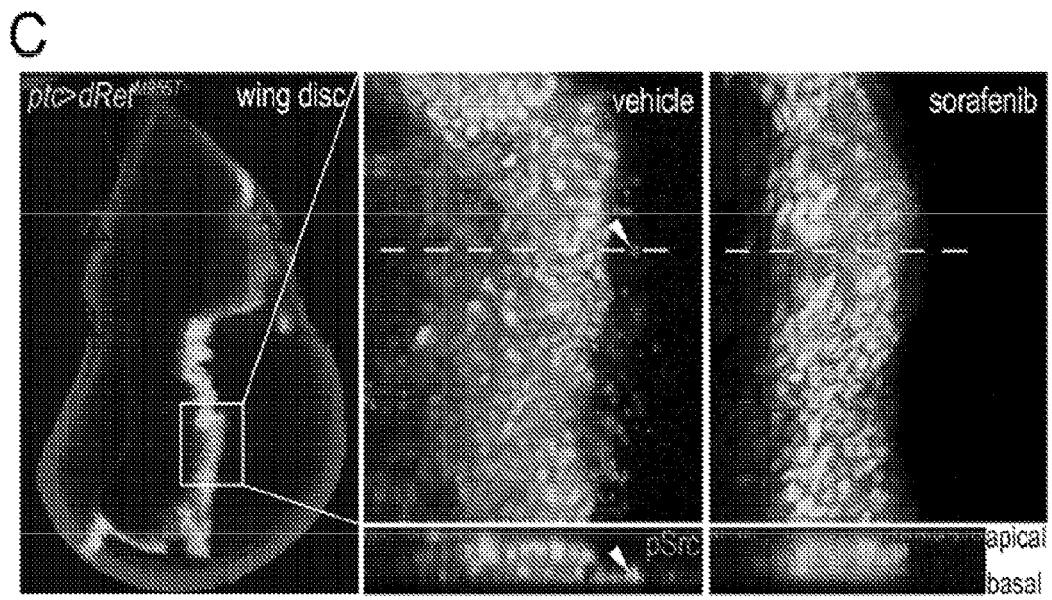
*FIGs. 53A-C*

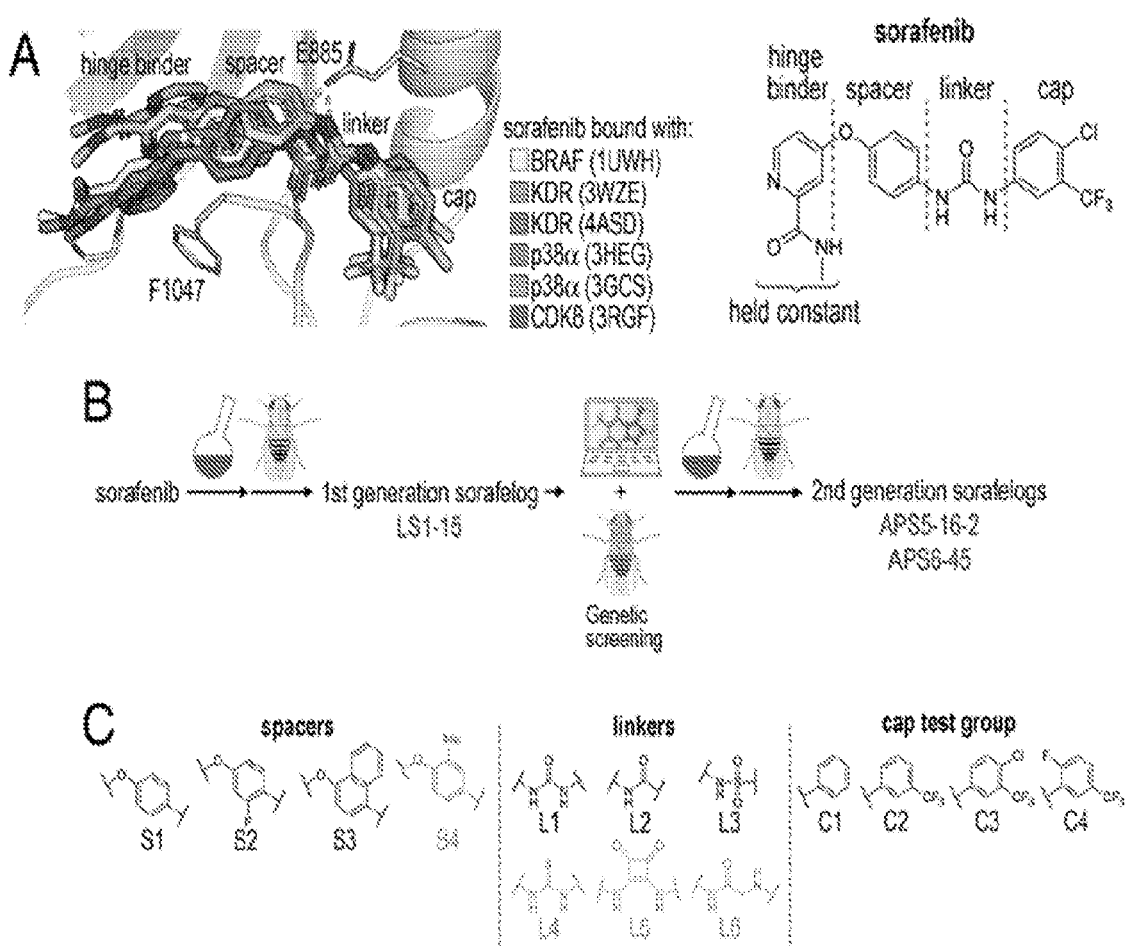
FIGs. 54A-C

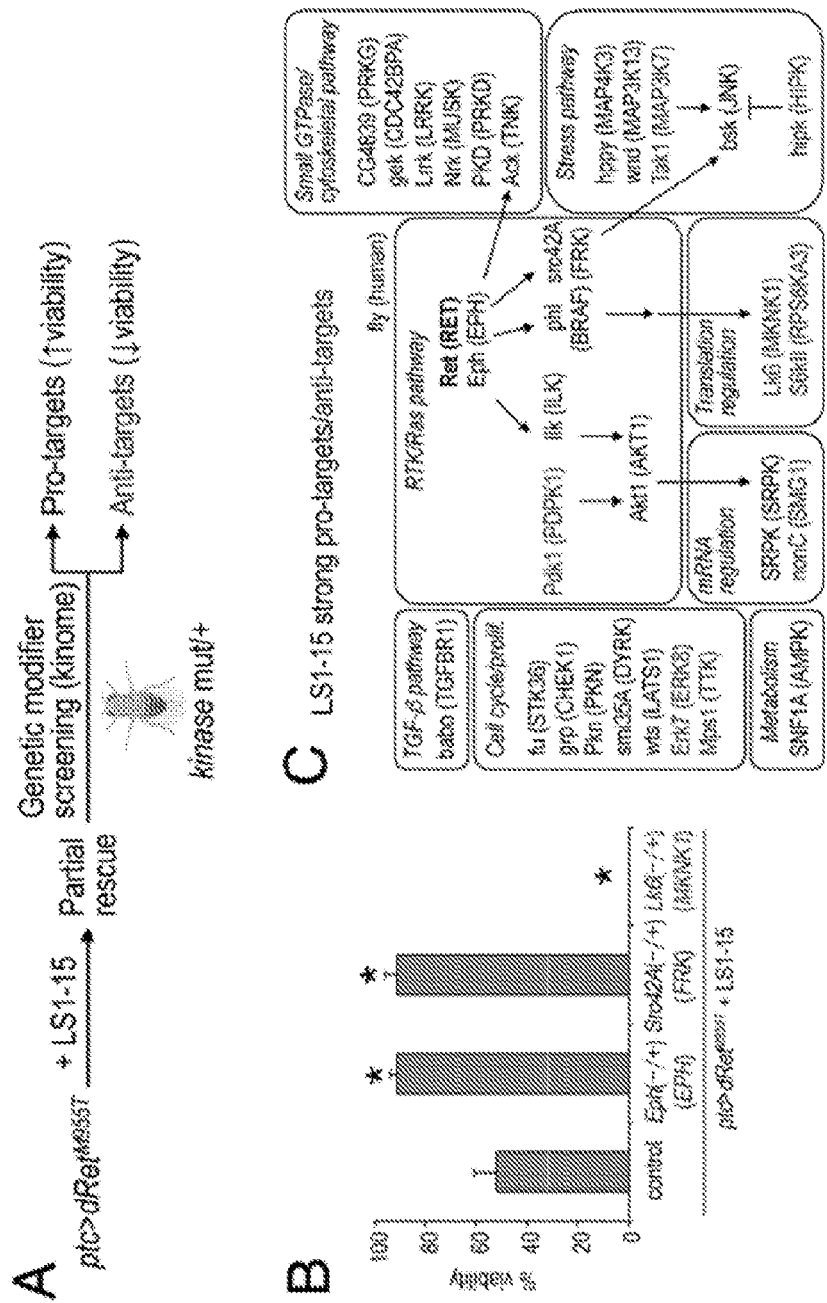
FIGs. 55A-C

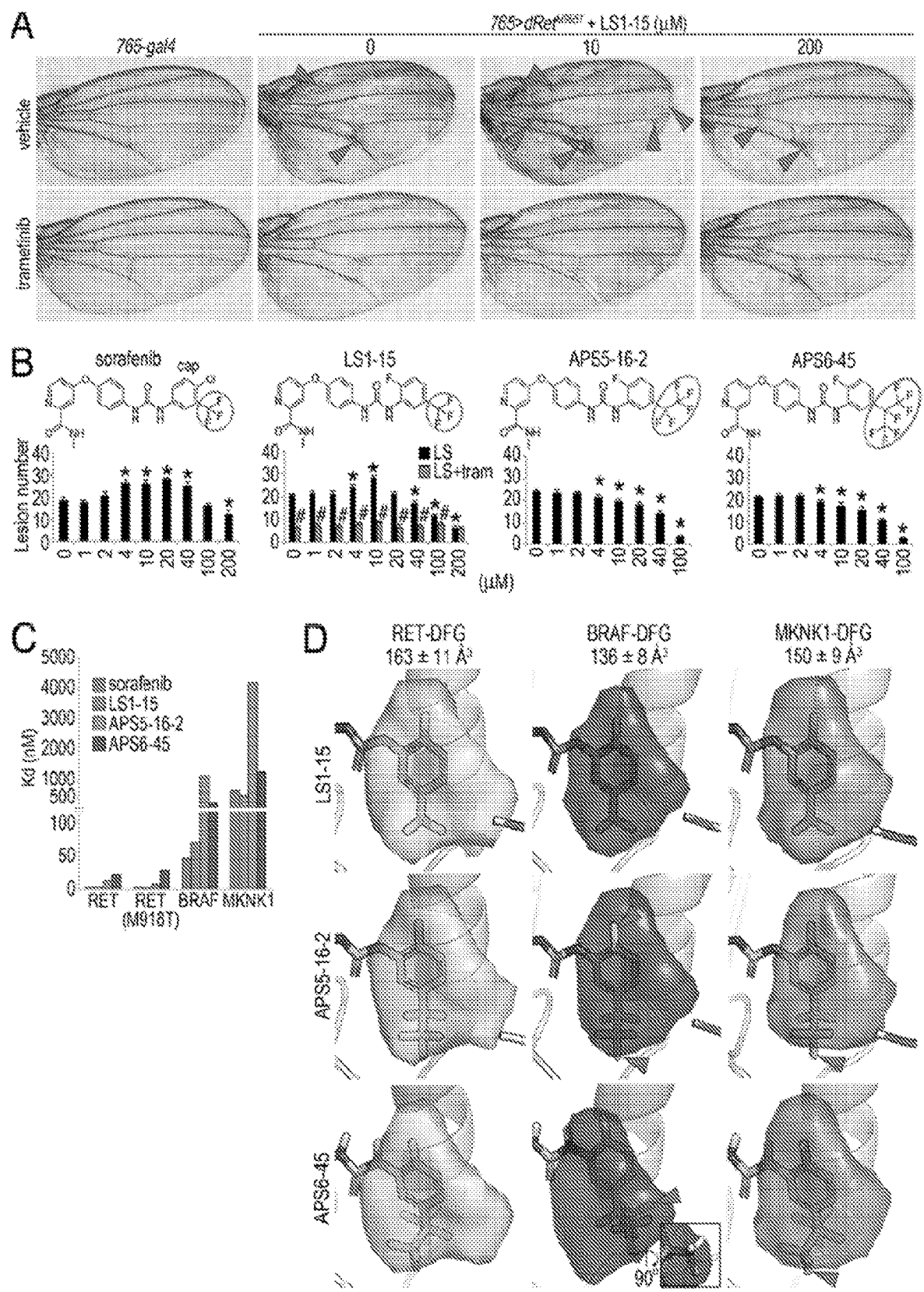
*FIGs. 56A-D*

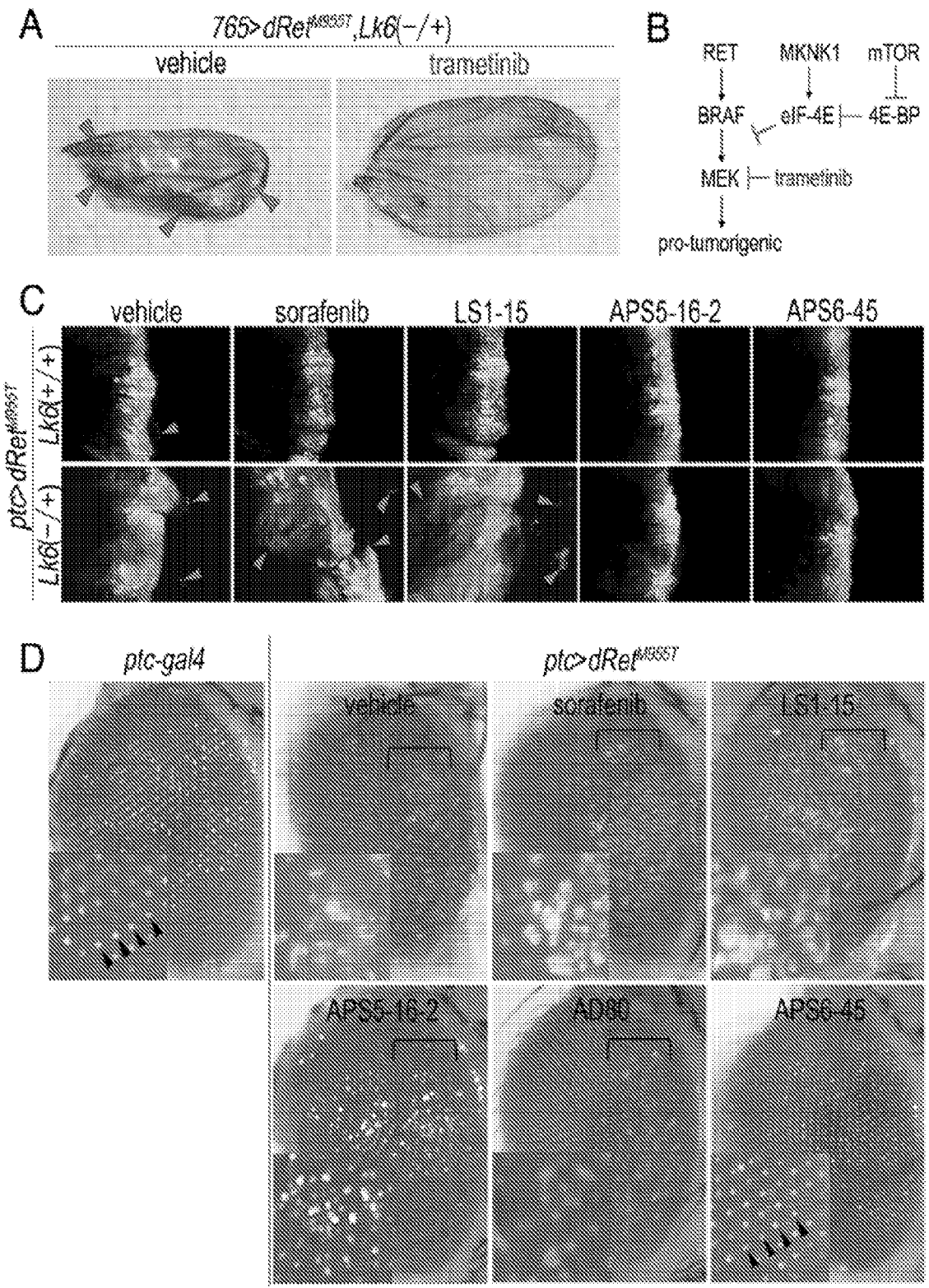
FIGs. 57A-D

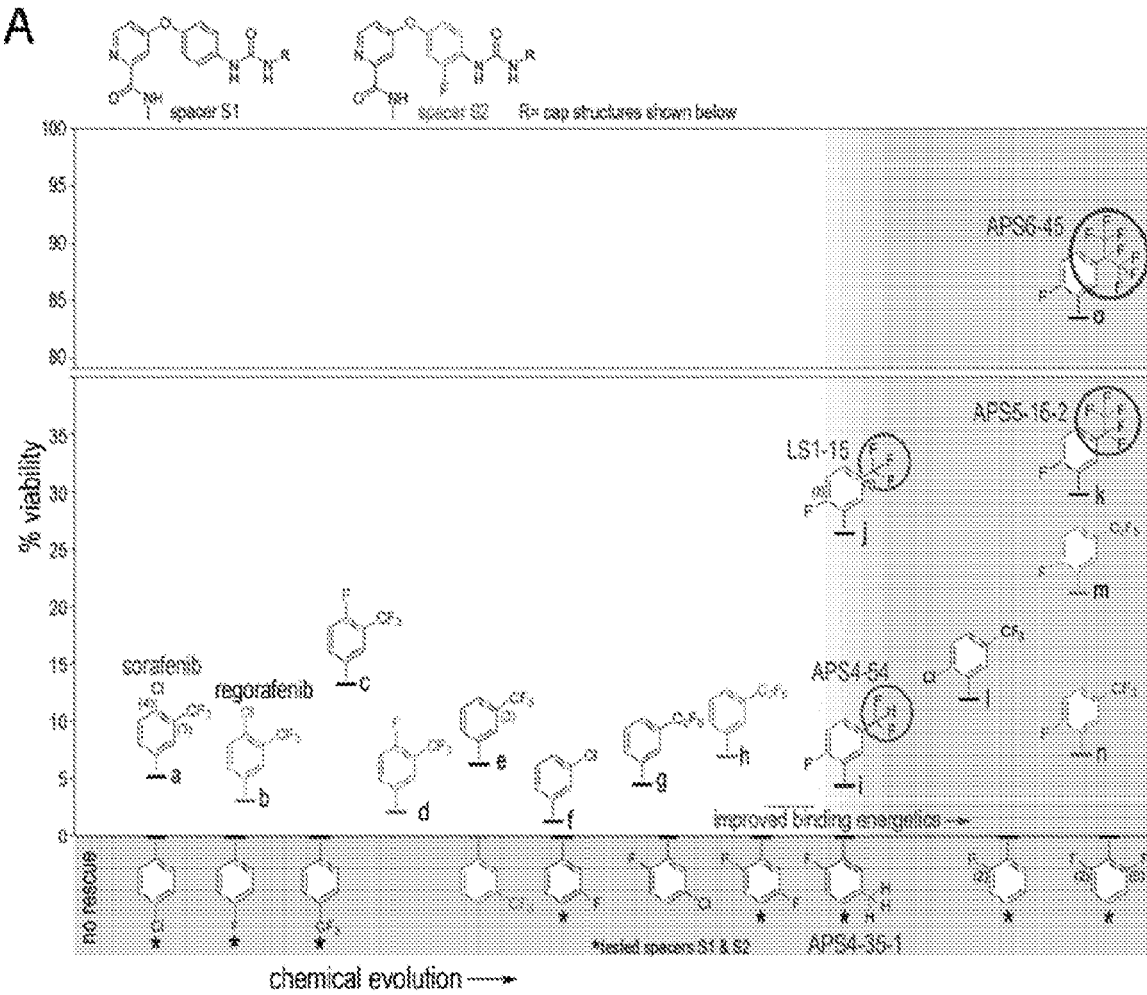
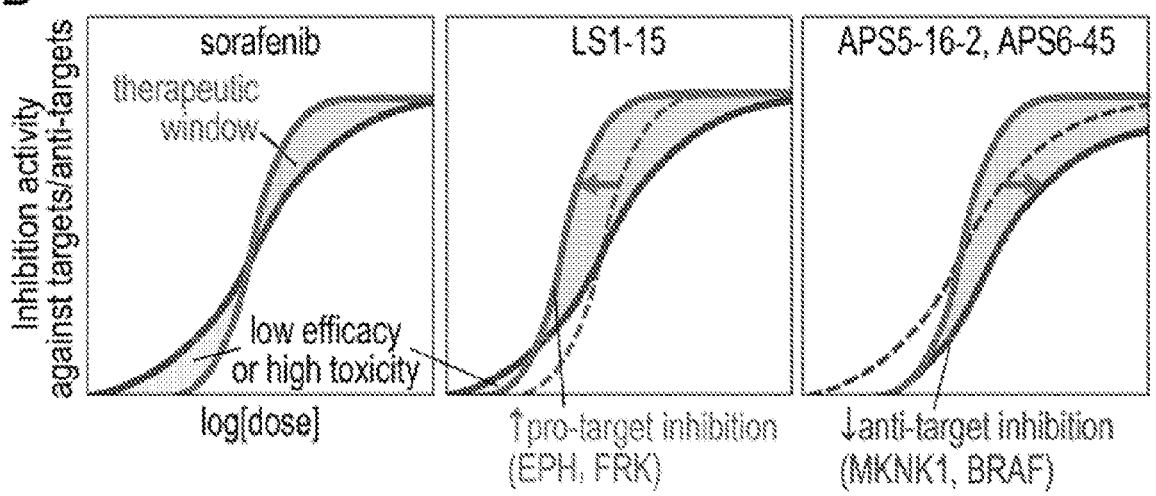
FIGs. 58A-B

Chromosome X

| Drugs | | | Gene symbol | | % viability | | | SE | | |
|---|---|---|---|---|---|---|---|---|---|---|
| - | soraf | L15 | Fly | Human | - | soraf | L15 | - | soraf | L15 |
| | | | control | | 3 | 18 | 20 | 1 | 1 | 4 |

*Pro-target for sorafenib*

| | | | | | | | | | | |
|---|---|---|---|---|---|---|---|---|---|---|
| * | M | | Pk17E | SGK494 | 19 | 67 | 43 | 4 | 5 | 18 |

*Pro-targets for LS1-15*

| | | | | | | | | | | |
|---|---|---|---|---|---|---|---|---|---|---|
| * | | M | sgg | GSK3A | 13 | 29 | 69 | 2 | 14 | 13 |
| * | | M | png | NEK11 | 26 | 35 | 63 | 8 | 4 | 7 |
| * | | M | tlk | TLK2 | 35 | 42 | 59 | 2 | 6 | 9 |
| * | | M | sev | ROS1 | 17 | 30 | 54 | 4 | 8 | 8 |
| * | | W | fs(1)h | BRD3 | 31 | 38 | 47 | 6 | 10 | 7 |
| * | | W | Cklalpha | CSNK1A1 (CK1a) | 37 | 14 | 43 | 3 | 10 | 1 |
| * | | W | Pink1 | PINK1 | 33 | 19 | 42 | 5 | 4 | 7 |
| | | W | mnb | DYRK1A | 2 | 29 | 36 | 1 | 5 | 1 |

*Pro-targets for both sorafenib and LS1-15*

| | | | | | | | | | | |
|---|---|---|---|---|---|---|---|---|---|---|
| * | S | S | phl | BRAF | 100 | 90 | 96 | 0 | 7 | 4 |
| * | S | S | fu | STK36 (FU) | 76 | 93 | 88 | 9 | 7 | 13 |
| * | S | S | SNF1A | PRKAA2 (AMPK) | 29 | 86 | 81 | 3 | 9 | 10 |
| * | M | M | Dsor1 | MEK | 78 | 55 | 80 | 6 | 3 | 20 |
| * | M | M | hop | JAK | 45 | 63 | 78 | 9 | 11 | 9 |
| * | W | M | Tao | TAOK1 | 24 | 46 | 75 | 12 | 17 | 3 |
| * | M | M | lic | MAP2K6 (MKK6) | 36 | 54 | 75 | 10 | 8 | 13 |
| * | W | M | rok | ROCK1 | 32 | 42 | 67 | 15 | 2 | 7 |
| | M | M | Drak | STK17A (DRAK1) | 14 | 64 | 65 | 9 | 9 | 6 |
| * | M | M | hep | MAP2K7 (MKK7) | 20 | 55 | 58 | 6 | 2 | 5 |
| * | M | W | mei-41 | ATR | 10 | 61 | 39 | 3 | 6 | 1 |
| | W | W | l(1)G0148 | CDC7 | 0 | 24 | 21 | 0 | 4 | 1 |

*FIG. 59*

Chromosomes 2, 3 and 4

| Drugs | | | Gene symbol | | % viability | | | SE | | |
|---|---|---|---|---|---|---|---|---|---|---|
| – | soraf | L15 | Fly | Human | – | soraf | L15 | – | soraf | L15 |
| | | | control | | 28 | 46 | 52 | 3 | 5 | 9 |

Pro-targets for sorafenib

| | | | | | | | | | | |
|---|---|---|---|---|---|---|---|---|---|---|
| | M | | ksr | KSR2 | 51 | 78 | 69 | 8 | 2 | 13 |
| | M | | Gcklll | STK24 (MST3) | 61 | 73 | 67 | 12 | 7 | 10 |
| * | M | | ird5 | IKBKB | 47 | 89 | 57 | 5 | 2 | 9 |
| * | M | | fray | STK39 (PASK) | 54 | 71 | 52 | 3 | 8 | 6 |
| | M | | Abl | ABL | 18 | 79 | 42 | 6 | 3 | 6 |
| | M | | Mekk1 | MAP3K4 (MTK1) | 12 | 72 | 38 | 4 | 5 | 5 |

Pro-targets for LS1-15

| | | | | | | | | | | |
|---|---|---|---|---|---|---|---|---|---|---|
| * | | M | wts | LATS1 (WARTS) | 70 | 56 | 96 | 10 | 4 | 4 |
| * | | M | Cad96Ca | KDR | 44 | 46 | 89 | 13 | 5 | 1 |
| | | M | Pkc53E | PRKCA | 55 | 51 | 87 | 11 | 5 | 2 |
| | | M | Ack-like | TNK1 | 42 | 55 | 87 | 6 | 4 | 2 |
| * | | M | CG7616 | ADCK5 | 84 | 63 | 86 | 3 | 7 | 3 |
| * | | M | cdc2c | CDK2 | 78 | 54 | 85 | 4 | 3 | 7 |
| | | M | gish | CSNK1G3 | 58 | 51 | 83 | 12 | 10 | 1 |
| * | | M | CaMKI | CAMK1D | 56 | 43 | 83 | 4 | 3 | 3 |
| * | | M | Drl-2 | RYK | 53 | 58 | 83 | 13 | 5 | 2 |
| * | | M | JIL-1 | RPS6KA5 (MSK1) | 75 | 32 | 83 | 5 | 11 | 5 |
| * | | M | cdc2 | CDK1 | 58 | 56 | 82 | 7 | 16 | 1 |
| * | | M | Pak | PAK1 | 65 | 30 | 81 | 3 | 5 | 2 |
| * | | M | Fps85D | FER | 72 | 50 | 81 | 2 | 13 | 7 |
| | | M | CG3216 | NPR1 | 37 | 39 | 80 | 2 | 10 | 4 |
| * | | M | shark | SYK | 63 | 48 | 80 | 13 | 7 | 10 |
| | | M | otk | PTK7 | 41 | 64 | 80 | 8 | 2 | 8 |
| * | | M | Cdk4 | CDK4/6 | 50 | 53 | 79 | 6 | 12 | 3 |
| * | | M | trbl | TRIB2 | 38 | 44 | 77 | 6 | 6 | 7 |
| * | | M | dnt | RYK | 33 | 80 | 75 | 3 | 6 | 2 |
| * | | M | Lkb1 | LKB1 | 61 | 61 | 74 | 8 | 7 | 2 |
| * | | M | gwl | MASTL (GWL) | 61 | 38 | 74 | 7 | 5 | 8 |
| | | M | sax | ACVR1 | 35 | 52 | 73 | 1 | 2 | 2 |
| | | M | CG8878 | VRK3 | 43 | 46 | 73 | 2 | 2 | 1 |
| * | | M | sti | CIT | 58 | 43 | 72 | 9 | 8 | 4 |
| * | | M | SAK | PLK4 | 64 | 39 | 72 | 7 | 5 | 6 |
| * | | M | Cdk12 | CDK12 | 66 | 47 | 72 | 2 | 2 | 6 |
| * | | M | nmo | NLK | 69 | 45 | 71 | 3 | 0 | 7 |
| | | W | Tor | MTOR | 43 | 46 | 70 | 9 | 9 | 5 |
| * | | W | CASK | CASK | 48 | 53 | 68 | 3 | 9 | 3 |
| | | W | polo | PLK1 | 39 | 24 | 68 | 9 | 12 | 5 |
| * | | W | S6k | RPS6KB1 (p70S6K) | 61 | 39 | 66 | 9 | 7 | 1 |
| | | W | msn | MINK1 | 42 | 34 | 66 | 6 | 4 | 1 |
| * | | W | Ddr | DDR2 | 49 | 37 | 65 | 6 | 12 | 4 |
| | | W | tefu | ATM | 29 | 61 | 62 | 4 | 2 | 1 |

*FIG. 59 (cont.)*

Chromosomes 2, 3 and 4 (continued)

*Pro-targets for both sorafenib and LS1-15*

| Drugs | | | Gene symbol | | % viability | | | SE | | |
|---|---|---|---|---|---|---|---|---|---|---|
| — | soraf | L15 | Fly | Human | — | soraf | L15 | — | soraf | L15 |
| | | | control | | 28 | 48 | 52 | 3 | 5 | 9 |
| * | | | babo | TGFBR1 (ALK5) | 98 | 96 | 100 | 2 | 2 | 0 |
| * | M | | Lrrk | LRRK1 | 94 | 87 | 98 | 2 | 3 | 1 |
| * | M | | hppy | MAP4K3 (GLK) | 95 | 89 | 97 | 1 | 5 | 1 |
| * | M | | Nrk | MUSK | 77 | 79 | 95 | 5 | 5 | 3 |
| * | W | | smi35A | DYRK4 | 64 | 70 | 95 | 10 | 8 | 3 |
| * | | | Pkn | PKN2 | 88 | 93 | 94 | 2 | 2 | 3 |
| * | M | | SRPK | SRPK | 77 | 89 | 94 | 7 | 11 | 4 |
| * | M | | PKD | PRKD1 | 83 | 84 | 94 | 4 | 3 | 1 |
| | M | | CG4839 | PRKG1 | 60 | 74 | 93 | 14 | 2 | 2 |
| * | M | | Ack | TNK2 | 70 | 71 | 93 | 1 | 6 | 4 |
| * | M | | Ilk | ILK | 85 | 78 | 93 | 1 | 5 | 6 |
| * | M | | gek | CDC42BPA | 47 | 81 | 92 | 8 | 2 | 1 |
| * | W | | grp | CHEK1 | 78 | 67 | 92 | 5 | 4 | 3 |
| | M | | wnd | MAP3K13 (LZK) | 33 | 82 | 92 | 5 | 5 | 4 |
| * | M | | srpk79D | SRPK | 88 | 87 | 92 | 6 | 4 | 4 |
| * | M | | Src42A | FRK | 88 | 80 | 91 | 6 | 9 | 5 |
| * | M | | bsk | JNK | 76 | 88 | 91 | 6 | 3 | 5 |
| * | M | | Eph | EPH | 72 | 64 | 91 | 2 | 4 | 3 |
| * | W | | Akt1 | AKT1 | 51 | 69 | 91 | 7 | 3 | 2 |
| * | M | M | Pka-C1 | PRKACA (PKA) | 56 | 71 | 90 | 4 | 4 | 7 |
| * | M | M | bt | TTN | 78 | 82 | 90 | 6 | 4 | 4 |
| | M | M | Bub1 | BUB1 | 45 | 80 | 90 | 4 | 13 | 2 |
| * | W | M | Sk2 | SPHK2 (SK2) | 67 | 68 | 89 | 1 | 8 | 7 |
| * | M | M | dco | CSNK1E | 90 | 72 | 89 | 8 | 8 | 6 |
| * | M | M | Cdk9 | CDK9 | 48 | 81 | 89 | 4 | 8 | 2 |
| * | W | M | Ret | RET | 73 | 69 | 88 | 3 | 4 | 6 |
| * | M | M | Pvr | FLT1 | 69 | 71 | 88 | 4 | 9 | 2 |
| * | M | M | Egfr | EGFR | 86 | 76 | 88 | 1 | 4 | 1 |
| * | M | M | Gyc32E | NPR2 | 61 | 76 | 87 | 8 | 4 | 4 |
| | W | M | Sik3 | SIK3 | 43 | 67 | 86 | 3 | 4 | 4 |
| * | M | M | hpo | STK3 (MST2) | 66 | 76 | 86 | 3 | 8 | 6 |
| * | M | M | CG1951 | SCYL2 | 31 | 71 | 86 | 8 | 14 | 1 |
| * | M | M | CG1344 | SCYL3 | 67 | 73 | 86 | 7 | 9 | 2 |
| * | W | M | CG7028 | PRPF4B | 57 | 65 | 86 | 4 | 5 | 2 |
| * | M | M | CG32944 | STK32B (YANK2) | 60 | 80 | 86 | 4 | 6 | 2 |
| * | W | M | CG43143 | NUAK1 | 62 | 69 | 84 | 4 | 7 | 6 |
| * | W | M | cdi | TESK2 | 82 | 66 | 83 | 6 | 12 | 12 |

*FIG. 59 (cont.)*

Chromosomes 2, 3 and 4 (continued)

| Drugs | | | Gene symbol | | % viability | | | SE | | |
|---|---|---|---|---|---|---|---|---|---|---|
| – | soraf | L15 | Fly | Human | – | soraf | L15 | – | soraf | L15 |
| | | | control | | 28 | 48 | 52 | 3 | 5 | 9 |
| * | M | M | Cdk8 | CDK8 | 84 | 78 | 83 | 4 | 5 | 4 |
| | W | M | CG3008 | RIOK3 | 49 | 69 | 83 | 9 | 2 | 3 |
| * | M | M | Stm-Mlck | MYLK | 61 | 85 | 83 | 2 | 4 | 2 |
| | M | M | Pdk | PDK3 | 16 | 71 | 83 | 4 | 16 | 6 |
| * | M | M | for | PRKG1 | 55 | 73 | 82 | 4 | 14 | 2 |
| | M | M | Pkg21D | PRKG2 | 41 | 73 | 82 | 7 | 3 | 4 |
| * | S | M | CkIIalpha | CSNK2A1 | 69 | 93 | 82 | 4 | 7 | 7 |
| * | S | M | p38c | MAPK11 (p38b) | 63 | 93 | 81 | 6 | 7 | 3 |
| | M | M | Unc-89 | SPEG | 68 | 78 | 81 | 1 | 9 | 10 |
| * | M | M | slik | STK10 (LOK) | 68 | 83 | 81 | 3 | 4 | 1 |
| * | M | M | CaMKII | CAMK2D | 72 | 78 | 81 | 6 | 9 | 8 |
| * | M | M | wit | BMPR2 | 78 | 74 | 81 | 1 | 2 | 1 |
| * | M | M | Fak | PTK2 (FAK) | 58 | 81 | 80 | 2 | 3 | 7 |
| * | M | M | Eip63E | CDK14 | 72 | 73 | 80 | 6 | 6 | 6 |
| | W | M | par-1 | MARK3 | 67 | 70 | 79 | 6 | 7 | 10 |
| | M | M | wee | WEE1 | 18 | 78 | 78 | 5 | 9 | 4 |
| * | M | M | Pi3K92E | PIK3CA | 59 | 72 | 78 | 5 | 7 | 3 |
| * | W | M | Pi3K68D | PIK3C2A | 49 | 63 | 78 | 8 | 10 | 6 |
| * | M | M | Nipped-A | TRRAP | 66 | 82 | 78 | 12 | 2 | 4 |
| * | M | M | Mkk4 | MAP2K4 (MKK4) | 56 | 75 | 78 | 4 | 6 | 12 |
| | W | M | Atg1 | ULK1 (ATG1) | 79 | 61 | 78 | 8 | 1 | 1 |
| * | W | M | Mpk2 | MAPK14 (p38a) | 82 | 51 | 78 | 1 | 1 | 2 |
| | W | M | p38b | MAPK11 (p38b) | 39 | 69 | 77 | 4 | 3 | 6 |
| * | W | M | yata | SCYL1 | 91 | 70 | 77 | 7 | 13 | 4 |
| | W | M | CG5790 | CDC7 | 31 | 61 | 76 | 9 | 13 | 3 |
| * | W | M | Gprk2 | GRK5 | 64 | 70 | 73 | 5 | 2 | 5 |
| * | W | M | Asator | TTBK1 (BDTK) | 60 | 67 | 72 | 9 | 7 | 4 |
| * | M | M | sqa | MYLK2 | 47 | 77 | 72 | 5 | 6 | 4 |
| | W | M | CG10738 | NPR1 | 45 | 64 | 71 | 5 | 6 | 2 |
| * | M | W | rl | MAPK1 (ERK) | 53 | 71 | 69 | 4 | 5 | 10 |
| | M | W | aPKC | PRKCI | 35 | 78 | 68 | 7 | 2 | 1 |
| | M | W | CG4629 | NIM1 | 29 | 79 | 68 | 2 | 2 | 10 |
| * | M | W | Src64B | SRC | 70 | 74 | 67 | 2 | 3 | 2 |
| | M | W | CG4945 | SBK2 | 25 | 76 | 67 | 9 | 1 | 0 |
| * | M | W | aux | GAK | 56 | 71 | 67 | 3 | 5 | 7 |
| | M | W | Nak | AAK1 | 42 | 77 | 66 | 5 | 7 | 5 |
| * | W | W | Pka-C3 | PRKX | 49 | 70 | 66 | 5 | 3 | 4 |
| | M | W | Btk29A | BTK | 60 | 81 | 63 | 2 | 4 | 4 |
| * | M | W | CG11221 | SBK1 | 31 | 86 | 56 | 5 | 7 | 6 |

*FIG. 59 (cont.)*

X chr
Chromosome X

| Drugs | | | Gene symbol | | % viability | | | SE | | |
|---|---|---|---|---|---|---|---|---|---|---|
| - | soraf | L15 | Fly | Human | - | soraf | L15 | - | soraf | L15 |
| | | | control | | 3 | 18 | 20 | 1 | 1 | 4 |

*Anti-targets for LS1-15*

| | | | | | | | | | | |
|---|---|---|---|---|---|---|---|---|---|---|
| | | | nonC | SMG1 | 3 | 31 | 2 | 3 | 10 | 2 |
| | | | LIMK1 | LIMK1 | 1 | 22 | 8 | 1 | 9 | 4 |

*Anti-targets for both sorafenib and LS1-15*

| | | | | | | | | | | |
|---|---|---|---|---|---|---|---|---|---|---|
| * | | | Erk7 | MAPK15 (ERK7) | 0 | 0 | 0 | 0 | 0 | 0 |
| | | | Tak1 | MAP3K7 (TAK1) | 3 | 8 | 2 | 3 | 4 | 2 |
| * | | | S6kII | RPS6KA3 (p90RSK) | 0 | 8 | 4 | 0 | 7 | 4 |

Chromosomes 2, 3 and 4

| | | | control | | 28 | 48 | 52 | 3 | 5 | 9 |
|---|---|---|---|---|---|---|---|---|---|---|

*Anti-target for sorafenib*

| | | | | | | | | | | |
|---|---|---|---|---|---|---|---|---|---|---|
| | | | csk | CSK | 43 | 22 | 58 | 11 | 5 | 6 |

*Anti-targets for LS1-15*

| | | | | | | | | | | |
|---|---|---|---|---|---|---|---|---|---|---|
| * | | | trc | STK38 | 3 | 34 | 14 | 1 | 12 | 2 |
| | | | ninaC | MYO3A | 14 | 48 | 25 | 2 | 3 | 4 |
| * | | | Pk92B | MAP3K15 (ASK3) | 16 | 40 | 36 | 4 | 8 | 1 |

*Anti-targets for both sorafenib and LS1-15*

| | | | | | | | | | | |
|---|---|---|---|---|---|---|---|---|---|---|
| * | | | Pdk1 | PDPK1 | 0 | 0 | 0 | 0 | 0 | 0 |
| * | | | hipk | HIPK2 | 0 | 0 | 0 | 0 | 0 | 0 |
| * | | | Mps1 | TTK | 1 | 0 | 0 | 1 | 0 | 0 |
| * | | | Lk6 | MKNK1 | 0 | 0 | 0 | 0 | 0 | 0 |
| | | | Pak3 | PAK3 | 14 | 6 | 20 | 8 | 4 | 2 |

KINASE INHIBITOR COMPOUNDS, COMPOSITIONS, AND METHODS OF TREATING CANCER

This application is a national stage application under 35 U.S.C. § 371 of PCT Application No. PCT/US2017/047383, filed Aug. 17, 2017, which claims the benefit of U.S. Provisional Patent Application Ser. No. 62/376,138, filed Aug. 17, 2016, which are hereby incorporated by reference in their entirety.

This invention was made with government support under grant numbers U54OD020353, R01-CA170495, and R01-CA109730 awarded by National Institutes of Health. The government has certain rights in the invention.

FIELD OF THE INVENTION

The present invention relates to kinase inhibitor compounds, compositions containing the compounds, and methods of treating cancer.

BACKGROUND OF THE INVENTION

In complex diseases such as cancer, drug combinations have the potential to provide durable treatment responses, minimize adverse events, and limit development of resistance (U.S. Department of Health and Human Services Food and Drug Administration, "Guidance for Industry. Codevelopment of Two or More New Investigational Drugs for Use in Combination," (June 2013)). A related approach to combination therapy is single agent polypharmacological drugs such as multi-targeted kinase inhibitors. However, a lack of systematic design approaches and a historical reliance on serendipity has limited the number of new polypharmacological drugs (Anighoro et al., "Polypharmacology: Challenges and Opportunities in Drug Discovery," *J. Med. Chem.* 57:7874-7887 (2014); Reddy et al., "Polypharmacology: Drug Discovery for the Future," *Expert Rev. Clin. Pharmacol.* 6:41-47 (2013)). An intentional, rational approach to polypharmacology, especially in the context of the whole animal, would significantly expand the ability to develop complex therapeutics. Further, achieving "balanced polypharmacology" in the context of the whole animal can reduce overall toxicity by balancing a drug's effects on cellular and tissue networks.

The present invention is directed to overcoming these and other deficiencies in the art.

SUMMARY OF THE INVENTION

One aspect of the present invention relates to a compound of formula (I) having the following structure:

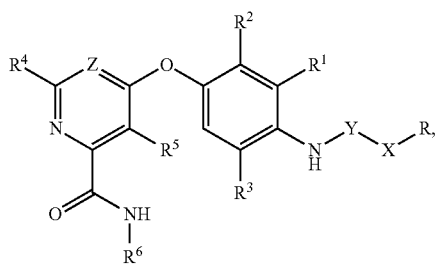

or a stereoisomer, pharmaceutically acceptable salt, oxide, or solvate thereof, wherein R is selected from the group consisting of $C_{1-6}$ alkyl, $C_{1-6}$ alkoxy, $-N(C_{1-6}$ alkyl$)_2$, $C_{3-6}$ cycloalkyl, aryl, heteroaryl, and heterocyclyl, wherein $C_{1-6}$ alkyl, $C_{3-6}$ cycloalkyl, aryl, heteroaryl, and heterocyclyl can be optionally substituted n times with $R^{13}$;

$R^1$ is H;
$R^2$ is H;
or $R^1$ and $R^2$ combine with the phenyl ring to which they are attached to form

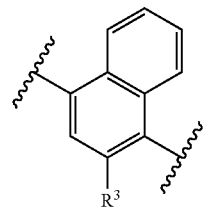

(a naphthyl group);

$R^3$ is H or halogen;
$R^4$ is H, halogen, or $C_1$-$C_6$ alkyl;
$R^5$ is H, halogen, or $C_1$-$C_6$ alkyl;
$R^6$ is $C_1$-$C_6$ alkyl;
X is optional and, if present, is NH;
Y is

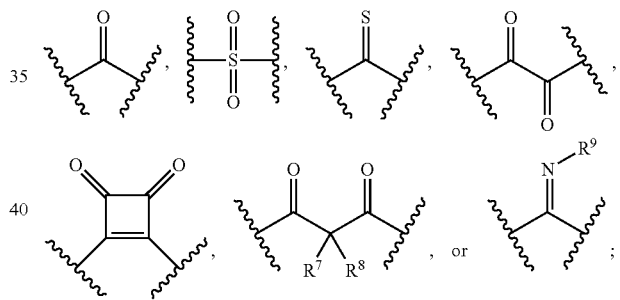

Z is $C(R^{12})$ or N;
$R^7$ is H or Me;
$R^8$ is H or Me;
or $R^7$ and $R^8$ are taken together with the carbon atom to which they are attached to form

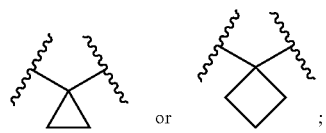 [SMILES: *C1(*)CC1 ; *C1(*)CCC1]

$R^9$ is H, $C_{1-6}$ alkyl, $C_{3-6}$ cycloalkyl, allyl, —CN, or

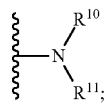

$R^{10}$ is H, $C_{1-6}$ alkyl, or $C_{3-6}$ cycloalkyl;

$R^{11}$ is H, $C_{1-6}$ alkyl, or $C_{3-6}$ cycloalkyl;
$R^{12}$ is H, halogen, or $C_1$-$C_6$ alkyl;
$R^{13}$ is selected independently at each occurrence thereof from the group consisting of H, halogen, $C_1$-$C_6$ alkyl, $CH_2F$, $CHF_2$, $CClF_2$, $CBrF_2$, $ClF_2$, $CF_3$, $C_2F_5$, $C_3F_7$, $C_4F_9$, $OCF_3$ and heterocyclyl; and
n is 1 to 5;
with the proviso that when
i) $R^1$ is H, $R^2$ is H, $R^3$ is H, $R^4$ is H, $R^5$ is H, $R^6$ is $CH_3$, Z is CH, X is NH, and Y is

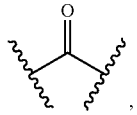 [SMILES: *C(*)=O]

R cannot be

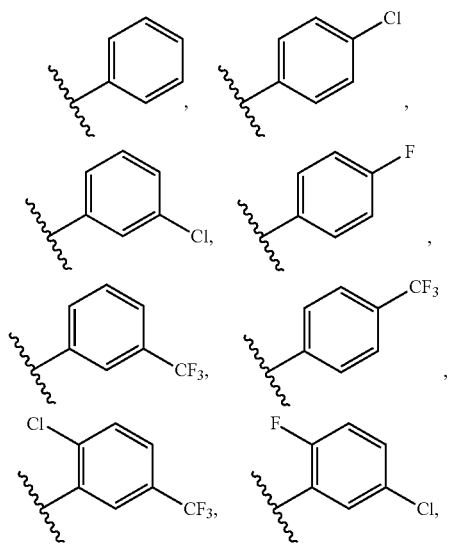

ii) $R^1$ is H, $R^2$ is H, $R^3$ is H, $R^4$ is H, $R^5$ is H, $R^6$ is $CH_3$, Z is CH, X is absent, and Y is

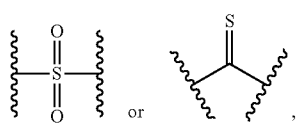

R cannot be

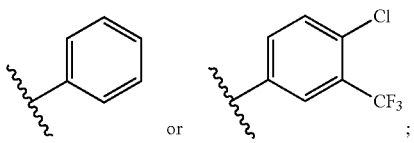 [SMILES: *c1ccccc1 ; *c1ccc(Cl)c(C(F)(F)F)c1]

iii) $R^1$ is H, $R^2$ is H, $R^3$ is H, $R^4$ is H, $R^5$ is H, $R^6$ is $CH_3$, Z is CH, Y is

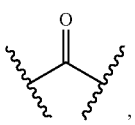 [SMILES: *C(*)=O]

and n is 2, R cannot be

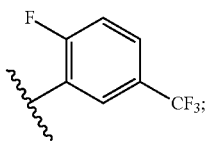 [SMILES: *c1cc(C(F)(F)F)ccc1F]

iv) $R^1$ is H, $R^2$ is H, $R^3$ is F, $R^4$ is H, $R^5$ is H, $R^6$ is $CH_3$, Z is CH, X is NH, Y is

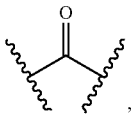 [SMILES: *C(*)=O]

and n is 2, R cannot be

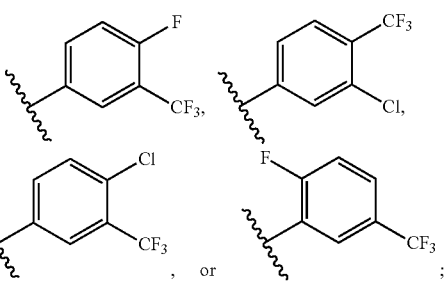

v) $R^1$ is H, $R^2$ is H, $R^3$ is H, $R^4$ is H, $R^5$ is H, $R^6$ is $CH_3$, Z is CH, X is absent, and Y is

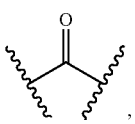 [SMILES: *C(*)=O]

R cannot be

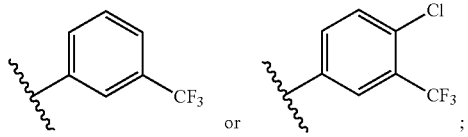 [SMILES: *c1cccc(C(F)(F)F)c1 ; *c1ccc(Cl)c(C(F)(F)F)c1]

or ;

and vi) $R^1$ is H, $R^2$ is H, $R^3$ is H, $R^4$ is H, $R^5$ is H, $R^6$ is $CH_3$, Z is CH, X is NH, and Y is

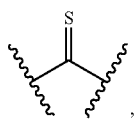 [SMILES: *C(*)=S]

,

R cannot be

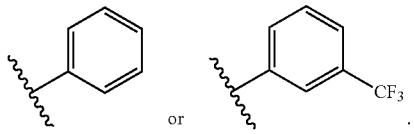 [SMILES: *c1ccccc1 ; *c1cccc(C(F)(F)F)c1]

or .

Another aspect of the present invention relates to a composition comprising the compound of formula (I) described herein and a carrier.

A further aspect of the present invention relates to a method of treating cancer in a subject. This method involves administering to a subject a compound of formula (I) having the following structure:

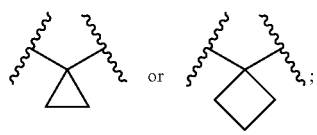 [SMILES: *C1(*)CC1 ; *C1(*)CCC1]
(I)

or a stereoisomer, pharmaceutically acceptable salt, oxide, or solvate thereof, wherein R is selected from the group consisting of $C_{1-6}$ alkyl, $C_{1-6}$ alkoxy, —N($C_{1-6}$ alkyl)$_2$, $C_{3-6}$ cycloalkyl, aryl, heteroaryl, and heterocyclyl, wherein $C_{1-6}$ alkyl, $C_{3-6}$ cycloalkyl, aryl, heteroaryl, and heterocyclyl can be optionally substituted n times with $R^{13}$;

$R^1$ is H;

$R^2$ is H;

or $R^1$ and $R^2$ combine with the phenyl ring to which they are attached to form

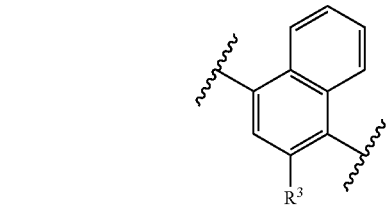

(a naphthyl group);

$R^3$ is H or halogen;

$R^4$ is H, halogen, or $C_1$-$C_6$ alkyl;

$R^5$ is H, halogen, or $C_1$-$C_6$ alkyl;

$R^6$ is $C_1$-$C_6$ alkyl;

X is optional and, if present, is NH;

Y is

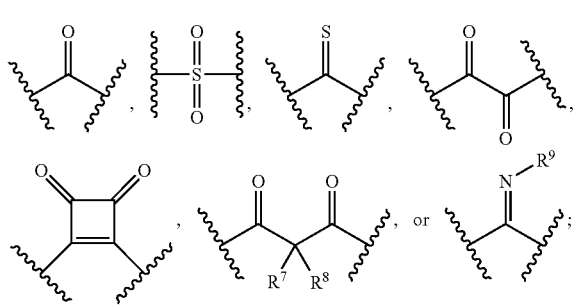

Z is $C(R^{12})$ or N;

$R^7$ is H or Me;

$R^8$ is H or Me;

or $R^7$ and $R^8$ are taken together with the carbon atom to which they are attached to form

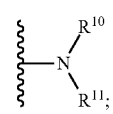

or ;

$R^9$ is H, $C_{1-6}$ alkyl, $C_{3-6}$ cycloalkyl, allyl, —CN, or $R^{10}$ is H, $C_{1-6}$ alkyl, or $C_{3-6}$ cycloalkyl;

$R^{11}$ is H, $C_{1-6}$ alkyl, or $C_{3-6}$ cycloalkyl;

$R^{12}$ is H, halogen, or $C_1$-$C_6$ alkyl;

$R^{13}$ is selected independently at each occurrence thereof from the group consisting of H, halogen, $C_1$-$C_6$ alkyl, $CH_2F$, $CHF_2$, $CClF_2$, $CBrF_2$, $ClF_2$, $CF_3$, $C_2F_5$, $C_3F_7$, $C_4F_9$, $OCF_3$, and heterocyclyl; and n is 1 to 5;

with the proviso that when i) $R^1$ is H, $R^2$ is H, $R^3$ is H, $R^4$ is H, $R^5$ is H, $R^6$ is $CH_3$, Z is CH, X is NH, and Y is

7

$$\text{(C=O group)},$$

R cannot be

[phenyl, 4-chlorophenyl, 3-chlorophenyl, 4-fluorophenyl, 3-trifluoromethylphenyl, 4-trifluoromethylphenyl, 2-chloro-5-trifluoromethylphenyl, 2-fluoro-5-chlorophenyl, benzo[1,3]dioxol-5-yl, 3,5-bis(trifluoromethyl)phenyl, 2-fluoro-3-trifluoromethylphenyl, or 4-chloro-3-trifluoromethylphenyl];

ii) $R^1$ is H, $R^2$ is H, $R^3$ is H, $R^4$ is H, $R^5$ is H, $R^6$ is CH$_3$, Z is CH, X is absent, and Y is

[sulfonyl (SO$_2$) or thiocarbonyl (C=S)],

R cannot be

[phenyl or 4-chloro-3-trifluoromethylphenyl];

iii) $R^1$ is H, $R^2$ is H, $R^3$ is H, $R^4$ is H, $R^5$ is H, $R^6$ is CH$_3$, Z is CH, Y is

8

$$\text{(C=O group)},$$

and n is 2, R cannot be

[2-fluoro-5-trifluoromethylphenyl];

iv) $R^1$ is H, $R^2$ is H, $R^3$ is F, $R^4$ is H, $R^5$ is H, $R^6$ is CH$_3$, Z is CH, X is NH, Y is $$\text{(C=O group)},$$

and n is 2, R cannot be

[4-fluoro-3-trifluoromethylphenyl, 4-trifluoromethyl-3-chlorophenyl, 4-chloro-3-trifluoromethylphenyl, or 4-fluoro-3-trifluoromethylphenyl];

v) $R^1$ is H, $R^2$ is H, $R^3$ is H, $R^4$ is H, $R^5$ is H, $R^6$ is CH$_3$, Z is CH, X is absent, and Y is $$\text{(C=O group)},$$

R cannot be

[3-trifluoromethylphenyl or 4-chloro-3-trifluoromethylphenyl];

and vi) $R^1$ is H, $R^2$ is H, $R^3$ is H, $R^4$ is H, $R^5$ is H, $R^6$ is CH$_3$, Z is CH, X is NH, and Y is

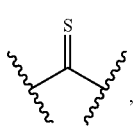 [SMILES: *C(*)=S]

R cannot be

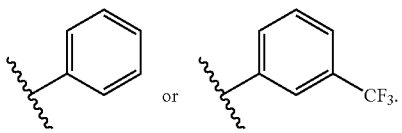 [SMILES: *c1ccccc1 ; *c1cccc(C(F)(F)F)c1]

Polypharmacological kinase inhibitors target biological networks at multiple nodes and through multiple pathways. Such drugs, including the clinically approved cancer therapeutic sorafenib, have historically been limited due to complexity of design, significant toxicity, and dosing problems. Avoiding these liabilities can reveal desirable properties such as the potential for low susceptibility to resistance and long-term responses in patients. However, few methods are available to intentionally design polypharmacological drugs. Using a multidisciplinary approach that combined chemical and genetic modifier screens, a discrete set of biological pro-targets and anti-targets of the FDA approved kinase inhibitor sorafenib in an established ptc>dRet$^{M955T}$ Drosophila model for medullary thyroid carcinoma was identified. It was demonstrated that Raf, the original intended sorafenib target, and MKNK1 are key pharmacological anti-targets that emerge as a result of higher-order complex assembly and pathway feedback, respectively. Combining this information with progressive synthetic refinement of lead compounds resulted in a new class of "sorafelogs" with diminished anti-target activity, and thereby strongly improved therapeutic index within a whole animal context. More generally, the application of this platform to a variety of diseases and candidate therapeutic leads can provide a rational, intentional path forward for the development of new classes of high efficacy/low toxicity polypharmacological drugs.

Drosophila was previously reported as a useful whole animal model for drug discovery and development (Vidal et al., "ZD6474 Suppresses Oncogenic RET Isoforms in a Drosophila Model for Type 2 Multiple Endocrine Neoplasia Syndromes and Papillary Thyroid Carcinoma," Cancer Res. 65:3538-3541 (2005); Rudrapatna et al., "Drosophila Cancer Models," Dev. Dyn. 241:107-118 (2012); Dar et al., "Chemical Genetic Discovery of Targets and Anti-Targets for Cancer Polypharmacology," Nature 486:80-84 (2012), which are hereby incorporated by reference in their entirety).

The present application relates to the use of genetic and chemical modifier screens in Drosophila to rationally improve the therapeutic index of the clinical cancer drug sorafenib. Combining a whole animal genetic modifier screen with computational and reiterative chemistry approaches resulted in development of novel sorafenib analogs ("sorafelogs") with optimized pro-target and anti-target profiles. Surprisingly, eliminating activity against Raf kinase led to a strong improvement of therapeutic index. In all, novel compounds with markedly improved therapeutic indices were developed in a rational, stepwise manner.

BRIEF DESCRIPTION OF THE DRAWINGS

FIGS. 53A-C show identification of sorafenib in drug screening using a *Drosophila* cancer model. FIG. 53A is a schematic illustration showing the quantitative "rescue-from-lethality" *Drosophila* platform used for drug and compound screening. In ptc>dRet$^{M955T}$ flies, the patched (ptc) promoter drives an oncogenic mutant isoform of *Drosophila* Ret (dRet$^{M955T}$) in several tissues, directing lethality prior to emergence as adults. Larvae consume candidate drugs; drug efficacy is quantified by dividing the number of rescued adults (A) by the number of total pupae (P). FIG. 53B is a graph showing testing of FDA-approved anti-cancer kinase inhibitors in ptc>dRet$^{M955T}$ flies. Two approved drugs for MTC are underlined. The best hit, sorafenib, promoted only ~5% rescue. Error bars, standard errors in triplicate. Asterisks, p<0.05 in Student's t-test reflects comparison with DMSO vehicle control. FIG. 53C shows results of an in vivo cell migration assay. Left panel, a developing wing disc harboring GFP-labeled, dRet$^{M955T}$-expressing transformed cells. Blue, DAPI staining outlines the wing disc margin. Middle top and right top, magnified apical images for vehicle and sorafenib treatments, respectively. Arrowhead indicates example of migrating cell. Bottom, virtual z-series of confocal images derived from the plane indicated by dotted lines in top panels; tissues are stained for phospho (p)-Src (red). Arrowheads indicate a migrating transformed cell expressing pSrc basally (red).

FIGS. 54A-D show generation and efficacy of sorafenib analogs, sorafelogs. FIG. 54A is a schematic illustration showing that Sorafenib is composed of four domains. Left panel shows the conformations of sorafenib when bound to various kinases in the DFG-out (i.e. inactive) conformation (grey); PDB ID of the shown structures is listed in parentheses. For example, when bound to BRAF, sorafenib (yellow version) interacts with the hinge region of the ATP-binding pocket and a conserved glutamate residue from the C-helix (E885) using hinge binder and linker regions, respectively. The cap group of sorafenib occupies the DFG-pocket, which was previously occupied by the phenylalanine (F1047) in the DFG-in (i.e. active) conformation. The right panel shows the chemical structure of sorafenib and a conceptual fragmentation into four simple building blocks amenable to a modular synthetic strategy. The hinge binder was not altered in these studies. FIG. 54B is a schematic illustration showing stepwise derivatization of sorafelogs. The first set of sorafelogs includes combinations between spacers/linkers/caps generated by medicinal chemistry. Drug screening experiments with ptc>dRet$^{M955T}$ flies identified LS1-15 as the best derivative; subsequent genetic screening revealed pro-targets and anti-targets for sorafenib and LS1-15. Computation compared physicochemical features between compounds such as intramolecular steric hindrance and modifications of the cap to prevent its binding to anti-targets, pointing to novel chemical spaces APS5-16-2 and APS6-45. FIG. 54C shows derivatized sorafenib segments. Grey structures: ineffective components as assessed in ptc>dRet$^{M955T}$ animals. FIG. 54D is a graph showing rescue of ptc>dRet$^{M955T}$ flies by sorafelogs. LS1-15 ("j") rescued viability significantly better than sorafenib (a) and regorafenib (b); additional fluorines (circled) and an absent chlorine (x) highlight the structural differences with sorafenib. APS5-16-2 carrying inflated cap also showed significant rescue (k), whereas APS6-45 with the largest cap shows the strongest efficacy (o) exceeding AD80. T, toxic dose for flies. Error bars, standard errors in triplicate. Lower case letters correspond to those in FIG. 58A.

FIGS. 55A-C show pro-target and anti-targets for LS1-15 identified through genetic screening. FIG. 55A is a schematic illustration showing a screening approach to identify genetic modifiers of LS1-15 efficacy in ptc>dRet$^{M955T}$ flies. Fly kinome genes were identified as "pro-targets" or "anti-targets" if as (−/+) heterozygotes they increased or decreased, respectively, the efficacy of LS1-15. FIG. 55B is a graph showing examples of LS1-15 pro-targets (EPH, FRK) and an anti-target (MKNK1). For example, removal of one functional copy of Lk6 (ptc>dRet$^{M955T}$, Lk6) in the presence of LS1-15 led to full lethality. FIG. 55C is a schematic illustration showing representative signaling and cellular pathways defined by pro-targets and anti-targets of LS1-15. Full data is presented in FIGS. 59 and 60. Shown are strong pro-targets and strong anti-targets giving >91% and <9% viability, respectively, as compared with ~50% viability of LS1-15-treated control flies at 23° C. Human orthologs are indicated (parentheses). Asterisks, p<0.05 in Student's t-test as compared with control.

FIGS. 56A-D show the development of novel sorafelogs APS5-16-2 and APS6-45 by reducing anti-targets MKNK1 and BRAF. FIG. 56A shows results of a Wing venation assay in adult flies. dRet$^{M955T}$ driven by the pan-wing disc driver 765-gal4 directed ectopic vein material (arrowheads); 765-gal4 alone is shown as control. Low-dose LS1-15 enhanced extra venation and also notching of the wing margin, whereas high dose suppressed both. MEK inhibitor trametinib strongly suppressed ectopic venation, demonstrating that ectopic venation is due to elevated Ras/Raf pathway activity. FIG. 56B shows quantification of wing venation assays. LS1-15 and sorafenib showed bipartite effects: low doses enhanced venation whereas high doses suppressed venation. APS5-16-2 and APS6-45, carrying bulky cap subgroups (circles), exclusively suppressed wing venation. Asterisks, p<0.05 as compared with vehicle control. #, p<0.05 as compared with LS1-15 mono-treatment. Error bars, standard errors in >15 wings. FIG. 56C is a graph showing Kd values for sorafelogs against human RET, its active mutant RET(M918T), and anti-targets BRAF and MKNK1. FIG. 56D shows DFG-pockets of human RET, BRAF, and MKNK1 in DFG-out configuration. The DFG-pocket is contoured by a colored surface, and is superimposed with the cap of LS1-15, APS5-16-2, or APS6-45. Arrowheads indicate representative steric clashes between the caps and the pockets; inset for DFG-BRAF shows a lateral view of APS6-45 to visualize clash. Errors, standard errors of ten calculations.

FIGS. 57A-D show that the novel sorafelog APS6-45 displayed exceptional efficacy. FIG. 57A shows that Lk6 mutation enhanced abnormal wing venation and affected overall wing structure. Arrowheads highlight excess wing vein materials. See FIG. 56A for controls. FIG. 57B is a schematic illustration showing one potential model of MKNK1 inhibition of Ras/MAPK pathway signaling. FIG. 57C shows effects of reducing Lk6 in the presence sorafelogs on cell migration. Wing discs heterozygous for Lk6 displayed enhanced dRet$^{M955T}$-induced cell migration, which was further enhanced by sorafenib and LS1-15 but not by APS5-16-2 or APS6-45. Arrowheads show migrating cells (apical views). FIG. 57D shows effects of compounds on a rough eye phenotype. ptc>dRet$^{M955T}$ exhibited a disarray of the ommatidial field in the anterior of the adult eye (brackets). APS6-45 strongly rescued the rough eye phenotype, leading to smoothly arrayed ommatidia similar to ptc-gal4 controls (arrowheads). Vehicle-treated control flies were dissecting from pupal cases as they did not survive until adulthood.

FIGS. 58A-B show the optimization of polypharmacology. FIG. 58A shows the chemical evolution of sorafenib. The x-axis shows progressing modification of the cap (-R). White area, caps to test internal steric hindrance. Shaded area, (2)-fluoridated compounds showing consistent SAR for the number of fluorines in the cap subgroups (circles). Asterisks, no rescue for both S1 and S2 spacers. FIG. 58B shows models for action mechanisms of each sorafelog. (Left) Sorafenib inhibits pro-targets such as RET. At low dose, however, such inhibition is not potent enough, and BRAF is even activated to cause toxicity. Such unwanted effects are abolished at higher concentration, but simultaneous inhibition of anti-targets limits the therapeutic window. (Middle) LS1-15 inhibits additional pro-targets EPH and FRK, generating a bigger therapeutic window than sorafenib. LS1-15 at low dose still causes toxicity because it activates BRAF as sorafenib does. (Right) APS5-16-2 and APS6-45 have reduced binding potency to an anti-target BRAF, thus prevents its activation at low dose. Another anti-target MKNK1 is also kept uninhibited, leading to more prominent therapeutic effects than sorafenib.

FIG. 59 is a table showing pro-targets of sorafenib and LS1-15. A list of genes whose heterozygosity causes a statistically significant increase in the survival of ptc>dRet$^{M955T}$ flies in the presence of drugs. ptc>dRet$^{M955T}$ flies were crossed with kinase-mutant flies, and the number of adults was divided by that of total pupae to calculate percent viability. Viabilities of kinase-proficient controls differ between data sets for different chromosomes due to swapped genders of parent flies in the crosses (FIGS. 62A-H). W, M, and S, statistically significantly weak, modest, and strong effects, respectively: for genes on X chromosome, weak (21-50% viability), moderate (51-80% viability), and strong effects (81-100% viability), respectively, and for genes on 2nd, 3rd, and 4th chromosomes, weak (51-70% viability), moderate (71-90% viability), and strong effects (91-100% viability), respectively. SE, standard error for three experimental replicates. Asterisks, statistically significant change in % viability by kinase mutations as compared with kinase-proficient control in the absence of drugs. -, soraf, and L15, vehicle-, sorafenib-, and LS1-15-treated flies, respectively.

FIG. 60 is a table showing anti-targets of sorafenib and LS1-15. A list of genes whose heterozygosity caused statistically significant decrease in % viability of ptc>dRet$^{M955T}$ flies in the presence of drugs. Same legend as in FIG. 59 except for W, M, and S for genes on X chromosome (weak (11-17% viability), moderate (6-10% viability), and strong effects (0-5% survival), respectively) or 2nd, 3rd, and 4th chromosomes (weak (30-47% viability), moderate (10-29% viability), and strong effects (0-9% viability), respectively).

FIG. 65A shows Venn diagrams displaying pro-targets and anti-targets for sorafenib and/or LS1-15. Shown are strong pro-targets and strong anti-targets whose heterozygosity give >91% and <9% viability, respectively, to ptc>dRet$^{M955T}$ flies in the presence of drugs. FIG. 65B is a graph showing that heterozygosity of Lk6 heterozygosity had no effect on viability of control flies. Control (w$^-$) flies or Lk6 heterozygotes (w$^-$; Lk6$^{-/+}$) larvae were treated with or without drugs. Percent viability was determined using numbers of pupae and adults. FIG. 65C is a graph showing distinct inhibition of pro-target kinases by sorafelogs. Percent inhibition of kinase activities were determined by in vitro assays.

FIG. 66A shows the effects of compounds sorafenib (400 μM), LS1-15 (200 μM), APS5-16-2 (100 μM), APS6-45 (100 μM), and AD80 (100 μM) on a fly rough eye phenotype. FIG. 66B illustrates the suppression of human MTC colony formation by APS5-16-2 and APS6-45. FIG. 66C illustrates the suppression of TT cell growth in nude mice in vivo by APS6-45. FIG. 66D shows percent changes in tumor volume on day 30 relative to pretreatment baselines. FIG. 66E illustrates the lack of effect of the treatment on mouse body weight.

DETAILED DESCRIPTION OF THE INVENTION

Figure 1:
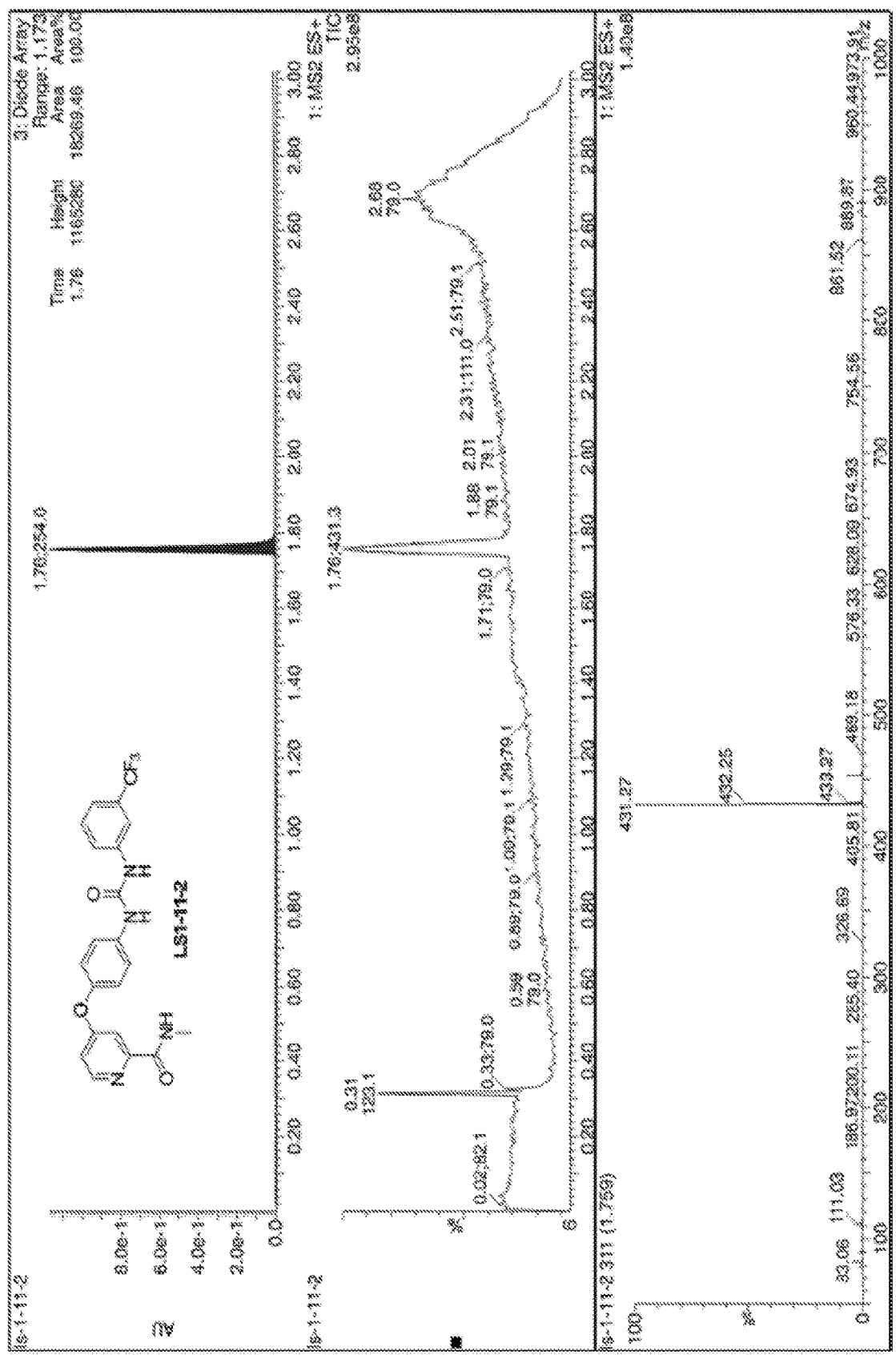
FIG. 1 shows LC-MS data for compound LS1-11-2.

The present invention involves a stepwise approach for balancing the polypharmacology of clinical kinase inhibitors. According to this approach, new kinase inhibitor compounds have been synthesized. The present invention is directed to such compounds, compositions containing the compounds, and methods of treating cancer.

One aspect of the present invention relates to a compound of formula (I) having the following structure:

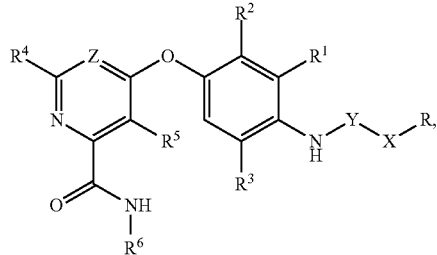
(I)

or a stereoisomer, pharmaceutically acceptable salt, oxide, or solvate thereof, wherein R is selected from the group consisting of $C_{1-6}$ alkyl, $C_{1-6}$ alkoxy, —N($C_{1-6}$ alkyl)$_2$, $C_{3-6}$ cycloalkyl, aryl, heteroaryl, and heterocyclyl, wherein $C_{1-6}$ alkyl, $C_{3-6}$ cycloalkyl, aryl, heteroaryl, and heterocyclyl can be optionally substituted n times with $R^{13}$;

$R^1$ is H;

$R^2$ is H;

or $R^1$ and $R^2$ combine with the phenyl ring to which they are attached to form

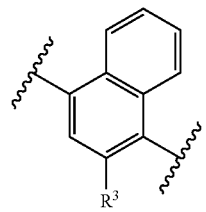

(a naphthyl group);

$R^3$ is H or halogen;

$R^4$ is H, halogen, or $C_1$-$C_6$ alkyl;

$R^5$ is H, halogen, or $C_1$-$C_6$ alkyl;

$R^6$ is $C_1$-$C_6$ alkyl;

X is optional and, if present, is NH;

Y is

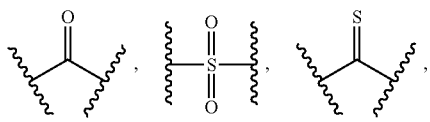

-continued

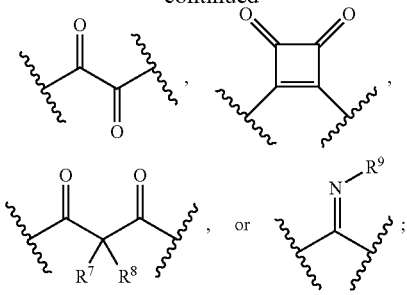

Z is $C(R^{12})$ or N;

$R^7$ is H or Me;

$R^8$ is H or Me;

or $R^7$ and $R^8$ are taken together with the carbon atom to which they are attached to form

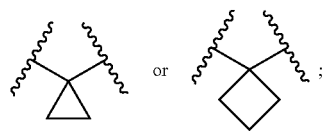 [SMILES: *C1(*)CC1 ; *C1(*)CCC1]

$R^9$ is H, $C_{1-6}$ alkyl, $C_{3-6}$ cycloalkyl, allyl, —CN, or

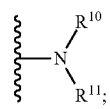

$R^{10}$ is H, $C_{1-6}$ alkyl, or $C_{3-6}$ cycloalkyl;

$R^{11}$ is H, $C_{1-6}$ alkyl, or $C_{3-6}$ cycloalkyl;

$R^{12}$ is H, halogen, or $C_1$-$C_6$ alkyl;

$R^{13}$ is selected independently at each occurrence thereof from the group consisting of H, halogen, $C_1$-$C_6$ alkyl, $CH_2F$, $CHF_2$, $CClF_2$, $CBrF_2$, $CIF_2$, $CF_3$, $C_2F_5$, $C_3F_7$, $C_4F_9$, $OCF_3$, and heterocyclyl; and n is 1 to 5;

with the proviso that when i) $R^1$ is H, $R^2$ is H, $R^3$ is H, $R^4$ is H, $R^5$ is H, $R^6$ is $CH_3$, Z is CH, X is NH, and Y is

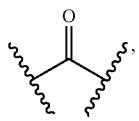

R cannot be

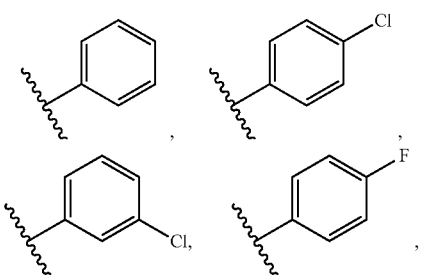

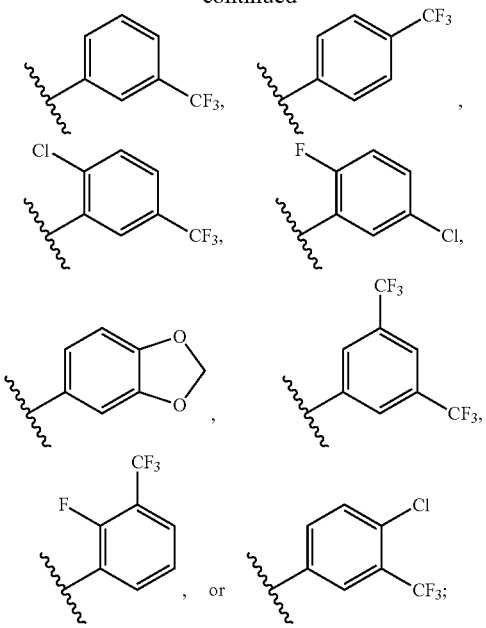

ii) $R^1$ is H, $R^2$ is H, $R^3$ is H, $R^4$ is H, $R^5$ is H, $R^6$ is CH$_3$, Z is CH, X is absent, and Y is

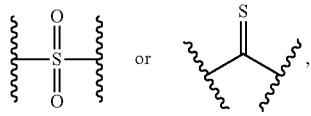

R cannot be

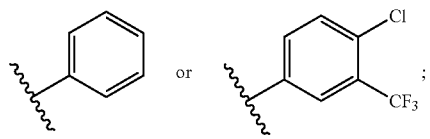 [SMILES: *c1ccccc1 ; *c1ccc(Cl)c(C(F)(F)F)c1]

iii) $R^1$ is H, $R^2$ is H, $R^3$ is H, $R^4$ is H, $R^5$ is H, $R^6$ is CH$_3$, Z is CH, Y is

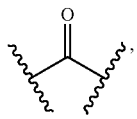 [SMILES: *C(*)=O]

and n is 2, R cannot be

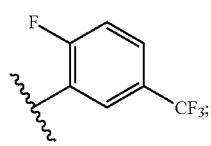 [SMILES: *c1cc(C(F)(F)F)ccc1F]

iv) $R^1$ is H, $R^2$ is H, $R^3$ is H, $R^4$ is H, $R^5$ is H, $R^6$ is CH$_3$, Z is CH, X is NH, Y is and n is 2, R cannot be v) $R^1$ is H, $R^2$ is H, $R^3$ is H, $R^4$ is H, $R^5$ is H, $R^6$ is CH$_3$, Z is CH, X is absent, and Y is R cannot be and vi) $R^1$ is H, $R^2$ is H, $R^3$ is H, $R^4$ is H, $R^5$ is H, $R^6$ is CH$_3$, Z is CH, X is NH, and Y is R cannot be As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs.

In the event that there is a plurality of definitions for a term herein, those in this section prevail unless stated otherwise.

As used herein, the term "halogen" means fluoro, chloro, bromo, or iodo.

The term "alkyl" means an aliphatic hydrocarbon group which may be straight or branched having about 1 to about 6 carbon atoms in the chain (or the number of carbons designated by "$C_{n\text{-}n}$", where n-n is the numerical range of carbon atoms). Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "cycloalkyl" means a non-aromatic, saturated or unsaturated, mono- or multi-cyclic ring system of about 3 to about 7 carbon atoms, preferably of about 5 to about 7 carbon atoms, and which may include at least one double bond. Exemplary cycloalkyl groups include, without limitation, cyclopropyl, cyclobutyl, cyclopentyl, cyclohexyl, cycloheptyl, cyclopropenyl, cyclobutenyl, cyclopentenyl, cyclophenyl, anti-bicyclopropane, and syn-tricyclopropane.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to six carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be

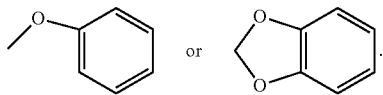

The term "aryl" means an aromatic monocyclic or multi-cyclic (polycyclic) ring system of 6 to about 19 carbon atoms, preferably of 6 to about 10 carbon atoms, and includes arylalkyl groups. The ring system of the aryl group may be optionally substituted. Representative aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

The term "heteroaryl" means an aromatic monocyclic or multi-cyclic ring system of about 5 to about 19 ring atoms, preferably about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "heterocyclyl" or "heterocycle" refers to a stable 3- to 18-membered ring (radical) of carbon atoms and from one to five heteroatoms selected from nitrogen, oxygen, and sulfur. The heterocycle may be a monocyclic or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., *Comprehensive Heterocyclic Chemistry: The Structure, Reactions, Synthesis and Use of Heterocyclic Compounds*, Vol. 1-8, Pergamon Press, N.Y. (1984), which is hereby incorporated by reference in its entirety.

The phrase "optionally substituted" indicates that a group may have a substituent at each substitutable atom of the group (including more than one substituent on a single atom), and the identity of each substituent is independent of the others.

The term "substituted" means that one or more hydrogen on a designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds. By "stable compound" it is meant a compound that is sufficiently robust to survive isolation to a useful degree of purity from a reaction mixture and formulation into an efficacious therapeutic agent.

By "compound(s) of the invention" and equivalent expressions, it is meant compounds herein described, which expression includes the prodrugs, the pharmaceutically acceptable salts, the oxides, and the solvates, e.g. hydrates, where the context so permits.

The term "treating" means amelioration or relief from the symptoms and/or effects associated with the diseases or disorders described herein.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. All tautomeric forms are also intended to be included.

As would be understood by a person of ordinary skill in the art, the recitation of "a compound" is intended to include salts, solvates, oxides, and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form.

The term "solvate" refers to a compound in the solid state, where molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

Inclusion complexes are described in *Remington, The Science and Practice of Pharmacy,* 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed by the present invention.

The term "pharmaceutically acceptable salt" refers to salts prepared from pharmaceutically acceptable non-toxic acids or bases including inorganic acids and bases and organic acids and bases.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

In one embodiment, in the compound of formula (I) R is

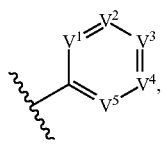

where
$V^1$ is $C(R^{14})$ or N;
$V^2$ is CH or N;
$V^3$ is $C(R^{15})$ or N;
$V^4$ is $C(R^{16})$ or N;
$V^5$ is CH or N;
$R^{14}$ is H or halogen;
$R^{15}$ is H or halogen; and
$R^{16}$ is $C_1$-$C_6$ alkyl substituted from 2 to 13 times with halogen;
where only one of $V^1$-$V^5$ is N.

In another embodiment, in the compound of formula (I) $R^{16}$ is $C_1$-$C_6$ alkyl substituted from 2 to 13 times with fluorine. According to this embodiment, $R^{16}$ may be selected from the group consisting of $CH_2F$, $CHF_2$, $CClF_2$, $CBrF_2$, $ClF_2$, $CF_3$, $C_2F_5$, $C_3F_7$, and $C_4F_9$.

In another embodiment, in the compound of formula (I) $R^{14}$ is F.

In yet another embodiment, in the compound of formula (I) $R^3$ is F.

In another embodiment, in the compound of formula (I) X is NH and Y is

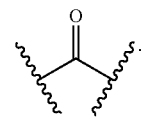

In a further embodiment, the compound of formula (I) is selected from the group consisting of

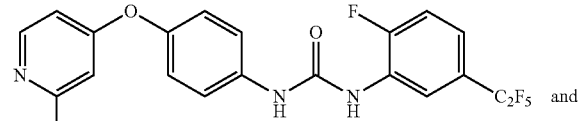 and

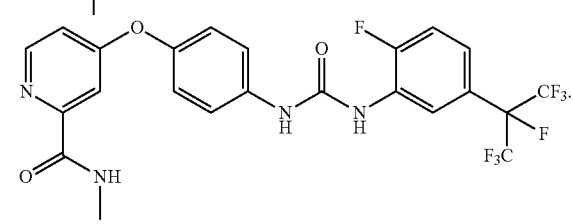

In another embodiment, the compound of formula (I) is selected from the group consisting of

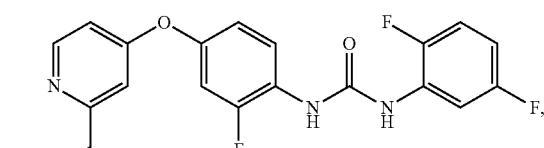

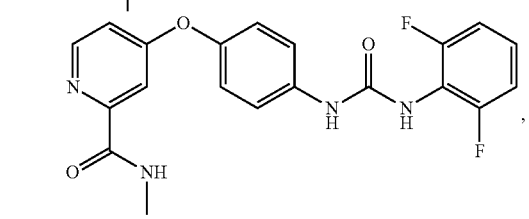

-continued
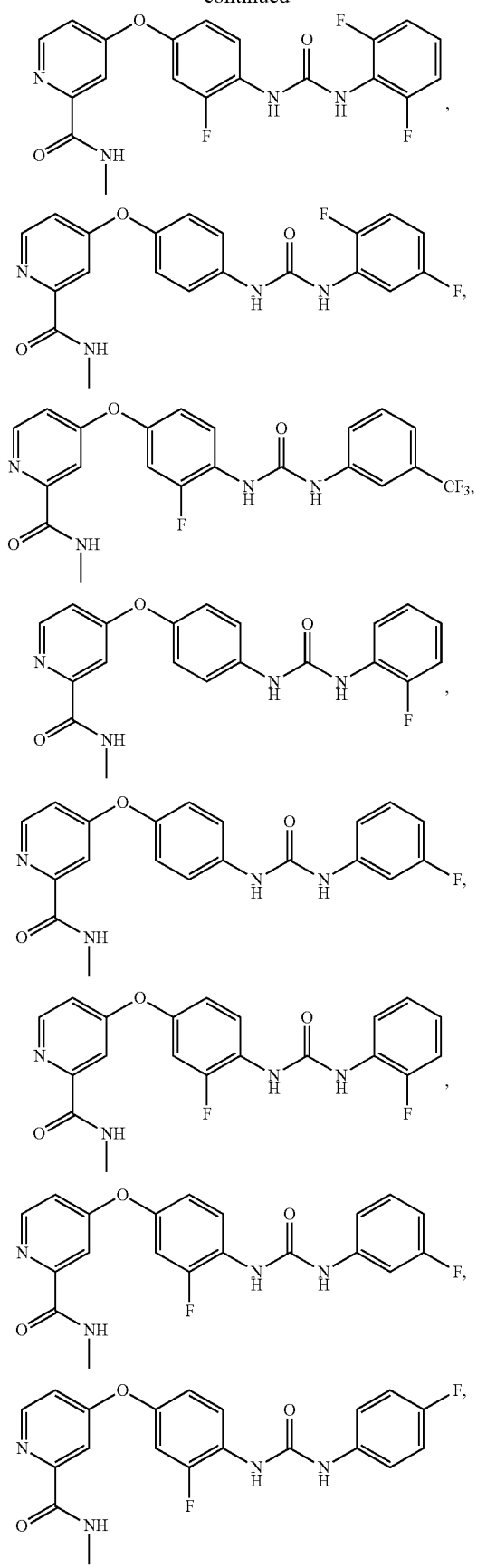
-continued
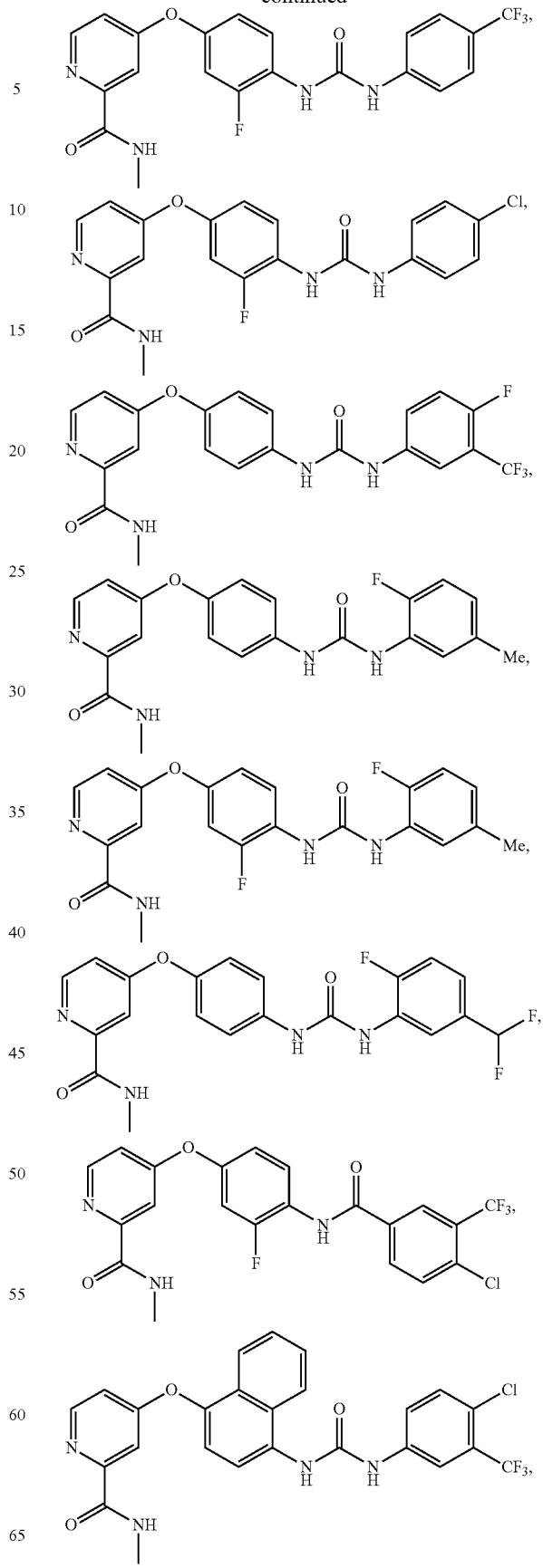

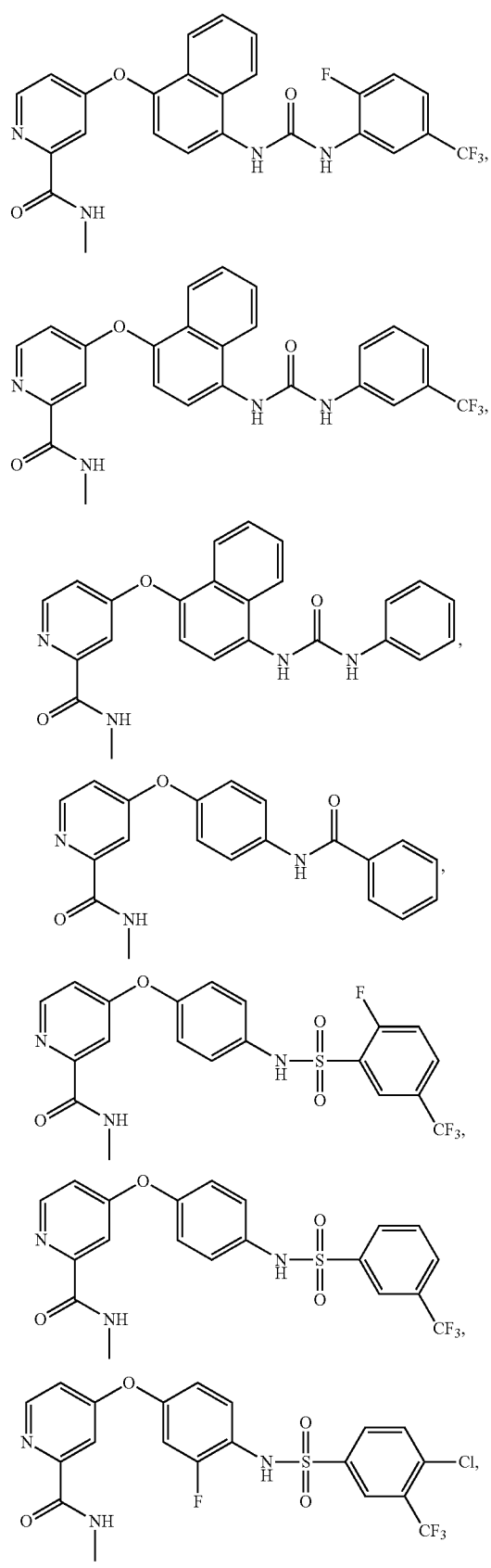
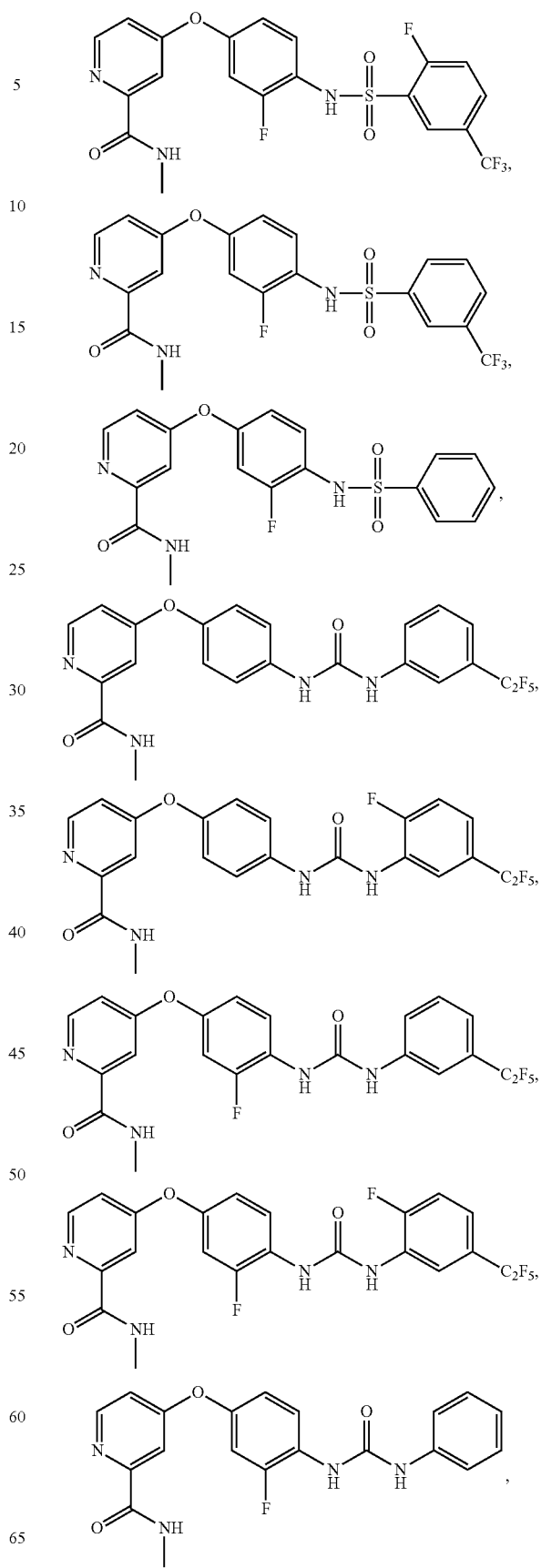

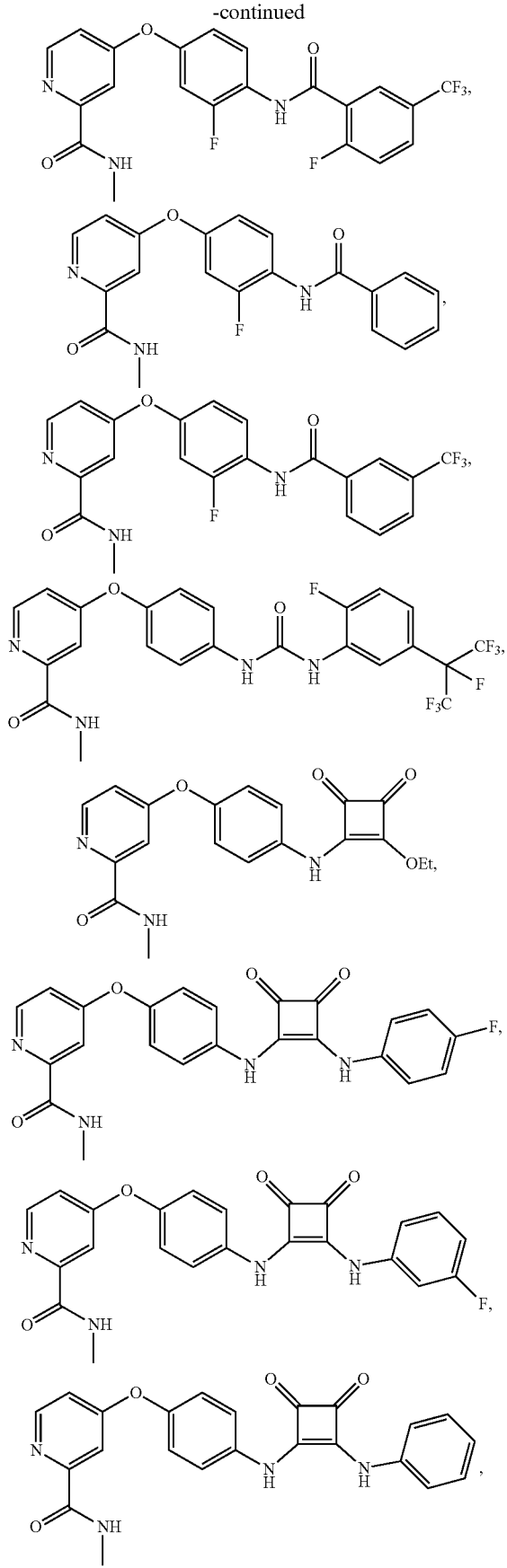
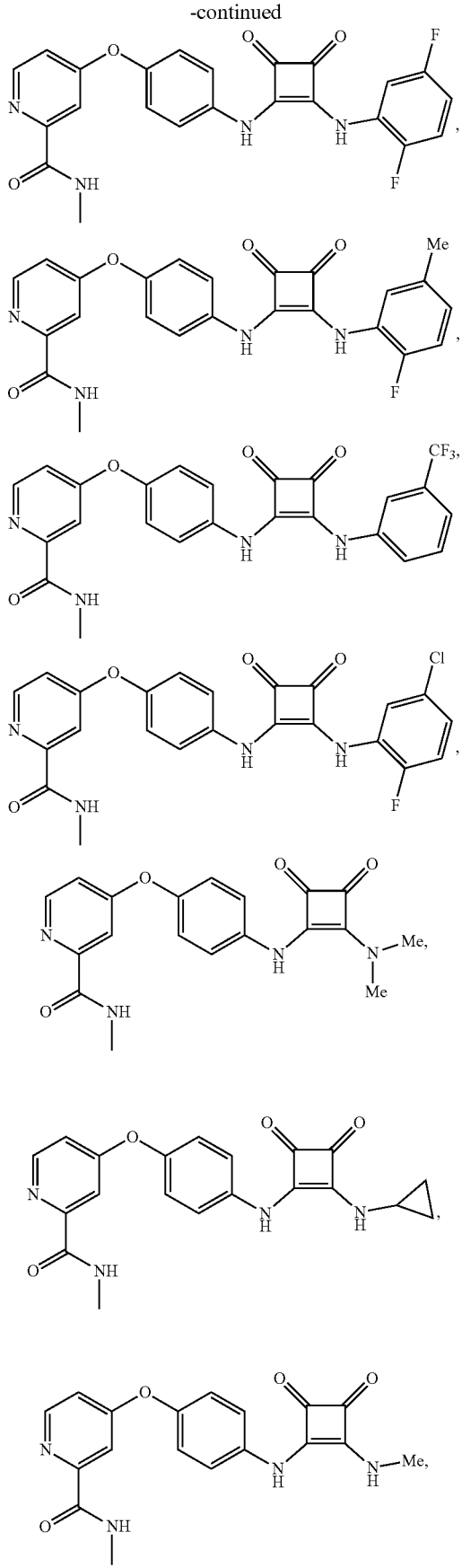

-continued
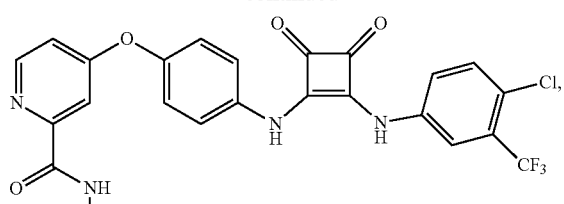
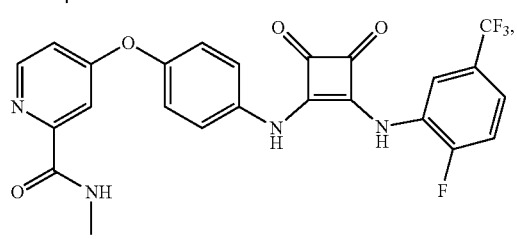
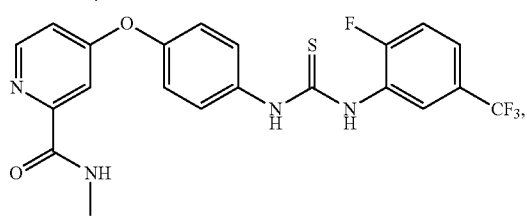
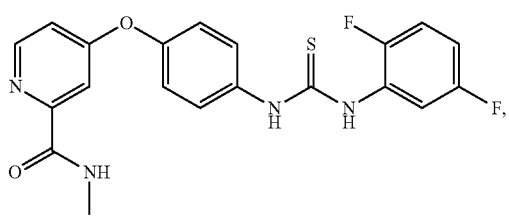
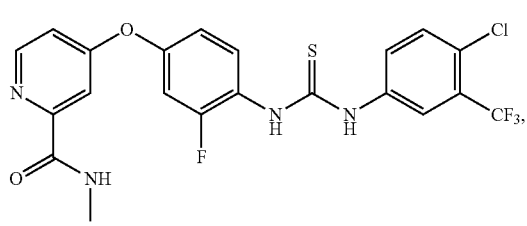
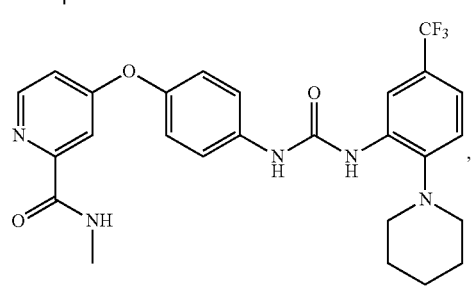
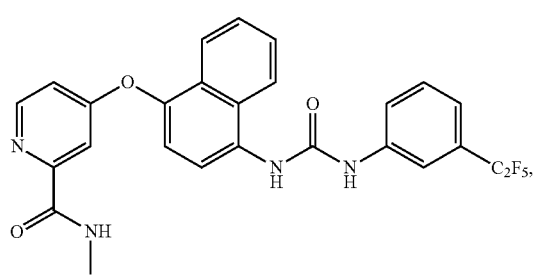
-continued
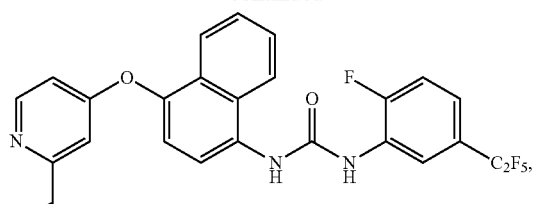
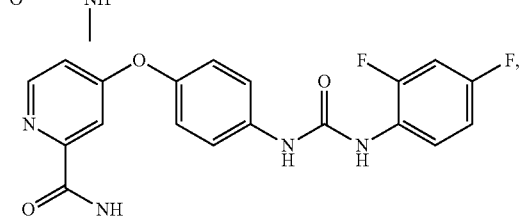
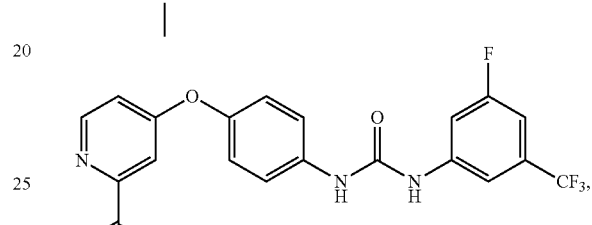
APS-5-69-1
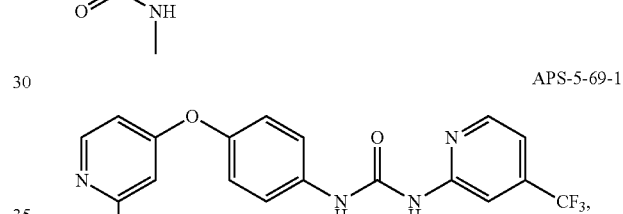
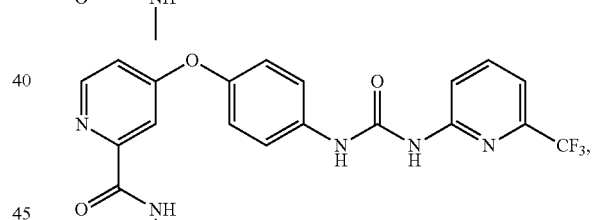
APS-5-69-3
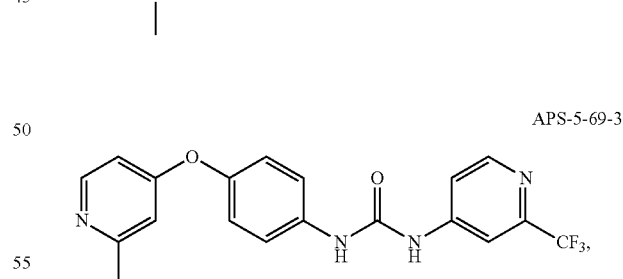
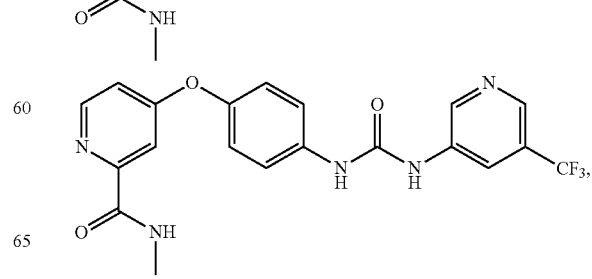

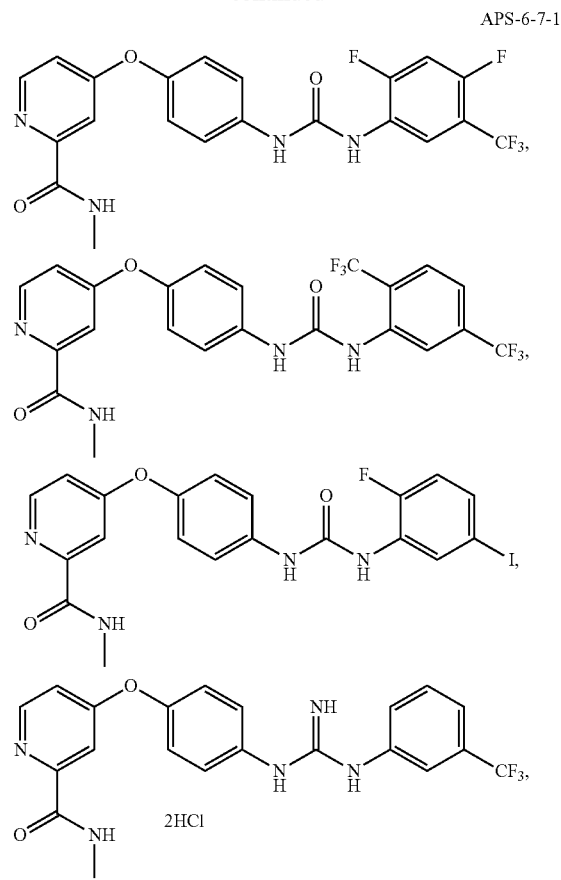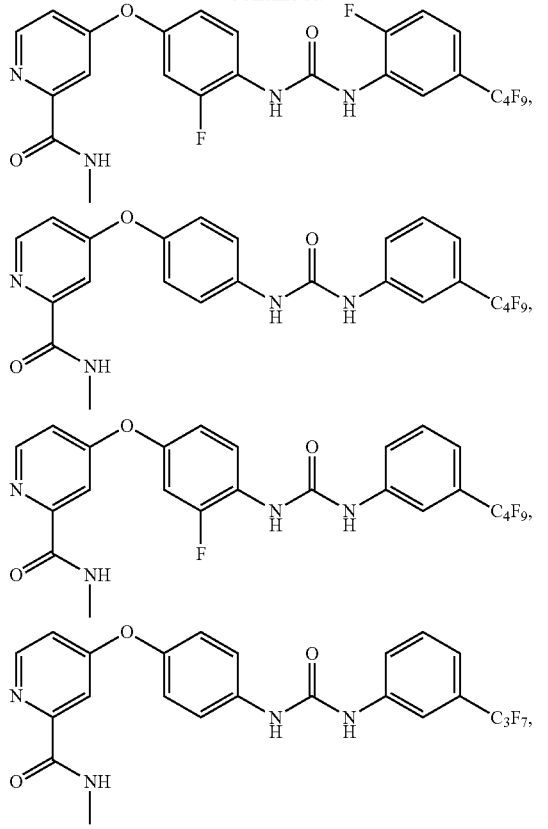

APS-7-44-1
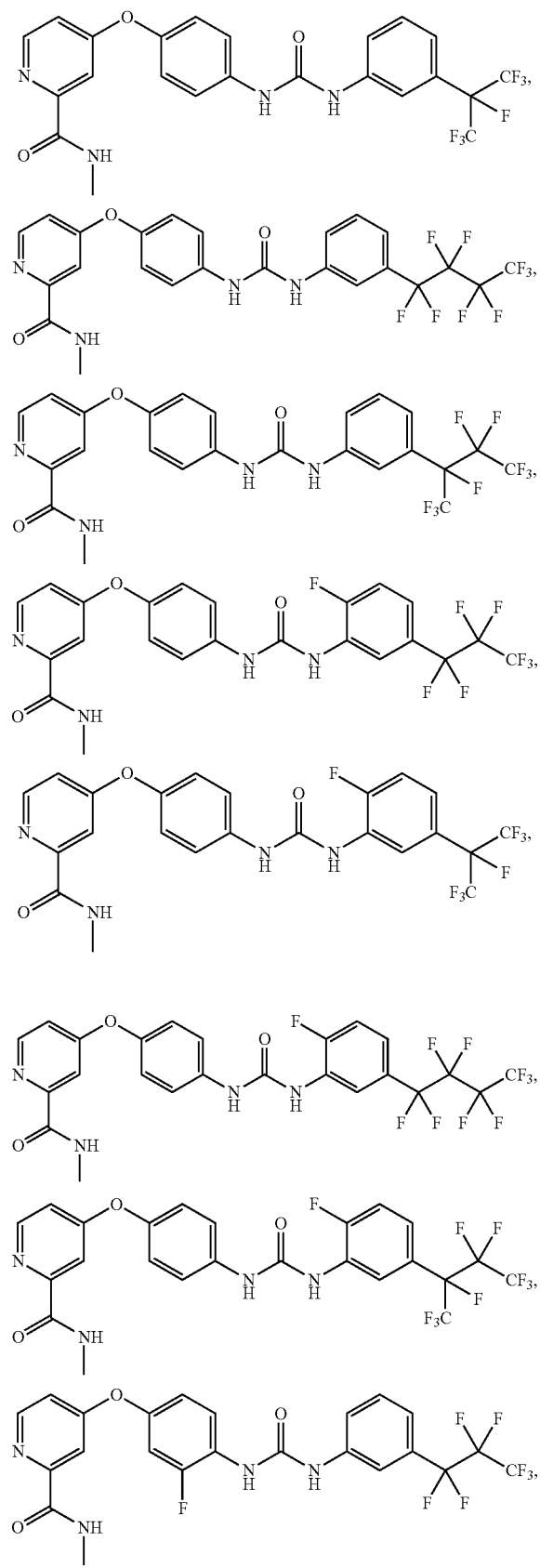
APS-7-45-1
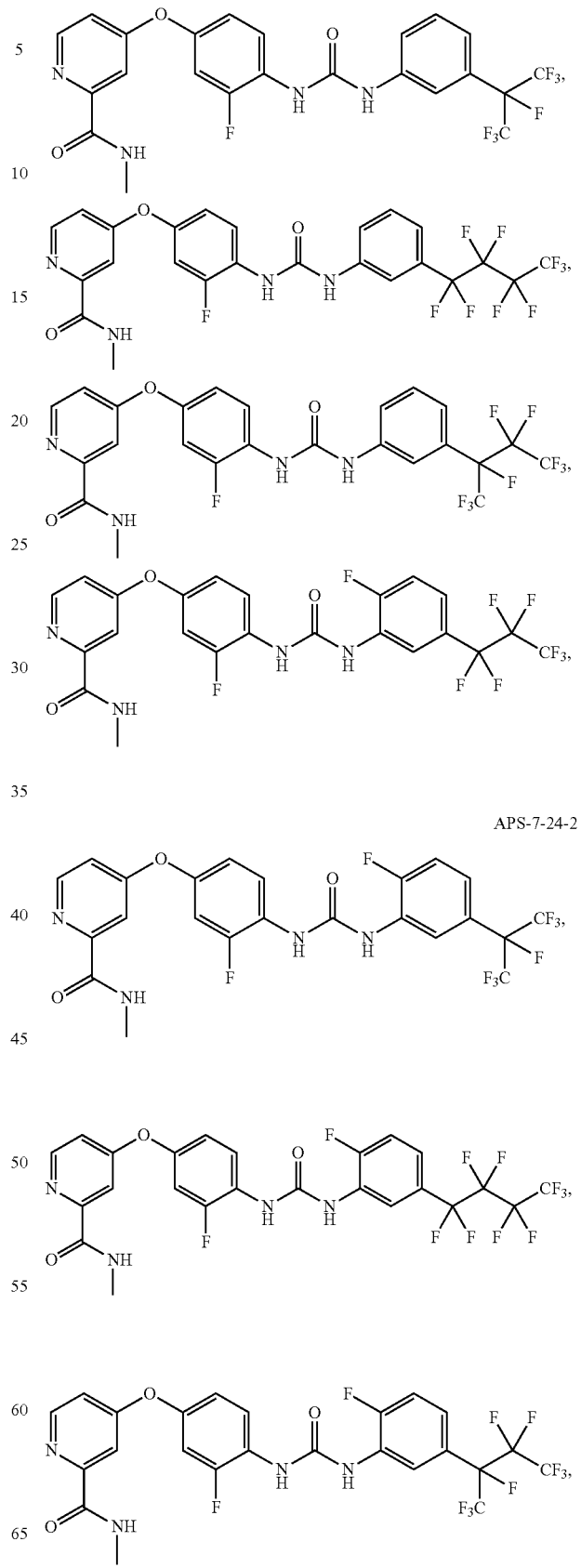
APS-7-24-2

-continued

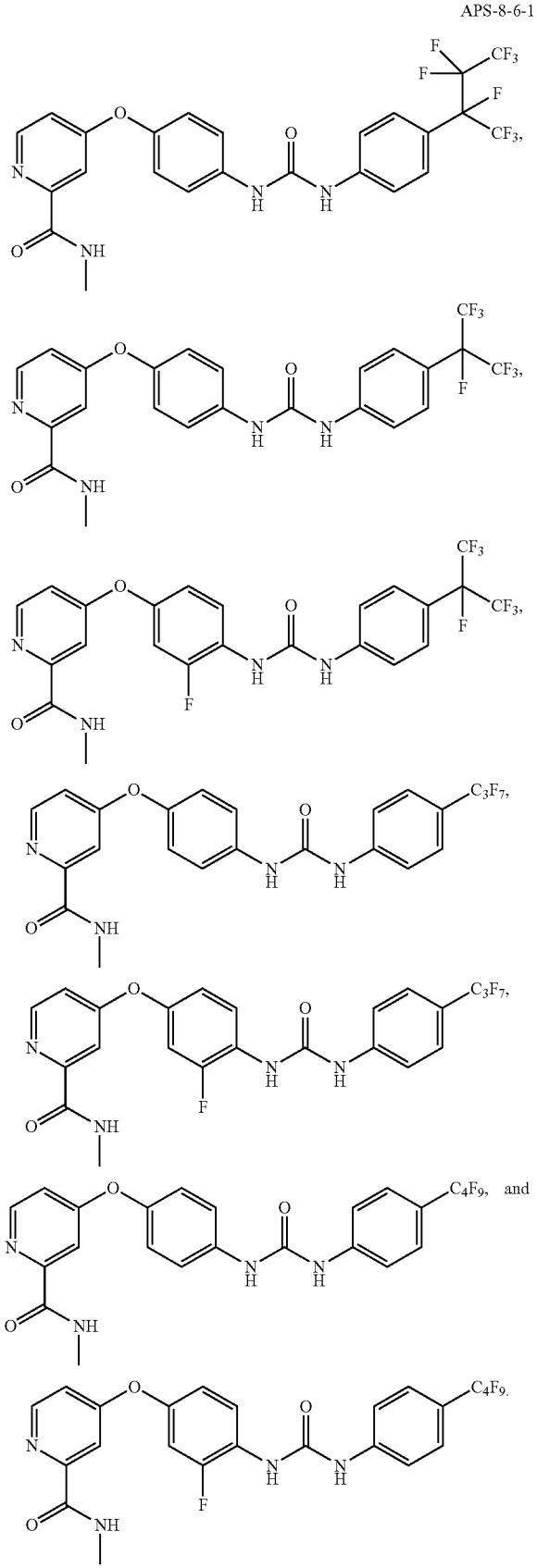

APS-8-6-1

Urea linker (L1) Sorafelogs of formula (I) can be prepared, e.g., by reacting an amine HB/SX with an acyl halide, acyl imidazole, or an activated ester (Scheme 1).

Scheme 1

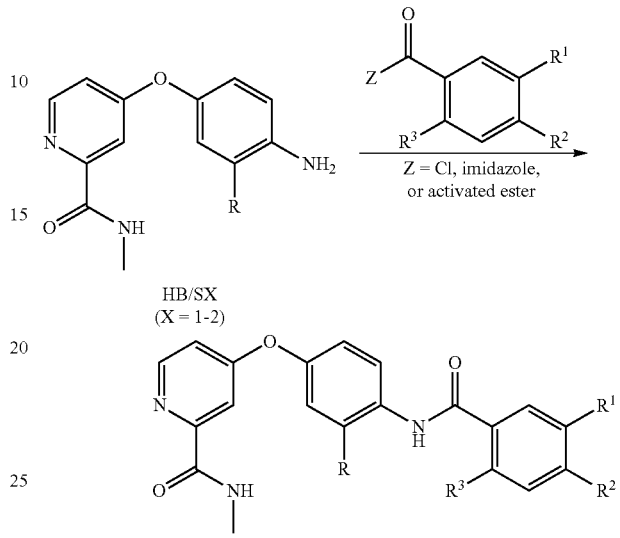

Reaction between an aniline and N,N-carbonyldiimidazole (CDI) leads to formation of an acyl imidazole (Scheme 2). Urea linker (L1) Sorafelogs can be prepared by reacting an acyl imidazole with an amine HB/SX.

Scheme 2

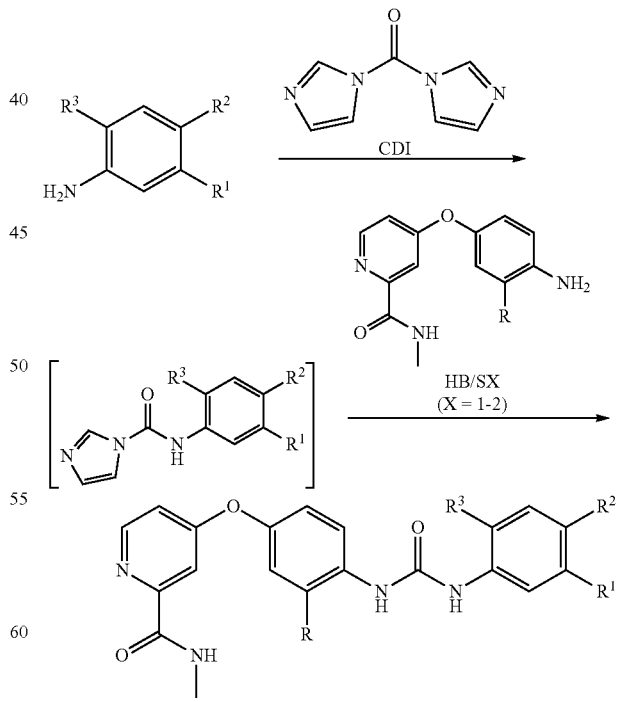

Urea Linker (L1) Sorafelogs of formula (I) can also be prepared by reacting an amine HB/SX with an isocyanate (Scheme 3).

Scheme 3

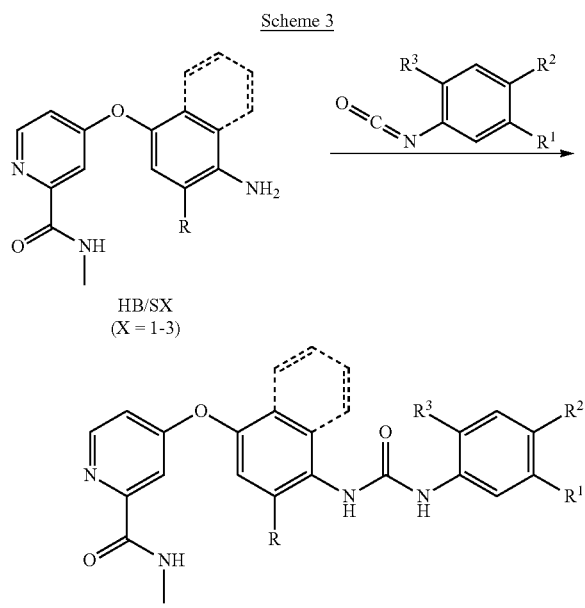

HB/SX
(X = 1-3)

Sulfonamide linker Sorafelogs of formula (I) can also be prepared by reacting an amine HB/SX with sulfonyl chloride derivatives (Scheme 4).

Scheme 4

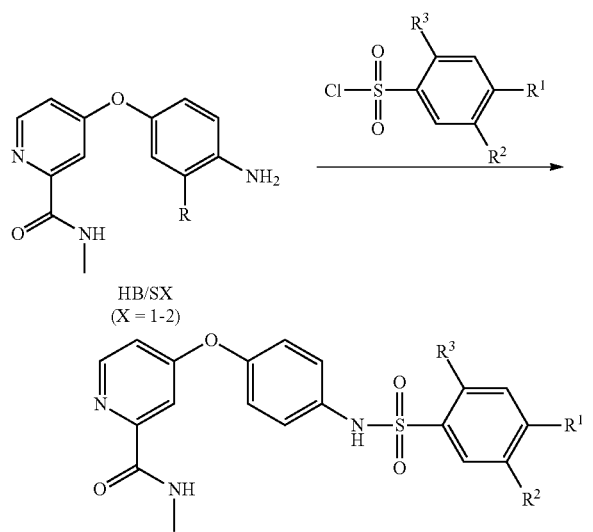

HB/SX
(X = 1-2)

The compounds of formula (I) (and the other compounds described herein made by the above process) can be isolated and purified in a known manner, for example, by subjecting the residue after distillation of the solvent to partition, extraction, re-precipitation, re-crystallization, or another purification method or combination of purification methods.

A further aspect of the present invention is directed to a composition comprising the compound of the present invention and a carrier.

In one embodiment, the carrier is a pharmaceutically-acceptable carrier, and a composition is a pharmaceutical composition.

By "pharmaceutical composition" it is meant a composition comprising a compound of the present invention and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term "pharmaceutically acceptable carrier" is used to mean any carrier, diluent, adjuvant, excipient, or vehicle, as described herein.

Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances.

Prevention of the action of microorganisms can be ensured by various antibacterial and antifungal agents, for example, parabens, chlorobutanol, phenol, sorbic acid, and the like.

It may also be desirable to include isotonic agents, for example sugars, sodium chloride, and the like.

Prolonged absorption of the injectable pharmaceutical form can be brought about by the use of agents delaying absorption, for example, aluminum monosterate and gelatin.

Examples of suitable carriers, diluents, solvents, or vehicles include water, ethanol, polyols, suitable mixtures thereof, vegetable oils (such as olive oil), and injectable organic esters such as ethyl oleate.

Examples of excipients include lactose, milk sugar, sodium citrate, calcium carbonate, and dicalcium phosphate.

Examples of disintegrating agents include starch, alginic acids, and certain complex silicates.

Examples of lubricants include magnesium stearate, sodium lauryl sulphate, talc, as well as high molecular weight polyethylene glycols.

Another aspect of the present invention relates to a method of treating cancer in a subject. This method involves administering to a subject a compound of formula (I) having the following structure:

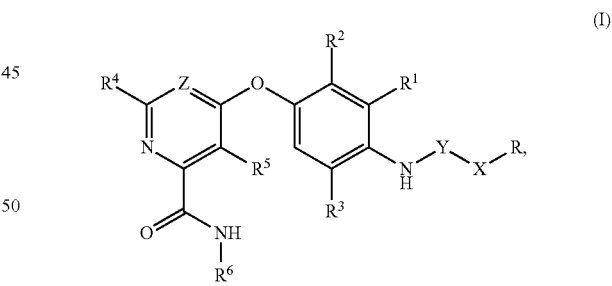

(I)

or a stereoisomer, pharmaceutically acceptable salt, oxide, or solvate thereof, where R, $R^1$, $R^2$, $R^3$, $R^4$, $R^5$, $R^6$, X, Y, Z, $R^7$, $R^8$, $R^9$, $R^{10}$, $R^{11}$, $R^{12}$, and $R^{13}$ are as defined herein.

Administering of compounds and/or pharmaceutical compositions to a subject may involve administering therapeutically effective amounts, which means an amount of compound effective in treating the stated conditions and/or disorders in a subject. Such amounts generally vary according to a number of factors well within the purview of ordinarily skilled artisans. These include, without limitation, the particular subject, as well as the subject's age, weight, height, general physical condition, and medical history, the particular compound used, as well as the carrier in which it is formulated and the route of administration selected for it; and, the nature and severity of the condition being treated.

Administering typically involves administering pharmaceutically acceptable dosage forms, which means dosage forms of compounds described herein, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in *Remington's Pharmaceutical Sciences*, Mack Publishing Co., Easton, Pa., latest edition, which is hereby incorporated by reference in its entirety.

Administering may be carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. Compounds may be administered alone or with suitable pharmaceutical carriers, and can be in solid or liquid form, such as tablets, capsules, powders, solutions, suspensions, or emulsions.

In carrying out this aspect of the present invention, suitable subjects to be treated include mammals, such as a human.

Cancers amenable to the treatment method of the present invention include, without limitation, Acute Lymphoblastic Leukemia (ALL), Acute Myeloid Leukemia (AML), Adrenocortical Carcinoma, Adrenal Cortex Cancer, Anal Cancer, Appendix Cancer, Astrocytomas, Atypical Teratoid/Rhabdoid Tumor, Basal Cell Carcinoma, Extrahepatic Bile Duct Cancer, Bladder Cancer, Bone Cancer, Brain Tumors, Breast Cancer, Bronchial Tumors, Burkitt Lymphoma, Carcinoid Tumor, Cardiac (Heart) Tumors, Cervical Cancer, Cholangiocarcinoma, Chronic Lymphocytic Leukemia (CLL), Chronic Myelogenous Leukemia (CML), Chronic Myeloproliferative Neoplasms, Colorectal Cancer, Cutaneous T-Cell Lymphoma, Ductal Carcinoma In Situ (DCIS), Endometrial Cancer, Ependymoma, Esophageal, Esthesioneuroblastoma, Ewing Sarcoma, Intraocular Melanoma, Retinoblastoma, Malignant Fibrous Histiocytoma of Bone, Osteosarcoma, Gallbladder Cancer, Gastric (Stomach) Cancer, Gastrointestinal Carcinoid Tumor, Gastrointestinal Stromal Tumors (GIST), Gestational Trophoblastic Disease, Gliomas, Hairy Cell Leukemia, Head and Neck Cancer, Hepatocellular (Liver) Cancer, Langerhans Cell Histiocytosis, Hodgkin Lymphoma, Hypopharyngeal Cancer, Intraocular Melanoma, Kaposi Sarcoma, Kidney cancer, Langerhans Cell Histiocytosis, Leukemia, Lung Cancer, Lymphoma, Medullary Thyroid Carcinoma, Melanoma, Intraocular (Eye) Melanoma, Merkel Cell Carcinoma, Malignant Mesothelioma, Metastatic Squamous Neck Cancer with Occult Primary, Multiple Endocrine Neoplasia Syndromes, Multiple Myeloma/Plasma Cell Neoplasms, Myelodysplastic Syndromes, Myelodysplastic/Myeloproliferative Neoplasms, and Chronic Myeloproliferative Neoplasms, Chronic Myelogenous Leukemia (CML), Acute Myeloid Leukemia (AML), Nasopharyngeal Cancer, Neuroblastoma, Non-Hodgkin Lymphoma, Non-Small Cell Lung Cancer, Oral Cancer, Lip and Oral Cavity Cancer, Oropharyngeal Cancer, Ovarian Cancer, Pancreatic Cancer and Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Primary Central Nervous System (CNS) Lymphoma, Prostate Cancer, Rectal Cancer, Renal Cell (Kidney) Cancer, Retinoblastoma, Rhabdomyosarcoma, Salivary Gland Cancer, Sarcoma, Sezary Syndrome, Small Cell Lung Cancer, Small Intestine Cancer, Soft Tissue Sarcoma, Squamous Cell Carcinoma, Squamous Neck Cancer, Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Urethral Cancer, Uterine Cancer, Endometrial and Uterine Sarcoma, Vaginal Cancer, Vulvar Cancer, Waldenstrom Macroglobulinemia, and Wilms Tumor.

In one particular embodiment of this aspect of the present invention, the treatment method is carried out to treat thyroid cancer, liver and renal cell cancer, or colorectal cancer.

EXAMPLES

Example 1

General Chemical Methods

All solvents were purchased from Sigma-Aldrich and were used as received. Anhydrous solvents were used for chemical reactions, and HPLC grade solvents were used for aqueous work-ups, recrystallizations, and chromatography. The palladium metal on solid support, used in hydrogenation reactions was purchased from Sigma-Aldrich as 10% w/w on activated carbon (dry basis), with 50% w/w water added (Degussa type), designated in procedures as "5% w/w on activated carbon." Other reagents were purchased from various vendors and were used as received. Reactions were run as described in the individual procedures using standard double manifold and syringe techniques. Glassware was dried by baking in an oven at 130° C. for 12 hours prior to use, or was flame-dried. The pH of aqueous solutions was estimated using pH paper. Vacuum filtrations were carried out using a house vacuum line (~100 torr). In the individual procedures, the phrases "concentration under vacuum" and "concentrated to dryness" mean that solvent was removed on a rotary evaporator using a diaphragm pump (with an automatic vacuum regulator) and remaining traces of volatiles were removed on a high-vacuum (<1 torr) oil pump. Unless specified otherwise, the term "flask" refers to the round-bottomed variety. Reactions were monitored by TLC using EMD silica gel 60 F254 (250 µm) glass-backed plates (visualized by UV fluorescence quenching and stained with basic $KMnO_4$ solution) and by liquid chromatography-tandem mass spectrometry (LC-MS). Analysis by reverse-phase LC-MS was carried out on a Waters Aquity I-Class UPLC system, with a C18 column (2.1×30 mm; 1.7 µm particle size), heated at 50° C., eluted at 0.6 mL/min, and using a 3 min linear gradient method with a mobile phase consisting of water/acetonitrile (0.1% v/v formic acid added to each): 95:5→1:99 (0-2.5 min), then 1:99 (2.5-3 min). Sample runs were monitored using alternating positive/negative electrospray ionization (50-1000 amu) and UV detection at 254 nm. Dimensions of plugs, pads, and columns for filtration or flash chromatography are reported as: ((diameter×length) cm). The 5¾ inch pipets (4 mL) used for filtration and micro scale flash chromatography were purchased from Fisher Scientific (product number 22-378-893). Automated preparative normal- and reverse-phase chromatography was carried out with an Interchim PuriFlash 450 purification system with a diode array detector (runs were monitored at 220-400 nm). Pre-packed silica gel cartridges (12, 25, and 40 g; 15 µm particle size) were employed for normal-phase (silica gel) chromatography, eluting at 20-30 mL/min. For reverse-phase chromatography, a C18 column (30×150 mm; 5 µm particle size) was used, eluting at 15-20 mL/min with a pressure limit of 50 bar. Carbon-decoupled $^1$H NMR spectra were recorded at 400 MHz on a Bruker spectrometer and are reported in ppm using the residual solvent signal (dimethylsulfoxide-d6=2.50 ppm) as an internal standard. Data are reported as: {(shift), [(s=singlet, d=doublet, dd=doublet of doublets, ddd=doublet of a doublet of doublets, t=triplet, dt-doublet of triplets, q=quartet, m=multiplet, br=broad, ap=apparent), (J=coupling constant in Hz), (integration)]}. Proton-decoupled $^{13}$C NMR spectra were recorded at 100 MHz on a Bruker spectrometer and are reported in ppm using the residual solvent signal (dimethylsulfoxide-d6=39.5 ppm) as an internal standard. Proton-decoupled $^{19}$F NMR spectra were recorded at 376 MHz on a Bruker spectrometer and are reported in ppm using added CFCl$_3$ (0.00 ppm) as an internal standard. Compounds with only one signal were integrated relative to a known amount of the internal standard.

Example 2

Preparation of 4-Chloro-N-methylpicolinamide (HB)

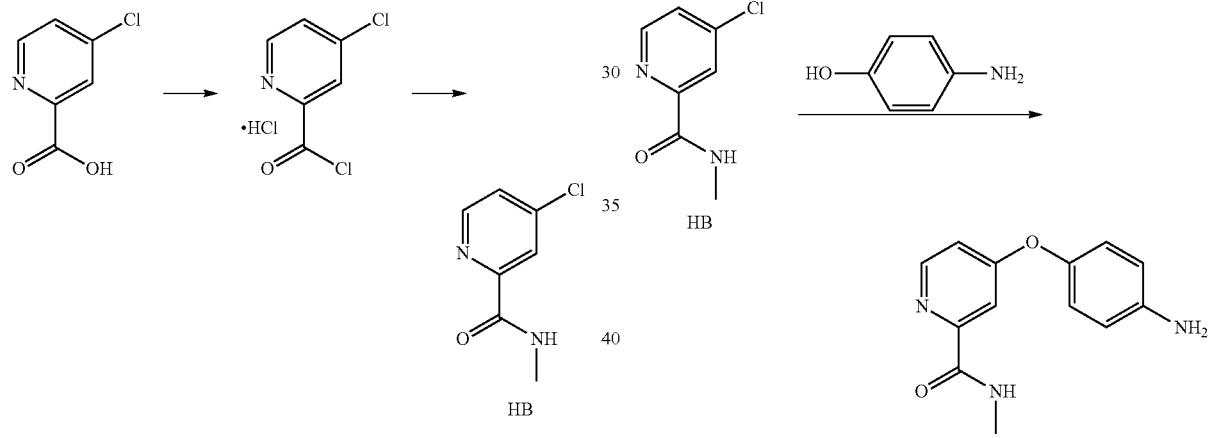

A flame-dried 250 mL flask, cooled under Ar, was charged with 4-chloropicolinic acid (10.0 g, 63.5 mmol), and THF (125 mL). The mixture was cooled to 0° C. and oxalyl chloride (6.70 mL, 79.2 mmol) was added dropwise over 5 min via syringe, followed by DMF (0.1 mL), which was added by syringe in one shot (CAUTION: rapid release of gas). After 30 min the reaction mixture was allowed to warm to room temperature and was stirred under a balloon of Ar for 15 hours. The resulting brown solution was concentrated on a rotary-evaporator; a drying tube filled with KOH pellets was used to trap residual HCl. The remaining oil was concentrated to dryness from toluene (3×10 mL) and then was dried further under high vacuum to provide a solid. The crude 4-chloropicolinoyl chloride hydrochloride salt was placed under Ar and THF (50 mL) was added. The dark solution was cooled to 0° C. and methylamine (160 mL, 2.0 M solution in THF, 320 mmol) was added dropwise over 20 min via syringe. After 5 min the reaction was allowed to warm to room temperature and was stirred for 16 hours. The reaction mixture was diluted with water (200 mL) and extracted with EtOAc (3×150 mL). The organic extracts were pooled, washed with water (100 mL) and brine (2×100 mL), dried (Na$_2$SO$_4$), and filtered. Concentration under vacuum gave ~11 g of a red-brown oil, which was purified by silica gel chromatography (40 g cartridge), eluting at 30 mL/min and using a linear gradient of hexanes/EtOAc: 100:0→0:100 over 30 column volumes. The appropriate fractions were pooled and concentrated to dryness. The remaining clear colorless oil (~10 g) was dissolved in a mixture of hexanes/CH$_2$Cl$_2$ (4:1; 150 mL) and allowed to stand at −20° C. for 12 hours. The resulting precipitate was isolated by vacuum filtration, washed with hexanes (2×30 mL) and air-dried to yield 8.90 g (82%) of the title compound as a white solid: $^1$H NMR (400 MHz, DMSO-d6) δ 8.85 (br ap d, J=3.4 Hz, 1H), 8.62 (dd, J=5.3, 0.6 Hz, 1H), 8.01 (dd, J=2.2, 0.6 Hz, 1H), 7.75 (dd, J=5.3, 2.2 Hz, 1H), 2.82 (d, J=4.9 Hz, 3H); $^{13}$C NMR (100 MHz, DMSO-d6) δ 163.1, 151.8, 150.0, 144.5, 126.3, 121.8, 26.1; LC-MS (ESI+) m/z: [M+H]$^+$ Calcd for C$_7$H$_8$ClN$_2$O, 171.0; Found 171.1.

Example 3

Preparation of 4-(4-Aminophenoxy)-N-methylpicolinamide (HB/S1)

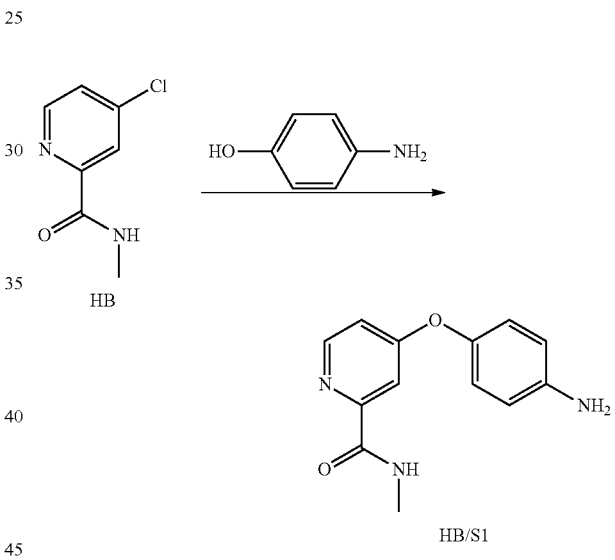

A two-necked 100 mL flask (equipped with an inlet adapter and septum) was flame-dried under vacuum and cooled under Ar. The flask was charged with 4-aminophenol (2.09 g, 19.2 mmol) and DMF (30 mL). To the stirred solution was added potassium tert-butoxide (2.14 g, 19.1 mmol) in portions over 1 min. The resulting light-brown mixture was stirred for 2 hours, then 4-chloro-N-methylpicolinamide (2.17 g, 12.7 mmol) was added in one portion, and the reaction was heated at 80° C. for 4 hours under a balloon of Ar. The reaction was allowed to cool to room temperature and then was poured into stirred ice-water (100 mL). Stirring was continued for 15 min and then the mixture was extracted with EtOAc (1×100 mL and 2×50 mL). The organic extracts were pooled, washed with 1 M KOH (3×50 mL), water (50 mL) and brine (2×50 mL), dried (Na$_2$SO4), and filtered. Concentration under vacuum gave 3.23 g of an orange oil, which was purified by silica gel chromatography (40 g cartridge), eluting at 30 mL/min and using a linear gradient of hexanes/EtOAc: 100:0→0:100 over 35 column volumes. Obtained 2.69 g (87%) of the title compound as an off-white solid: $^1$H NMR (400 MHz, DMSO-d$_6$) δ 8.73 (br q, J=4.6 Hz, 1H), 8.45 (d, J=5.6 Hz, 1H), 7.34 (d, J=2.5 Hz, 1H), 7.06 (dd, J=5.5, 2.6 Hz, 1H), 6.86 (d, J=8.8 Hz, 2H), 6.64 (d, J=8.8 Hz, 2H), 5.17 (s, 2H), 2.78 (d, J=4.9 Hz, 3H); $^{13}$C NMR (100 MHz, DMSO-$d_6$) δ 166.8, 163.9, 152.3, 150.1, 146.9, 142.8, 121.6, 114.9, 113.7, 108.3, 26.0; LC-MS (ESI+) m/z: [M+H]$^+$ Calcd for $C_{13}H_{14}N_3O_2$, 244.1; Found 244.2.

Example 4

Preparation of 4-(4-Amino-3-fluorophenoxy)-N-methylpicolinamide (HB/S2)

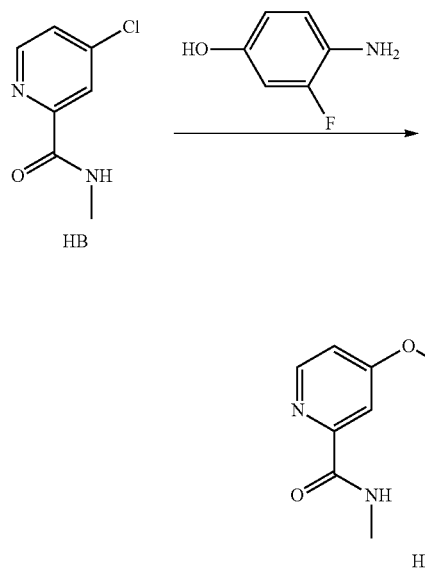

An oven-dried two-necked 100 mL flask (equipped with an inlet adapter and septum) under Ar, was charged with 4-amino-3-fluorophenol (1.12 g, 8.81 mmol) and DMF (18 mL). To the stirred solution was added potassium tert-butoxide (978 mg, 8.72 mmol) in portions over 2 min. The resulting dark-purple mixture was stirred for 3 hours, then 4-chloro-N-methylpicolinamide (1.06 g, 6.21 mmol) was added in one portion, and the reaction was heated at 90° C. for 10 hours under a balloon of Ar. The reaction was allowed to cool to room temperature and then was poured into stirred ice-water (50 mL). Stirring was continued for 15 min and then the mixture was extracted with EtOAc (3×50 mL). The organic extracts were pooled, washed with 1 M KOH (3×50 mL), water (50 mL) and brine (2×50 mL), dried (Na$_2$SO$_4$), and filtered. Concentration under vacuum gave a brown solid, which was purified by silica gel chromatography (40 g cartridge), eluting at 30 mL/min and using a linear gradient of hexanes/EtOAc: 100:0→0:100 over 38 column volumes. Obtained 882 mg (54%) of the title compound as a light-brown solid: $^1$H NMR (400 MHz, DMSO-$d_6$) δ 8.74 (br q, J=4.6 Hz, 1H), 8.47 (d, J=5.6 Hz, 1H), 7.35 (d, J=2.5 Hz, 1H), 7.09 (dd, J=5.6, 2.7 Hz, 1H), 7.01 (dd, J=11.9, 2.6 Hz, 1H), 6.81-6.89 (m, 1H), 6.76-6.80 (m, 1H), 5.22 (br s, 2H), 2.78 (d, J=4.9 Hz, 3H); $^{19}$F NMR (376 MHz, DMSO-$d_6$) δ −130.7 (s, 1F); LC-MS (ESI+) m/z: [M+H]$^+$ Calcd for $C_{13}H_{13}FN_3O_2$, 262.1; Found 262.1.

Example 5

Preparation of 4-((4-Aminonaphthalen-1-yl)oxy)-N-methylpicolinamide (HB/S3)

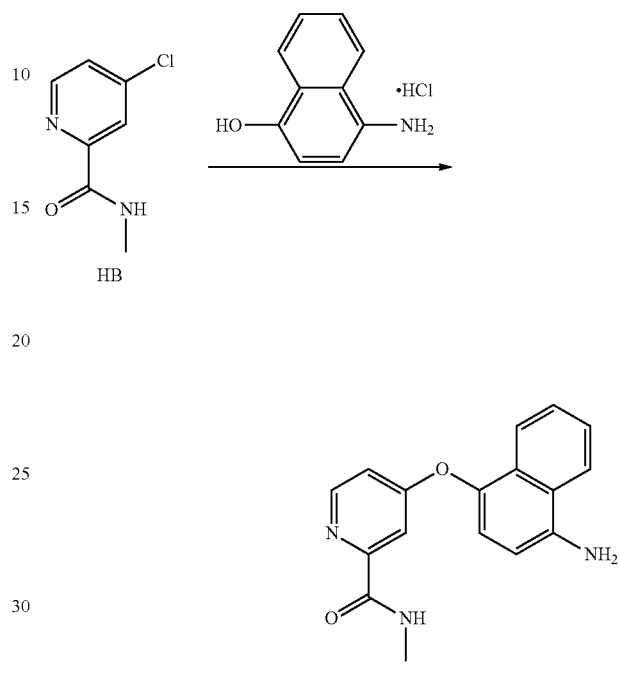

An oven-dried two-necked 100 mL flask (equipped with an inlet adapter and septum) under Ar was charged with 4-aminonaphthalen-1-ol hydrochloride (1.33 g, 6.80 mmol) and DMF (8 mL). To the stirred solution was added potassium tert-butoxide (1.52 g, 13.5 mmol) in portions over 2 min. The resulting dark-purple mixture was stirred for 3 hours, then 4-chloro-N-methylpicolinamide (640 mg, 3.75 mmol) was added in one portion, and the reaction was heated at 80° C. for 3 hours under a balloon of Ar. The reaction was allowed to cool to room temperature and then was poured into stirred ice-water (50 mL). Stirring was continued for 15 min and then the mixture was extracted with EtOAc (3×50 mL). The organic extracts were pooled, washed with 1 M KOH (3×50 mL), water (50 mL) and brine (2×50 mL), dried (Na$_2$SO$_4$), and filtered. Concentration under vacuum gave a brown semi-solid, which was purified by silica gel chromatography (40 g cartridge), eluting at 30 mL/min and using a linear gradient of hexanes/EtOAc: 100:0→0:100 over 38 column volumes. The solid obtained was triturated with EtOAc and isolated by vacuum filtration; the collected solid was washed with EtOAc (×1) and hexanes (×2) then air-dried. Obtained 640 mg (58%) of the title compound as a light-brown solid: $^1$H NMR (400 MHz, DMSO-$d_6$) δ 8.72 (br q, J=4.9 Hz, 1H), 8.46 (dd, J=5.6, 0.5 Hz, 1H), 8.15-8.21 (m, 1H), 7.55-7.61 (m, 1H), 7.40-7.48 (m, 2H), 7.28 (d, J=2.5 Hz, 1H), 7.10-7.15 (m, 2H), 6.71 (d, J=8.1 Hz, 1H), 5.89 (br s, 2H), 2.75 (d, J=4.9 Hz, 3H); $^{13}$C NMR (100 MHz, DMSO-$d_6$) δ 167.2, 163.8, 152.4, 150.3, 143.6, 138.0, 126.8, 126.6, 124.5, 123.4, 123.3, 120.8, 119.0, 113.5, 108.2, 106.3, 26.0; LC-MS (ESI+) m/z: [M+H]$^+$ Calcd for $C_{17}H_{16}N_3O_2$, 294.1; Found 294.2.

Example 6

General Procedure for Synthesis of Urea Linker (L1) Sorafelogs Employing an Isocyanate

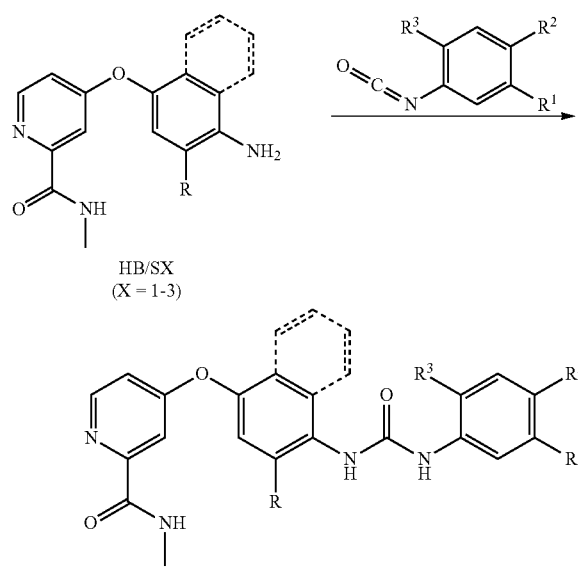

To a stirred solution of HB/SX (X=1-3) and CH$_2$Cl$_2$ (0.1-0.5 M), in a flame-dried vial under Ar was added the isocyanate (neat or as a solution in CH$_2$Cl$_2$) dropwise by syringe over 1-3 min. The headspace above the reaction was blanketed with Ar, the vial was sealed with a screw cap (wrapped with Teflon tape) and the reaction was stirred until judged complete by LC-MS analysis of a reaction aliquot diluted with MeOH. The product typically precipitated out of solution and was isolated by vacuum filtration; the collected solid was washed with CH$_2$Cl$_2$ (×2) and hexanes (×2), then air-dried, and finally dried under high vacuum. Specific reaction details and characterization data for Sorafelogs prepared by this synthetic strategy are described below.

Example 7

Preparation of N-Methyl-4-(4-(3-phenylureido)phenoxy)picolinamide (S1/L1/C1 (APS3-2))

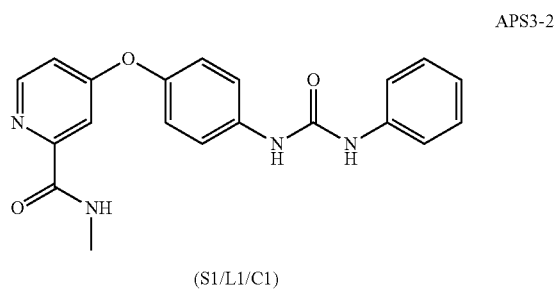 [SMILES: CNC(=O)c1cc(Oc2ccc(NC(=O)Nc3ccccc3)cc2)ccn1]

In an 8 mL vial from isocyanatobenzene (30.0 µL, 0.276 mmol) and HB/S1 (65.0 mg, 0.267 mmol) in CH$_2$Cl$_2$ (0.6 mL). Stirred for 18 hours and isolated by vacuum filtration.

Obtained 85.4 mg (88%) of the title compound as a white solid: $^1$H NMR (400 MHz, DMSO-d$_6$) δ 8.81 (s, 1H), 8.76 (br ap d, J=4.9 Hz, 1H), 8.70 (s, 1H), 8.50 (d, J=5.4 Hz, 1H), 7.58 (d, J=8.8 Hz, 2H), 7.46 (d, J=7.6 Hz, 1H), 7.38 (d, J=2.7 Hz, 1H), 7.29 (dd, J=7.8, 7.8 Hz, 2H), 7.10-7.20 (m, 3H), 6.98 (dd, J=7.4, 7.4 Hz, 1H), 2.79 (d, J=4.9 Hz, 3H); $^{13}$C NMR (100 MHz, DMSO-d$_6$) δ 166.0, 163.8, 152.6, 152.4, 150.4, 147.4, 139.6, 137.6, 128.8, 121.9, 121.4, 119.9, 118.3, 114.0, 108.6, 26.0; LC-MS (ESI+) m/z: [M+H]$^+$ Calcd for C$_{20}$H$_{19}$N$_4$O$_3$, 363.2; Found 363.2.

Example 8

Preparation of N-Methyl-4-(4-(3-(3-(trifluoromethyl)phenyl)ureido) phenoxy)picolinamide (S1/L1/C2 (LS1-11-2))

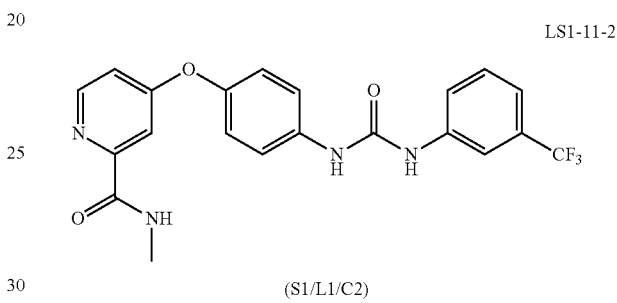

Figure 2:
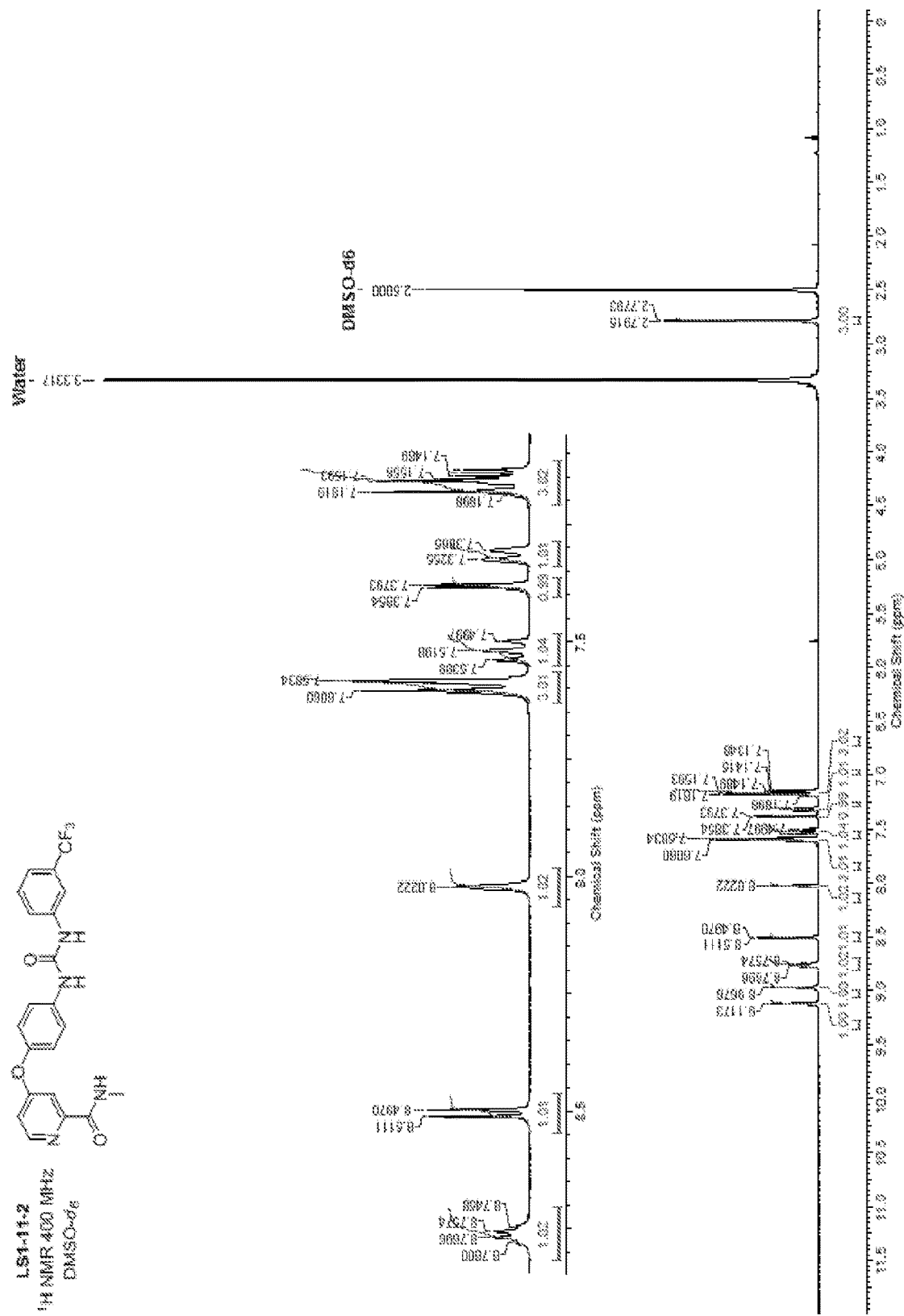
FIG. 2 shows $^1$H NMR spectra for compound LS1-11-2.

In a 4 mL vial from 1-isocyanato-3-(trifluoromethyl)benzene (21.2 µL, 0.154 mmol) and HB/S1 (36.8 mg, 0.151 mmol) in CH$_2$Cl$_2$ (0.5 mL). Stirred for 24 hours and isolated the product by vacuum filtration. Obtained 53.4 mg (84%) of the title compound as a white powder: $^1$H NMR (400 MHz, DMSO-d$_6$) δ 9.12 (s, 1H), 8.97 (s, 1H), 8.76 (br q, J=4.9 Hz, 1H), 8.50 (d, J=5.6 Hz, 1H), 8.02 (s, 1H), 7.56-7.63 (m, 3H), 7.52 (dd, J=7.8, 7.8 Hz, 1H), 7.38 (d, J=2.4 Hz, 1H), 7.32 (d, J=7.6 Hz, 1H), 7.17 (d, J=9.0 Hz, 2H), 7.15 (dd, J=5.6, 2.7 Hz, 1H), 2.79 (d, J=4.9 Hz, 3H); $^{19}$F NMR (376 MHz, DMSO-d$_6$) δ −60.8 (s, 3F); LC-MS (ESI+) m/z: [M+H]$^+$ Calcd for C$_{21}$H$_{18}$F$_3$N$_4$O$_3$, 431.1; Found 431.3 (FIGS. 1-2).

Example 9

Preparation of N-Methyl-4-(4-(3-(3-(trifluoromethyl)phenyl)ureido) phenoxy)picolinamide (S1/L1/C3 (Sorafenib))

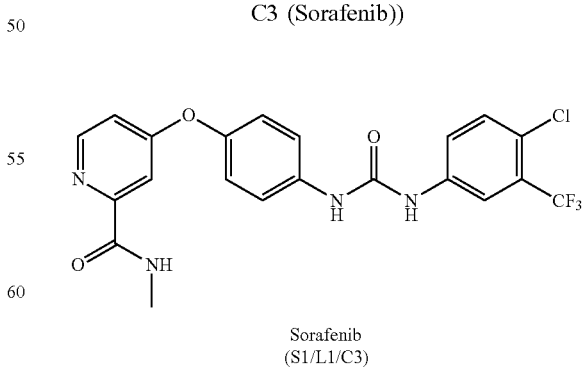

Figure 3:
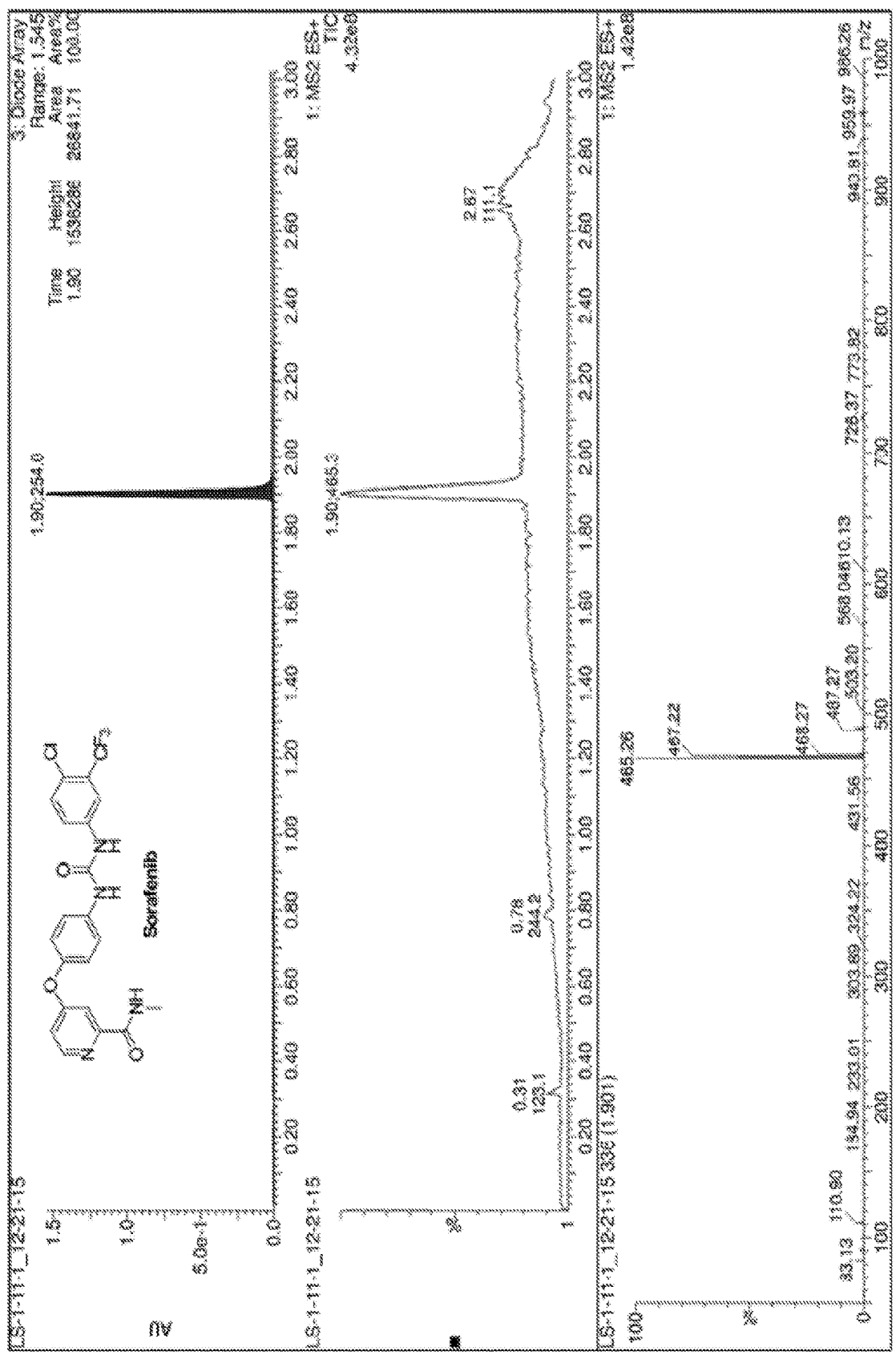
FIG. 3 shows LC-MS data for Sorafenib.
Figure 4:
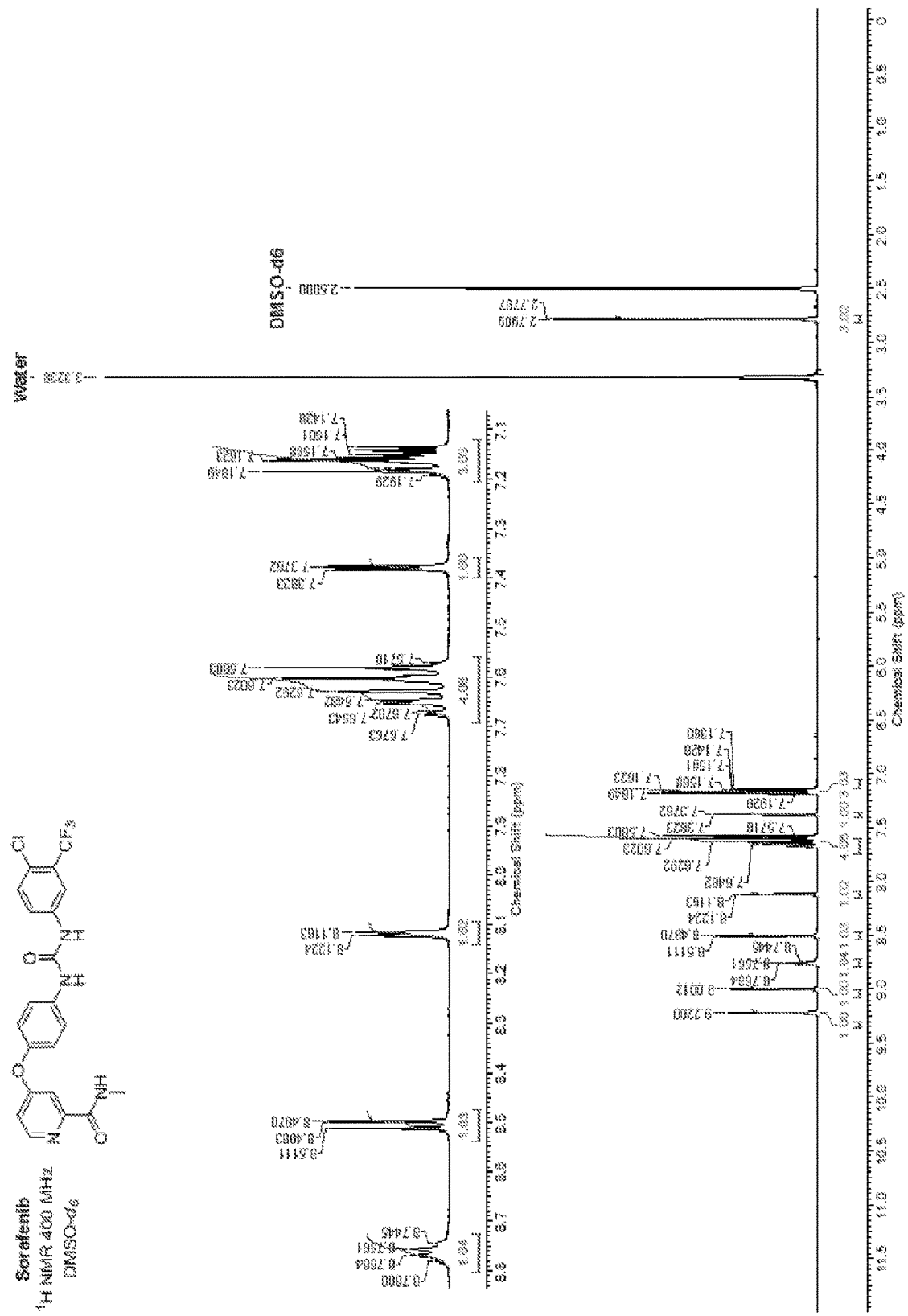
FIG. 4 shows $^1$H NMR spectra for Sorafenib.

A solution of 1-chloro-4-isocyanato-2-(trifluoromethyl)benzene (463 mg, 2.09 mmol) and CH$_2$Cl$_2$ (5 mL) was added to a solution of HB/S1 (500 mg, 2.06 mmol) and CH$_2$Cl$_2$ (5 mL) in a 20 mL vial. Stirred for 24 hours and the product was isolated by vacuum filtration. Obtained 889 mg (93%) of the title compound as a white powder (Bankston et al., "A Scalable Synthesis of BAY 43-9006: A Potent Raf Kinase Inhibitor for the Treatment of Cancer," *Org. Process Res. Dev.* 6:777-781 (2002), which is hereby incorporated by reference in its entirety): $^1$H NMR (400 MHz, DMSO-d$_6$) δ 9.22 (s, 1H), 9.00 (s, 1H), 8.76 (br q, J=4.9 Hz, 1H), 8.50 (d, J=5.6 Hz, 1H), 8.12 (d, J=2.4 Hz, 1H), 7.69-7.56 (m, 4H), 7.38 (d, J=2.4 Hz, 1H), 7.17 (d, J=9.0 Hz, 2H), 7.15 (dd, J=5.6, 2.7 Hz, 1H), 2.78 (d, J=4.9 Hz, 3H); $^{19}$F NMR (376 MHz, DMSO-d$_6$) δ −61.0 (s, 3F); LC-MS (ESI+) m/z: [M+H]$^+$ Calcd for C$_{21}$H$_{17}$ClF$_3$N$_4$O$_3$, 465.1; Found 465.3 (FIGS. 3-4).

Example 10

Preparation of 4-(4-(3-(2-Fluoro-5-(trifluoromethyl) phenyl)ureido) phenoxy)-N-methylpicolinamide (S1/L1/C4 (LS1-15))

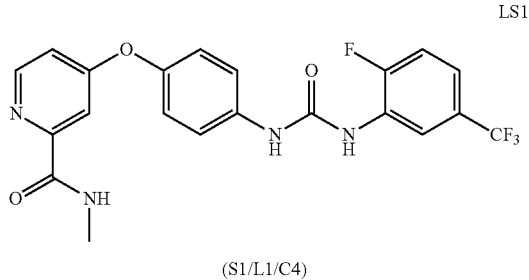

(S1/L1/C4)

Figure 5:
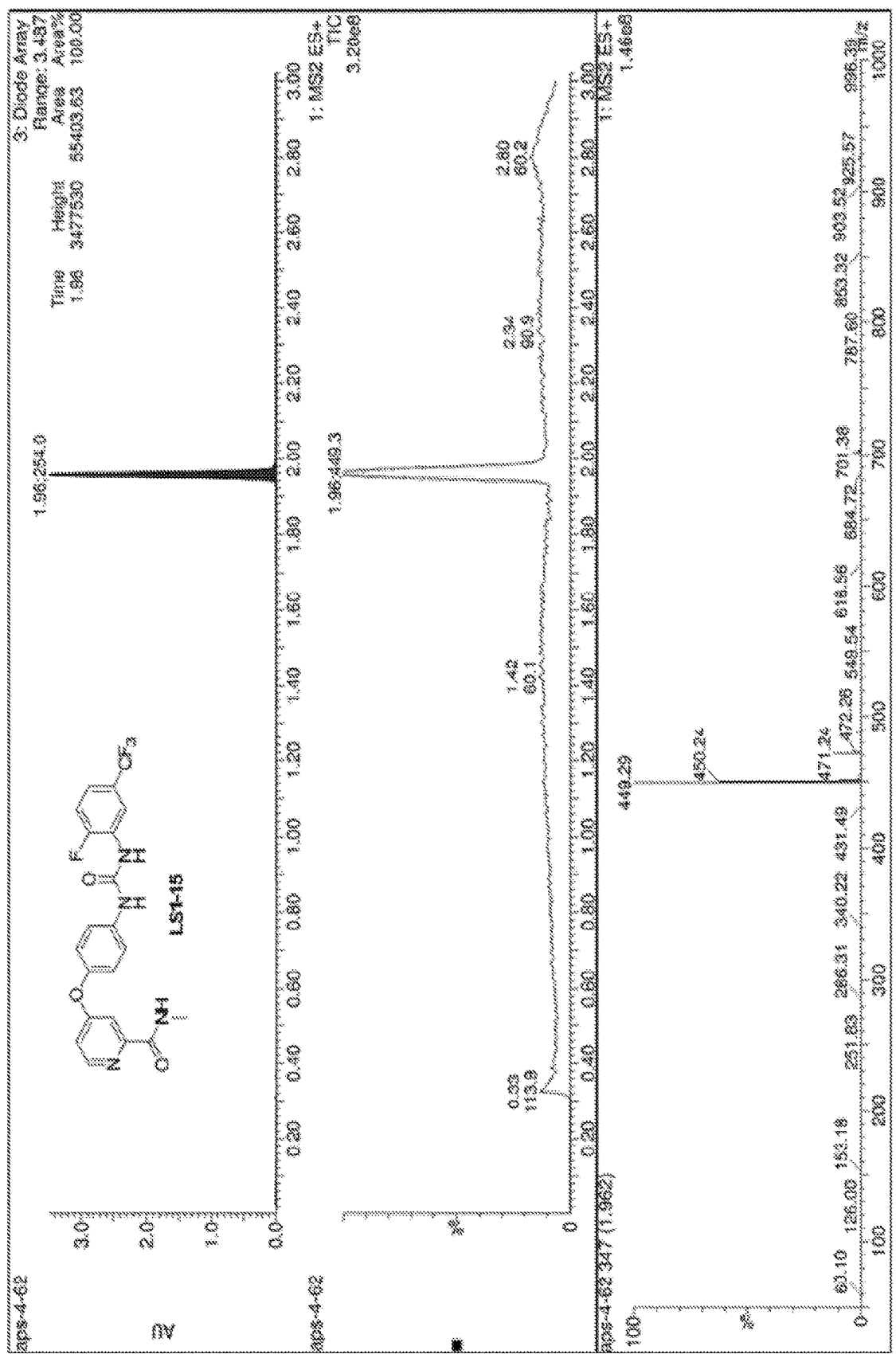
FIG. 5 shows LC-MS data for compound LS1-15.
Figure 6:
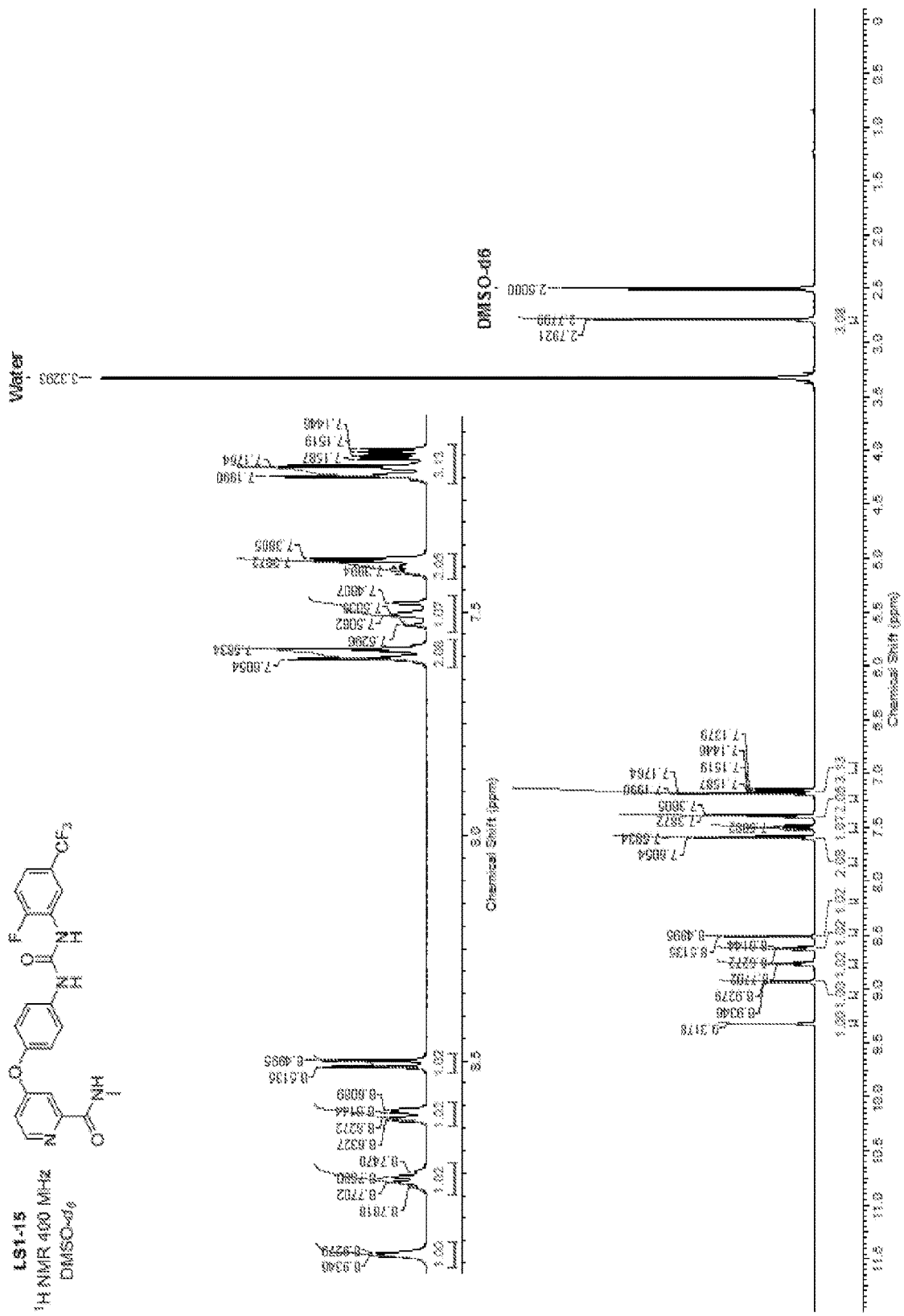
FIG. 6 shows $^1$H NMR spectra for compound LS1-15.

In a 20 mL vial from 1-fluoro-2-isocyanato-4-(trifluoromethyl)benzene (720 μL, 4.98 mmol) and HB/S1 (1.09 g, 4.48 mmol) in CH$_2$Cl$_2$ (16 mL). Stirred for 72 hours and isolated by vacuum filtration. Obtained 1.92 g (96%) of the title compound as a white powder: $^1$H NMR (400 MHz, DMSO-d$_6$) δ 9.32 (s, 1H), 8.93 (d, J=2.7 Hz, 1H), 8.76 (br q, J=4.9 Hz, 1H), 8.62 (dd, J=7.3, 2.2 Hz, 1H), 8.51 (d, J=5.6 Hz, 1H), 7.59 (d, J=8.8 Hz, 2H), 7.51 (dd, J=10.6, 8.9 Hz, 1H), 7.37-7.43 (m, 2H), 7.19 (d, J=9.0 Hz, 2H), 7.15 (dd, J=5.6, 2.7 Hz, 1H), 2.79 (d, J=4.9 Hz, 3H); $^{19}$F NMR (376 MHz, DMSO-d$_6$) δ −60.2 (s, 3F), −123.7 (s, 1F); LC-MS (ESI+) m/z: [M+H]$^+$ Calcd for C$_{21}$H$_{17}$F$_4$N$_4$O$_3$, 449.1; Found 449.3 (FIGS. 5-6).

Example 11

Preparation of 4-(3-Fluoro-4-(3-phenylureido)phenoxy)-N-methylpicolinamide (S2/L1/C1 (APS6-18))

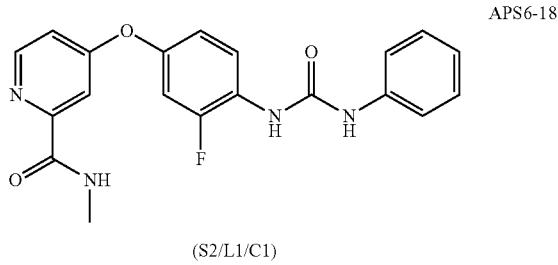 [SMILES: CNC(=O)c1cc(Oc2ccc(NC(=O)Nc3ccccc3)c(F)c2)ccn1]

(S2/L1/C1)

In an 8 mL vial from isocyanatobenzene (50.0 μL, 0.460 mmol) and HB/S2 (100 mg, 0.383 mmol) in CH$_2$Cl$_2$ (1 mL). Stirred for 24 hours and isolated by vacuum filtration. Obtained 115 mg (79%) of the title compound as a white solid: $^1$H NMR (400 MHz, DMSO-d$_6$) δ 9.08 (s, 1H), 8.78 (br q, J=4.4 Hz, 1H), 8.63 (d, J=1.7 Hz, 1H), 8.52 (d, J=5.6 Hz, 1H), 8.24 (t, J=9.0 Hz, 1H), 7.47 (d, J=7.6 Hz, 2H), 7.42 (d, J=2.4 Hz, 1H), 7.27-7.35 (m, 3H), 7.18 (dd, J=5.5, 2.6 Hz, 1H), 7.06 (dd, J=8.9, 1.6 Hz, 1H), 6.99 (t, J=7.3 Hz, 1H), 2.79 (d, J=4.9 Hz, 3H); $^{19}$F NMR (376 MHz, DMSO-d$_6$) δ −125.1 (s, 1F); LC-MS (ESI+) m/z: [M+H]$^+$ Calcd for C$_{20}$H$_{18}$FN$_4$O$_3$, 381.1; Found 381.2.

Example 12

Preparation of 4-(3-Fluoro-4-(3-(3-(trifluoromethyl) phenyl)ureido) phenoxy)-N-methylpicolinamide (S2/L1/C2 (APS4-4-2))

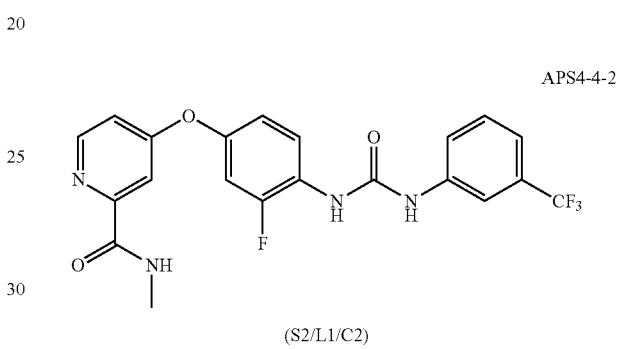

(S2/L1/C2)

In an 8 mL vial from 1-isocyanato-3-(trifluoromethyl) benzene (45.0 μL, 0.327 mmol) and HB/S2 (78.4 mg, 0.300 mmol) in CH$_2$Cl$_2$ (1 mL). Stirred for 24 hours and isolated by vacuum filtration. Obtained 57.4 mg (43%) of the title compound as a white solid: $^1$H NMR (400 MHz, DMSO-d$_6$) δ 9.43 (s, 1H), 8.78 (br q, J=4.6 Hz, 1H), 8.71 (d, J=1.7 Hz, 1H), 8.53 (dd, J=5.6, 0.5 Hz, 1H), 8.19 (t, J=9.0 Hz, 1H), 8.04 (s, 1H), 7.50-7.59 (m, 2H), 7.42 (d, J=2.7 Hz, 1H), 7.31-7.37 (m, 2H), 7.18 (dd, J=5.5, 2.6 Hz, 1H), 7.07 (ddd, J=8.9, 2.7, 1.1 Hz, 1H), 2.79 (d, J=4.9 Hz, 3H); $^{19}$F NMR (376 MHz, DMSO-d$_6$) δ −60.9 (s, 3F), −124.3 (s, 1F); LC-MS (ESI+) m/z: [M+H]$^+$ Calcd for C$_{21}$H$_{17}$F$_4$N$_4$O$_3$, 449.1; Found 449.2.

Example 13

Preparation of 4-(4-(3-(4-Chloro-3-(trifluoromethyl) phenyl)ureido)-3-fluorophenoxy)-N-methylpicolinamide (S2/L1/C3 (Regorafenib))

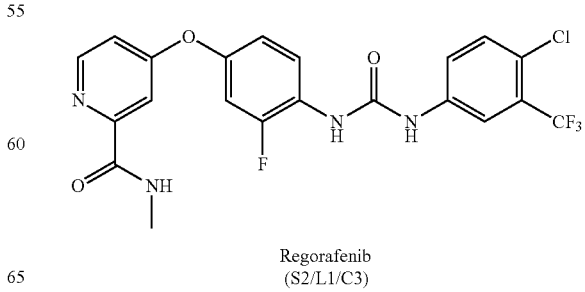

Regorafenib
(S2/L1/C3)

Figure 7:
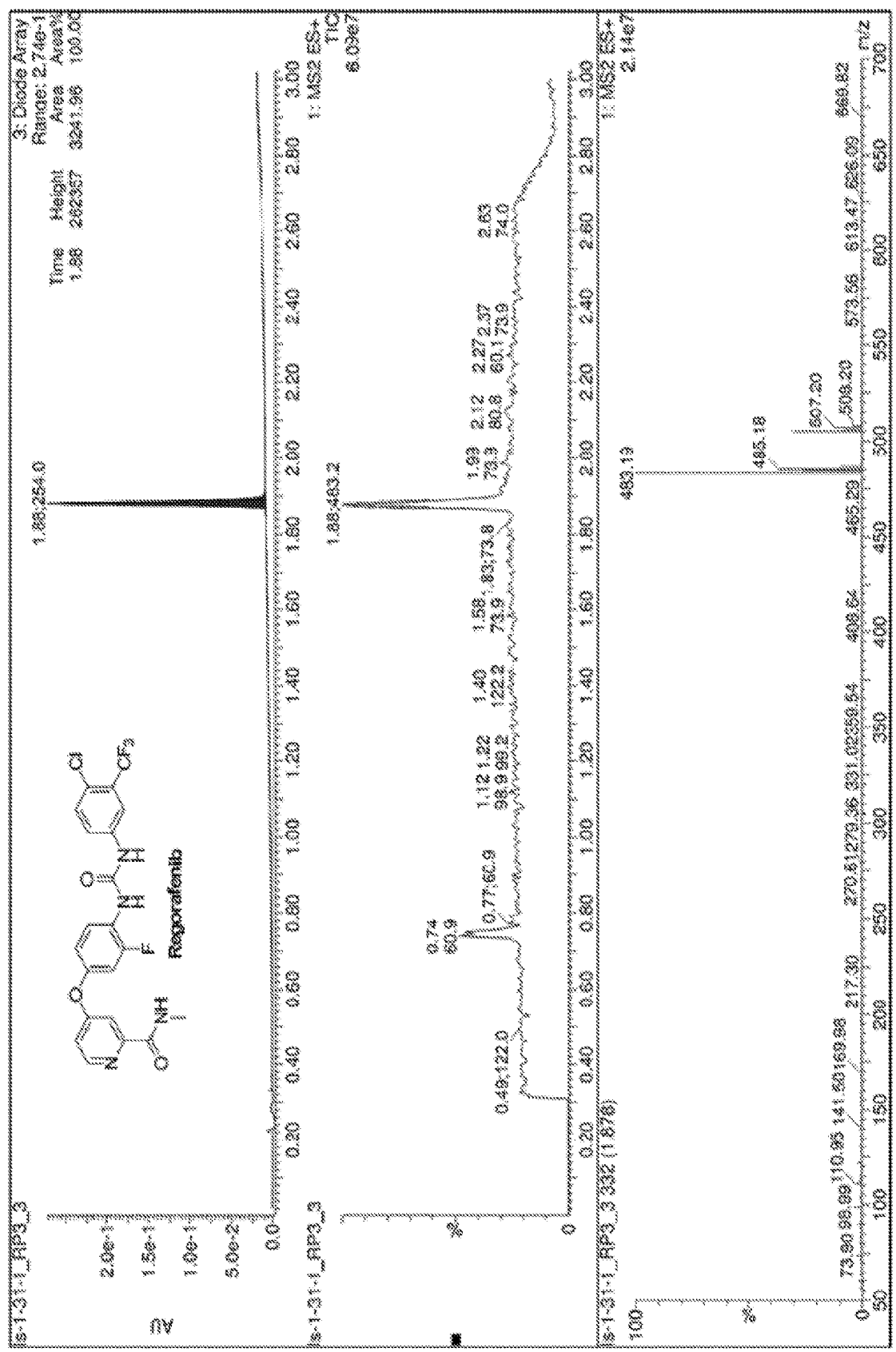
FIG. 7 shows LC-MS data for Regorafenib.
Figure 8:
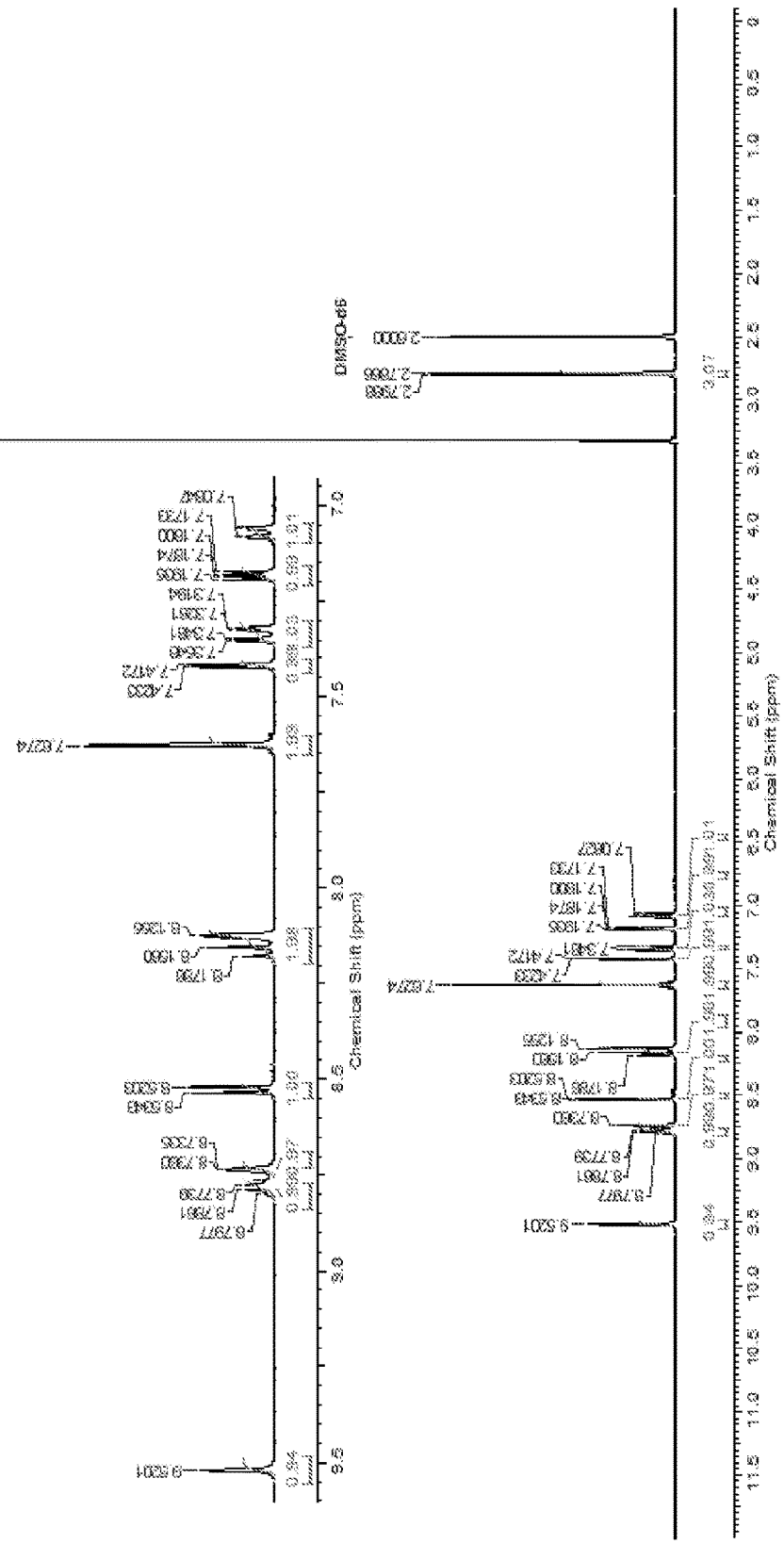
FIG. 8 shows $^1$H NMR spectra for Regorafenib.

A solution of 1-chloro-4-isocyanato-2-(trifluoromethyl)benzene (384 mg, 1.73 mmol) and CH$_2$Cl$_2$ (2.5 mL) was added to a solution of HB/S2 (450 mg, 1.72 mmol) and CH$_2$Cl$_2$ (2.5 mL) in an 8 mL vial. Stirred for 24 hours and isolated the product by vacuum filtration. Obtained 720 mg (87%) of the title compound as a white powder: $^1$H NMR (400 MHz, DMSO-d$_6$) δ 9.52 (s, 1H), 8.78 (br q, J=4.8 Hz, 1H), 8.73 (d, J=1.0 Hz, 1H), 8.53 (d, J=5.6 Hz, 1H), 8.10-8.20 (m, 2H), 7.63 (s, 2H), 7.42 (d, J=2.5 Hz, 1H), 7.34 (dd, J=11.5, 2.7 Hz, 1H), 7.18 (dd, J=5.5, 2.6 Hz, 1H), 7.07 (dd, J=8.8, 1.5 Hz, 1H), 2.79 (d, J=4.9 Hz, 3H); $^{19}$F NMR (100 MHz, DMSO-d$_6$) δ −61.1 (s, 3F), −124.0 (s, 1F); LC-MS (ESI+) m/z: [M+H]$^+$ Calcd for C$_{21}$H$_{16}$ClF$_4$N$_4$O$_3$, 483.1; Found 483.2 (FIGS. 7-8).

Example 14

Preparation of 4-(3-Fluoro-4-(3-(2-fluoro-5-(trifluoromethyl)phenyl) ureido)phenoxy)-N-methylpicolinamide (S2/L1/C4 (APS3-69-1))

APS-3-69-1

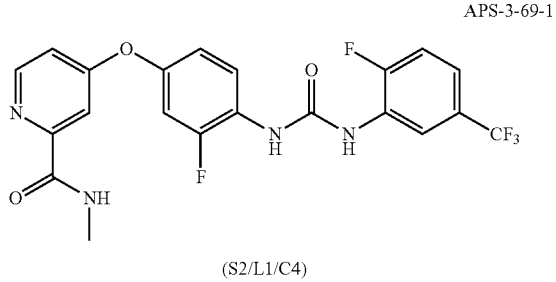 [SMILES: CNC(=O)c1cc(Oc2ccc(NC(=O)Nc3cc(C(F)(F)F)ccc3F)c(F)c2)ccn1]

(S2/L1/C4)

Figure 9:
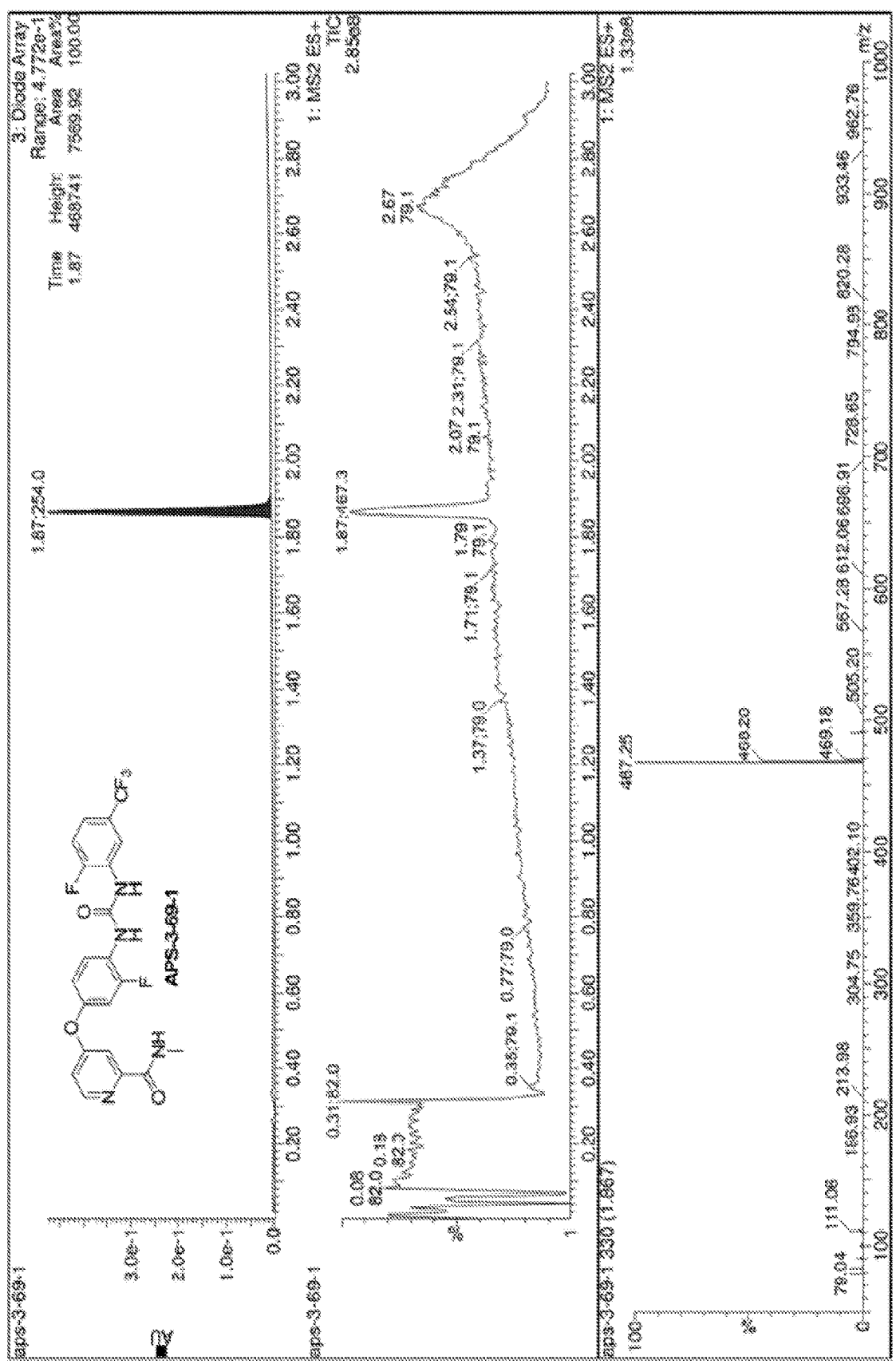
FIG. 9 shows LC-MS data for compound APS-3-69-1.
Figure 10:
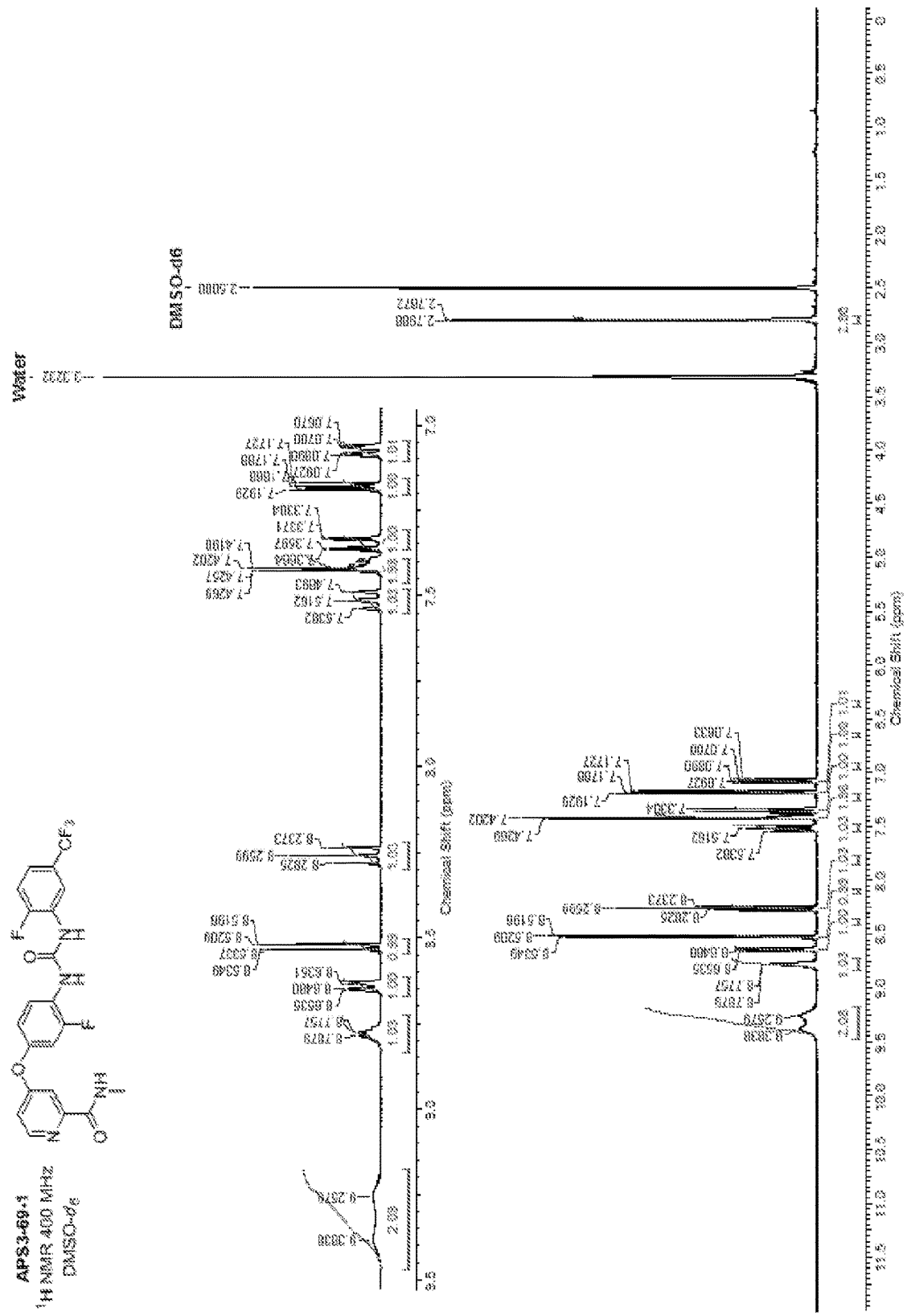
FIG. 10 shows $^1$H NMR spectra for compound APS-3-69-1.

In a 4 mL vial from 1-fluoro-2-isocyanato-4-(trifluoromethyl)benzene (31.0 μL, 0.214 mmol) and HB/S2 (52.3 g, 0.200 mmol) in CH$_2$Cl$_2$ (1 mL). Stirred for 18 hours and isolated by vacuum filtration. Obtained 82.6 mg (88%) of the title compound as a white powder: $^1$H NMR (400 MHz, DMSO-d$_6$) δ 9.38 (br s, 1H), 9.26 (br s, 1H), 8.78 (br ap d, J=4.9 Hz, 1H), 8.64 (dd, J=7.3, 2.2 Hz, 1H), 8.53 (dd, J=5.6, 0.5 Hz, 1H), 8.26 (dd, J=9.1, 9.1 Hz, 1H), 7.51 (dd, J=10.7, 8.9 Hz, 1H), 7.38-7.44 (m, 2H), 7.35 (dd, J=11.7, 2.7 Hz, 1H), 7.18 (dd, J=5.6, 2.4 Hz, 1H), 7.08 (ddd, J=9.0, 2.6, 1.4 Hz, 1H), 2.79 (d, J=4.7 Hz, 3H); $^{19}$F NMR (376 MHz, DMSO-d$_6$) δ −60.3 (s, 3F), −123.5 (s, 1F), −124.6 (s, 1F); LC-MS (ESI+) m/z: [M+H]$^+$ Calcd for C$_{21}$H$_{16}$F$_5$N$_4$O$_3$, 467.1; Found 467.3 (FIGS. 9-10).

Example 15

Preparation of N-Methyl-4-((4-(3-phenylureido)naphthalen-1-yl)oxy)picolinamide (S3/L1/C1 (APS4-61-4))

APS4-61-4

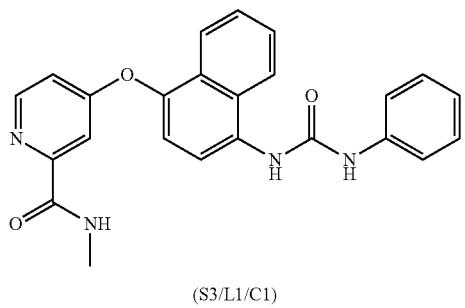

(S3/L1/C1)

In an 8 mL vial from isocyanatobenzene (45.0 μL, 0.414 mmol) and HB/S3 (100 mg, 0.341 mmol) in CH$_2$Cl$_2$ (2 mL). Stirred for 72 hours and isolated by vacuum filtration. Obtained 135 mg (96%) of the title compound as a light-purple solid: $^1$H NMR (400 MHz, DMSO-d$_6$) δ 9.10 (s, 1H), 8.88 (s, 1H), 8.76 (br q, J=4.8 Hz, 1H), 8.52 (dd, J=5.6, 0.5 Hz, 1H), 8.24 (d, J=8.6 Hz, 1H), 8.08 (d, J=8.3 Hz, 1H), 7.83 (dd, J=8.3, 0.7 Hz, 1H), 7.70 (ddd, J=8.4, 7.0, 1.2 Hz, 1H), 7.56-7.62 (m, 1H), 7.53 (dd, J=8.7, 1.1 Hz, 2H), 7.41 (d, J=8.3 Hz, 1H), 7.28-7.35 (m, 3H), 7.22 (dd, J=5.6, 2.7 Hz, 1H), 6.97-7.03 (m, 1H), 2.76 (d, J=4.9 Hz, 3H); $^{13}$C NMR (100 MHz, DMSO-d$_6$) δ 166.4, 163.7, 152.9, 152.5, 150.5, 144.0, 139.7, 132.8, 128.9, 127.4, 127.1, 126.8, 126.6, 122.3, 121.9, 121.5, 118.2, 117.8, 117.6, 113.8, 108.4, 26.0; LC-MS (ESI+) m/z: [M+H]$^+$ Calcd for C$_{24}$H$_{21}$N$_4$O$_3$, 413.2; Found 413.3.

Example 16

Preparation of N-Methyl-4-((4-(3-(3-(trifluoromethyl)phenyl) ureido)naphthalen-1-yl)oxy)picolinamide (S3/L1/C2 (APS4-61-3))

APS4-61-3

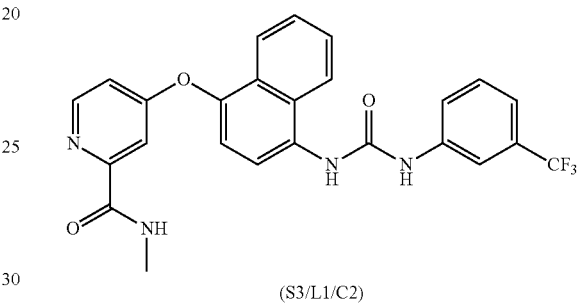

(S3/L1/C2)

In an 8 mL vial from 1-isocyanato-3-(trifluoromethyl)benzene (55.0 μL, 0.399 mmol) and HB/S3 (100 mg, 0.341 mmol) in CH$_2$Cl$_2$ (3 mL). Stirred for 72 hours and isolated by vacuum filtration. Obtained 133 mg (78%) of the title compound as a light-pink solid: $^1$H NMR (400 MHz, DMSO-d$_6$) δ 9.45 (s, 1H), 8.97 (s, 1H), 8.76 (br q, J=4.6 Hz, 1H), 8.53 (d, J=5.6 Hz, 1H), 8.23 (d, J=8.6 Hz, 1H), 8.09 (s, 1H), 8.03 (d, J=8.3 Hz, 1H), 7.84 (d, J=7.8 Hz, 1H), 7.71 (ddd, J=8.4, 7.0, 1.2 Hz, 1H), 7.52-7.66 (m, 3H), 7.42 (d, J=8.3 Hz, 1H), 7.31-7.36 (m, 2H), 7.22 (dd, J=5.6, 2.7 Hz, 1H), 2.76 (d, J=4.9 Hz, 3H); $^{19}$F NMR (376 MHz, DMSO-d$_6$) δ −60.9 (s, 3F); LC-MS (ESI+) m/z: [M+H]$^+$ Calcd for C$_{25}$H$_{20}$F$_3$N$_4$O$_3$, 481.2; Found 481.3.

Example 17

Preparation of 4-((4-(3-(4-Chloro-3-(trifluoromethyl)phenyl)ureido) naphthalen-1-yl)oxy)-N-methylpicolinamide (S3/L1/C3 (APS4-61-1))

APS-4-61-1

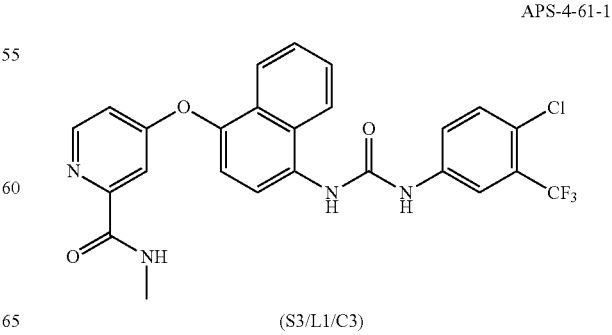

(S3/L1/C3)

Figure 11:
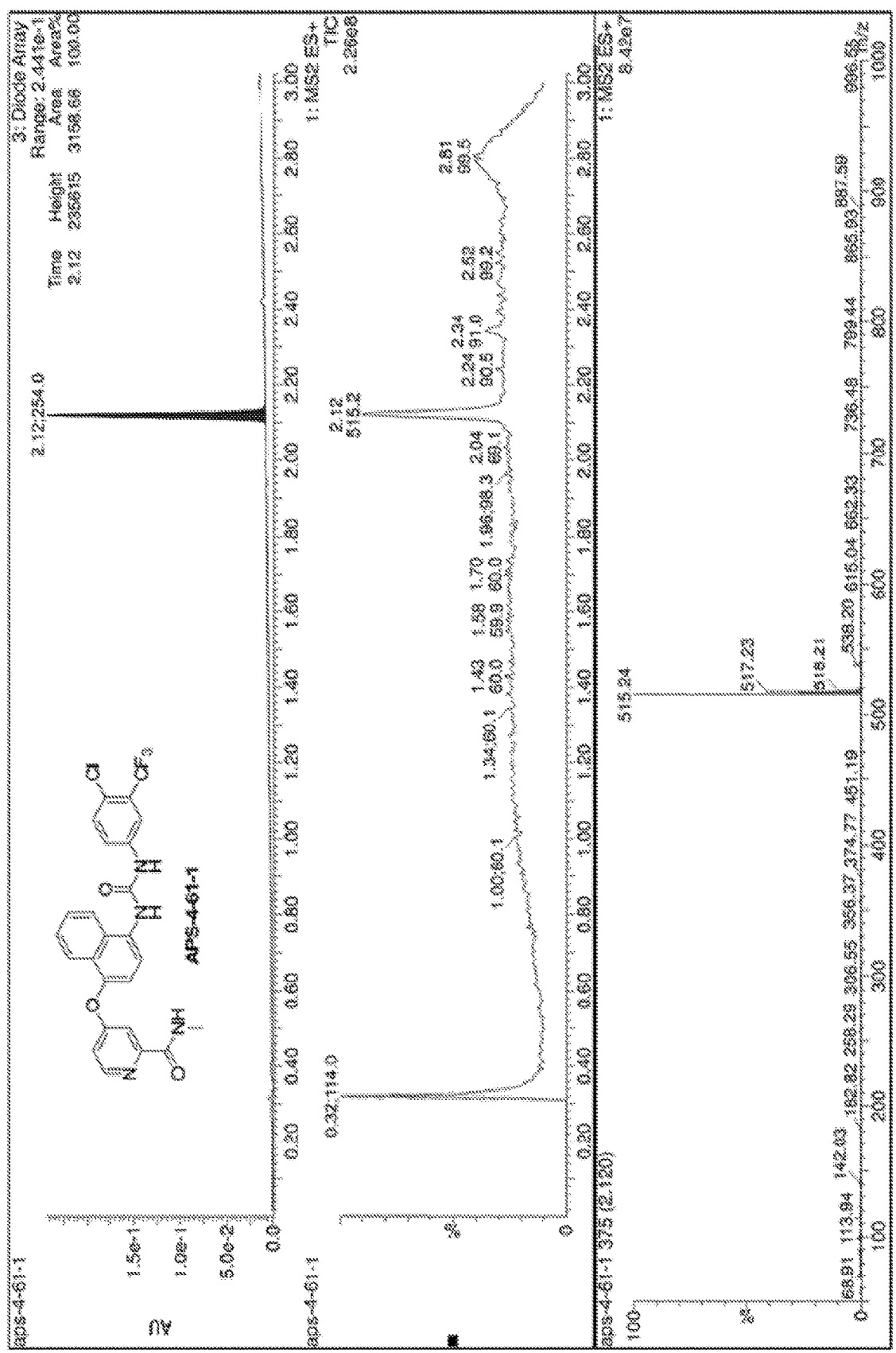
FIG. 11 shows LC-MS data for compound APS-4-61-1.
Figure 12:
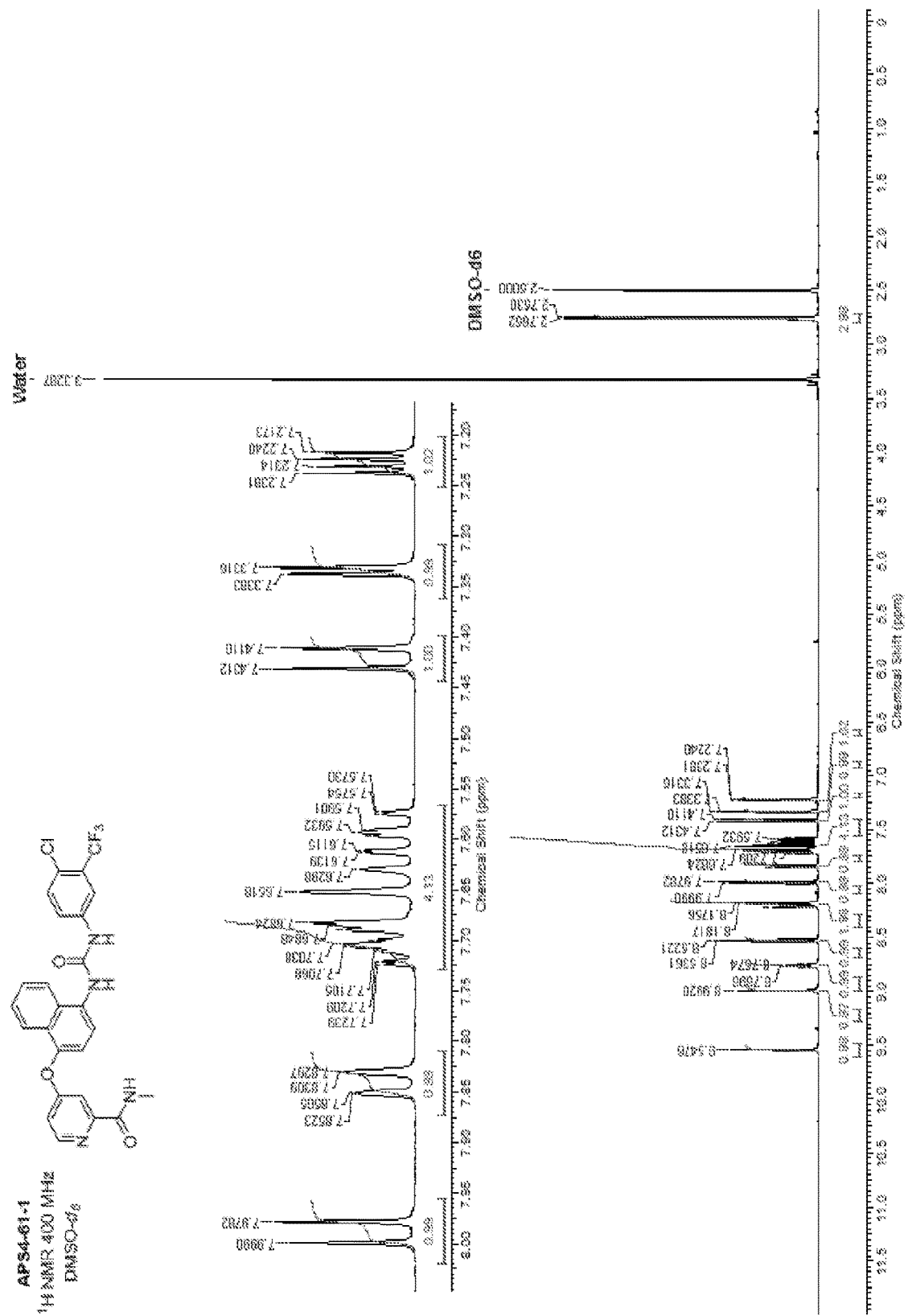
FIG. 12 shows $^1$H NMR spectra for compound APS-4-61-1.

A solution of 1-chloro-4-isocyanato-2-(trifluoromethyl) benzene (83.1 mg, 0.375 mmol) and $CH_2Cl_2$ (0.5 mL) was added to a solution of HB/S3 (100 mg, 0.341 mmol) and $CH_2Cl_2$ (0.5 mL) in an 8 mL vial. Stirred for 72 hours and isolated by vacuum filtration. Obtained 136 mg (77%) of the title compound as a light-pink solid: $^1H$ NMR (400 MHz, DMSO-$d_6$) δ 9.55 (s, 1H), 8.99 (s, 1H), 8.76 (br q, J=4.9 Hz, 1H), 8.53 (dd, J=5.6, 0.5 Hz, 1H), 8.21 (d, J=8.6 Hz, 1H), 8.18 (d, J=2.4 Hz, 1H), 7.99 (d, J=8.3 Hz, 1H), 7.84 (dd, J=8.4, 0.6 Hz, 1H), 7.57-7.73 (m, 4H), 7.42 (d, J=8.1 Hz, 1H), 7.33 (d, J=2.7 Hz, 1H), 7.23 (dd, J=5.6, 2.7 Hz, 1H), 2.76 (d, J=4.9 Hz, 3H); $^{19}F$ NMR (376 MHz, DMSO-$d_6$) δ −61.0 (s, 3F); LC-MS (ESI+) m/z: $[M+H]^+$ Calcd for $C_{25}H_{19}F_3N_4O_3$, 515.1; Found 515.2 (FIGS. 11-12).

Example 18

Preparation of 4-((4-(3-(2-Fluoro-5-(trifluoromethyl)phenyl)ureido) naphthalen-1-yl)oxy)-N-methylpicolinamide (S3/L1/C4 (APS4-61-2))

APS4-61-2

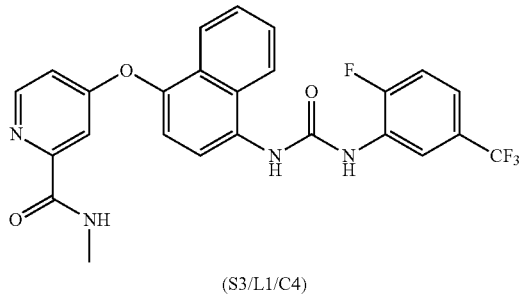

(S3/L1/C4)

In an 8 mL vial from 1-fluoro-2-isocyanato-4-(trifluoromethyl)benzene (55.0 μL, 0.380 mmol) and HB/S3 (100 mg, 0.341 mmol) in $CH_2Cl_2$ (3 mL). Stirred for 72 hours and isolated by vacuum filtration. Obtained 139 mg (85%) of the title compound as a light-purple solid: $^1H$ NMR (400 MHz, DMSO-$d_6$) δ 9.43 (d, J=2.7 Hz, 1H), 9.37 (s, 1H), 8.76 (br q, J=4.9 Hz, 1H), 8.70 (dd, J=7.3, 2.2 Hz, 1H), 8.53 (d, J=5.6 Hz, 1H), 8.28 (d, J=8.6 Hz, 1H), 8.12 (d, J=8.3 Hz, 1H), 7.85 (dd, J=8.4, 0.6 Hz, 1H), 7.72 (ddd, J=8.4, 7.0, 1.2 Hz, 1H), 7.61 (ddd, J=8.2, 7.0, 1.0 Hz, 1H), 7.54 (dd, J=10.8, 9.0 Hz, 1H), 7.43 (d, J=8.3 Hz, 2H), 7.33 (d, J=2.7 Hz, 1H), 7.22 (dd, J=5.6, 2.7 Hz, 1H), 2.76 (d, J=4.9 Hz, 3H); $^{19}F$ NMR (376 MHz, DMSO-$d_6$) δ −60.3 (s, 3F), −123.7 (s, 1F); LC-MS (ESI+) m/z: $[M+H]^+$ Calcd for $C_{25}H_{19}F_4N_4O_3$, 499.1; Found 499.3.

Example 19

Preparation of 4-(4-(3-(4-Chlorophenyl)ureido)phenoxy)-N-methylpicolinamide 2,2,2-trifluoroacetate (LS1-14)

LS1-14

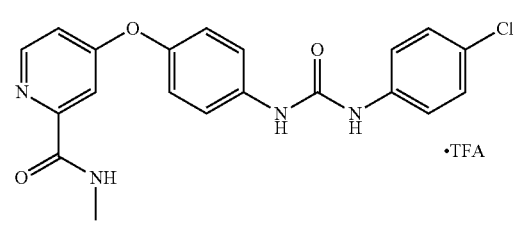

A solution of 1-chloro-4-isocyanatobenzene (23.7 mg, 0.154 mmol) and $CH_2Cl_2$ (0.3 mL) was added to a solution of HB/S1 (36.8 mg, 0.151 mmol) and $CH_2Cl_2$ (0.3 mL) in a 4 mL vial. Stirred for 14 hours and isolated the precipitate by vacuum filtration. The slightly impure white solid was purified by reverse-phase chromatography, eluting at 20 mL/min and using a linear gradient of $H_2O$ (with 0.1% v/v TFA)/MeCN: 80:20→5:95 over 20 minutes. Obtained 57.4 (74%) of the title compound as a white solid: $^1H$ NMR (400 MHz, DMSO-$d_6$) δ 8.86 (d, J=1.5 Hz, 1H), (br ap d, J=4.7 Hz, 1H), 8.50 (d, J=5.6 Hz, 1H), 7.57 (d, J=9.1 Hz, 2H), 7.50 (d, J=9.1 Hz, 2H), 7.38 (d, J=2.2 Hz, 1H), 7.33 (d, J=9.0 Hz, 2H), 7.11-7.20 (m, 3H), 2.78 (d, J=4.9 Hz, 3H); $^{13}C$ NMR (100 MHz, DMSO-$d_6$) δ 166.0, 16.8, 152.5, 152.4, 150.4, 147.5, 138.6, 137.4, 128.6, 125.4, 121.4, 120.1, 119.8, 114.0, 108.6, 26.0; LC-MS (ESI+) m/z: $[M+H]^+$ Calcd for $C_{22}H_{18}ClN_4O_3$, 397.1; Found 397.2.

Example 20

Preparation of 4-(4-(3-(2,5-Difluorophenyl)ureido)-3-fluorophenoxy)-N-methylpicolinamide (APS3-69-2)

APS3-69-2

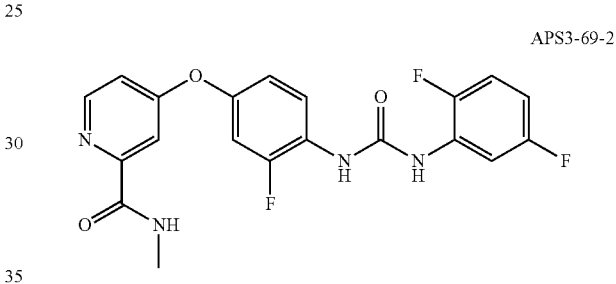

In an 8 mL vial from 1,4-difluoro-2-isocyanatobenzene (25.0 μL, 0.213 mmol) and HB/S2 (52.3 mg, 0.200 mmol) in $CH_2Cl_2$ (1 mL). Stirred for 24 hours and isolated by vacuum filtration. Obtained 75.2 mg (90%) of the title compound as an off-white solid: $^1H$ NMR (400 MHz, DMSO-$d_6$) δ 9.27 (br s, 1H), 8.78 (br q, J=4.7 Hz, 1H), 8.53 (dd, J=5.6, 0.5 Hz, 1H), 8.25 (dd, J=9.2, 9.2 Hz, 1H), 8.06 (ddd, J=11.1, 6.5, 3.2 Hz, 1H), 7.42 (dd, J=2.7, 0.5 Hz, 1H), 7.27-7.38 (m, 2H), 7.18 (dd, J=5.6, 2.7 Hz, 1H), 7.08 (ddd, J=9.0, 2.8, 1.2 Hz, 1H), 6.84 (ddt, J=8.9, 8.0, 3.5 Hz, 1H), 2.79 (d, J=4.7 Hz, 3H); $^{19}F$ NMR (376 MHz, DMSO-$d_6$) δ −116.2 (s, 1F), −124.7 (s, 1F), −134.8 (s, 1F); LC-MS (ESI+) m/z: $[M+H]^+$ Calcd for $C_{20}H_{16}F_3N_4O_3$, 417.1; Found 417.2.

Example 21

Preparation of 4-(4-(3-(2,6-Difluorophenyl)ureido) phenoxy)-N-methylpicolinamide (APS4-3-1)

APS4-3-1

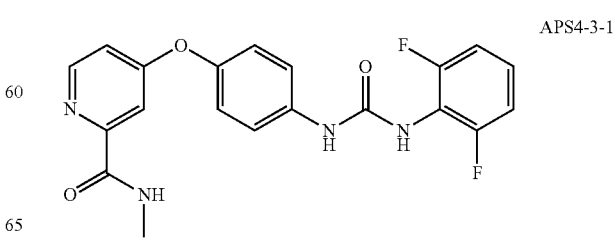

A solution of 1,3-difluoro-2-isocyanatobenzene (50.0 mg, 0.322 mmol) and CH$_2$Cl$_2$ (0.3 mL) was added to a solution of HB/S1 (73.0 mg, 0.300 mmol) and CH$_2$Cl$_2$ (0.8 mL) in an 8 mL vial. Stirred for 48 hours and isolated the precipitate by vacuum filtration. Obtained 111 mg (93%) of the title compound as a white solid: $^1$H NMR (400 MHz, DMSO-d$_6$) δ 9.10 (s, 1H), 8.76 (br ap d, J=4.7 Hz, 1H), 8.50 (d, J=5.6 Hz, 1H), 8.16 (s, 1H), 7.58 (d, J=8.8 Hz, 2H), 7.39 (d, J=2.5 Hz, H), 7.26-7.36 (m, 1H), 7.10-7.20 (m, 5H), 2.79 (d, J=4.9 Hz, 3H); $^{19}$F NMR (376 MHz, DMSO-d$_6$) δ −118.4-−118.3 (m, 2F); LC-MS (ESI+) m/z: [M+H]$^+$ Calcd for C$_{20}$H$_{17}$F$_2$N$_4$O$_3$, 399.1; Found 399.2.

Example 22

Preparation of 4-(4-(3-(2,6-Difluorophenyl)ureido)-3-fluorophenoxy)-N-methylpicolinamide (APS4-3-2)

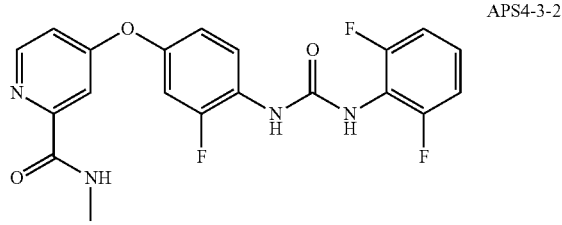 [SMILES: CNC(=O)c1cc(Oc2ccc(NC(=O)Nc3c(F)cccc3F)c(F)c2)ccn1]

APS4-3-2

A solution of 1,3-difluoro-2-isocyanatobenzene (50.0 mg, 0.322 mmol) and CH$_2$Cl$_2$ (0.3 mL) was added to a solution of HB/S2 (78.4 mg, 0.300 mmol) and CH$_2$Cl$_2$ (0.8 mL) in an 8 mL vial. Stirred for 48 hours and isolated the precipitate by vacuum filtration. Obtained 114 mg (91%) of the title compound as a white solid: $^1$H NMR (400 MHz, DMSO-d$_6$) δ 8.88 (br s, 1H), 8.78 (br ap d, J=4.7 Hz, 1H), 8.47-8.58 (m, 2H), 8.15 (dd, J=9.2 Hz, 1H), 7.43 (d, J=2.5 Hz, 1H), 7.27-7.38 (m, 2H), 7.12-7.22 (m, 3H), 7.05 (d, J=8.8 Hz, 1H), 2.79 (d, J=4.9 Hz, 3H); $^{19}$F NMR (376 MHz, DMSO-d$_6$) δ −118.4-−118.3 (m, 2F), −124.7 (s, 1F); LC-MS (ESI+) m/z: [M+H]$^+$ Calcd for C$_{20}$H$_{16}$F$_3$N$_4$O$_3$, 417.1; Found 417.1.

Example 23

Preparation of 4-(4-(3-(2,5-Difluorophenyl)ureido)phenoxy)-N-methylpicolinamide (APS4-4-1)

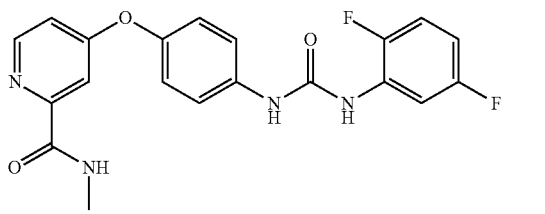

APS4-4-1

In an 8 mL vial from 1,4-difluoro-2-isocyanatobenzene (38.0 μL, 0.324 mmol) and HB/S1 (73.0 mg, 0.300 mmol) in CH$_2$Cl$_2$ (1 mL). Stirred for 24 hours and isolated by vacuum filtration. Obtained 113 mg (94%) of the title compound as an off-white solid: $^1$H NMR (400 MHz, DMSO-d$_6$) δ 9.29 (s, 1H), 8.80 (br s, 1H), 8.76 (br q, J=4.9 Hz, 1H), 8.50 (d, J=5.6 Hz, 1H), 8.05 (ddd, J=11.1, 6.5, 3.2 Hz, 1H), 7.58 (d, J=8.8 Hz, 2H), 7.38 (d, J=2.4 Hz, 1H), 7.30 (ddd, J=10.9, 9.1, 5.1 Hz, 1H), 7.19 (d, J=8.8 Hz, 2H), 7.15 (dd, J=5.6, 2.4 Hz, 1H), 6.78-6.88 (m, 1H), 2.79 (d, J=4.9 Hz, 3H); $^{19}$F NMR (376 MHz, DMSO-d$_6$) δ −116.3 (s, 1F), −135.2 (s, 1F); LC-MS (ESI+) m/z: [M+H]$^+$ Calcd for C$_{20}$H$_{17}$F$_2$N$_4$O$_3$, 399.1; Found 399.2.

Example 24

Preparation of 4-(4-(3-(2-Fluorophenyl)ureido)phenoxy)-N-methylpicolinamide (APS4-9-1)

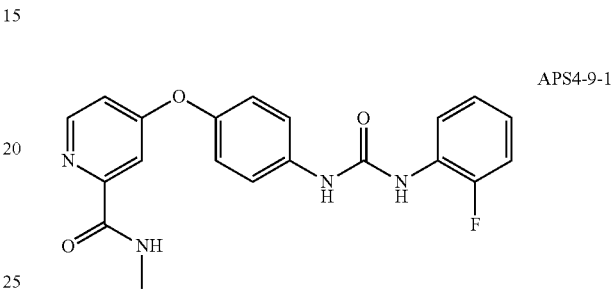

APS4-9-1

In an 8 mL vial from 1-fluoro-2-isocyanatobenzene (40.0 μL, 0.357 mmol) and HB/S1 (73.0 mg, 0.300 mmol) in CH$_2$Cl$_2$ (1 mL). Stirred for 48 hours and isolated by vacuum filtration. Obtained 110 mg (96%) of the title compound as a white solid: $^1$H NMR (400 MHz, DMSO-d$_6$) δ 9.22 (s, 1H), 8.76 (br q, J=4.9 Hz, 1H), 8.58 (d, J=2.5 Hz, 1H), 8.50 (ddd, J=8.2, 8.2, 1.4 Hz, 1H) 7.58 (d, J=9.1 Hz, 2H), 7.39 (d, J=2.5 Hz, 1H), 7.24 (ddd, J=11.6, 8.2, 1.4 Hz, 1H), 7.11-7.20 (m, 4H), 6.97-7.05 (m, 1H), 2.79 (d, J=4.9 Hz, 3H); $^{19}$F NMR (376 MHz, DMSO-d$_6$) δ −129.5 (s, 1F); LC-MS (ESI+) m/z: [M+H]$^+$ Calcd for C$_{20}$H$_{18}$FN$_4$O$_3$, 381.1; Found 381.2.

Example 25

Preparation of 4-(4-(3-(3-Fluorophenyl)ureido)phenoxy)-N-methylpicolinamide (APS4-9-2)

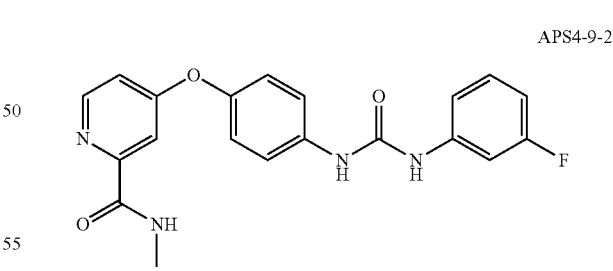

APS4-9-2

In an 8 mL vial from 1-fluoro-3-isocyanatobenzene (41.0 μL, 0.359 mmol) and HB/S1 (73.0 mg, 0.300 mmol) in CH$_2$Cl$_2$ (1 mL). Stirred for 48 hours and isolated by vacuum filtration. Obtained 111 mg (97%) of the title compound as a white solid: $^1$H NMR (400 MHz, DMSO-d$_6$) δ 8.96 (br s, 1H), 8.90 (br s, 1H), 8.76 (br ap d, J=4.6 Hz, 1H), 8.50 (d, J=5.6 Hz, 1H), 7.58 (d, J=8.8 Hz, 2H), 7.50 (ddd, J=11.9, 2.0, 2.0 Hz, 1H), 7.38 (d, J=2.5 Hz, 1H), 7.31 (dd, J=8.1, 8.1 Hz, 1H), 7.09-7.21 (m, 4H), 6.79 (ddd, J=8.5, 2.1, 2.1 Hz, 1H), 2.79 (d, J=4.9 Hz, 3H); $^{19}$F NMR (376 MHz, DMSO-d$_6$) δ −111.8 (s, 1F); LC-MS (ESI+) m/z: [M+H]$^+$ Calcd for C$_{20}$H$_{18}$FN$_4$O$_3$, 381.1; Found 381.2.

Example 26

Preparation of 4-(4-(3-(4-Fluorophenyl)ureido)phenoxy)-N-methylpicolinamide (APS4-9-3)

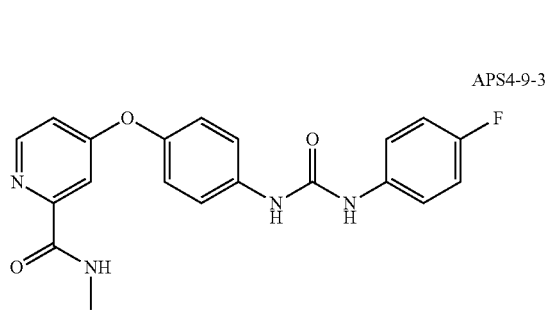 [SMILES: CNC(=O)c1cc(Oc2ccc(NC(=O)Nc3ccc(F)cc3)cc2)ccn1]

APS4-9-3

In an 8 mL vial from 1-fluoro-4-isocyanatobenzene (41.0 μL, 0.359 mmol) and HB/S1 (73.0 mg, 0.300 mmol) in CH$_2$Cl$_2$ (1 mL). Stirred for 48 hours and isolated by vacuum filtration. Obtained 109 mg (96%) of the title compound as a white solid: $^1$H NMR (400 MHz, DMSO-d$_6$) δ 8.67-8.87 (m, 3H), 8.50 (d, J=5.6 Hz, 1H), 7.57 (d, J=8.8 Hz, 2H), 7.43-7.52 (m, 2H), 7.38 (d, J=2.2 Hz, 1H), 7.08-7.20 (m, 5H), 2.79 (d, J=4.9 Hz, 3H); $^{19}$F NMR (376 MHz, DMSO-d$_6$) δ −121.0 (s, 1F); LC-MS (ESI+) m/z: [M+H]$^+$ Calcd for C$_{20}$H$_{18}$FN$_4$O$_3$, 381.1; Found 381.2.

Example 27

Preparation of N-Methyl-4-(4-(3-(4-(trifluoromethyl)phenyl)ureido) phenoxy)picolinamide (APS4-9-4)

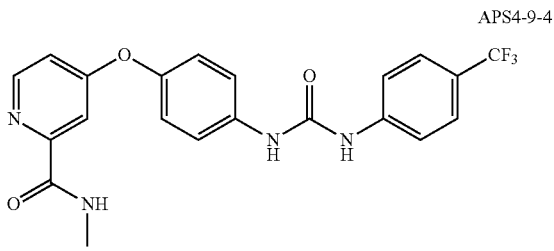 [SMILES: CNC(=O)c1cc(Oc2ccc(NC(=O)Nc3ccc(C(F)(F)F)cc3)cc2)ccn1]

APS4-9-4

In an 8 mL vial from 1-isocyanato-4-(trifluoromethyl)benzene (51.0 μL, 0.357 mmol) and HB/S1 (73.0 mg, 0.300 mmol) in CH$_2$Cl$_2$ (1 mL). Stirred for 48 hours and isolated by vacuum filtration. Obtained 123 mg (95%) of the title compound as a white solid: $^1$H NMR (400 MHz, DMSO-d$_6$) δ 9.15 (s, 1H), 8.95 (s, 1H), 8.76 (br q, J=4.6 Hz, 1H), 8.47-8.53 (m, 1H), 7.66-7.70 (m, 2H), 7.62-7.66 (m, 2H), 7.60 (d, J=8.8 Hz, 2H), 7.39 (d, J=2.2 Hz, 1H), 7.18 (d, J=8.8 Hz, 2H), 7.15 (dd, J=5.6, 2.4 Hz, 1H), 2.79 (d, J=4.9 Hz, 3H); $^{19}$F NMR (376 MHz, DMSO-d$_6$) δ −59.6 (s, 3F); LC-MS (ESI+) m/z: [M+H]$^+$ Calcd for C$_{20}$H$_{18}$F$_3$N$_4$O$_3$, 431.1; Found 431.2.

Example 28

Preparation of 4-(3-Fluoro-4-(3-(2-fluorophenyl)ureido)phenoxy)-N-methylpicolinamide (APS4-9-5)

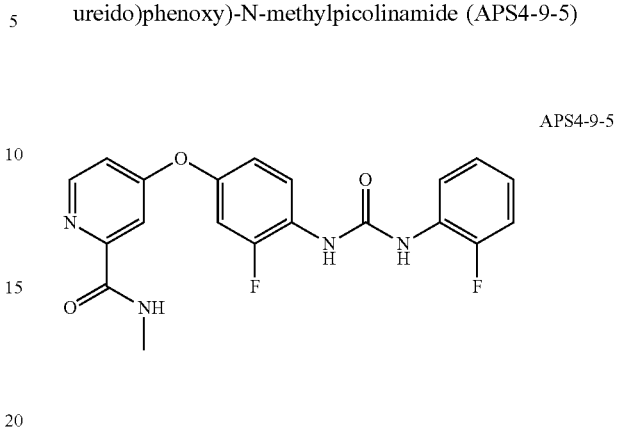

APS4-9-5

In an 8 mL vial from 1-fluoro-2-isocyanatobenzene (40.0 μL, 0.357 mmol) and HB/S2 (78.4 mg, 0.300 mmol) in CH$_2$Cl$_2$ (1 mL). Stirred for 48 hours and isolated by vacuum filtration. Obtained 108 mg (90%) of the title compound as an off-white solid: $^1$H NMR (400 MHz, DMSO-d$_6$) δ 9.12 (br s, 1H), 9.06 (br s, 1H), 8.78 (d, J=3.9 Hz, 1H), 8.52 (d, J=5.6 Hz, 1H), 8.27 (t, J=9.0 Hz, 1H), 8.18 (t, J=8.1 Hz, 1H), 7.42 (br s, 1H), 7.33 (d, J=12.2 Hz, 1H), 7.25 (t, J=8.8 Hz, 1H), 7.11-7.21 (m, 2H), 6.98-7.11 (m, 2H), 2.79 (d, J=4.2 Hz, 3H); $^{19}$F NMR (376 MHz, DMSO-d$_6$) δ −124.9 (s, 1F), −129.3 (s, 1F); LC-MS (ESI+) m/z: [M+H]$^+$ Calcd for C$_{20}$H$_{17}$F$_2$N$_4$O$_3$, 399.1; Found 399.2.

Example 29

Preparation of 4-(3-Fluoro-4-(3-(3-fluorophenyl)ureido)phenoxy)-N-methylpicolinamide (APS4-9-6)

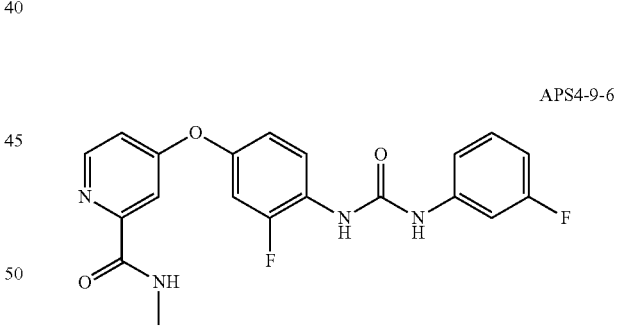

APS4-9-6

In an 8 mL vial from 1-fluoro-3-isocyanatobenzene (41.0 μL, 0.359 mmol) and HB/S2 (78.4 mg, 0.300 mmol) in CH$_2$Cl$_2$ (1 mL). Stirred for 48 hours and isolated by vacuum filtration. Obtained 110 mg (92%) of the title compound as an off-white solid: $^1$H NMR (400 MHz, DMSO-d$_6$) δ 9.31 (s, 1H), 8.80 (br q, J=4.6 Hz, 1H), 8.70 (d, J=2.0 Hz, 1H), 8.53 (d, J=5.4 Hz, 1H), 8.20 (t, J=9.2 Hz, 1H), 7.51 (dt, J=12.0, 2.2 Hz, 1H), 7.42 (d, J=2.4 Hz, 1H), 7.28-7.37 (m, 2H), 7.18 (dd, J=5.6, 2.7 Hz, 1H), 7.04-7.14 (m, 2H), 6.81 (td, J=8.4, 2.7 Hz, 1H), 2.79 (d, J=4.9 Hz, 3H); $^{19}$F NMR (376 MHz, DMSO-d$_6$) δ −111.6 (s, 1F), −124.6 (s, 1F); LC-MS (ESI+) m/z: [M+H]$^+$ Calcd for C$_{20}$H$_{17}$F$_2$N$_4$O$_3$, 399.1; Found 399.2.

Example 30

Preparation of 4-(3-Fluoro-4-(3-(4-fluorophenyl)ureido)phenoxy)-N-methylpicolinamide (APS4-9-7)

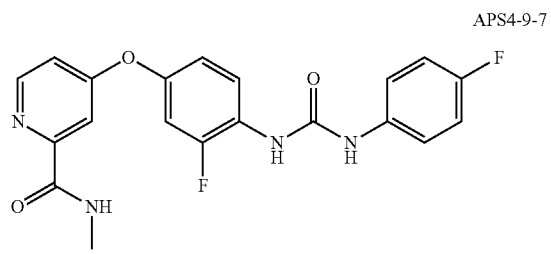 [SMILES: CNC(=O)c1cc(Oc2ccc(NC(=O)Nc3ccc(F)cc3)c(F)c2)ccn1]

APS4-9-7

In an 8 mL vial from 1-fluoro-4-isocyanatobenzene (41.0 µL, 0.359 mmol) and HB/S2 (78.4 mg, 0.300 mmol) in CH$_2$Cl$_2$ (1 mL). Stirred for 48 hours and isolated a precipitate by vacuum filtration. The slightly impure solid was recrystallized from a mixture of EtOAc/EtOH/hexanes (1:1:1, ~2 mL). Obtained 71.5 mg (60%) of the title compound as an off-white solid: $^1$H NMR (400 MHz, DMSO-d$_6$) δ 9.10 (s, 1H), 8.77 (br q, J=4.8 Hz, 1H), 8.60 (d, J=2.2 Hz, 1H), 8.52 (d, J=5.6 Hz, 1H), 8.21 (t, J=9.0 Hz, 1H), 7.44-7.51 (m, 2H), 7.42 (d, J=2.4 Hz, 1H), 7.31 (dd, J=11.5, 2.7 Hz, 1H), 7.10-7.20 (m, 3H), 7.06 (ddd, J=8.9, 2.7, 1.3 Hz, 1H), 2.79 (d, J=4.9 Hz, 3H); $^{19}$F NMR (376 MHz, DMSO-d$_6$) δ −120.7 (s, 1F), −124.9 (s, 1F); LC-MS (ESI+) m/z: [M+H]$^+$ Calcd for C$_{20}$H$_{17}$F$_2$N$_4$O$_3$, 399.1; Found 399.2.

Example 31

Preparation of 4-(3-Fluoro-4-(3-(4-(trifluoromethyl)phenyl)ureido) phenoxy)-N-methylpicolinamide (APS4-9-8)

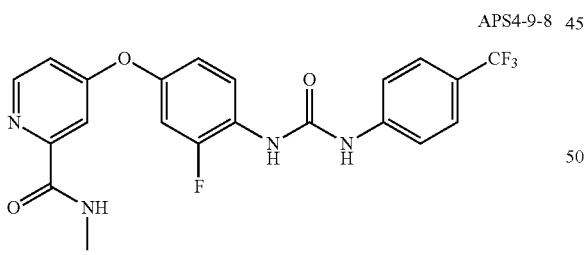

APS4-9-8

In an 8 mL vial from 1-isocyanato-4-(trifluoromethyl)benzene (51.0 µL, 0.357 mmol) and HB/S2 (78.4 mg, 0.300 mmol) in CH$_2$Cl$_2$ (1 mL). Stirred for 48 hours and isolated by vacuum filtration. Obtained 117 mg (87%) of the title compound as a white solid: $^1$H NMR (400 MHz, DMSO-d$_6$) δ 9.48 (s, 1H), 8.70-8.83 (m, 2H), 8.53 (d, J=5.6 Hz, 1H), 8.20 (t, J=9.0 Hz, 1H), 7.62-7.70 (m, 4H), 7.42 (d, J=2.4 Hz, 1H), 7.34 (dd, J=11.6, 2.6 Hz, 1H), 7.18 (dd, J=5.6, 2.7 Hz, 1H), 7.08 (dd, J=8.9, 1.3 Hz, 1H), 2.79 (d, J=4.9 Hz, 3H); $^{19}$F NMR (376 MHz, DMSO-d$_6$) δ −59.7 (s, 3F), −124.4 (s, 1F); LC-MS (ESI+) m/z: [M+H]$^+$ Calcd for C$_{21}$H$_{17}$F$_4$N$_4$O$_3$, 449.1; Found 449.2.

Example 32

Preparation of 4-(4-(3-(4-Chlorophenyl)ureido)-3-fluorophenoxy)-N-methylpicolinamide (APS4-32)

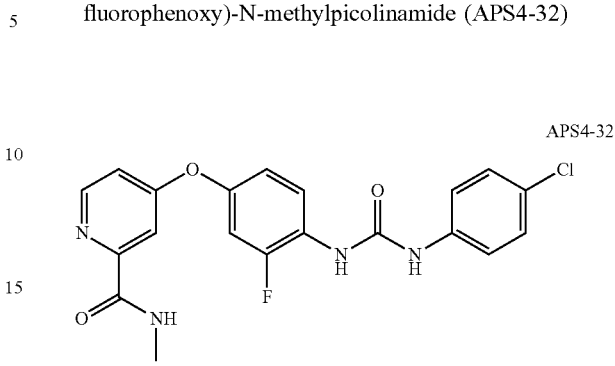

APS4-32

A solution of 1-chloro-4-isocyanatobenzene (82.3 mg, 0.536 mmol) and CH$_2$Cl$_2$ (1 mL) was added to a solution of HB/S2 (100 mg, 0.383 mmol) and CH$_2$Cl$_2$ (0.5 mL) in an 8 mL vial. Stirred for 24 hours and isolated the precipitate by vacuum filtration. Obtained 155 mg (97%) of the title compound as a white solid: $^1$H NMR (400 MHz, DMSO-d$_6$) δ 9.21 (s, 1H), 8.78 (br q, J=4.9 Hz, 1H), 8.65 (d, J=2.0 Hz, 1H), 8.52 (d, J=5.6 Hz, 1H), 8.20 (t, J=9.2 Hz, 1H), 7.50 (d, J=8.8 Hz, 2H), 7.42 (d, J=2.4 Hz, 1H), 7.29-7.38 (m, 3H), 7.18 (dd, J=5.5, 2.6 Hz, 1H), 7.07 (d, J=8.8 Hz, 1H), 2.79 (d, J=4.9 Hz, 3H); $^{19}$F NMR (376 MHz, DMSO-d6) δ −124.8 (s, 1F); LC-MS (ESI+) m/z: [M+H]$^+$ Calcd for C$_{20}$H$_{17}$ClFN$_4$O$_3$, 415.1; Found 415.2.

Example 33

Preparation of 4-(4-(3-(2-Chloro-5-(trifluoromethyl)phenyl)ureido) phenoxy)-N-methylpicolinamide (APS4-70-1)

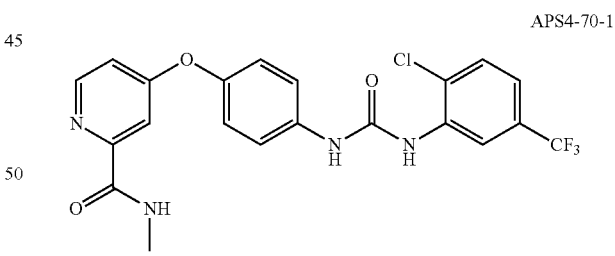

APS4-70-1

Figure 13:
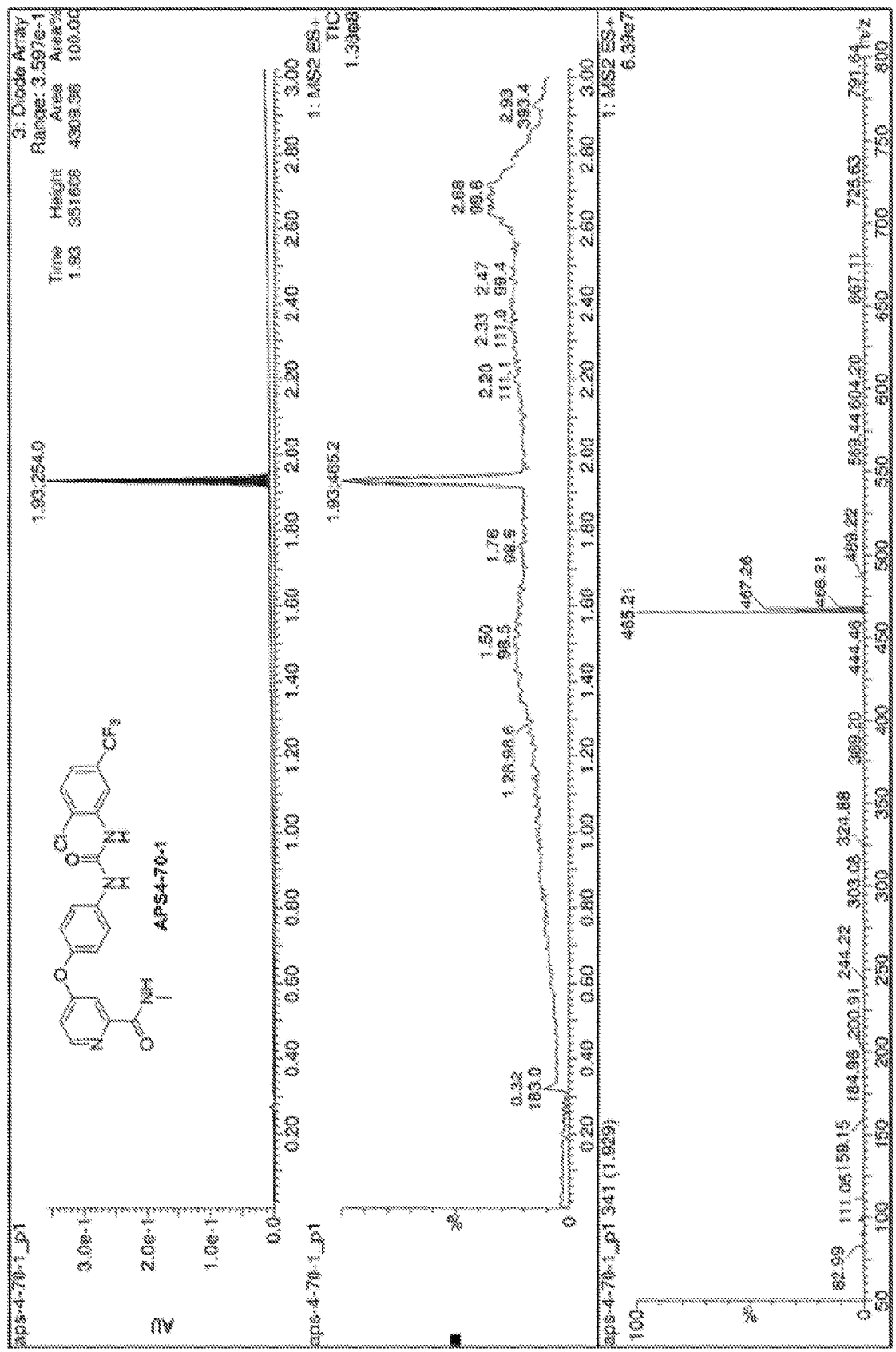
FIG. 13 shows LC-MS data for compound APS4-70-1.
Figure 14:
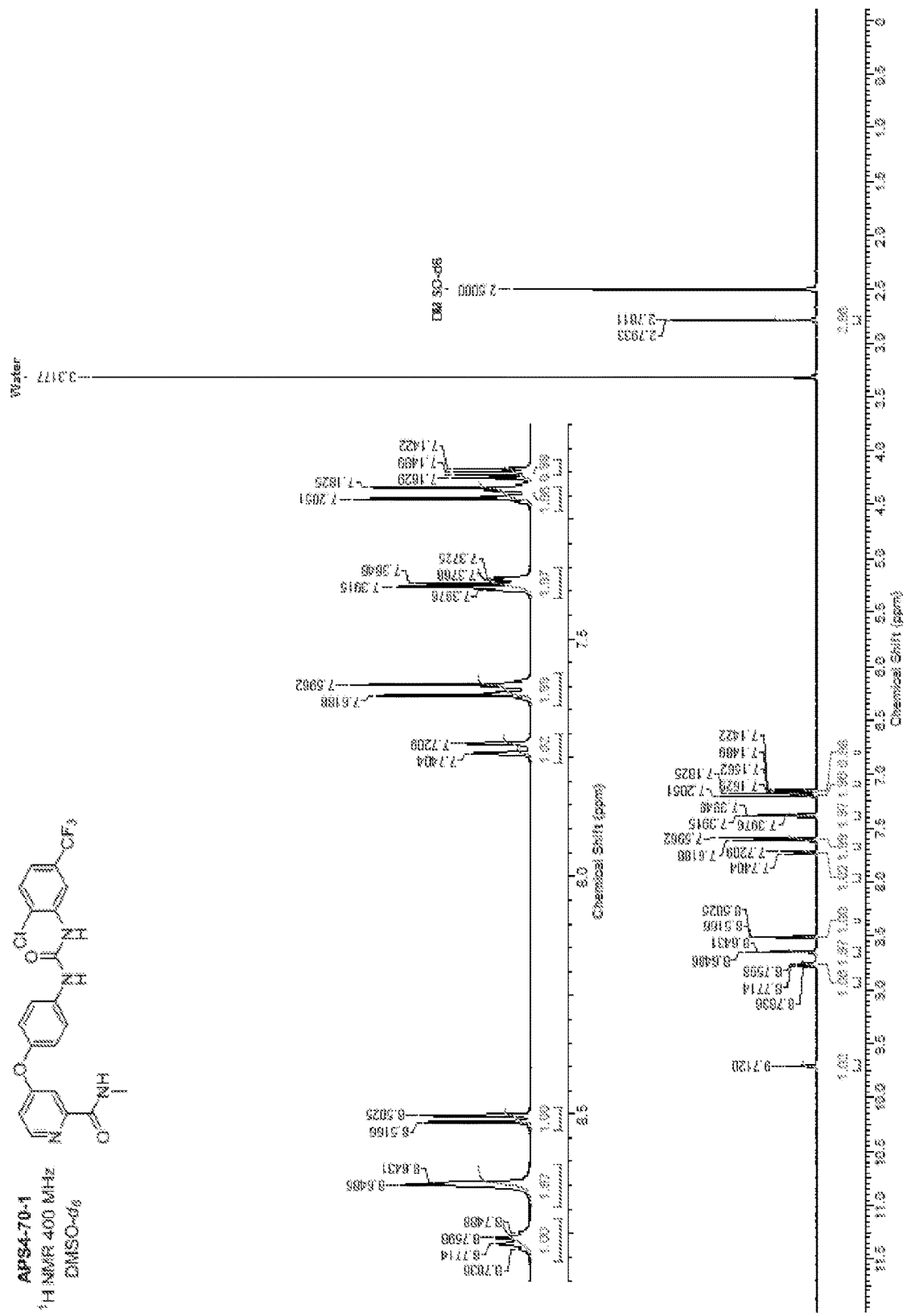
FIG. 14 shows $^1$H NMR spectra for compound APS4-70-1.

In a 4 mL vial from 1-chloro-2-isocyanato-4-(trifluoromethyl)benzene (27.0 µL, 0.180 mmol) and HB/S1 (36.5 mg, 0.150 mmol) in CH$_2$Cl$_2$ (0.6 mL). Stirred for 14 hours and isolated by vacuum filtration. Obtained 54.5 mg (78%) of the title compound as a white powder: $^1$H NMR (400 MHz, DMSO-d$_6$) δ 9.71 (s, 1H), 8.77 (br q, J=4.6 Hz, 1H), 8.65 (d, J=2.2 Hz, 2H), 8.51 (d, J=5.6 Hz, 1H), 7.73 (d, J=7.8 Hz, 1H), 7.61 (d, J=9.0 Hz, 2H), 7.36-7.41 (m, 2H), 7.19 (d, J=9.0 Hz, 2H), 7.15 (dd, J=5.6, 2.7 Hz, 1H), 2.79 (d, J=4.9 Hz, 3H); $^{19}$F NMR (376 MHz, DMSO-d$_6$) δ −60.9 (s, 3F); LC-MS (ESI+) m/z: [M+H]$^+$ Calcd for C$_{21}$H$_{17}$ClF$_3$N$_4$O$_3$, 465.1; Found 465.2 (FIGS. 13-14).

Example 34

Preparation of 4-(4-(3-(3-Chlorophenyl)ureido)phenoxy)-N-methylpicolinamide (APS4-70-2)

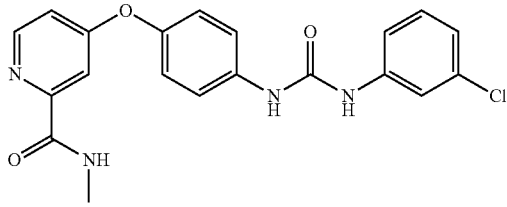

APS4-70-2

Figure 15:
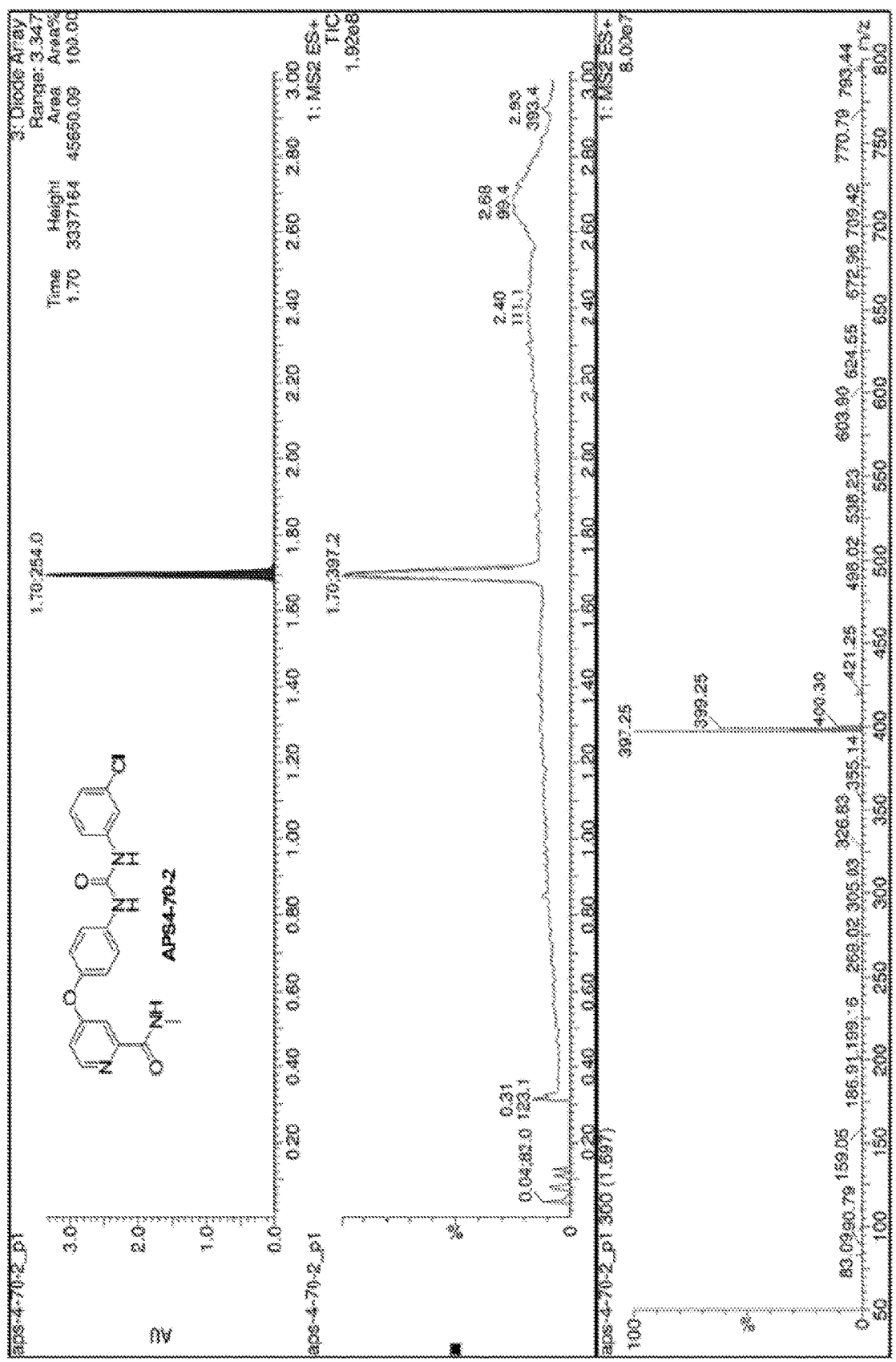
FIG. 15 shows LC-MS data for compound APS4-70-2.
Figure 16:
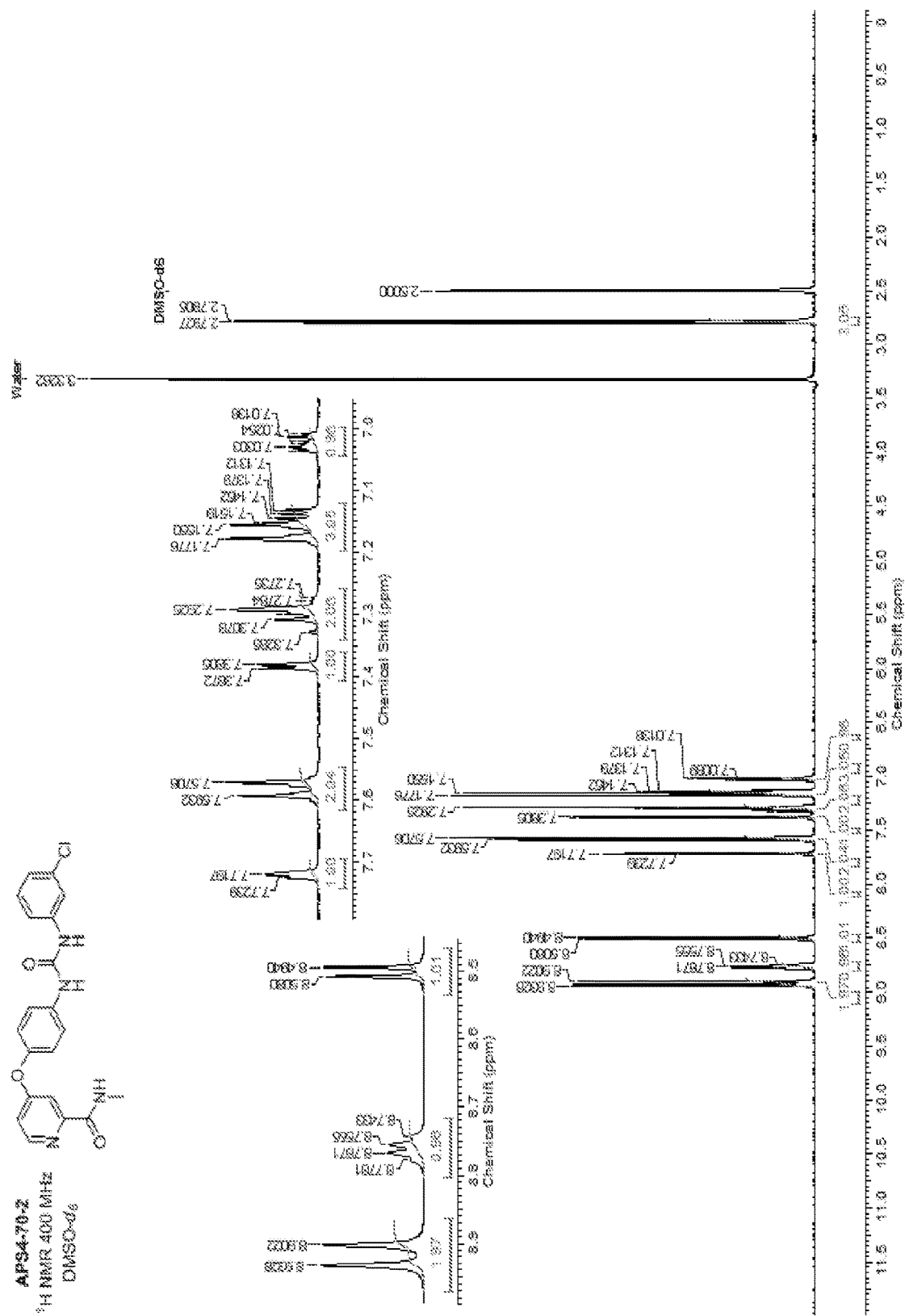
FIG. 16 shows $^1$H NMR spectra for compound APS4-70-2.

In a 4 mL vial from 1-chloro-3-isocyanatobenzene (22.0 µL, 0.181 mmol) and HB/S1 (36.5 mg, 0.150 mmol) in CH$_2$Cl$_2$ (0.6 mL). Stirred for 14 hours and then diluted with Et$_2$O (3 mL). The resulting precipitate was isolated by vacuum filtration and washed with hexanes. Obtained 50.7 mg (85%) of the title compound as a white powder: $^1$H NMR (400 MHz, DMSO-d$_6$) δ 8.92 (d, J=12.2 Hz, 2H), 8.76 (br q, J=4.7 Hz, 1H), 8.50 (d, J=5.6 Hz, 1H), 7.69-7.74 (m, 1H), 7.58 (d, J=9.0 Hz, 2H), 7.38 (d, J=2.7 Hz, 1H), 7.26-7.34 (m, 2H), 7.12-7.20 (m, 3H), 7.02 (dt, J=6.5, 2.2 Hz, 1H), 2.79 (d, J=4.9 Hz, 3H); $^{13}$C NMR (100 MHz, DMSO-d$_6$) δ 166.0, 163.8, 152.43, 152.42, 150.4, 147.6, 141.2, 137.3, 133.2, 130.4, 121.49, 121.45, 120.2, 117.6, 116.7, 114.0, 108.7, 26.0; LC-MS (ESI+) m/z: [M+H]$^+$ Calcd for C$_{20}$H$_{18}$ClN$_4$O$_3$, 397.1; Found 397.3 (FIGS. 15-16).

Example 35

General Procedure for the Synthesis of Urea Linker (L1) Sorafelogs Employing an Aniline and N,N-Carbonyldiimidazole (CDI)

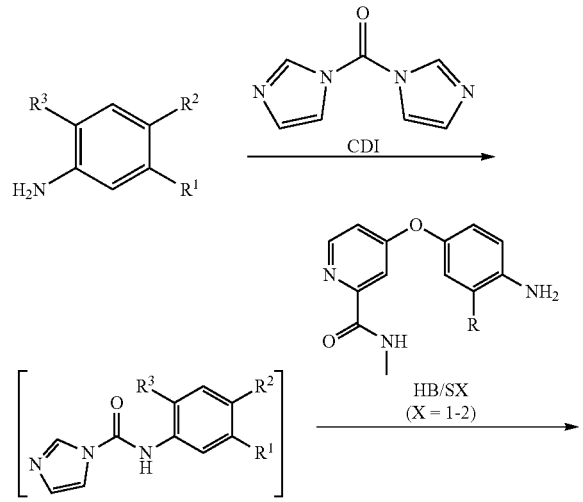

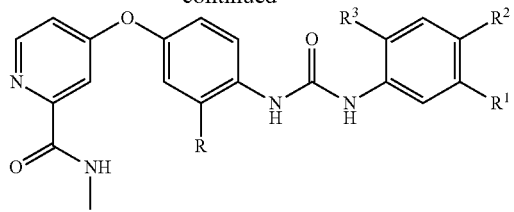

The aniline (neat or as a solution in CH$_2$Cl$_2$) was added dropwise over 10 min by syringe to a 0° C. solution of CDI (0.2-1.0 M) and CH$_2$Cl$_2$, in a flame-dried vial (equipped with a sepcap) under Ar. For 2-substituted anilines the cooling bath was removed after 15 min, while for other anilines (without a 2-substituent) reactions were allowed to gradually warm to room temperature as the bath melted (typically 2-3 hours). Reactions were stirred until formation of the acyl-imidazole intermediate was complete; progress was monitored by quenching reaction aliquots into MeOH and observing the conversion of the aniline to the methylcarbamate. After 12-24 hours, solid HB/SX (X=1-2) was added in one portion and the reaction was stirred under Ar for an additional 1-24 hours. For some reactions the product precipitated out of solution and was isolated by vacuum filtration; the collected solid was washed with CH$_2$Cl$_2$ (×2) and hexanes (×2) and air-dried. When the product did not precipitate out of solution, the crude reaction mixture was purified directly by chromatography. All products were dried under high vacuum for >24 hours.

Example 36

Preparation of 4-(4-(3-(4-Fluoro-3-(trifluoromethyl)phenyl)ureido) phenoxy)-N-methylpicolinamide (APS4-34-1)

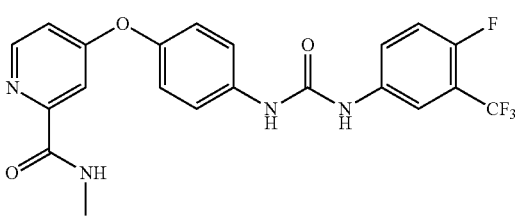

APS4-34-1

Figure 17:
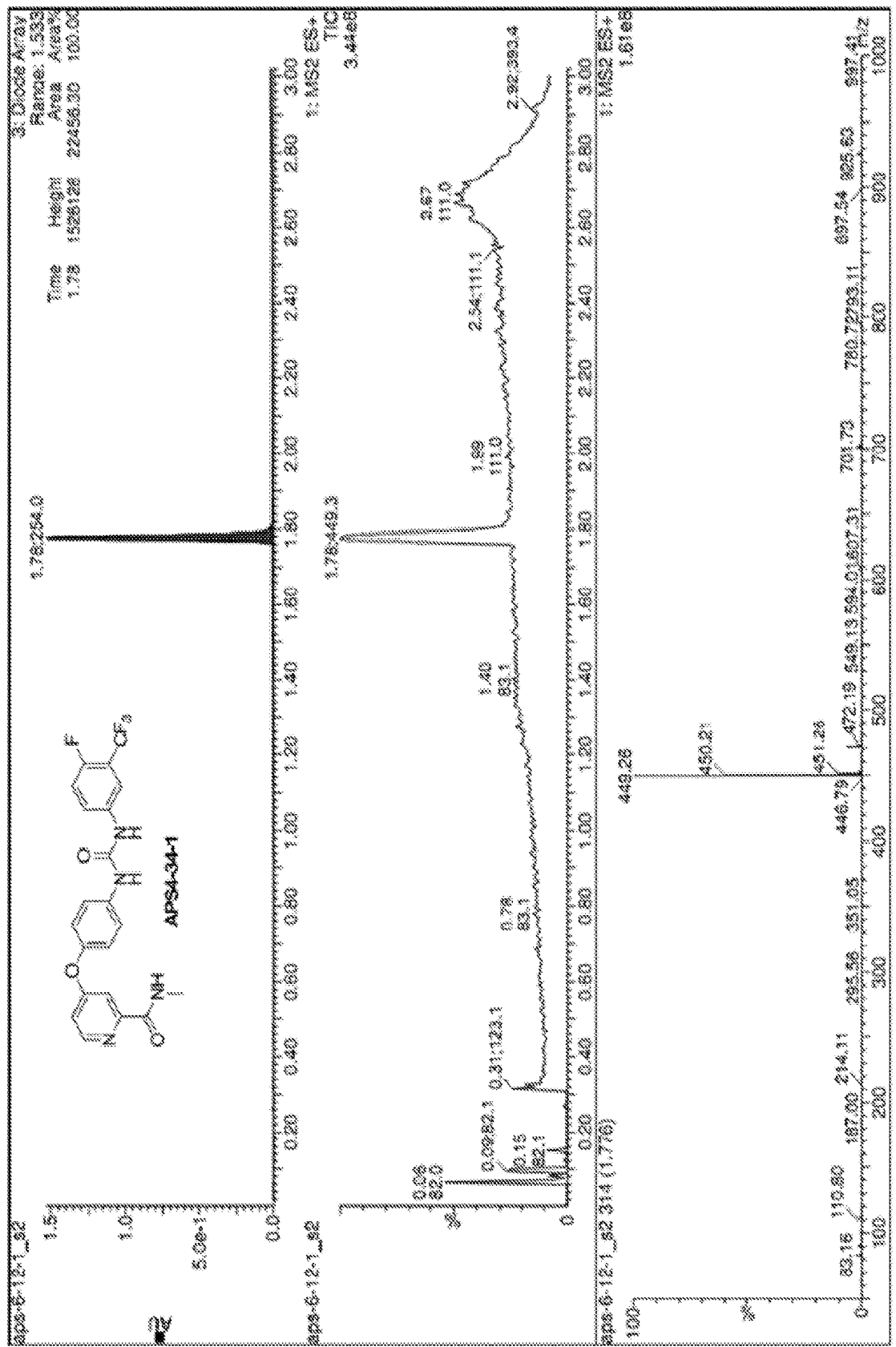
FIG. 17 shows LC-MS data for compound APS4-34-1.
Figure 18:
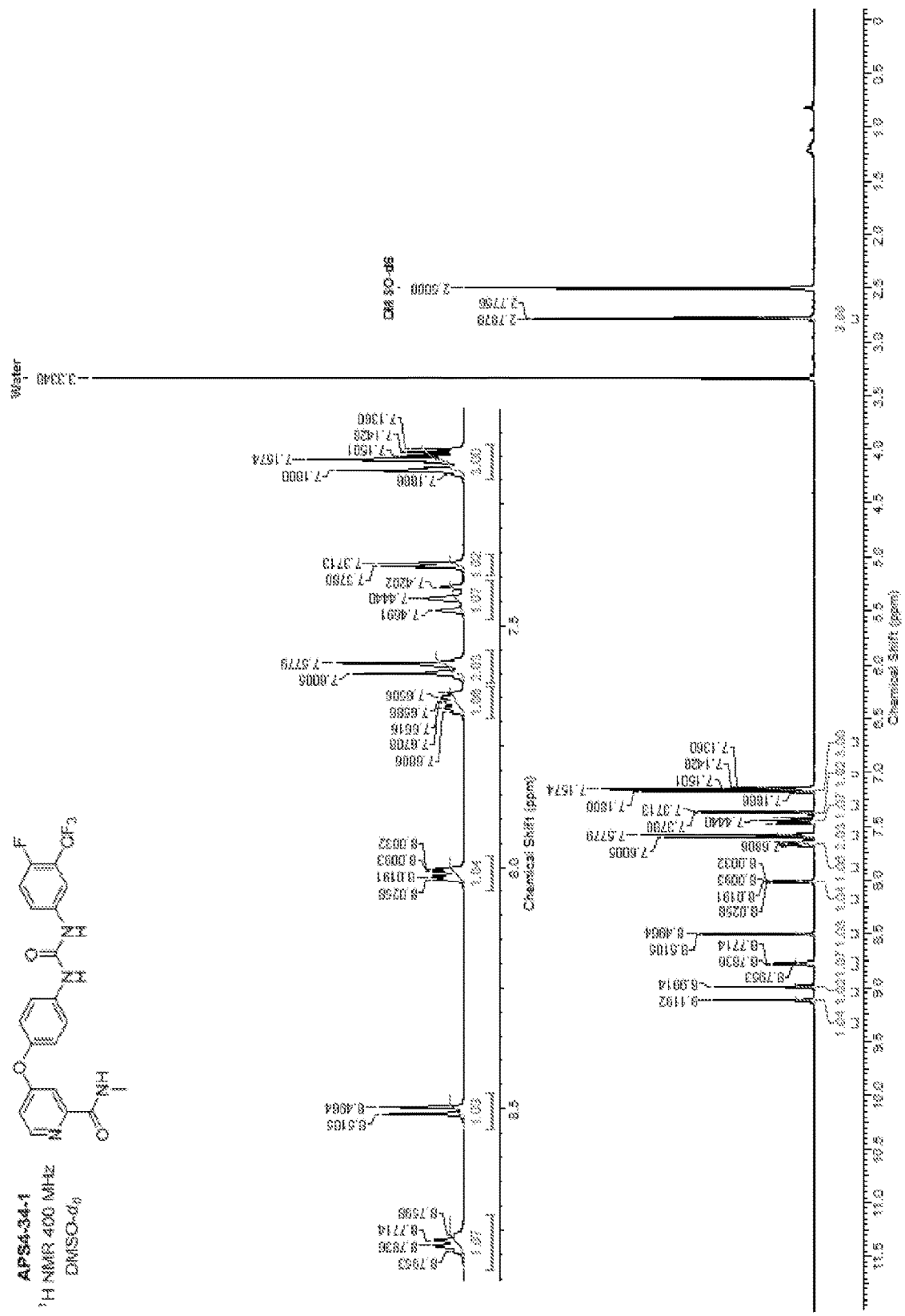
FIG. 18 shows $^1$H NMR spectra for compound APS4-34-1.

4-Fluoro-3-(trifluoromethyl)aniline (39.0 µL, 0.303 mmol) was added neat to CDI (51.6 mg, 0.318 mmol) and CH$_2$Cl$_2$ (1 mL) in a 4 mL vial. The reaction was allowed to warm to room temperature after 10 min and stirred for 16 hours, then HB/S1 (73.8 mg, 0.303 mmol) was added in one portion and stirring was continued for 12 hours. Purified by silica gel chromatography (12 g cartridge), eluting at 20 mL/min, and using a linear gradient of hexanes/EtOAc: 100:0→30:100 over 27 column volumes. Obtained 105 mg (77%) of the title compound as a white solid: $^1$H NMR (400 MHz, DMSO-d$_6$) δ 9.12 (s, 1H), 8.99 (s, 1H), 8.78 (br q, J=4.6 Hz, 1H), 8.50 (d, J=5.6 Hz, 1H), 8.01 (dd, J=6.5, 2.6 Hz, 1H), 7.66 (dt, J=8.3, 3.8 Hz, 1H), 7.59 (d, J=9.0 Hz, 2H), 7.44 (t, J=9.8 Hz, 1H), 7.37 (d, J=2.7 Hz, 1H), 7.12-7.20 (m, 3H), 2.78 (d, J=4.9 Hz, 3H); $^{19}$F NMR (376 MHz, DMSO-d$_6$) δ -59.8--59.7 (m, 3F), -124.5--124.2 (m, 1F); LC-MS (ESI+) m/z: [M+H]$^+$ Calcd for C$_{21}$H$_{17}$F$_4$N$_4$O$_3$, 449.1; Found 449.3 (FIGS. 17-18).

Example 37

Preparation of 4-(3-Fluoro-4-(3-(4-fluoro-3-(trifluoromethyl)phenyl) ureido)phenoxy)-N-methylpicolinamide (APS4-34-2)

APS4-34-2

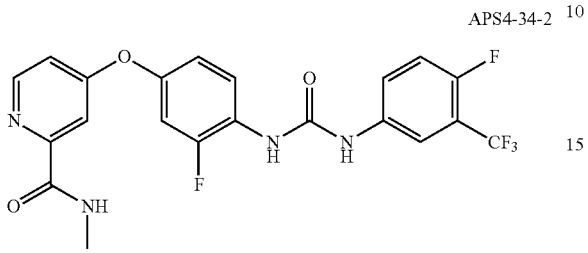

Figure 19:
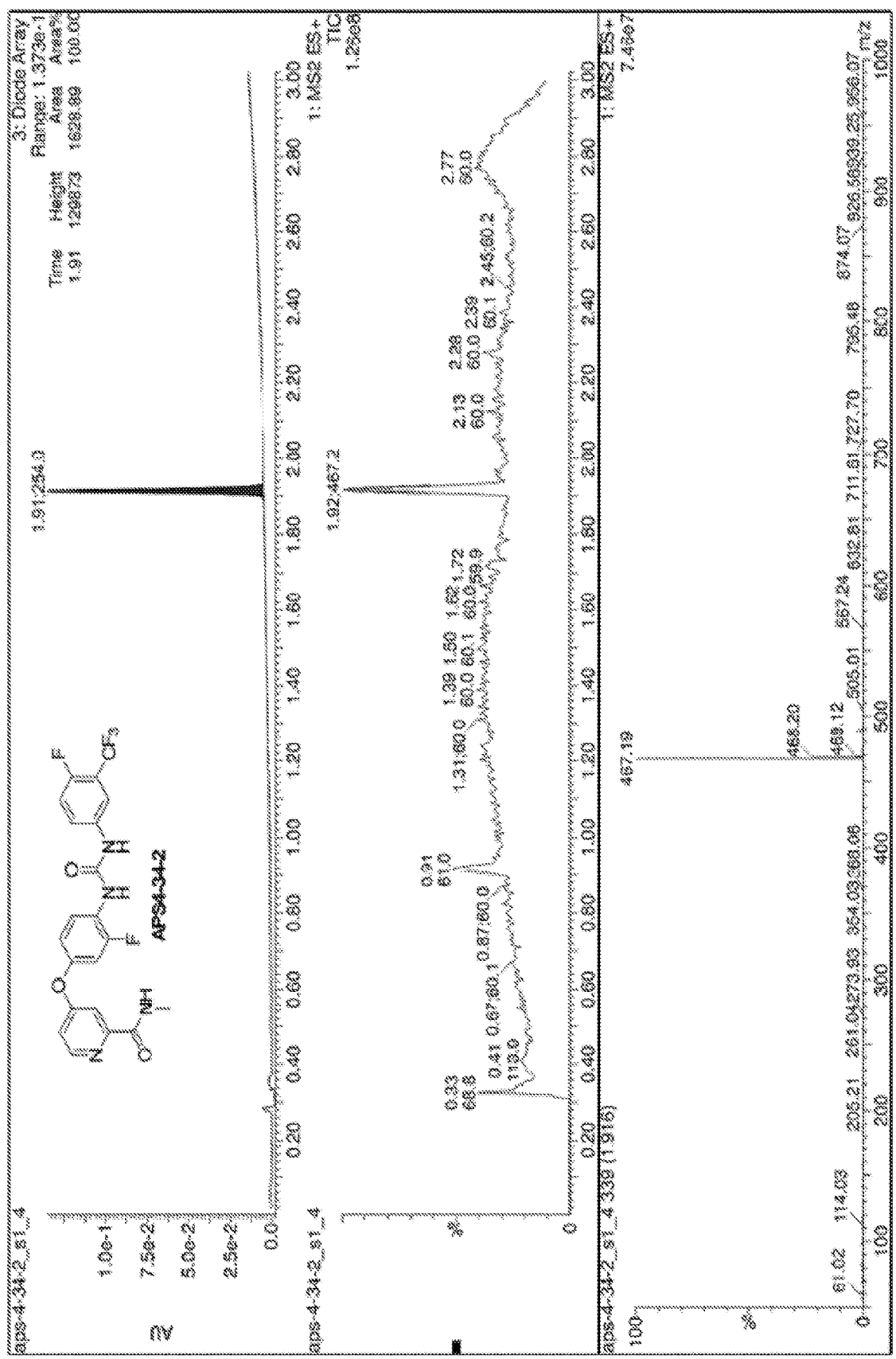
FIG. 19 shows LC-MS data for compound APS4-34-2.
Figure 20:
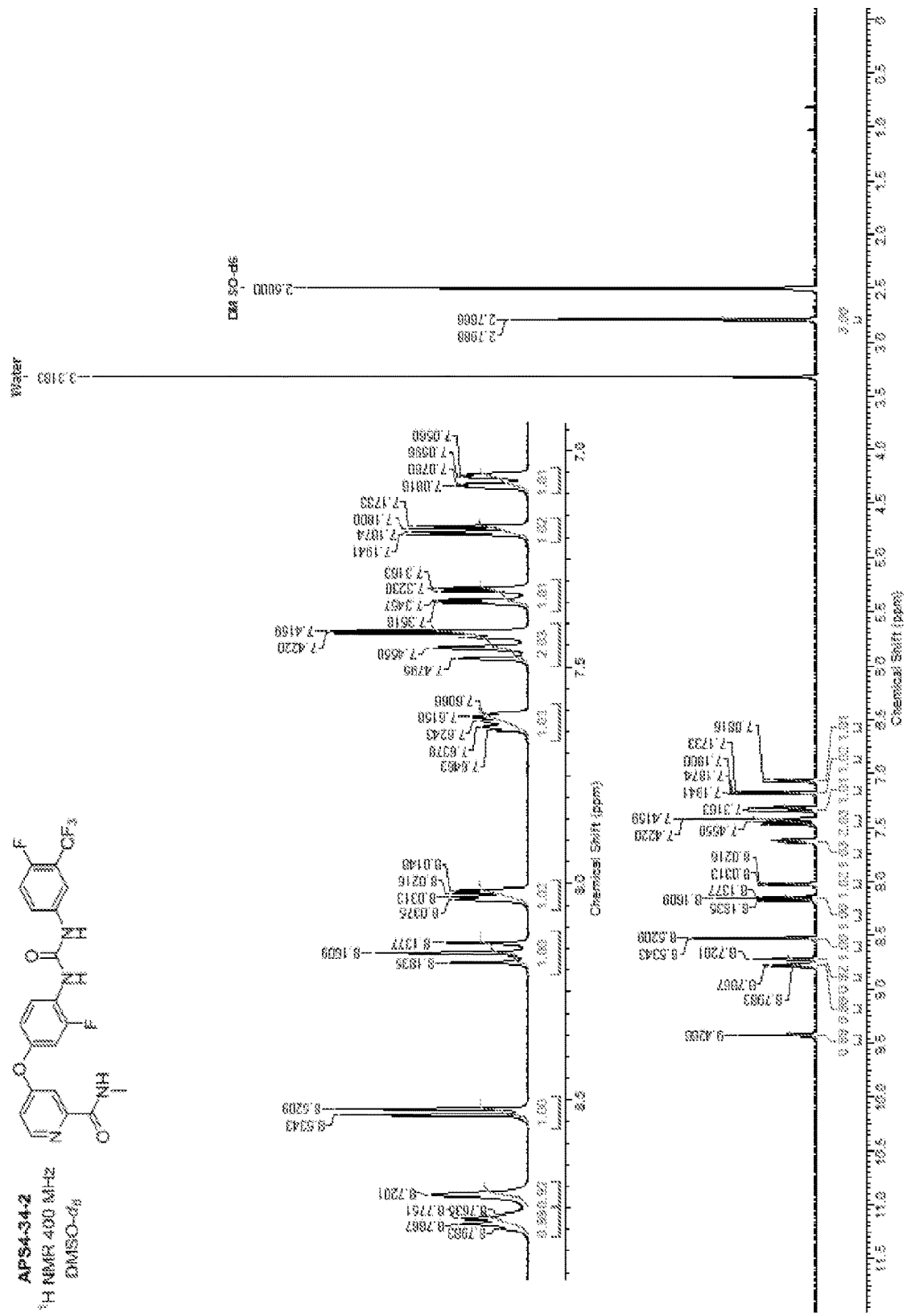
FIG. 20 shows $^1$H NMR spectra for compound APS4-34-2.

4-Fluoro-3-(trifluoromethyl)aniline (39.0 μL, 0.303 mmol) was added neat to CDI (51.6 mg, 0.318 mmol) and CH$_2$Cl$_2$ (1 mL) in an 4 mL vial. The reaction was allowed to warm to room temperature after 10 min and stirred for 16 hours, then HB/S2 (79.1 mg, 0.303 mmol) was added in one portion and stirring was continued for 12 hours. Purified by silica gel chromatography (12 g cartridge), eluting at 20 mL/min and using a linear gradient of hexanes/EtOAc: 100:0→0:100 over 27 column volumes. Obtained 84.6 mg (60%) of the title compound as a white solid: $^1$H NMR (400 MHz, DMSO-d$_6$) δ 9.43 (s, 1H), 8.78 (br q, J=4.6 Hz, 1H), 8.72 (s, 1H), 8.53 (d, J=5.4 Hz, 1H), 8.16 (t, J=9.2 Hz, 1H), 8.03 (dd, J=6.5, 2.6 Hz, 1H), 7.59-7.67 (m, 1H), 7.40-7.50 (m, 2H), 7.33 (dd, J=11.6, 2.6 Hz, 1H), 7.18 (dd, J=5.6, 2.7 Hz, 1H), 7.07 (dd, J=8.8, 1.5 Hz, 1H), 2.79 (d, J=4.9 Hz, 3H); $^{19}$F NMR (376 MHz, DMSO-d$_6$) δ -59.8--59.7 (m, 3F), -124.0--123.9 (m, 1F), -124.1 (s, 1F); LC-MS (ESI+) m/z: [M+H]$^+$ Calcd for C$_{21}$H$_{16}$F$_5$N$_4$O$_3$, 467.1; Found 467.2 (FIGS. 19-20).

Example 38

Preparation of 4-(4-(3-(2-Fluoro-5-methylphenyl) ureido)phenoxy)-N-methylpicolinamide (APS4-35-1)

APS4-35-1

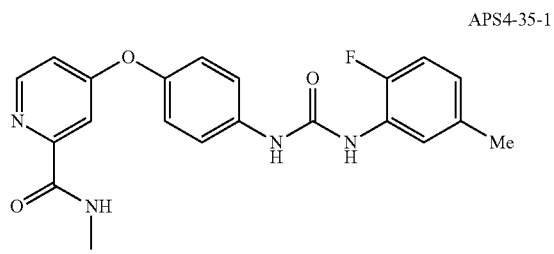 [SMILES: CNC(=O)c1cc(Oc2ccc(NC(=O)Nc3cc(C)ccc3F)cc2)ccn1]

2-Fluoro-5-methylaniline (34.0 μL, 0.301 mmol) was added neat to CDI (51.0 mg, 0.315 mmol) and CH$_2$Cl$_2$ (1.0 mL) in a 4 mL vial. The reaction was allowed to warm to room temperature after 10 min and stirred for 16 hours, then HB/S1 (73.0 mg, 0.300 mmol) was added in one portion and stirring was continued for 12 hours. Purified by silica gel chromatography (25 g cartridge), eluting at 20 mL/min and using a linear gradient of hexanes/EtOAc: 100:0→0:100 over 27 column volumes. Obtained 73.5 mg (62%) of the title compound as a white solid: $^1$H NMR (400 MHz, DMSO-d$_6$) δ 9.21 (s, 1H), 8.76 (br q, J=4.8 Hz, 1H), 8.45-8.56 (m, 2H), 7.98 (dd, J=7.8, 2.0 Hz, 1H), 7.58 (d, J=8.8 Hz, 2H), 7.38 (d, J=2.7 Hz, 1H), 7.07-7.20 (m, 4H), 6.78-6.84 (m, 1H), 2.79 (d, J=4.9 Hz, 3H), 2.27 (s, 3H); $^{19}$F NMR (376 MHz, DMSO-d$_6$) δ -134.2 (s, 1F); LC-MS (ESI+) m/z: [M+H]$^+$ Calcd for C$_{21}$H$_{20}$FN$_4$O$_3$, 395.2; Found 395.3.

Example 39

Preparation of 4-(3-Fluoro-4-(3-(2-fluoro-5-methylphenyl)ureido)phenoxy)-N-methylpicolinamide (APS4-35-2)

APS4-35-2

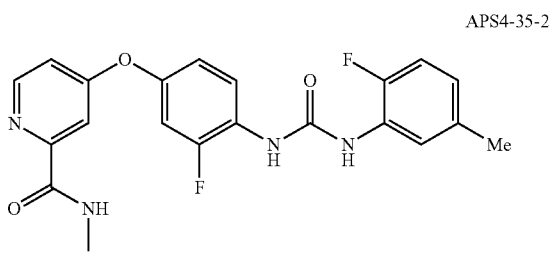 [SMILES: CNC(=O)c1cc(Oc2ccc(NC(=O)Nc3cc(C)ccc3F)c(F)c2)ccn1]

2-Fluoro-5-methylaniline (34.0 μL, 0.301 mmol) was added neat to CDI (51.0 mg, 0.315 mmol) and CH$_2$Cl$_2$ (1.0 mL) in a 4 mL vial. The reaction was allowed to warm to room temperature after 10 min and was stirred for 16 hours, then HB/S2 (78.4 mg, 0.300 mmol) as added in one portion and stirring was continued for 12 hours. Purified by silica gel chromatography (25 g cartridge), eluting at 20 mL/min and using a linear gradient of hexanes/EtOAc: 100:0→0:100 over 27 column volumes. Obtained 68.2 mg (55%) of the title compound as a white solid: $^1$H NMR (400 MHz, DMSO-d$_6$) δ 9.11 (s, 1H), 8.99 (s, 1H), 8.78 (d, J=4.9 Hz, 1H), 8.52 (d, J=5.6 Hz, 1H), 8.27 (t, J=9.0 Hz, 1H), 8.01 (d, J=6.4 Hz, 1H), 7.42 (d, J=2.4 Hz, 1H), 7.33 (dd, J=11.7, 2.4 Hz, 1H), 7.18 (dd, J=5.6, 2.4 Hz, 1H), 7.12 (dd, J=11.4, 8.4 Hz, 1H), 7.06 (dd, J=8.8, 1.5 Hz, 1H), 6.82 (ddd, J=5.4, 2.8, 2.8 Hz, 1H), 2.79 (d, J=4.6 Hz, 3H), 2.27 (s, 3H); $^{19}$F NMR (376 MHz, DMSO-d$_6$) δ -124.9 (s, 1F), -134.0 (s, 1F); LC-MS (ESI+) m/z: [M+H]$^+$ Calcd for C$_{21}$H$_{19}$F$_2$N$_4$O$_3$, 413.1; Found 413.3.

Example 40

Preparation of 4-(4-(3-(5-(Difluoromethyl)-2-fluorophenyl)ureido)phenoxy)-N-methylpicolinamide (APS4-54)

APS4-54

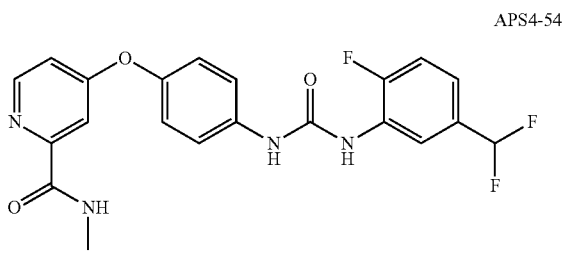 [SMILES: CNC(=O)c1cc(Oc2ccc(NC(=O)Nc3cc(C(F)F)ccc3F)cc2)ccn1]

Figure 21:
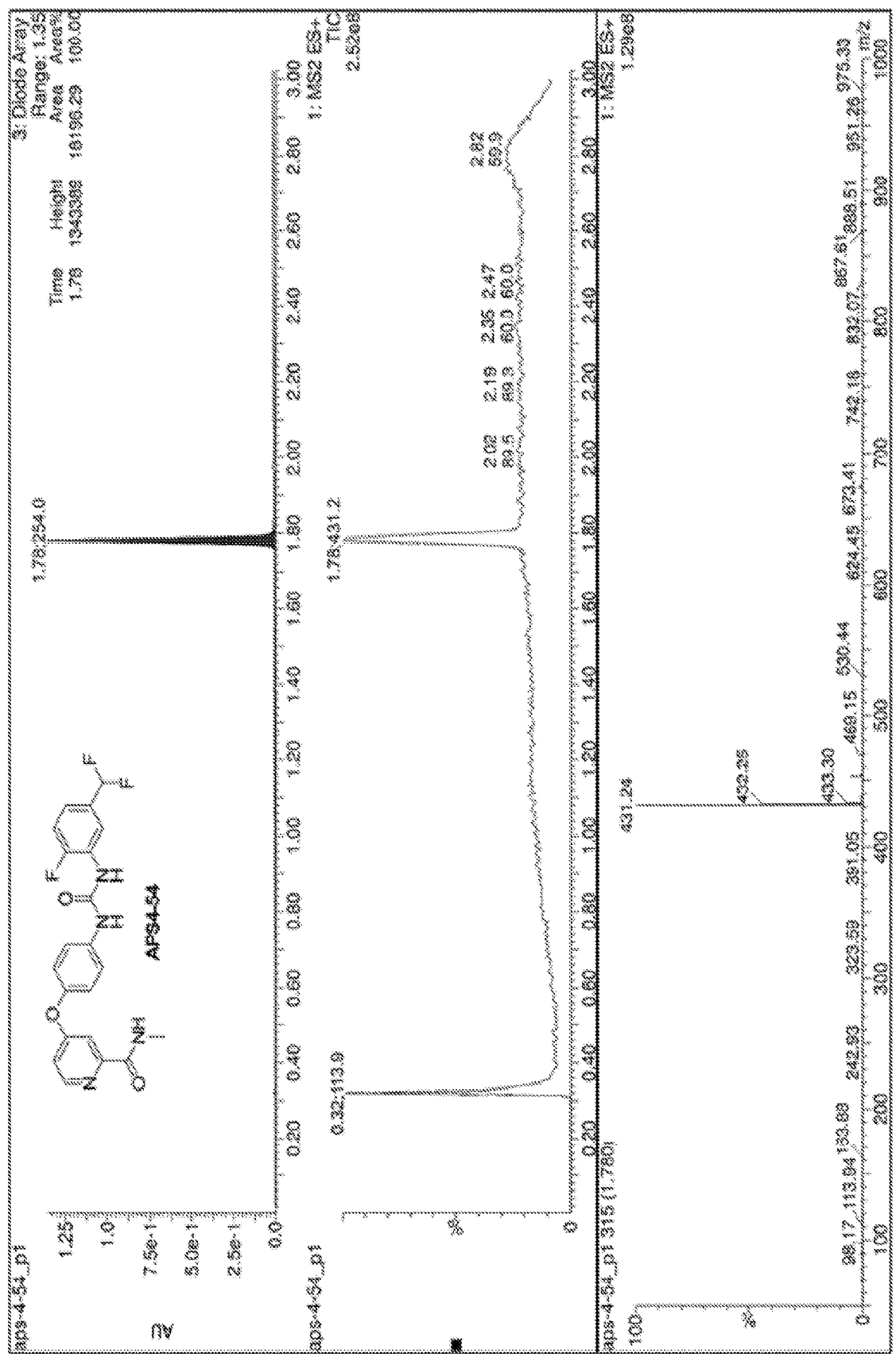
FIG. 21 shows LC-MS data for compound APS4-54.
Figure 22:
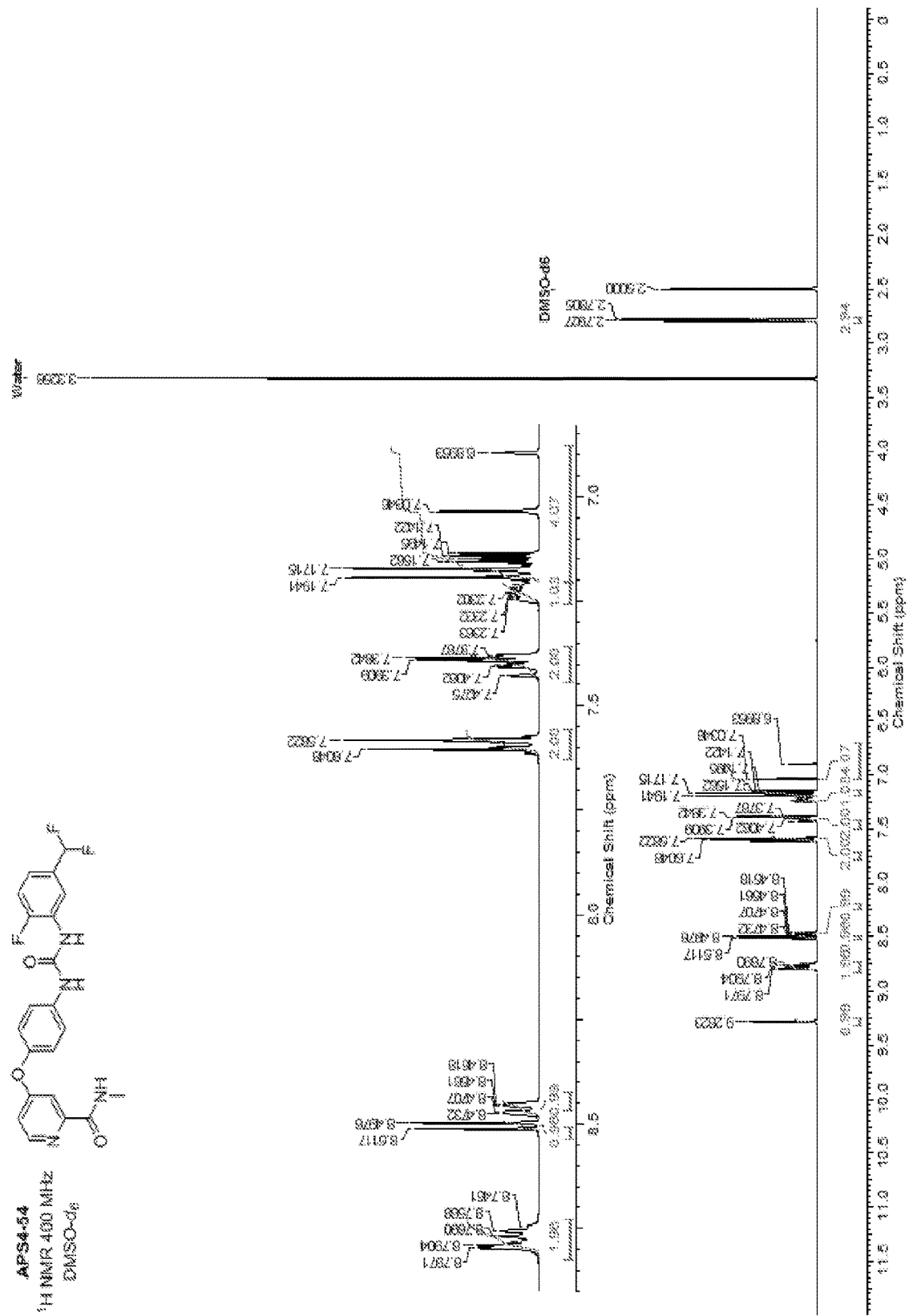
FIG. 22 shows $^1$H NMR spectra for compound APS4-54.

A solution of 5-(difluoromethyl)-2-fluoroaniline (APS4-53; 100 mg, 0.621 mmol) and CH$_2$Cl$_2$ (1 mL) was added to a 0° C. solution of CDI (106 mg, 0.654 mmol) and CH$_2$Cl$_2$ (1 mL) in an 8 mL vial. After 10 min, the reaction was allowed to warm to room temperature and was stirred for 22 hours, then HB/S1 (151 mg, 0.621 mmol) was added and stirring was continued for 14 hours. The product precipitated and was isolated by vacuum filtration. Obtained 199 mg (75%) of the title compound as a white solid: $^1$H NMR (400 MHz, DMSO-d$_6$) δ 9.28 (s, 1H), 8.73-8.82 (m, 2H), 8.50 (d, J=5.6 Hz, 1H), 8.46 (dd, J=7.2, 1.3 Hz, 1H), 7.59 (d, J=9.0 Hz, 2H), 7.36-7.45 (m, 2H), 7.20-7.26 (m, 1H), 7.18 (d, J=9.0 Hz, 2H), 7.15 (dd, J=5.6, 2.7 Hz, 1H), 7.03 (t, J$_{HF}$=55.7 Hz, 1H), 2.79 (d, J=4.9 Hz, 3H); $^{19}$F NMR (376 MHz, DMSO-d$_6$) δ −108.2 (s, 2F), −126.1 (s, 1F); LC-MS (ESI+) m/z: [M+H]$^+$ Calcd for C$_{21}$H$_{18}$F$_3$N$_4$O$_3$, 431.1; Found 431.2 (FIGS. 21-22).

Example 41

Preparation of 4-Fluoro-3-nitrobenzaldehyde (APS4-48)

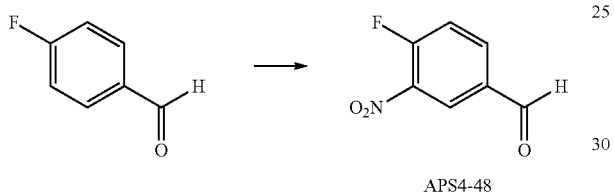

APS4-48

A 50 mL flask was charged with 4-fluorobenzaldehyde (2.20 mL, 20.5 mmol) and concentrated sulfuric acid (10 mL). The solution was cooled to 0° C. and fuming nitric acid (1.10 mL, 90% w/w in water, 23.3 mmol) was added dropwise over 5 min by pipet. The reaction was stirred for 2.5 hours and allowed to warm as the ice-bath melted. The reaction was poured into rapidly stirred ice-water (150 mL), and was stirred for an additional 15 min. The resulting precipitate was collected by vacuum filtration, and the collected solid was washed with water (2×10 mL). Air-drying provided 1.84 g (53%) of the title compound as a white solid: $^1$H NMR (400 MHz, DMSO-d$_6$) δ 10.07 (s, 1H), 8.68 (dd, J=7.5, 2.1 Hz, 1H), 8.33 (ddd, J=8.6, 4.3, 2.2 Hz, 1H), 7.82 (dd, J=11.0, 8.6 Hz, 1H); $^{19}$F NMR (376 MHz, DMSO-d$_6$) δ −109.6 (s, 1F); LC-MS (ESI+) m/z: [M+H]$^+$ Calcd for C$_7$H$_5$FNO$_3$, 170.0; Found 170.1.

Example 42

Preparation of 4-(Difluoromethyl)-1-fluoro-2-nitrobenzene (APS4-50)

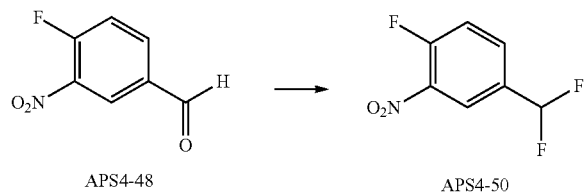 [SMILES: O=Cc1ccc(F)c([N+](=O)[O-])c1 ; O=[N+]([O-])c1cc(C(F)F)ccc1F]

APS4-48     APS4-50

A flame-dried 50 mL flask cooled under Ar was charged with 4-fluoro-3-nitrobenzaldehyde (APS4-48; 715 mg, 4.23 mmol) and CH$_2$Cl$_2$ (12 mL). The solution was cooled to −78° C. and (diethylamino)sulfur trifluoride (DAST; 1.12 mL, 8.48 mmol) was added dropwise over 3 min via syringe. The resulting bright-yellow heterogeneous reaction was allowed to stir at −78° C. for 3 hours; over this time the reaction became homogeneous and light-red in color. The cooling bath was removed and the solution was allowed to warm to room temperature. The reaction was stirred at room temperature for 16 hours and then was quenched with water (10 mL). The pH of the aqueous layer was adjusted to ~7 with saturated NaHCO$_3$ solution and the mixture was extracted with CH$_2$Cl$_2$ (2×50 mL). The organic extracts were pooled, dried (Na$_2$SO$_4$) and filtered. Concentration under vacuum gave 790 mg of an orange oil, which was purified by silica gel chromatography (25 g cartridge), eluting at 20 mL/min and using a linear gradient of hexanes/EtOAc: 100:0→0:100 over 18 column volumes. Obtained 608 mg (75%) of the title compound as a yellow oil: $^1$H NMR (400 MHz, DMSO-d$_6$) δ 8.37-8.41 (m, 1H), 8.03-8.08 (m, 1H), 7.73-7.80 (m, 1H), 7.17 (t, J$_{HF}$=55.3 Hz, 1H); $^{19}$F NMR (376 MHz, DMSO-d$_6$) δ −109.8 (s, 2F), −114.8 (s, 1F).

Example 43

Preparation of 5-(Difluoromethyl)-2-fluoroaniline (APS4-53)

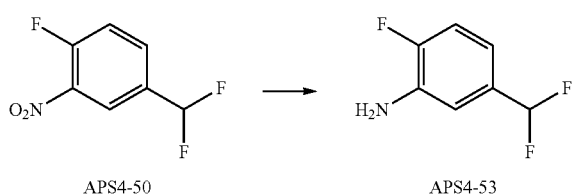 [SMILES: O=[N+]([O-])c1cc(C(F)F)ccc1F ; Nc1cc(C(F)F)ccc1F]

APS4-50     APS4-53

A 50 mL flask was charged sequentially with 4-(difluoromethyl)-1-fluoro-2-nitrobenzene (597 mg, 3.12 mmol), MeOH (15 mL), and iron powder (871 mg, 15.6 mmol). The mixture was stirred at room temperature and an aqueous solution of HCl (8.0 mL, 4.0 M solution in water, 32 mmol) was added dropwise over 1-2 min. After 1 hour the reaction was decanted from the unreacted iron, and the remaining solution was diluted with CH$_2$Cl$_2$ (50 mL) and water (50 mL). The pH of the aqueous phase was adjusted to ~7 with 6 N NaOH (~5.3 mL), then the mixture was transferred to a separatory funnel, the layers were separated, and the aqueous phase was extracted with CH$_2$Cl$_2$ (2×30 mL). The organic extracts were pooled, dried (Na$_2$SO$_4$), and filtered. Concentration under vacuum gave a yellow oil, which was purified by silica gel chromatography (25 g cartridge), eluting at 20 mL/min and using a linear gradient of hexanes/EtOAc: 100:0→0:100 over 20 column volumes. Obtained 257 mg (51%) of the title compound as a clear colorless oil: $^1$H NMR (400 MHz, DMSO-d$_6$) δ 7.04-7.13 (m, 1H), 6.91-6.97 (m, 1H), 6.86 (t, J$_{HF}$=56.1 Hz, 1H), 6.66-6.72 (m, 1H), 5.42 (br s, 2H); 19F NMR (376 MHz, DMSO-d$_6$) δ −108.0 (s, 2F), −131.5 (s, 1F); LC-MS (ESI+) m/z: [M+H]$^+$ Calcd for C$_7$H$_7$F$_3$N, 162.1 Found 162.1.

Example 44

Preparation of N-Methyl-4-(4-(3-(3-(perfluoroethyl)phenyl)ureido) phenoxy)picolinamide (APS5-16-1)

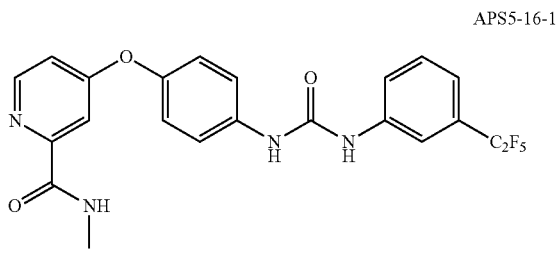

APS5-16-1

Figure 23:
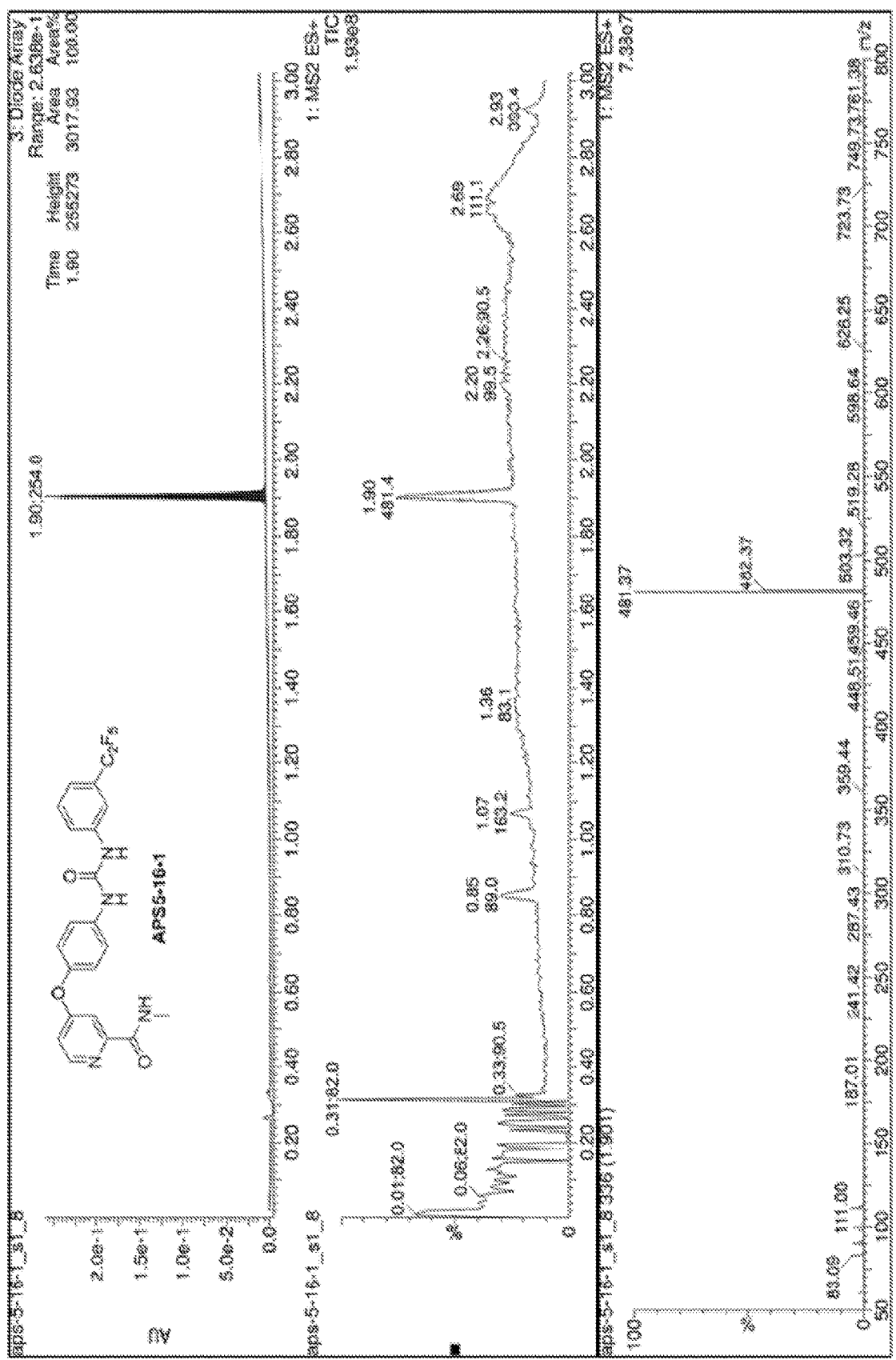
FIG. 23 shows LC-MS data for compound APS5-16-1.
Figure 24:
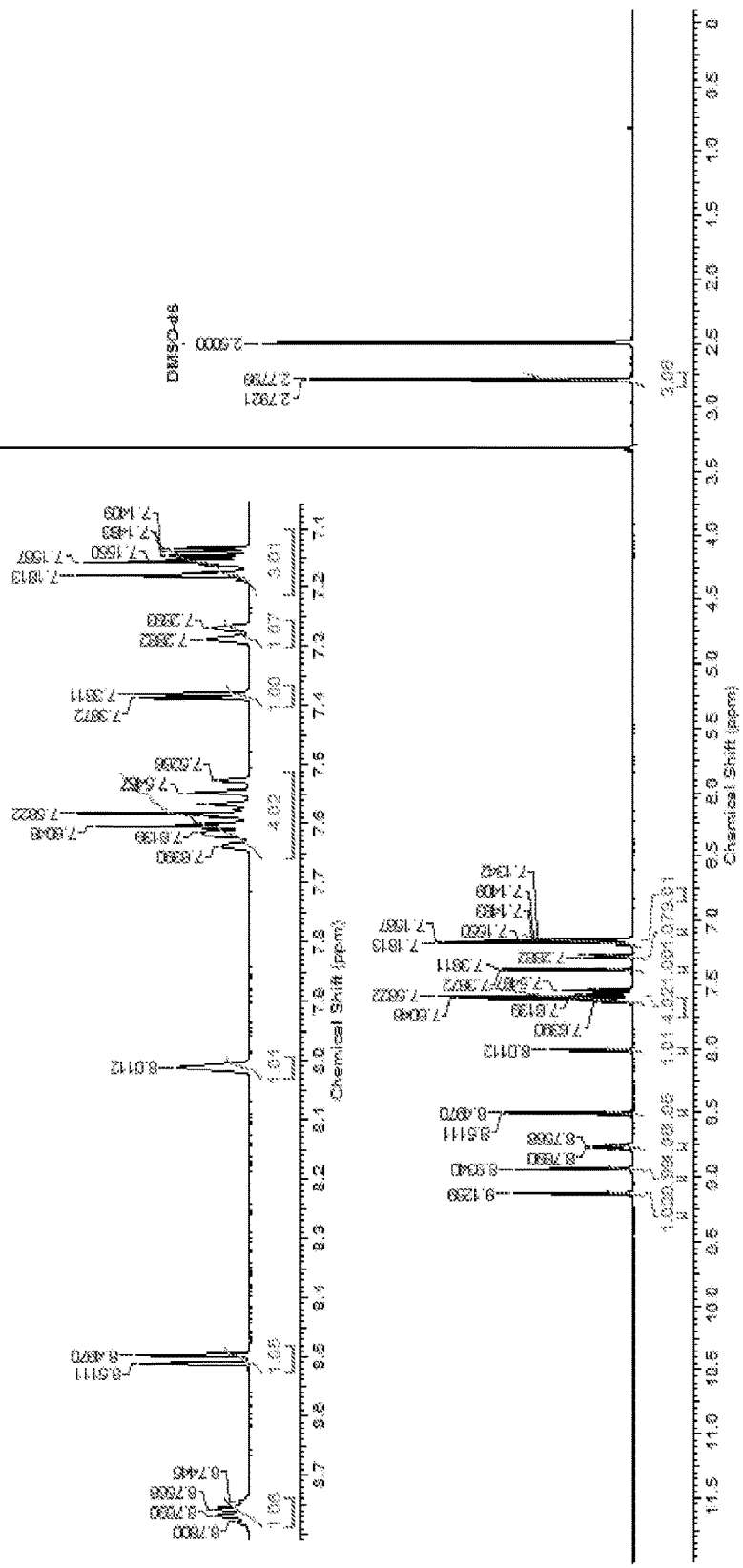
FIG. 24 shows $^1$H NMR spectra for compound APS5-16-1.

A solution of 3-(perfluoroethyl)aniline (APS5-9; 158 mg, 0.748 mmol) and CH$_2$Cl$_2$ (2 mL) was added to a 0° C. solution of CDI (122 mg, 0.752 mmol) and CH$_2$Cl$_2$ (1.5 mL) in an 8 mL vial. The reaction was allowed to warm to room temperature over 2 hours and was stirred for 20 hours, then HB/S1 (173 mg, 0.711 mmol) was added in one portion and stirring was continued for 8 hours. Purified by silica gel chromatography (25 g cartridge), eluting at 20 mL/min and using a linear gradient of CH$_2$Cl$_2$/EtOAc: 100:0→0:100 over 24 column volumes. Obtained 203 mg (59%) of the title compound as a white solid: $^1$H NMR (400 MHz, DMSO-d$_6$) δ 9.13 (s, 1H), 8.93 (s, 1H), 8.76 (br q, J=4.7 Hz, 1H), 8.50 (d, J=5.6 Hz, 1H), 8.01 (s, 1H), 7.61-7.65 (m, 1H), 7.59 (d, J=9.0 Hz, 2H), 7.52-7.57 (m, 1H), 7.38 (d, J=2.4 Hz, 1H), 7.28 (d, J=7.8 Hz, 1H), 7.13-7.20 (m, 3H), 2.79 (d, J=4.9 Hz, 3H); $^{19}$F NMR (376 MHz, DMSO-d$_6$) δ −83.6−−83.5 (m, 3F), −113.2−113.1 (m, 2F); LC-MS (ESI+) m/z: [M+H]$^+$ Calcd for C$_{22}$H$_{18}$F$_5$N$_4$O$_3$, 481.1; Found 481.4 (FIGS. 23-24).

Example 45

Preparation of 1-Nitro-3-(perfluoroethyl)benzene (APS5-4)

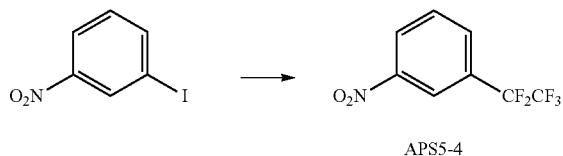

APS5-4

The synthesis was carried out following a known procedure (Serizawa et al., "Direct Synthesis of Pentafluoroethyl Copper From Pentafluoropropionate as an Economical C$_2$F$_5$ Source: Application to Pentafluoroethylation of Arylboronic Acids and Aryl Bromides," Org. Lett. 16:3456-3459 (2014), which is hereby incorporated by reference in its entirety). A 25 mL Schlenk flask (equipped with a 10 mL solid addition funnel) was flame-dried under vacuum and cooled under Ar. The flask was charged with copper(I) chloride (424 mg, 4.28 mmol; transferred in an Ar-purged glove bag) and DMF (15 mL). Sodium tert-butoxide (824 mg, 8.57 mmol; transferred in an Ar-purged glove bag) was added via the addition funnel in portions over 10 min. After replacing the addition funnel with a septum, the mixture was stirred at room temperature for 2 hours, and then was heated at 50° C. while ethyl 2,2,3,3,3-pentafluoropropanoate (635 μL, 4.29 mmol) was added dropwise by syringe over 2 min. The reaction was stirred at 50° C. for 3 hours and then cooled to 0° C. Triethylamine trihydrofluoride (265 μL, 1.63 mmol) was added dropwise over 1-2 min by syringe, which resulted in a nearly homogeneous solution. Stirring was continued at 0° C. for 5 min, and then at room temperature for 20 min. Solid 1-iodo-3-nitrobenzene (508 mg, 2.04 mmol) was added in one-portion and the reaction was heated at 80° C. for 12 hours, under a balloon of Ar. After the reaction had cooled to room temperature, 1 M HCl (~10 mL) was added in portions over 1-2 min by pipet. The mixture was diluted with water (50 mL) and Et$_2$O (50 mL), and then was filtered through a pad (3×3 cm) of Celite under vacuum. The filter-cake was washed with Et$_2$O (10 mL) and the combined filtrates were transferred to a separatory funnel. The layers were separated and the aqueous phase was extracted with Et$_2$O (2×30 mL). The organic extracts were pooled, washed with a 60:40 mixture of saturated NH$_4$Cl solution/concentrated NH$_4$OH solution (2×50 mL), half saturated NaCl solution (2×50 mL) and brine (50 mL), dried (MgSO$_4$), and filtered. Concentration under vacuum gave ~500 mg of an orange oil, which was used without further purification (see synthesis of APS5-9).

Example 46

Preparation of 3-(Perfluoroethyl)aniline (APS5-9)

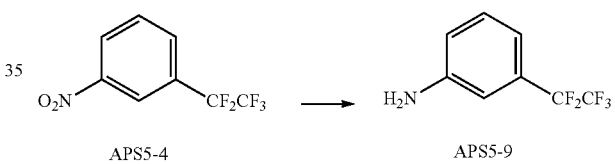

APS5-4     APS5-9

To a 100 mL flask containing the crude 1-nitro-3-(perfluoroethyl)benzene (APS5-4, ~2.04 mmol; from the reaction described above) was added MeOH (30 mL) and iron powder (570 mg, 10.2 mmol). The mixture was cooled to 0° C., and concentrated HCl (2.0 mL, 24 mmol) was added dropwise by pipet over 1-2 min. The reaction was allowed to warm to room temperature over 3 hours, and was stirred for an additional 3 hours. The reaction was decanted from the unreacted iron, diluted with water (50 mL) and CH$_2$Cl$_2$ (50 mL), and then the pH of the aqueous phase was adjusted to ~7 with 1 M KOH (24-25 mL). The mixture was vacuum-filtered through a pad of Celite/sand (50:50), and the filter-cake was washed with CH$_2$Cl$_2$ (30 mL). The combined filtrates were transferred to a separatory funnel, the layers were separated, and the aqueous phase was extracted with CH$_2$Cl$_2$ (2×25 mL). The organic extracts were pooled, dried (Na$_2$SO$_4$), and filtered. The filtrate was concentrated under vacuum to leave 492 mg of an orange liquid, which was purified by silica gel chromatography (25 g cartridge) eluting at 20 mL/min and using a linear gradient of hexanes/CH$_2$Cl$_2$: 100:0→0:100 over 22 column volumes. Obtained 316 mg (73%) of the title compound as a pale-yellow liquid: $^1$H NMR (400 MHz, DMSO-d$_6$) δ 7.22 (t, J=8.2 Hz, 1H), 6.78-6.84 (m, 2H), 6.72 (d, J=7.8 Hz, 1H), 5.57 (br s, 2H); $^{19}$F NMR (376 MHz, DMSO-d$_6$) δ −83.6−−83.5 (m, 3F), −113.3−−113.2 (m, 2F); LC-MS (ESI+) m/z: [M+H]$^+$ Calcd for C$_8$H$_7$F$_5$N, 212.1; Found 212.1.

Example 47

Preparation of 4-(4-(3-(2-Fluoro-5-(perfluoroethyl)phenyl)ureido)phenoxy)-N-methylpicolinamide (APS5-16-2)

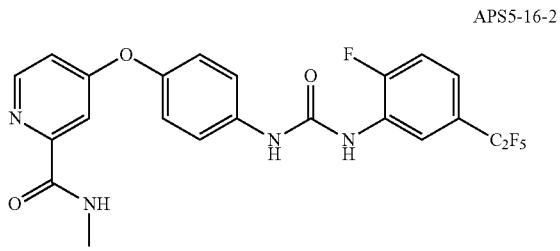

APS5-16-2

Figure 25:
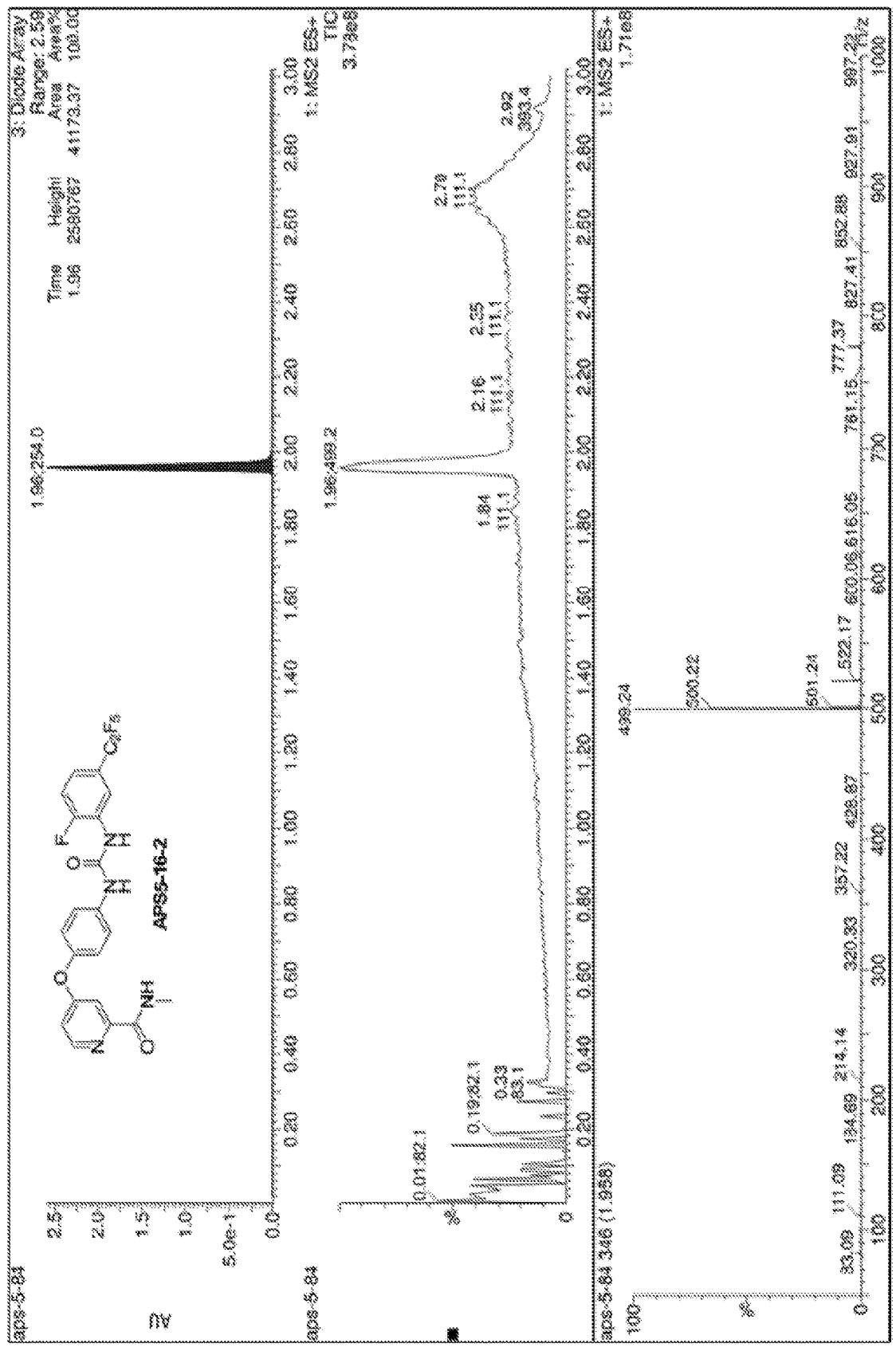
FIG. 25 shows LC-MS data for compound APS5-16-2.
Figure 26:
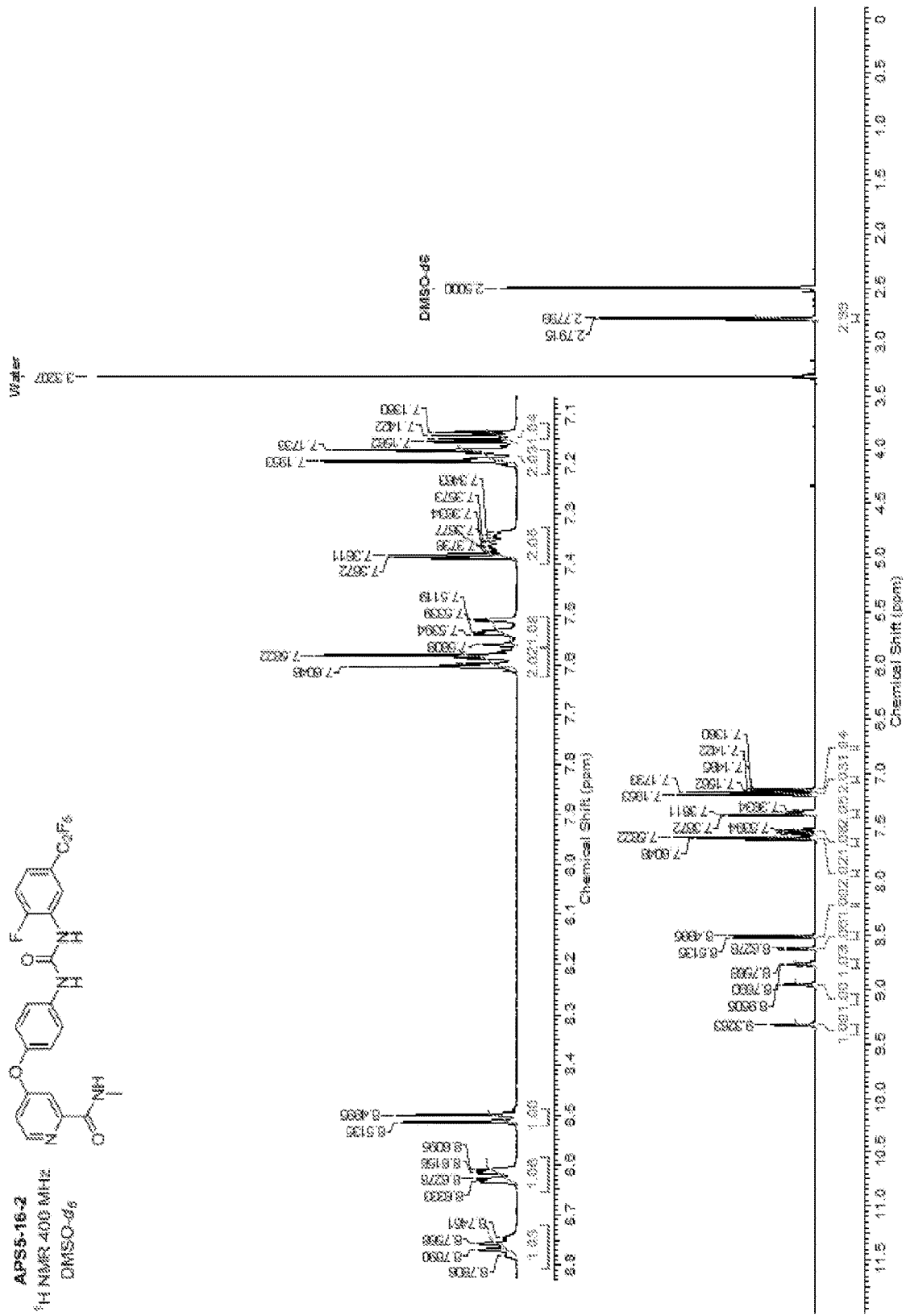
FIG. 26 shows $^1$H NMR spectra for compound APS5-16-2.

A solution of 2-fluoro-5-(perfluoroethyl)aniline (APS5-11; 213 mg, 0.930 mmol) and $CH_2Cl_2$ (1 mL) was added to a 0° C. solution of CDI (151 mg, 0.931 mmol) and $CH_2Cl_2$ (2 mL) in an 8 mL vial. After 10 min the reaction was allowed to warm to room temperature and was stirred for 20 hours, then HB/S1 (215 mg, 0.884 mmol) was added and stirring was continued for 8 hours. Purified by silica gel chromatography (25 g cartridge), eluting at 20 mL/min and using a linear gradient of $CH_2Cl_2$/EtOAc: 100:0→0:100 over 33 column volumes. Obtained 242 mg (55%) of the title compound as a white solid: $^1$H NMR (400 MHz, DMSO-$d_6$) δ 9.33 (s, 1H), 8.95 (br s, 1H), 8.76 (br q, J=4.6 Hz, 1H), 8.62 (dd, J=7.2, 2.3 Hz, 1H), 8.51 (d, J=5.6 Hz, 1H), 7.59 (d, J=9.0 Hz, 2H), 7.54 (dd, J=10.9, 8.7 Hz, 1H), 7.38 (d, J=2.4 Hz, 1H), 7.35 (ddd, J=8.6, 4.3, 2.6 Hz, 1H), 7.18 (d, J=8.8 Hz, 2H), 7.15 (dd, J=5.5, 2.6 Hz, 1H), 2.79 (d, J=4.6 Hz, 3H); $^{19}$F NMR (376 MHz, DMSO-$d_6$) δ −83.6--−83.5 (m, 3F), −112.6--−112.5 (m, 2F), −123.4 (s, 1F); LC-MS (ESI+) m/z: [M+H]$^+$ Calcd for $C_{22}H_{17}F_6N_4O_3$, 499.1; Found 499.2 (FIGS. 25-26).

Example 48

Preparation of 1-Fluoro-2-nitro-4-(perfluoroethyl)benzene (APS5-7)

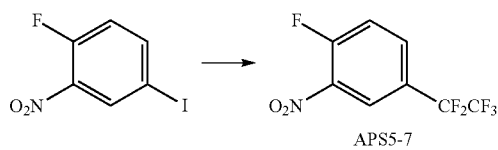

APS5-7

The synthesis was carried out following a known procedure (Serizawa et al., "Direct Synthesis of Pentafluoroethyl Copper from Pentafluoropropionate as an Economical $C_2F_5$ Source: Application to Pentafluoroethylation of Arylboronic Acids and Aryl Bromides," *Org. Lett.* 16:3456-3459 (2014), which is hereby incorporated by reference in its entirety). A 25 mL Schlenk flask (equipped with a 10 mL solid addition funnel) was flame-dried under vacuum and cooled under Ar. The flask was charged with copper(I) chloride (516 mg, 5.21 mmol; transferred in an Ar-purged glove bag) and DMF (18 mL). Sodium tert-butoxide (1.01 g, 10.4 mmol; transferred in a glove bag) was added via the addition funnel in portions over 10 min. After replacing the addition funnel with a septum, the mixture was stirred at room temperature for 2.5 hours, and then was heated at 50° C. while ethyl 2,2,3,3,3-pentafluoropropanoate (770 µL, 5.21 mmol) was added dropwise by syringe over 2-3 min. The reaction was stirred at 50° C. for 3 hours and then was cooled to 0° C. Triethylamine trihydrofluoride (325 µL, 1.99 mmol) was added dropwise over 1-2 min by syringe, which resulted in a nearly homogeneous solution. Stirring was continued at 0° C. for 5 min, and then at room temperature for 15 min. Solid 1-fluoro-4-iodo-2-nitrobenzene (662 mg, 2.48 mmol) was added in one-portion and the reaction was heated at 80° C. for 12 hours, under a balloon of Ar. After the reaction had cooled to room temperature, 1 M HCl (~15 mL) was added in portions over 1-2 min by pipet. The mixture was diluted with water (50 mL) and $Et_2O$ (50 mL), and then was filtered through a pad (3×3 cm) of Celite under vacuum. The filter-cake was washed with $Et_2O$ (20 mL) and the combined filtrates were transferred to a separatory funnel. The layers were separated and the aqueous phase was extracted with $Et_2O$ (2×30 mL). The organic extracts were pooled, washed with a 60:40 mixture of saturated $NH_4Cl$ solution/concentrated $NH_4OH$ solution (3×50 mL), half saturated NaCl solution (2×50 mL) and brine (50 mL), dried ($MgSO_4$), and filtered. Concentration under vacuum gave ~670 mg of an orange oil, which was used without further purification (see synthesis of APS5-11).

Example 49

Preparation of 2-Fluoro-5-(perfluoroethyl)aniline (APS5-11)

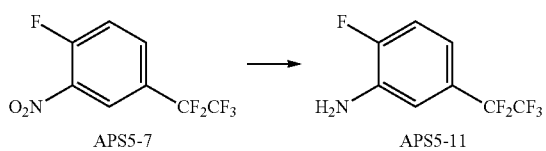

APS5-7　　　　　　　APS5-11

To a 100 mL flask, containing the crude 1-fluoro-2-nitro-4-(perfluoroethyl)benzene (APS5-7, ~2.48 mmol; from the reaction described above), was added MeOH (40 mL) and iron powder (693 mg, 12.4 mmol). The mixture was cooled to 0° C., and concentrated HCl (2.1 mL, 26 mmol) was added dropwise by pipet over 1-2 min. The reaction was allowed to warm to room temperature over 3 hours, and was stirred for an additional 3 hours. The reaction was decanted from the unreacted iron, diluted with water (75 mL) and $CH_2Cl_2$ (75 mL), and the pH of the aqueous phase was adjusted to ~7 with 6 M NaOH (~4.3 mL). The resulting mixture was vacuum-filtered through a pad of Celite/sand (50:50), and the filter-cake was washed with $CH_2Cl_2$ (30 mL). The combined filtrates were transferred to a separatory funnel, the layers were separated, and the aqueous phase was extracted with $CH_2Cl_2$ (2×30 mL). The organic extracts were pooled, dried ($Na_2SO_4$), and filtered. The filtrate was concentrated under vacuum to leave 840 mg of an orange-brown oil, which was purified by silica gel chromatography (25 g cartridge), eluting at 20 mL/min and using a linear gradient of hexanes/EtOAc: 100:0→75:25 over 24 column volumes. Obtained 426 mg (75%) of the title compound as an orange liquid: $^1$H NMR (400 MHz, DMSO-$d_6$) δ 7.21 (dd, J=1.2, 8.6 Hz, 1H), 7.05 (dd, J=8.2, 2.3 Hz, 1H), 6.74-6.81 (m, 1H), 5.65 (br s, 2H); $^{19}$F NMR (376 MHz, DMSO-$d_6$) δ −83.7--−83.7 (m, 3F), −112.6--−112.5 (m, 2F), −129.2 (s, 1F); LC-MS (ESI+) m/z: [M+H]$^+$ Calcd for $C_8H_6F_6N$, 230.0; Found 230.2.

Example 50

Preparation of 4-(4-(3-(5-Chloro-2-fluorophenyl)ureido)phenoxy)-N-methylpicolinamide (APS5-17-1)

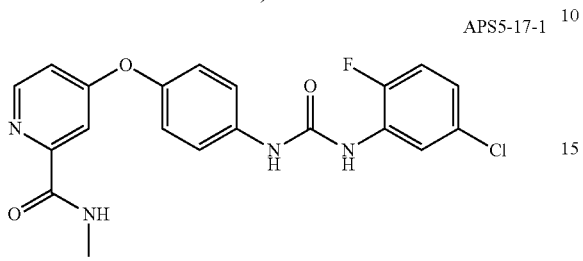

APS5-17-1

5-Chloro-2-fluoroaniline (46.5 μL, 0.431 mmol) was added neat to CDI (70.0 mg, 0.432 mmol) and $CH_2Cl_2$ (1.5 mL) in an 8 mL vial. The reaction was allowed to warm to room temperature over 10 min, and was stirred for 12 hours, then HB/S1 (100 mg, 0.411 mmol) was added in one portion and stirring was continued for 4 hours. The product precipitated out of solution and was isolated by vacuum filtration. Obtained 60.0 mg (35%) of the title compound as a white solid: $^1$H NMR (400 MHz, DMSO-$d_6$) δ 9.28 (s, 1H), 8.71-8.84 (m, 2H), 8.50 (d, J=5.6 Hz, 1H), 8.28 (dd, J=7.1, 2.7 Hz, 1H), 7.58 (d, J=9.0 Hz, 2H), 7.38 (d, J=2.4 Hz, 1H), 7.31 (dd, J=11.2, 8.8 Hz, 1H), 7.18 (d, J=9.0 Hz, 2H), 7.14 (dd, J=5.6, 2.7 Hz, 1H), 7.03-7.09 (m, 1H), 2.79 (d, J=4.6 Hz, 3H); $^{19}$F NMR (376 MHz, DMSO-$d_6$) δ −131.5 (s, 1F); LC-MS (ESI+) m/z: [M+H]$^+$ Calcd for $C_{20}H_{17}ClFN_4O_3$, 415.1; Found 415.3.

Example 51

Preparation of 4-(4-(3-(Benzo[d][1,3]dioxol-5-yl)ureido)phenoxy)-N-methylpicolinamide 2,2,2-trifluoroacetate (APS5-17-2)

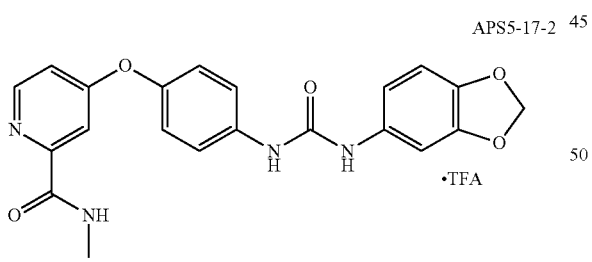

APS5-17-2

A solution of 3,4-methylenedioxyaniline (59.2 mg, 0.432 mmol) and $CH_2Cl_2$ (1 mL) was added (over 45 min) to a 0° C. solution of CDI (70.0 mg, 0.432 mmol) and $CH_2Cl_2$ (0.5 mL) in an 8 mL vial. The reaction was allowed to warm to room temperature over 2 hours, and stirred for 12 hours, then HB/S1 (100 mg, 0.411 mmol) was added in one portion and stirring was continued for 4 hours. The reaction was concentrated under vacuum and purified by reverse-phase chromatography, eluting at 18 mL/min and using a linear gradient of $H_2O$ (with 0.1% v/v TFA)/MeCN: 95:5→0:100 over 42 minutes. Obtained 48.4 mg (23%) of the title compound as a white solid: $^1$H NMR (400 MHz, DMSO-$d_6$) δ 8.72-8.79 (m, 2H), 8.59 (s, 1H), 8.50 (d, J=5.9 Hz, 1H), 7.56 (d, J=9.0 Hz, 2H), 7.38 (d, J=2.4 Hz, 1H), 7.21 (d, J=2.0 Hz, 1H), 7.11-7.18 (m, 3H), 6.83 (d, J=8.3 Hz, 1H), 6.77 (dd, J=8.3, 2.2 Hz, 1H), 5.97 (s, 2H), 2.78 (d, J=4.9 Hz, 3H); $^{13}$C NMR (100 MHz, DMSO-$d_6$) δ 166.0, 163.8, 152.7, 152.4, 150.3, 147.3, 147.2, 142.1, 137.6, 134.0, 121.4, 119.9, 114.0, 111.1, 108.6, 108.1, 101.0, 100.8, 26.0; LC-MS (ESI+) m/z: [M+H]$^+$ Calcd for $C_{21}H_{19}N_4O_5$, 407.1; Found 407.3.

Example 52

Preparation of 4-(3-Fluoro-4-(3-(3-(perfluoroethyl)phenyl)ureido) phenoxy)-N-methylpicolinamide (APS5-31-3)

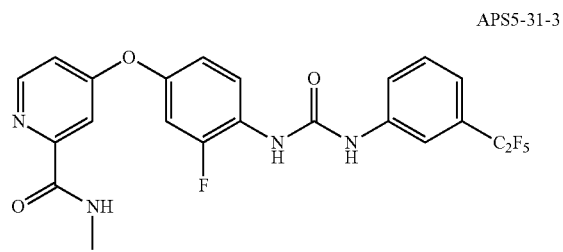

APS5-31-3

Figure 27:
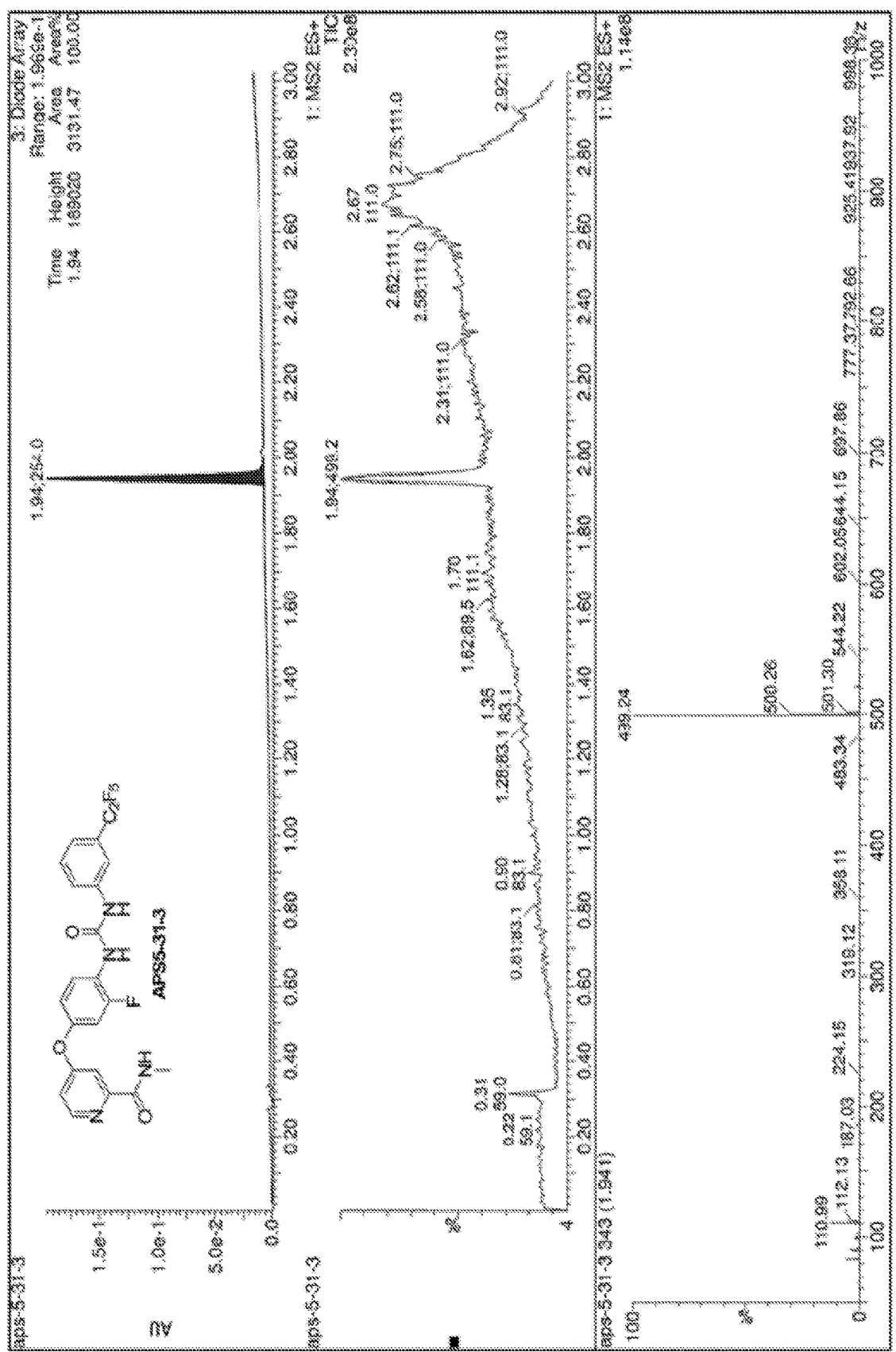
FIG. 27 shows LC-MS data for compound APS5-31-3.
Figure 28:
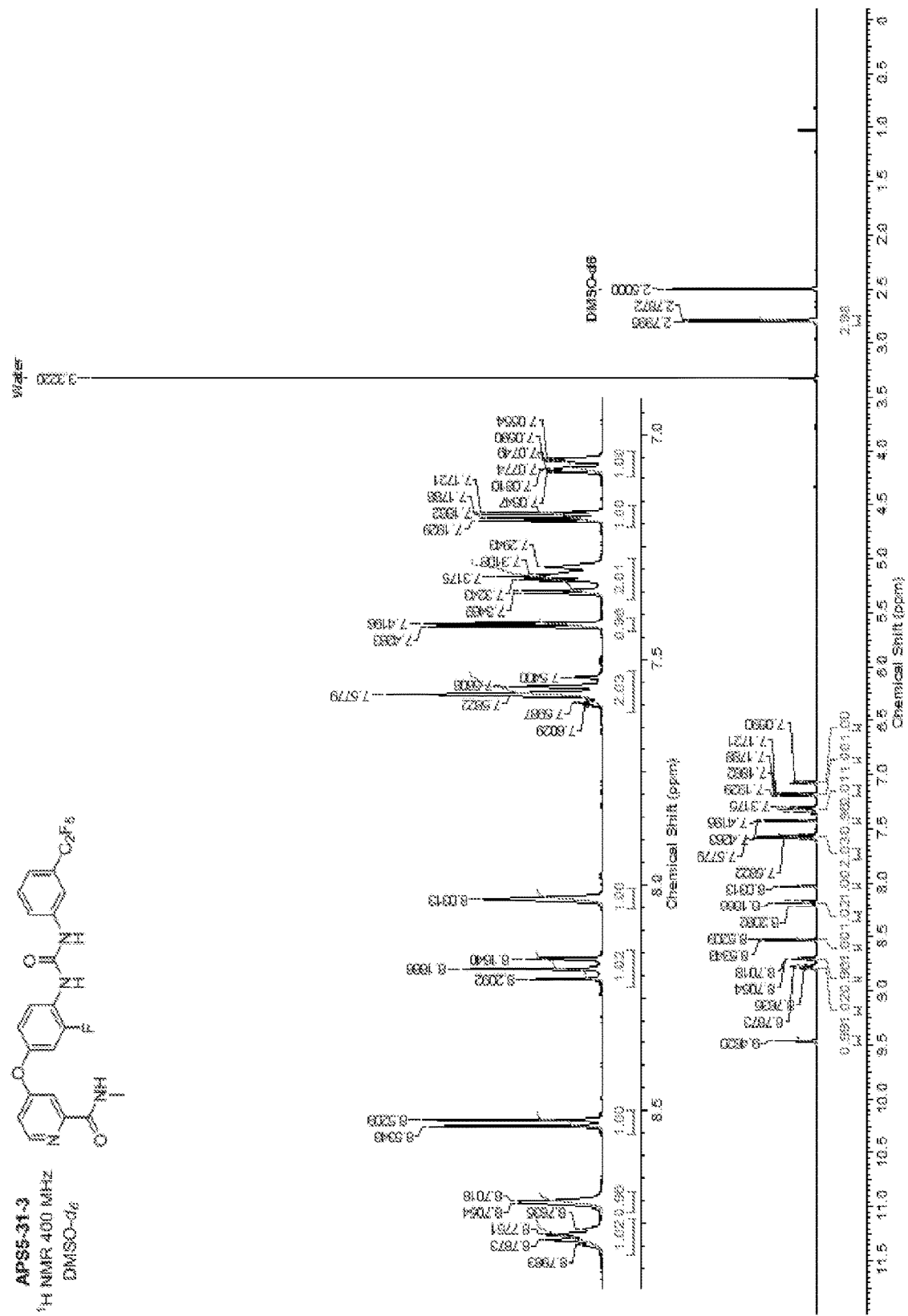
FIG. 28 shows $^1$H NMR spectra for compound APS5-31-3.

A solution of 3-(perfluoroethyl)aniline (APS5-9; 52.7 mg, 0.250 mmol) and $CH_2Cl_2$ (0.5 mL) was added to a 0° C. solution of CDI (40.5 mg, 0.250 mmol) and $CH_2Cl_2$ (0.5 mL) in an 8 mL vial. The reaction was allowed to warm to room temperature over 2 hours, and was stirred for 24 hours, then HB/S2 (58.5 mg, 0.227 mmol) was added, and stirring was continued for 24 hours. Purified by silica gel chromatography (25 g cartridge), eluting at 20 mL/min and using a linear gradient of $CH_2Cl_2$/EtOAc: 100:0→0:100 over 24 column volumes. Obtained 64.0 mg (57%) of the title compound as a white solid: $^1$H NMR (400 MHz, DMSO-$d_6$) δ 9.46 (s, 1H), 8.78 (br q, J=4.6 Hz, 1H), 8.70 (d, J=1.5 Hz, 1H), 8.53 (d, J=5.4 Hz, 1H), 8.19 (t, J=9.0 Hz, 1H), 8.03 (s, 1H), 7.52-7.62 (m, 2H), 7.42 (d, J=2.7 Hz, 1H), 7.28-7.37 (m, 2H), 7.18 (dd, J=5.6, 2.7 Hz, 1H), 7.07 (ddd, J=8.9, 2.6, 1.2 Hz, 1H), 2.79 (d, J=4.9 Hz, 3H); $^{19}$F NMR (376 MHz, DMSO-$d_6$) δ −83.6--−83.5 (m, 3F), −113.2--−113.1 (m, 2F), −124.3 (s, 1F); LC-MS (ESI+) m/z: [M+H]$^+$ Calcd for $C_{22}H_{17}F_6N_4O_3$, 499.1; Found 499.2 (FIGS. 27-28).

Example 53

Preparation of 4-(3-Fluoro-4-(3-(2-fluoro-5-(perfluoroethyl)phenyl) ureido)phenoxy)-N-methylpicolinamide (APS5-31-4)

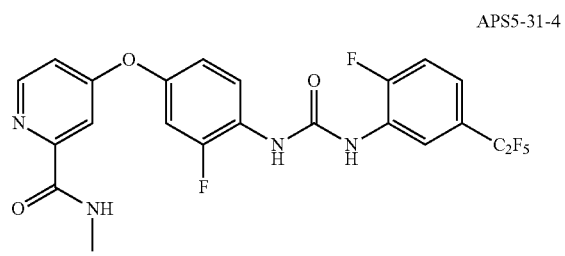

APS5-31-4

Figure 29:
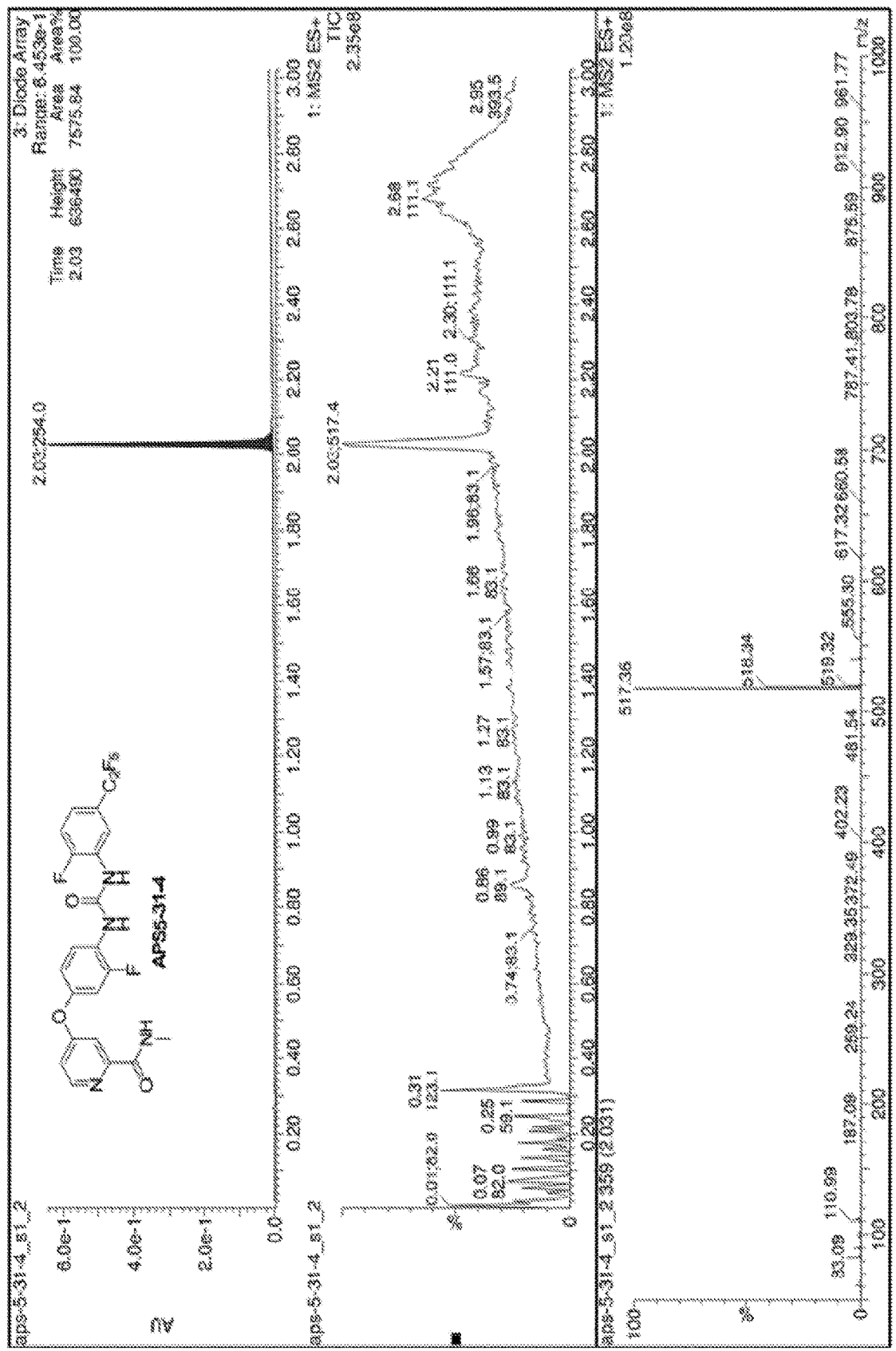
FIG. 29 shows LC-MS data for compound APS5-31-4.
Figure 30:
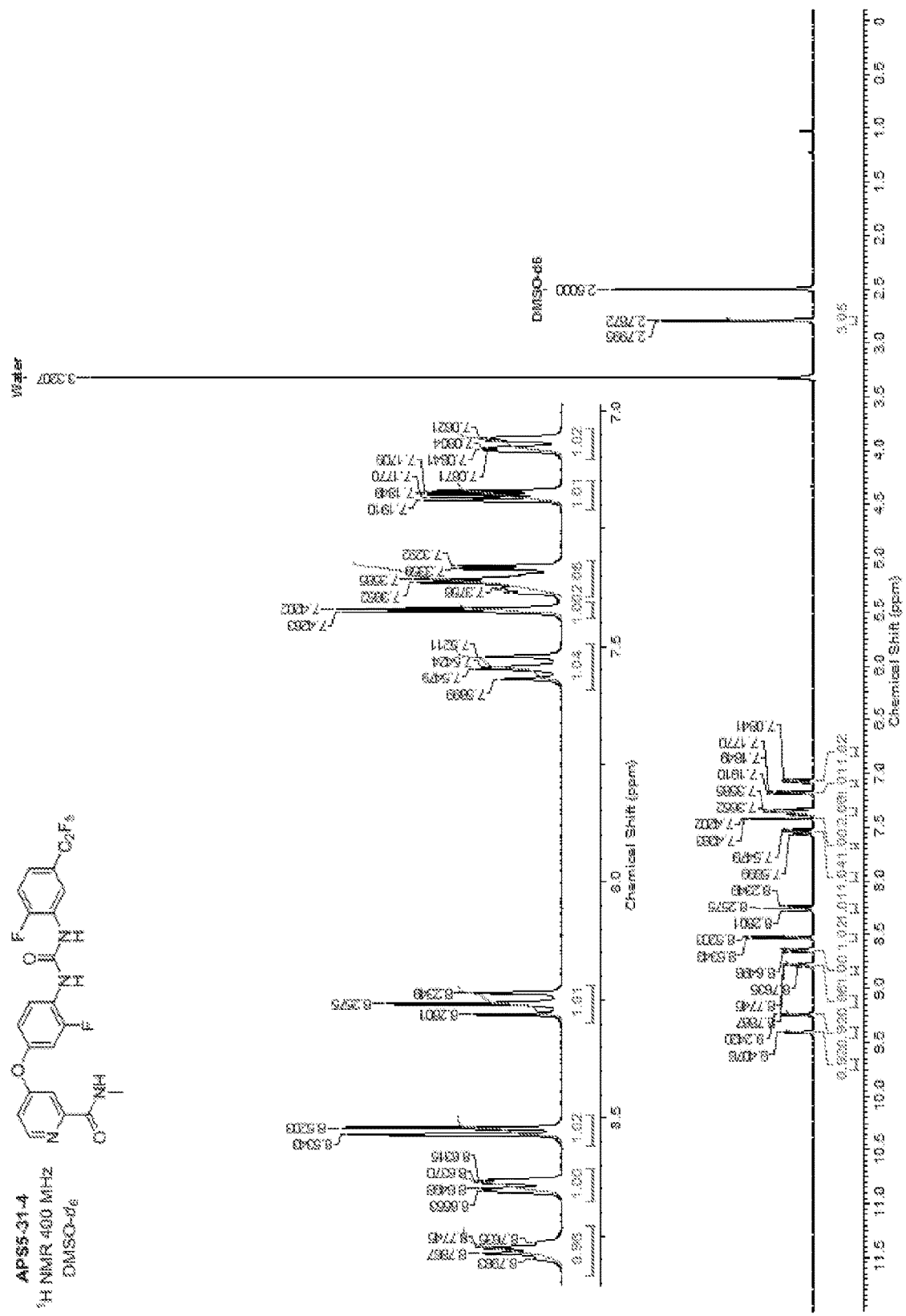
FIG. 30 shows $^1$H NMR spectra for compound APS5-31-4.

A solution of 2-fluoro-5-(perfluoroethyl)aniline (APS5-11; 71.0 mg, 0.310 mmol) and CH$_2$Cl$_2$ (0.5 mL) was added to a 0° C. solution of CDI (50.3 mg, 0.310 mmol) and CH$_2$Cl$_2$ (0.5 mL) in an 8 mL vial. After 10 min, the reaction was allowed to warm to room temperature, and was stirred for 24 hours, then HB/S2 (73.6 mg, 0.282 mmol) was added and stirring was continued for 24 hours. Purified by silica gel chromatography (25 g cartridge), eluting at 20 mL/min and using a linear gradient of CH$_2$Cl$_2$/EtOAc: 100:0→0:100 over 24 column volumes. Obtained 47.0 mg (32%) of the title compound as a white solid: $^1$H NMR (400 MHz, DMSO-d$_6$) δ 9.41 (br s, 1H), 9.24 (s, 1H), 8.78 (br q, J=4.5 Hz, 1H), 8.64 (dd, J=7.3, 2.2 Hz, 1H), 8.53 (d, J=5.6 Hz, 1H), 8.26 (t, J=9.0 Hz, 1H), 7.55 (dd, J=10.9, 8.7 Hz, 1H), 7.42 (d, J=2.4 Hz, 1H), 7.32-7.40 (m, 2H), 7.18 (dd, J=5.6, 2.4 Hz, 1H), 7.07 (dt, J=8.8, 1.3 Hz, 1H), 2.79 (d, J=4.9 Hz, 3H); $^{19}$F NMR (376 MHz, DMSO-d$_6$) δ -83.6--83.5 (m, 3F), -112.6--112.5 (m, 2F), -123.2 (s, 1F), -124.6 (s, 1F); LC-MS (ESI+) m/z: [M+H]$^+$ Calcd for C$_{22}$H$_{16}$F$_7$N$_4$O$_3$, 517.1; Found 517.3 (FIGS. 29-30).

Example 54

Preparation of 4-(4-(3-(2-Fluoro-5-(perfluoropropan-2-yl)phenyl)ureido)phenoxy)-N-methylpicolinamide (APS6-45)

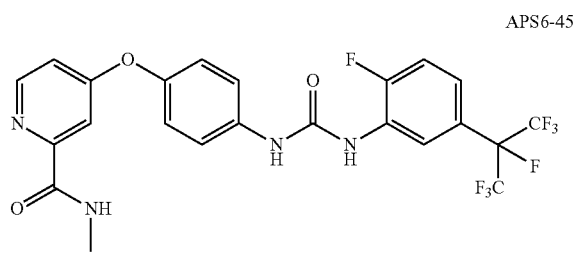 [SMILES: CNC(=O)c1cc(Oc2ccc(NC(=O)Nc3cc(C(F)(C(F)(F)F)C(F)(F)F)ccc3F)cc2)ccn1]

APS6-45

Figure 31:
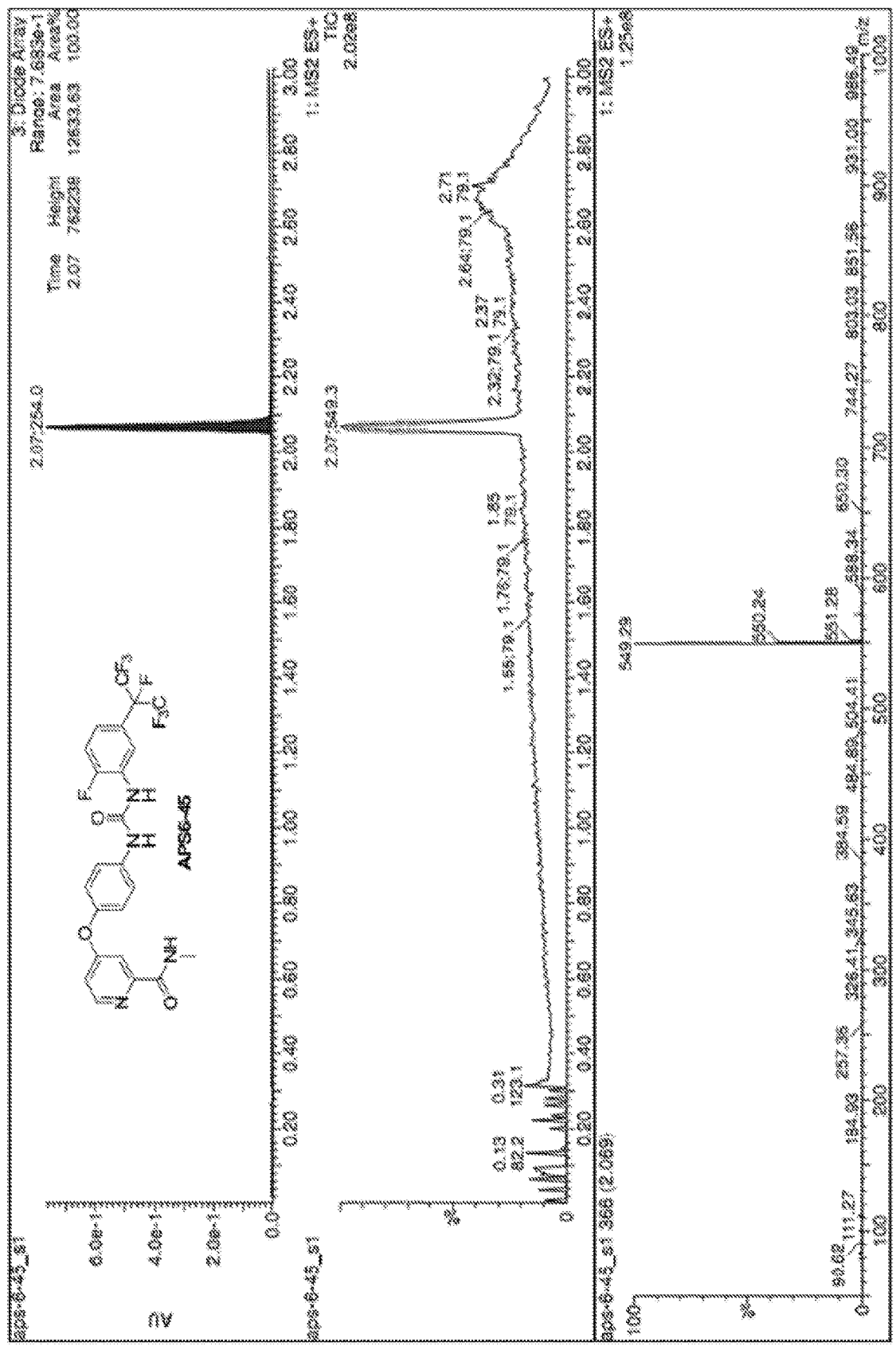
FIG. 31 shows LC-MS data for compound APS6-45.
Figure 32:
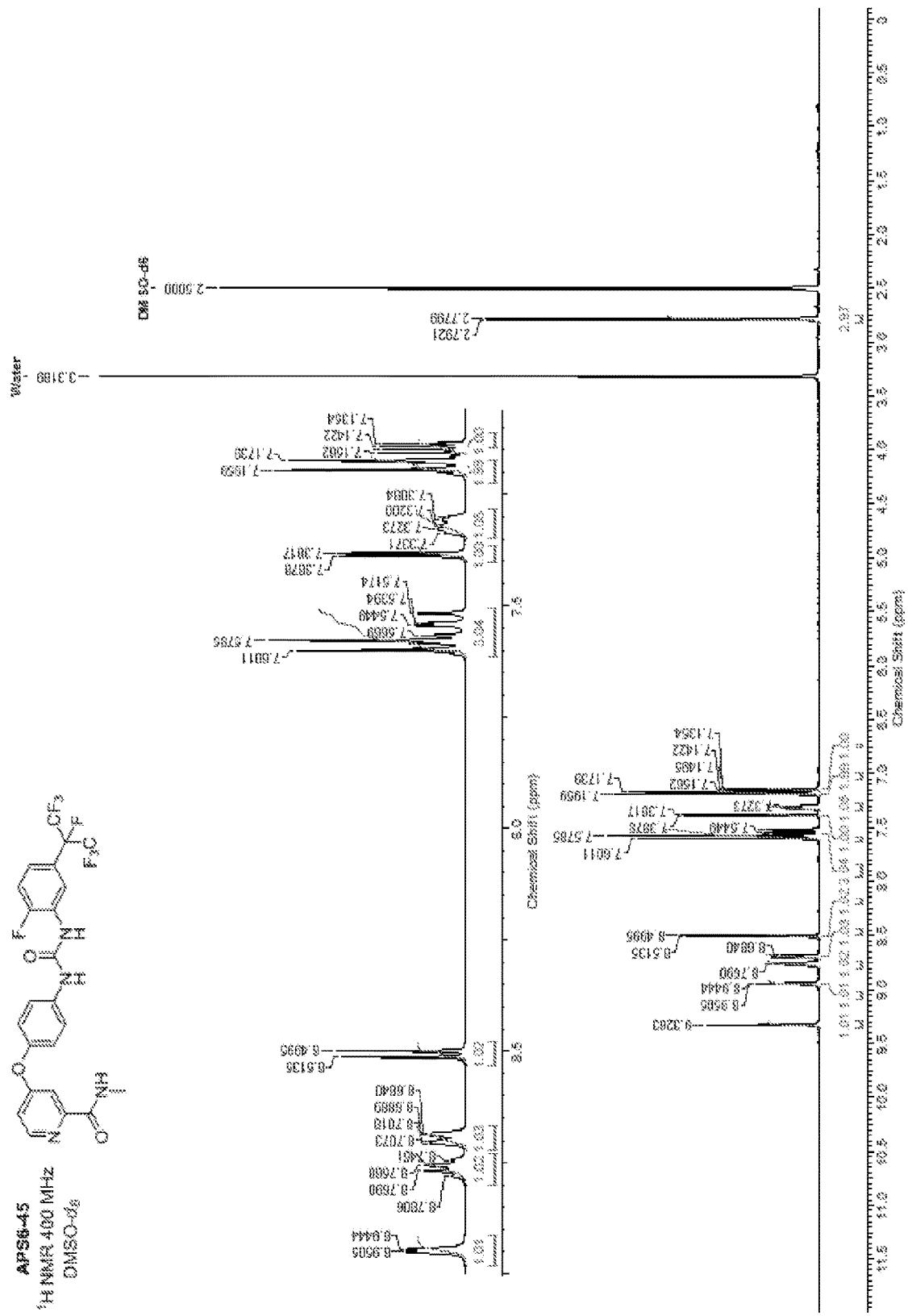
FIG. 32 shows $^1$H NMR spectra for compound APS6-45.

A solution of 2-fluoro-5-(perfluoropropan-2-yl)aniline (APS6-39; 115 mg, 0.412 mmol) and CH$_2$Cl$_2$ (0.6 mL) was added to a 0° C. solution of CDI (70.0 mg, 0.432 mmol) and CH$_2$Cl$_2$ (0.4 mL) in a 4 mL vial. After 10 min, the reaction was allowed to warm to room temperature, and was stirred for 24 hours, then HB/S1 (100 mg, 0.411 mmol) was added in one portion and stirring was continued for 4 hours. Purified by silica gel chromatography (25 g cartridge), eluting at 20 mL/min and using a linear gradient of CH$_2$Cl$_2$/EtOAc: 100:0→0:100 over 30 column volumes. Obtained 142 mg (63%) of the title compound as a white solid: $^1$H NMR (400 MHz, DMSO-d$_6$) δ 9.33 (s, 1H), 8.95 (d, J=2.4 Hz, 1H), 8.76 (br q, J=4.6 Hz, 1H), 8.70 (dd, J=7.2, 2.1 Hz, 1H), 8.51 (d, J=5.6 Hz, 1H), 7.51-7.62 (m, 3H), 7.38 (d, J=2.4 Hz, 1H), 7.28-7.35 (m, 1H), 7.18 (d, J=8.8 Hz, 2H), 7.15 (dd, J=5.6, 2.7 Hz, 1H), 2.79 (d, J=4.9 Hz, 3H); $^{19}$F NMR (376 MHz, DMSO-d$_6$) δ -74.7 (d, J=6.8 Hz, 6F), -124.8 (s, 1F), -180.1--179.9 (m, 1F); LC-MS (ESI+) m/z: [M+H]$^+$ Calcd for C$_{23}$H$_{17}$F$_8$N$_4$O$_3$, 549.1; Found 549.3 (FIGS. 31-32).

Example 55

Preparation of 1-Fluoro-2-nitro-4-(perfluoropropan-2-yl)benzene (APS6-36)

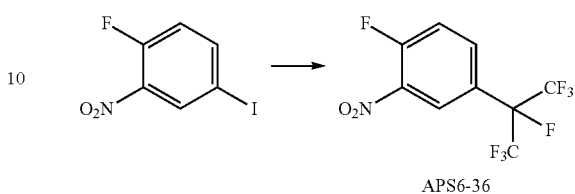

APS6-36

The synthesis was carried out following a known procedure (Guin et al., "Highly Enantioselective Hetero-Diels-Alder Reaction of 1,3-Bis-(silyoxy)-1,3-dienes With Aldehydes Catalyzed by Chiral Disulfonimide," *Angew. Chem. Int. Ed. Engl.* 51:8859-8863 (2012), which is hereby incorporated by reference in its entirety). To a mixture of 1-fluoro-4-iodo-2-nitrobenzene (1.25 g, 4.68 mmol), activated copper powder (1.20 g, 18.9 mmol) and dry DMF (13 mL; deoxygenated by bubbling Ar for 10 min) was added heptafluoro-2-iodopropane (1.00 mL, 7.03 mmol) via syringe over 1 min. The mixture was stirred under Ar and heated at 100° C. for 48 hours. The reaction mixture was allowed to cool to room temperature and then was filtered through a pad (3×3 cm) of Celite under vacuum; washed pad with Et$_2$O (2×20 mL). The combined filtrates were diluted with Et$_2$O (100 mL), then washed with a 60:40 mixture of saturated NH$_4$Cl solution/coned NH$_4$OH solution (3×30 mL), water (2×30 mL) and brine (2×30 mL), dried (MgSO$_4$), and filtered. Concentration under vacuum gave 1.38 g of an orange semi-solid, which was purified by silica gel chromatography (25 g cartridge), eluting at 20 mL/min and using a linear gradient of hexanes/CH$_2$Cl$_2$: 100:0→80:20 over 25 column volumes. Obtained 860 mg (59%) of the title compound as a colorless oil: $^1$H NMR (400 MHz, DMSO-d$_6$) δ 8.36 (dd, J=6.6, 2.4 Hz, 1H), 8.16 (dt, J=8.7, 3.1 Hz, 1H), 7.86-7.94 (m, 1H); $^{19}$F NMR (376 MHz, DMSO-d$_6$) δ -74.6 (d, J=6.8 Hz, 6F), -112.9 (s, 1F), -180.1--179.9 (m, 1F).

Example 56

Preparation of 2-Fluoro-5-(perfluoropropan-2-yl)aniline (APS6-39)

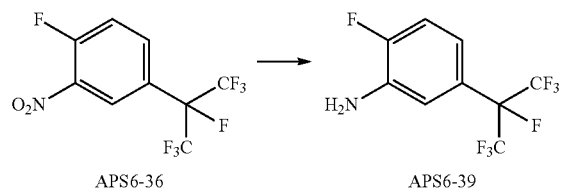 [SMILES: O=[N+]([O-])c1cc(C(F)(C(F)(F)F)C(F)(F)F)ccc1F ; Nc1cc(C(F)(C(F)(F)F)C(F)(F)F)ccc1F]

APS6-36          APS6-39

A 50 mL flask was charged with 1-fluoro-2-nitro-4-(perfluoropropan-2-yl)benzene (APS6-36; 665 mg, 2.15 mmol), MeOH (15 mL), and iron powder (720 mg, 12.9 mmol). The mixture was cooled to 0° C., and concentrated HCl (2.1 mL, 26 mmol) was added dropwise by pipet over 5 min. The reaction was allowed to warm to room temperature over 30 min, and was stirred for an additional 3 hours. The reaction was vacuum-filtered through a pad (2×2 cm) of Celite to remove unreacted iron powder and the pad was washed with MeOH (5 mL). The combined filtrates were diluted with water (75 mL) and CH$_2$Cl$_2$ (75 mL), and the pH of the aqueous phase was adjusted to 7-8 with 6 M NaOH solution (~4.3 mL). The resulting mixture was vacuum-filtered through a pad (4×4 cm total size) of sand (3×4 cm) layered on top of Celite (1×4 cm) and the filter-cake was washed with CH$_2$Cl$_2$ (30 mL). The combined filtrates were transferred to a separatory funnel, the layers were separated, and the aqueous phase was extracted with CH$_2$Cl$_2$ (2×50 mL). The organic extracts were pooled, dried (Na$_2$SO$_4$), and filtered. The filtrate was concentrated under vacuum to leave an oil, which was purified by silica gel chromatography (25 g cartridge), eluting at 20 mL/min and using a linear gradient of hexanes/CH$_2$Cl$_2$: 100:0→50:50 over 25 column volumes. Obtained 473 mg (79%) of the title compound as a colorless oil: $^1$H NMR (400 MHz, DMSO-d$_6$) δ 7.21 (dd, J=11.2, 8.6 Hz, 1H), 7.07 (dd, J=8.2, 1.8 Hz, 1H), 6.71-6.78 (m, 1H), 5.65 (br s, 2H); $^{19}$F NMR (376 MHz, DMSO-d$_6$) δ −74.8 (d, J=6.8 Hz, 6F), −130.6 (s, 1F), −180.4--180.2 (m, 1F); LC-MS (ESI+) m/z: [M+H]$^+$ Calcd for C$_9$H$_6$F$_8$N, 280.1; Found 280.2.

Example 57

General Synthetic Strategy for the Preparation of Amide Linker (L2) Sorafelogs

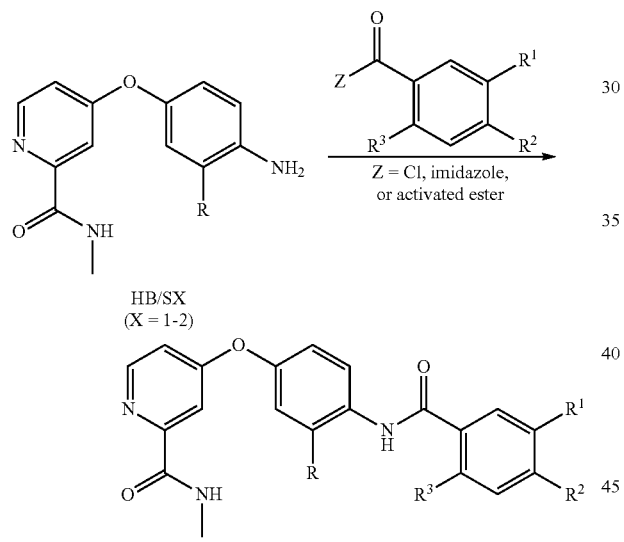

Example 58

Preparation of 4-(4-Benzamidophenoxy)-N-methyl-picolinamide (S1/L2/C1 (APS4-64-2))

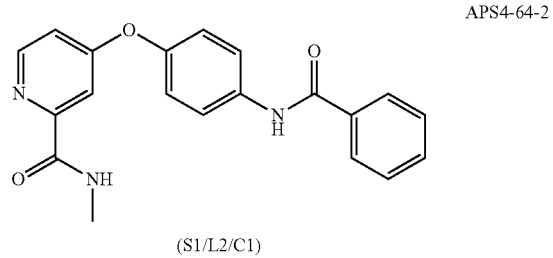 [SMILES: CNC(=O)c1cc(Oc2ccc(NC(=O)c3ccccc3)cc2)ccn1]

Figure 33:
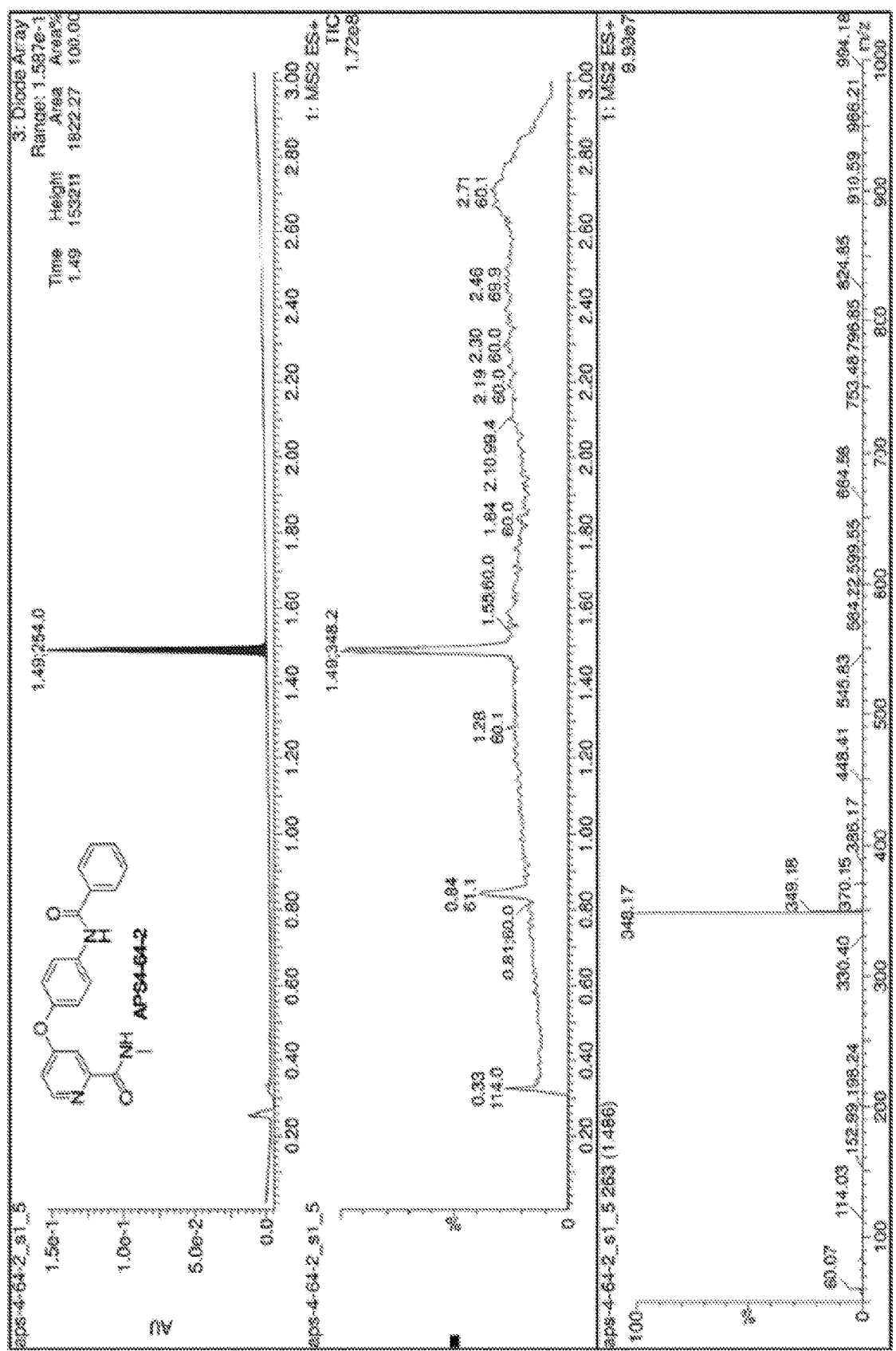
FIG. 33 shows LC-MS data for compound APS4-64-2.
Figure 34:
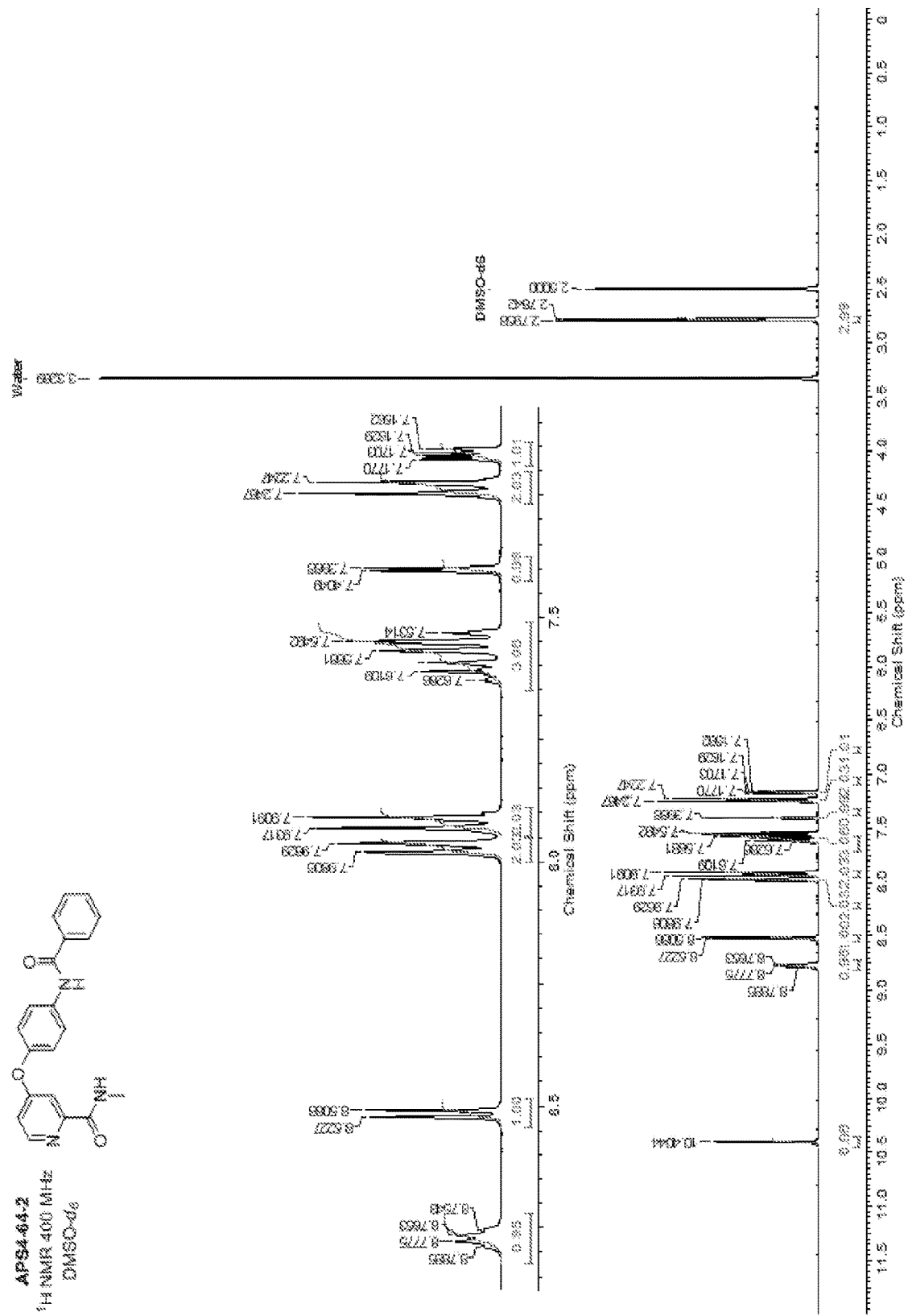
FIG. 34 shows $^1$H NMR spectra for compound APS4-64-2.

A flame-dried 8 mL vial, under Ar, was charged with HB/S1 (60.0 mg, 0.247 mmol) and CH$_2$Cl$_2$ (1 mL), and then benzoyl chloride (35.0 μL, 0.302 mmol) was added dropwise to the stirred solution over 1 min. To the resulting mixture was added pyridine (25.0 μL, 0.309 mmol), which produced a clear solution. The reaction was stirred for 14 hours, then MeOH (1 mL) was added and stirring was continued for 30 min. The solution was concentrated to dryness and the remaining material was purified by silica gel chromatography (12 gram cartridge), eluting at 20 mL/min and using a linear gradient of hexanes/EtOAc: 100:0→0:100 over 24 column volumes. Obtained 39.6 mg (46%) of the title compound as an off-white solid: $^1$H NMR (400 MHz, DMSO-d$_6$) δ 10.40 (s, 1H), 8.77 (br q, J=4.4 Hz, 1H), 8.52 (d, J=5.6 Hz, 1H), 7.95-8.00 (m, 2H), 7.92 (d, J=9.0 Hz, 2H), 7.51-7.65 (m, 3H), 7.40 (d, J=2.4 Hz, 1H), 7.24 (d, J=8.8 Hz, 2H), 7.17 (dd, J=5.6, 2.7 Hz, 1H), 2.79 (d, J=4.6 Hz, 3H); $^{13}$C NMR (100 MHz, DMSO-d$_6$) δ 165.9, 165.6, 163.8, 152.5, 150.4, 148.8, 137.0, 134.9, 131.6, 128.4, 127.7, 122.1, 121.3, 114.1, 108.7, 26.0; LC-MS (ESI+) m/z: [M+H]$^+$ Calcd for C$_{20}$H$_{18}$N$_3$O$_3$, 348.1; Found 348.2 (FIGS. 33-34).

Example 59

Preparation of N-Methyl-4-(4-(3-(trifluoromethyl) benzamido) phenoxy)picolinamide (S1/L2/C2 (APS4-64-1))

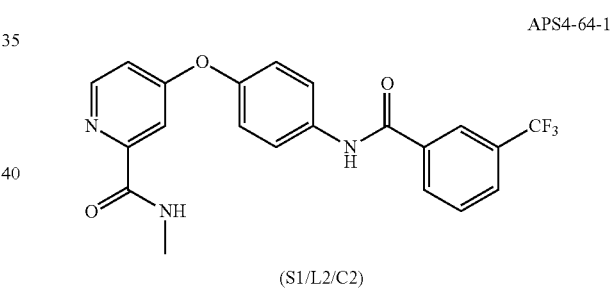

Figure 35:
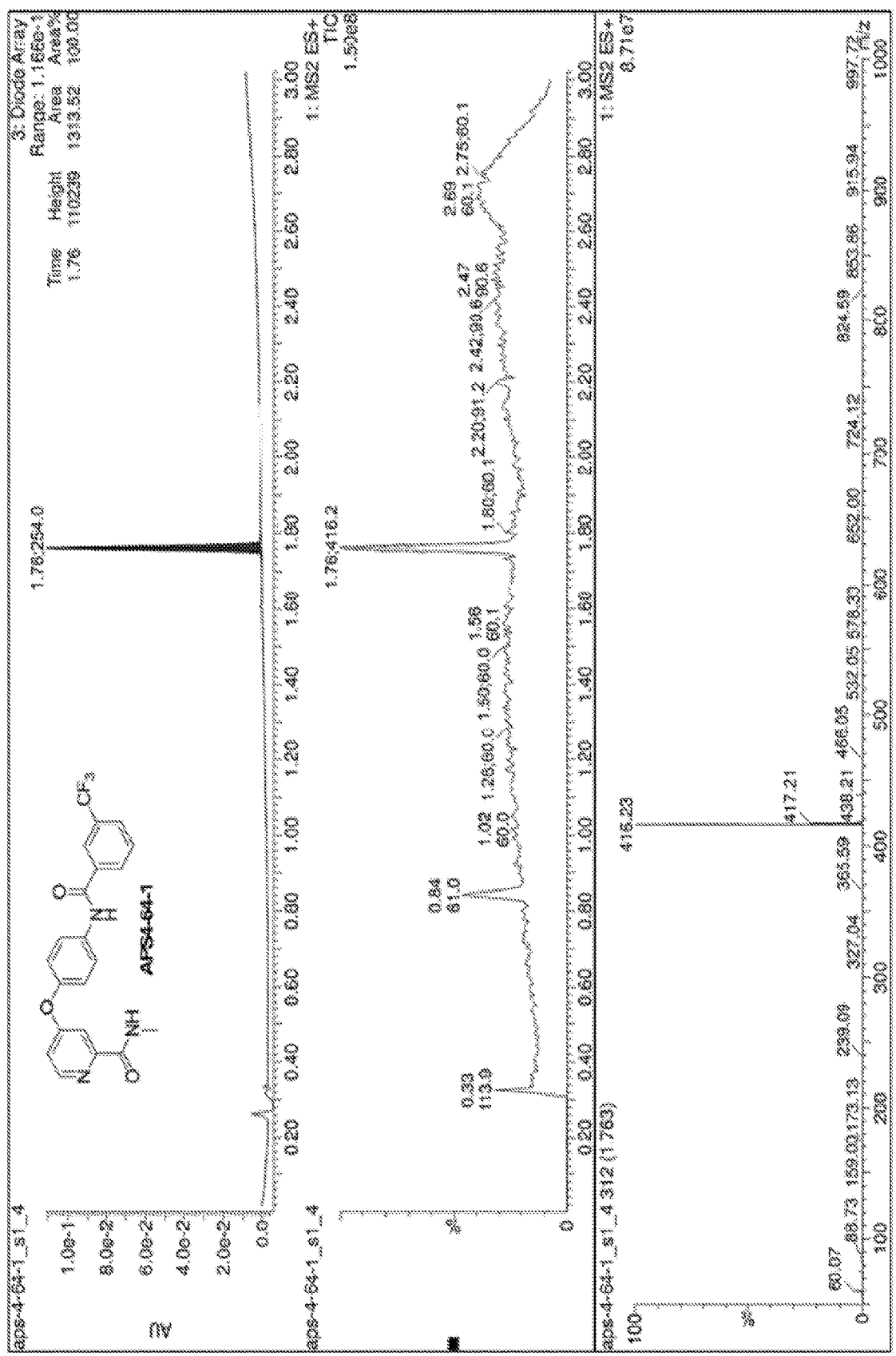
FIG. 35 shows LC-MS data for compound APS4-64-1.
Figure 36:
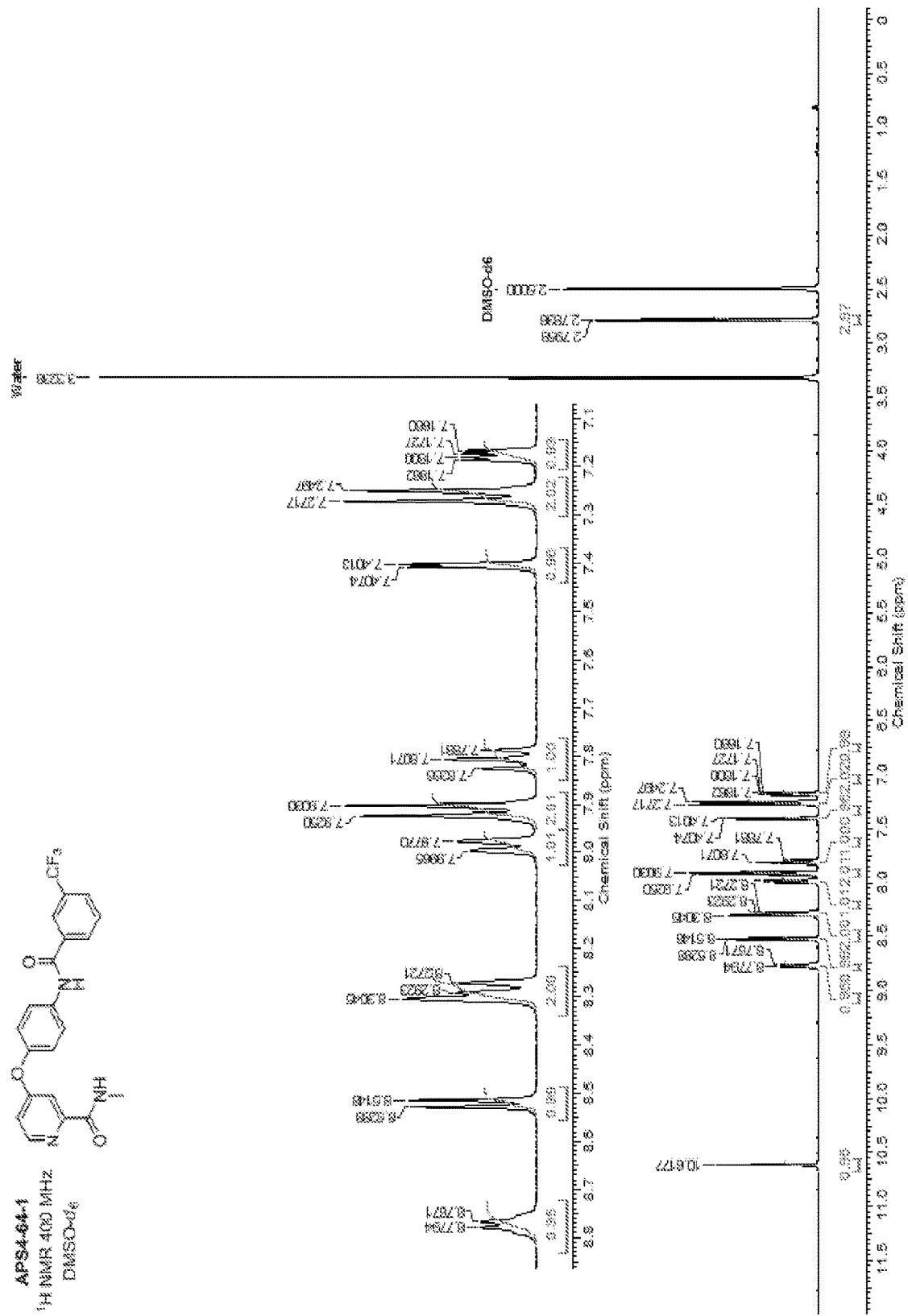
FIG. 36 shows $^1$H NMR spectra for compound APS4-64-1.

A flame-dried 8 mL vial, under Ar, was charged with HB/S1 (60.0 mg, 0.247 mmol) and CH$_2$Cl$_2$ (1 mL), and then 3-(trifluoromethyl)benzoyl chloride (45.0 μL, 0.298 mmol) was added dropwise to the stirred solution dropwise over 1 min. To the resulting mixture was added pyridine (25.0 μL, 0.309 mmol), which produced a clear solution. The reaction was stirred for 14 hours, then MeOH (1 mL) was added, and stirring was continued for 30 min. The solution was concentrated to dryness and the remaining material was purified by silica gel chromatography (12 gram cartridge), eluting at 20 mL/min and using a linear gradient of hexanes/EtOAc: 100:0→0:100 over 24 column volumes. Obtained 75.8 mg (74%) of the title compound as an off-white solid: $^1$H NMR (400 MHz, DMSO-d$_6$) δ 10.62 (s, 1H), 8.77 (d, J=4.9 Hz, 1H), 8.52 (d, J=5.6 Hz, 1H), 8.24-8.34 (m, 2H), 7.99 (d, J=7.8 Hz, 1H), 7.91 (d, J=8.8 Hz, 2H), 7.76-7.85 (m, 1H), 7.40 (d, J=2.4 Hz, 1H), 7.26 (d, J=8.8 Hz, 2H), 7.18 (dd, J=5.5, 2.6 Hz, 1H), 2.79 (d, J=4.9 Hz, 3H); $^{19}$F NMR (376 MHz, DMSO-d$_6$) δ −60.6 (s, 3F); LC-MS (ESI+) m/z: [M+H]$^+$ Calcd for C$_{21}$H$_{17}$F$_3$N$_3$O$_3$, 416.1; Found 416.2 (FIGS. 35-36).

Example 60

Preparation of 4-(4-(4-Chloro-3-(trifluoromethyl)benzamido) phenoxy)-N-methylpicolinamide (S1/L2/C3 (LS1-37))

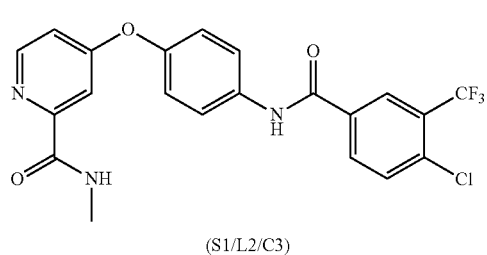

LS1-37

(S1/L2/C3)

An oven-dried 8 mL vial, under Ar, was charged with 4-chloro-3-(trifluoromethyl)benzoic acid (138 mg, 0.615 mmol) and CDI (100 mg, 0.617 mmol), then THF (1 mL) was added with stirring, which resulted in rapid evolution of gas. The solution was stirred at room temperature for 1 hour and then heated at 45° C. for 2 hours. After the solution had cooled to room temperature, HB/S1 (100 mg, 0.411 mmol) was added in one portion and stirring was continued for 2 hours. The reaction was diluted with MeOH (3 mL) and purified by reverse-phase chromatography, eluting at 20 mL/min and using a linear gradient of H$_2$O/MeCN: 90:10→5:95 over 26 minutes. Obtained 177 mg (96%) of the title compound as a white solid: $^1$H NMR (400 MHz, DMSO-d$_6$) δ 10.66 (br s, 1H), 8.77 (br q, J=4.9 Hz, 1H), 8.52 (d, J=5.6 Hz, 1H), 8.40 (d, J=1.7 Hz, 1H), 8.27 (dd, J=8.3, 2.0 Hz, 1H), 7.94 (d, J=8.3 Hz, 1H), 7.90 (d, J=9.0 Hz, 2H), 7.40 (d, J=2.7 Hz, 1H), 7.26 (d, J=9.0 Hz, 2H), 7.17 (dd, J=5.5, 2.6 Hz, 1H), 2.79 (d, J=4.9 Hz, 3H); $^{19}$F NMR (376 MHz, DMSO-d$_6$) δ −60.8 (s, 3F); LC-MS (ESI+) m/z: [M+H]$^+$ Calcd for C$_{21}$H$_{16}$ClF$_3$N$_3$O$_3$, 450.1; Found 450.2.

Example 61

Preparation of 4-(4-(2-Fluoro-5-(trifluoromethyl)benzamido)phenoxy)-N-methylpicolinamide (S1/L2/C4 (APS4-63-1))

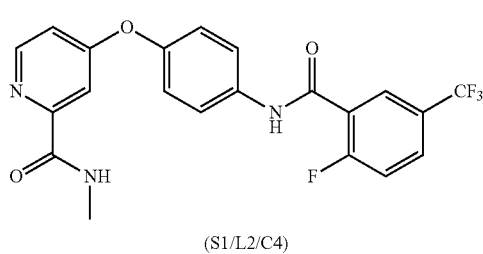

APS4-63-1

(S1/L2/C4)

Figure 37:
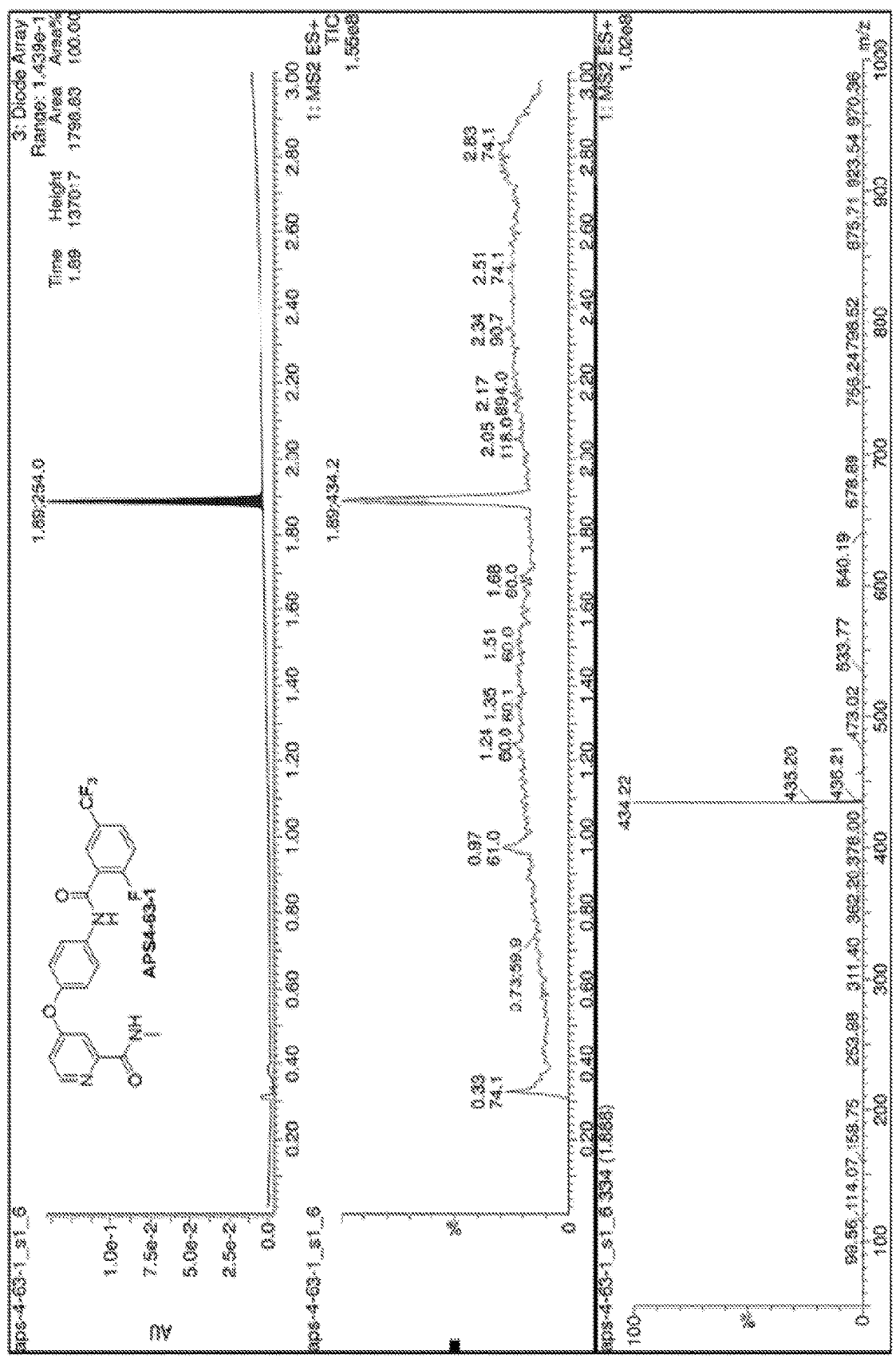
FIG. 37 shows LC-MS data for compound APS4-63-1.
Figure 38:
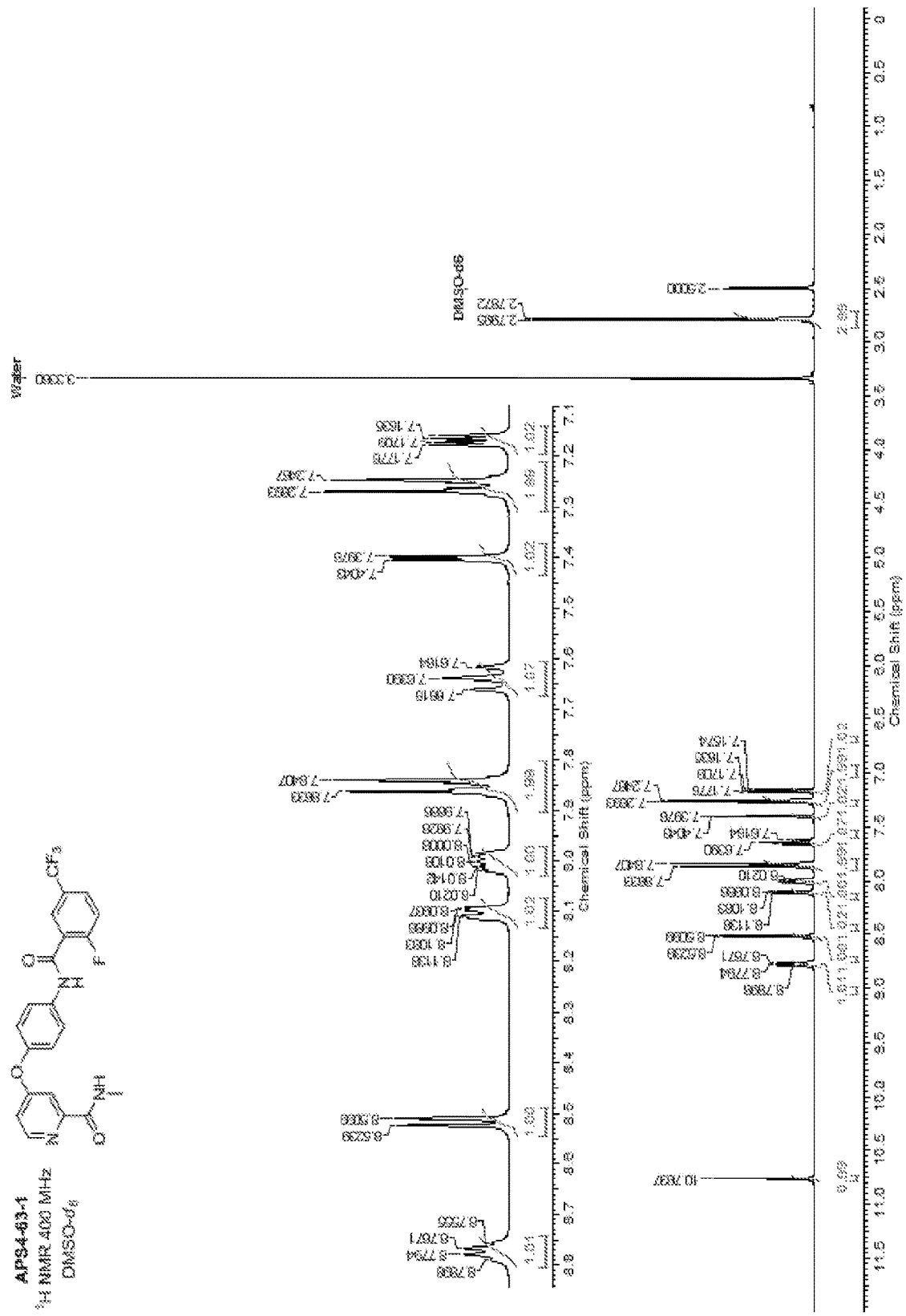
FIG. 38 shows $^1$H NMR spectra for compound APS4-63-1.

To a solution of 2-fluoro-5-(trifluoromethyl)benzoic acid (75.3 mg, 0.364 mmol), HATU (140 mg, 0.368 mmol), and DMF (1 mL), in an 8 mL vial, was added DIPEA (70.0 μL, 0.402 mmol) dropwise by syringe over 1 min. The solution was stirred for 30 min, then HB/S1 (80.0 mg, 0.329 mmol) was added in one portion and stirring was continued for 12 hours. The reaction was diluted with a saturated solution of NaHCO$_3$ (20 mL) and extracted with CH$_2$Cl$_2$ (3×20 mL). The organic extracts were pooled, dried (Na$_2$SO$_4$), filtered, and concentrated. The crude product was purified by silica gel chromatography (25 gram cartridge), eluting at 20 mL/min and using a linear gradient of hexanes/EtOAc: 100:0→0:100 over 18 column volumes. Obtained 139 mg (97%) of the title compound as a tan solid: $^1$H NMR (400 MHz, DMSO-d$_6$) δ 10.76 (s, 1H), 8.77 (br q, J=4.9 Hz, 1H), 8.52 (d, J=5.6 Hz, 1H), 8.10 (dd, J=6.1, 2.2 Hz, 1H), 8.00 (ddd, J=8.5, 4.3, 2.6 Hz, 1H), 7.85 (d, J=9.0 Hz, 2H), 7.64 (t, J=9.2 Hz, 1H), 7.40 (d, J=2.7 Hz, 1H), 7.26 (d, J=9.0 Hz, 2H), 7.17 (dd, J=5.5, 2.6 Hz, 1H), 2.79 (d, J=4.9 Hz, 3H); $^{19}$F NMR (376 MHz, DMSO-d$_6$) δ −60.9 (s, 3F), −108.3 (s, 1F); LC-MS (ESI+) m/z: [M+H]$^+$ Calcd for C$_{21}$H$_{16}$F$_4$N$_3$O$_3$, 434.1; Found 434.2 (FIGS. 37-38).

Example 62

Preparation of 4-(4-Benzamido-3-fluorophenoxy)-N-methylpicolinamide (S2/L2/C1 (APS6-22-1))

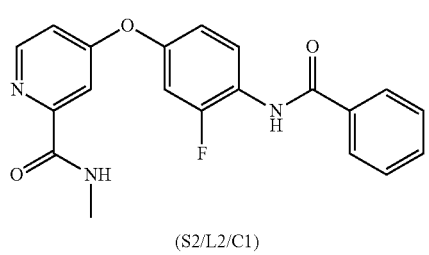

APS6-22-1

(S2/L2/C1)

A flame-dried 8 mL vial, under Ar, was charged with HB/S2 (100 mg, 0.383 mmol) and CH$_2$Cl$_2$ (1.5 mL), and then benzoyl chloride (65.0 μL, 0.560 mmol) was added to the stirred solution dropwise by syringe over 1 min. To the resulting mixture was added triethylamine (80.0 μL, 0.574 mmol), which produced a clear solution. The reaction was stirred for 12 hours, then MeOH (2 mL) was added and stirring was continued for 30 min. The solution was concentrated to dryness and the remaining material was purified by silica gel chromatography (12 gram cartridge), eluting at 25 mL/min and using a linear gradient of hexanes/EtOAc: 100:0→0:100 over 30 column volumes. Obtained 89.6 mg (64%) of the title compound as a white solid: $^1$H NMR (400 MHz, DMSO-d$_6$) δ 10.20 (s, 1H), 8.80 (br ap d, J=4.9 Hz, 1H), 8.56 (d, J=5.6 Hz, 1H), 7.99 (d, J=7.1 Hz, 2H), 7.72 (t, J=8.7 Hz, 1H), 7.59-7.66 (m, 1H), 7.51-7.59 (m, 2H), 7.46 (d, J=2.7 Hz, 1H), 7.37 (dd, J=10.9, 2.6 Hz, 1H), 7.23 (dd, J=5.5, 2.6 Hz, 1H), 7.13 (dd, J=8.7, 1.8 Hz, 1H), 2.80 (d, J=4.6 Hz, 3H); $^{19}$F NMR (376 MHz, DMSO-d$_6$) δ −115.9 (s, 1F); LC-MS (ESI+) m/z: [M+H]$^+$ Calcd for C$_{20}$H$_{17}$FN$_3$O$_3$, 366.1; Found 366.2.

Example 63

Preparation of 4-(3-Fluoro-4-(3(trifluoromethyl) benzamido)phenoxy)-N-methylpicolinamide (S2/L2/C2 (APS6-22-2))

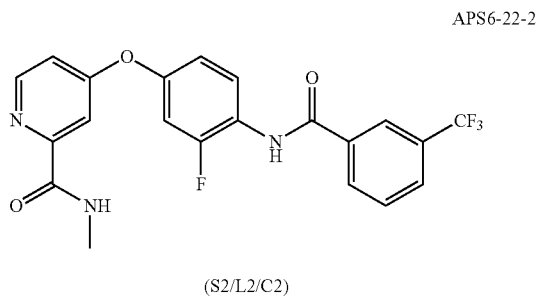 [SMILES: CNC(=O)c1cc(Oc2ccc(NC(=O)c3cccc(C(F)(F)F)c3)c(F)c2)ccn1]

(S2/L2/C2)

APS6-22-2

A flame-dried 8 mL vial, under Ar, was charged with HB/S2 (100 mg, 0.383 mmol) and CH$_2$Cl$_2$ (1.5 mL), and then 3-(trifluoromethyl)benzoyl chloride (85.0 µL, 0.564 mmol) was added to the stirred solution dropwise over 1 min. To the resulting mixture was added triethylamine (80.0 µL, 0.574 mmol), which produced a clear solution. The reaction was stirred for 12 hours, then MeOH (2 mL) was added and stirring was continued for 30 min. The solution was concentrated to dryness and the remaining material was purified by silica gel chromatography (12 gram cartridge), eluting at 20 mL/min and using a linear gradient of hexanes/EtOAc: 100:0→0:100 over 24 column volumes. Obtained 72.9 mg (44%) of the title compound as a white solid: $^1$H NMR (400 MHz, DMSO-d$_6$) δ 10.49 (s, 1H), 8.80 (br q, J=4.6 Hz, 1H), 8.56 (d, J=5.6 Hz, 1H), 8.33 (s, 1H), 8.29 (d, J=7.8 Hz, 1H), 8.00 (d, J=7.8 Hz, 1H), 7.78-7.85 (m, 1H), 7.74 (t, J=8.7 Hz, 1H), 7.46 (d, J=2.4 Hz, 1H), 7.39 (dd, J=11.0, 2.7 Hz, 1H), 7.24 (dd, J=5.6, 2.4 Hz, 1H), 7.15 (dd, J=8.7, 1.6 Hz, 1H), 2.80 (d, J=4.9 Hz, 3H); $^{19}$F NMR (376 MHz, DMSO-d$_6$) δ −60.7 (s, 3F), −115.9 (s, 1F); LC-MS (ESI+) m/z: [M+H]$^+$ Calcd for C$_{21}$H$_{16}$F$_4$N$_3$O$_3$, 434.1; Found 434.3.

Example 64

Preparation of 4-(4-(4-Chloro-3-(trifluoromethyl) benzamido)-3-fluorophenoxy)-N-methylpicolinamide (S2/L2/C3 (APS4-58))

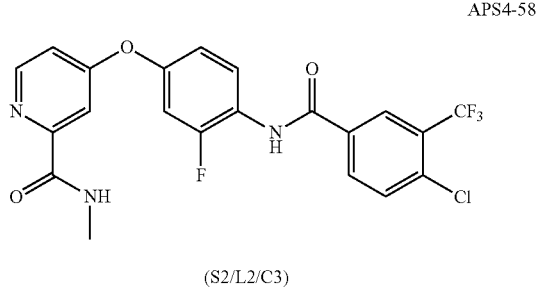 [SMILES: CNC(=O)c1cc(Oc2ccc(NC(=O)c3ccc(Cl)c(C(F)(F)F)c3)c(F)c2)ccn1]

(S2/L2/C3)

APS4-58

To a solution of 4-chloro-3-(trifluoromethyl)benzoic acid (52.5 mg, 0.234 mmol), 1-[bis(dimethylamino)methylene]-1H-1,2,3-triazolo[4,5-b]pyridinium 3-oxide hexafluorophosphate, (HATU; 88.9 mg, 0.234 mmol), and DMF (1 mL), in an 8 mL vial, was added N,N-diisopropylethylamine (DIPEA; 45.0 µL, 0.258 mmol) dropwise by syringe over 1 min. The solution was stirred for 2 hours, then HB/S2 (55.5 mg, 0.212 mmol) was added in one portion and stirring was continued for 18 hours. The solution was diluted with MeOH (5 mL) and purified by reverse-phase chromatography, eluting at 20 mL/min and using a linear gradient of H$_2$O/MeCN: 90:10→0:100 over 25 minutes. The product obtained from chromatography was slightly impure and was recrystallized from MeOH (1 mL) to provide 57.9 mg (58%) of the title compound as a white solid: $^1$H NMR (400 MHz, DMSO-d$_6$) δ 10.55 (s, 1H), 8.80 (br q, J=4.4 Hz, 1H), 8.56 (d, J=5.6 Hz, 1H), 8.42 (d, J=1.7 Hz, 1H), 8.27 (dd, J=8.3, 2.0 Hz, 1H), 7.95 (d, J=8.3 Hz, 1H), 7.74 (t, J=8.8 Hz, 1H), 7.46 (d, J=2.7 Hz, 1H), 7.39 (dd, J=11.0, 2.7 Hz, 1H), 7.24 (dd, J=5.6, 2.7 Hz, 1H), 7.15 (dt, J=8.6, 1.3 Hz, 1H), 2.80 (d, J=4.9 Hz, 3H); $^{19}$F NMR (376 MHz, DMSO-d$_6$) δ −60.9 (s, 3F), −116.0 (s, 1F); LC-MS (ESI+) m/z: [M+H]$^+$ Calcd for C$_{21}$H$_{15}$ClF$_4$N$_3$O$_3$, 468.1; Found 468.2.

Example 65

Preparation of 4-(3-Fluoro-4-(2-fluoro-5-(trifluoromethyl)benzamido) phenoxy)-N-methylpicolinamide (S2/L2/C4 (APS6-21))

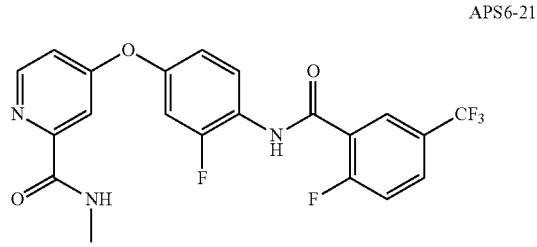

APS6-21

(S2/L2/C4)

To a solution of 2-fluoro-5-(trifluoromethyl)benzoic acid (96.0 mg, 0.461 mmol), HATU (175 mg, 0.460 mmol) and DMF (1 mL), in an 8 mL vial, was added DIPEA (80.0 µL, 0.459 mmol) dropwise over 1 min. The solution was stirred for 2 hours, then HB/S2 (100 mg, 0.383 mmol) was added in one portion and stirring was continued for 14 hours. The solution was diluted with MeOH (5 mL) and purified by reverse-phase chromatography, eluting at 20 mL/min and using a linear gradient of H$_2$O/MeCN: 90:10→0:100 over 42 minutes. Obtained 93.0 mg (54%) of the title compound as a white solid: $^1$H NMR (400 MHz, DMSO-d$_6$) δ 10.50 (s, 1H), 8.80 (br ap d, J=4.6 Hz, 1H), 8.55 (d, J=5.6 Hz, 1H), 8.10 (d, J=4.4 Hz, 1H), 7.99-8.05 (m, 1H), 7.95 (t, J=8.8 Hz, 1H), 7.63 (t, J=9.2 Hz, 1H), 7.46 (d, J=2.4 Hz, 1H), 7.39 (dd, J=11.0, 2.4 Hz, 1H), 7.23 (dd, J=5.4, 2.4 Hz, 1H), 7.15 (dd, J=8.8, 1.5 Hz, 1H), 2.80 (d, J=4.9 Hz, 3H); $^{19}$F NMR (376 MHz, DMSO-d$_6$) δ −60.1 (s, 3F), −107.6 (s, 1F), −117.6 (s, 1F); LC-MS (ESI+) m/z: [M+H]$^+$ Calcd for C$_{21}$H$_{15}$F$_5$N$_3$O$_3$, 452.1; Found 452.3.

Example 66

General Procedure for the Synthesis of Sulfonamide Linker Sorafelogs Employing a Sulfonyl Chloride

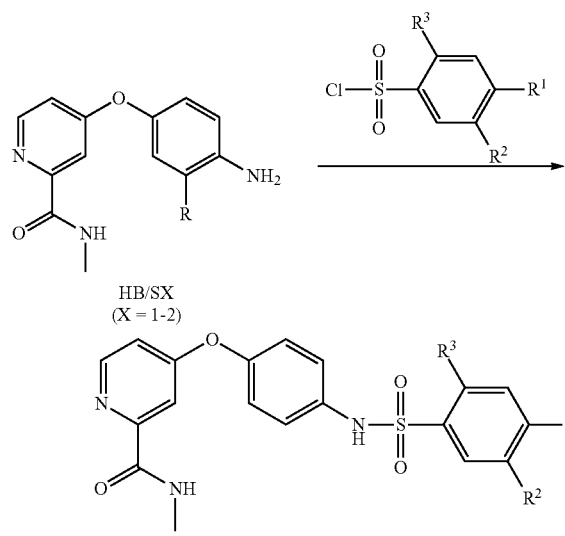

HB/SX
(X = 1-2)

A flame-dried 8 mL vial, cooled under Ar, was charged with HB/SX (X=1-2) and CH$_2$Cl$_2$ (0.5-1 mL). To the stirred solution were sequentially added the sulfonyl chloride (neat or as a solution in 0.5 mL CH$_2$Cl$_2$) and pyridine; both were added dropwise via syringe over 1 min. The headspace above the reaction was blanketed with Ar, the vial was sealed with a screw cap (wrapped with Teflon tape) and the reaction was stirred for 24 hours. All reactions in this group were purified by silica gel chromatography (12 gram cartridge), eluting at 20 mL/min and using a linear gradient of CH$_2$Cl$_2$/EtOAc: 100:0→0:100 over 20 column volumes. All products were dried under high vacuum for >24 hours. Specific details and characterization data for Sorafelogs prepared by this synthetic strategy are given below.

Example 67

Preparation of N-Methyl-4-(4-phenylsulfonamido) phenoxy) picolinamide (S1/L3/C1 (APS4-67-4))

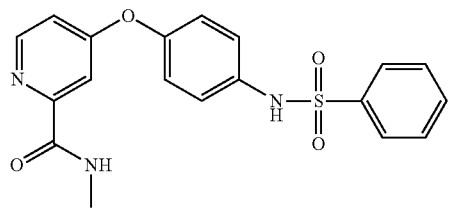

(S1/L3/C1)

Figure 39:
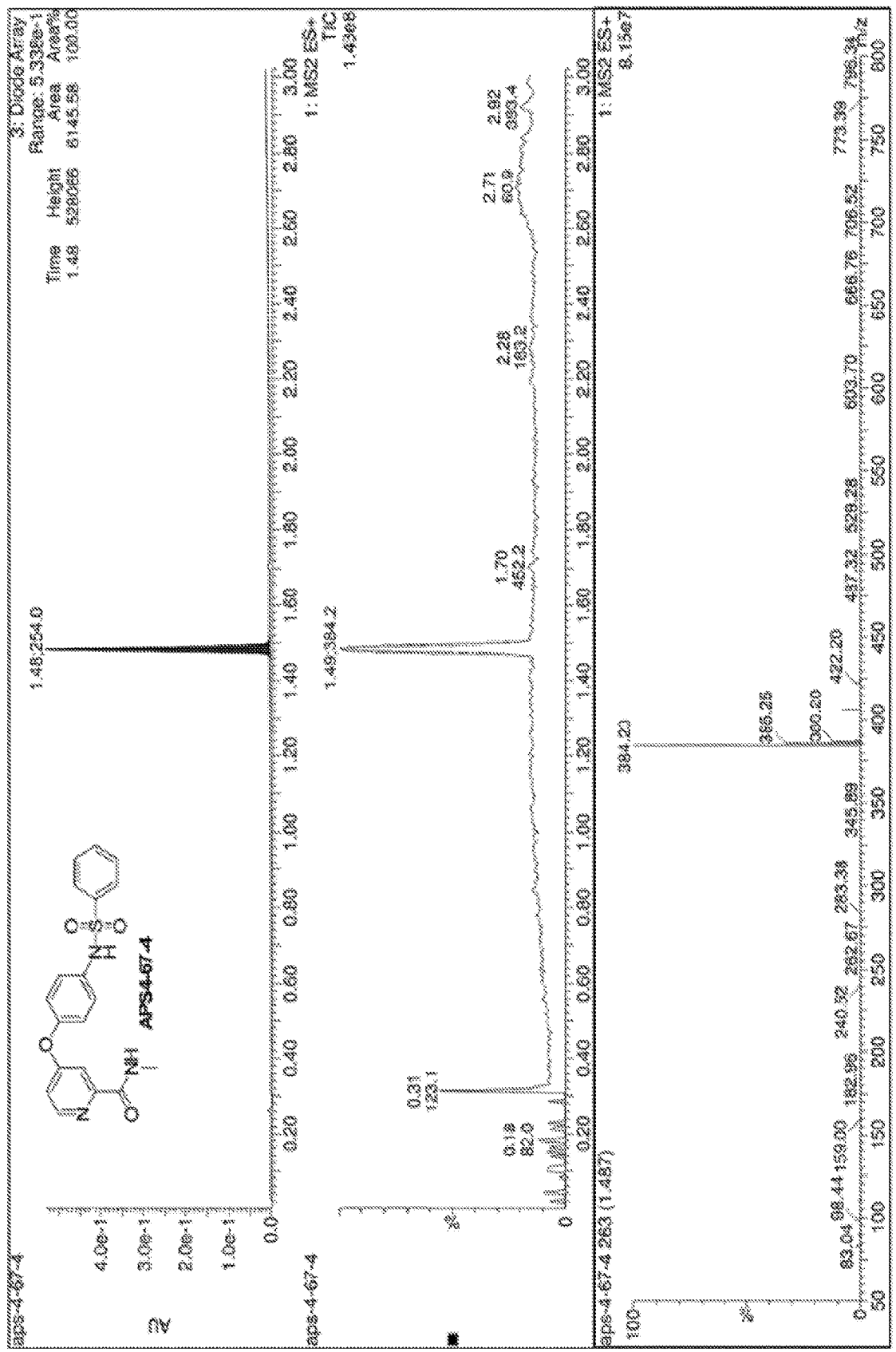
FIG. 39 shows LC-MS data for compound APS4-67-4.
Figure 40:
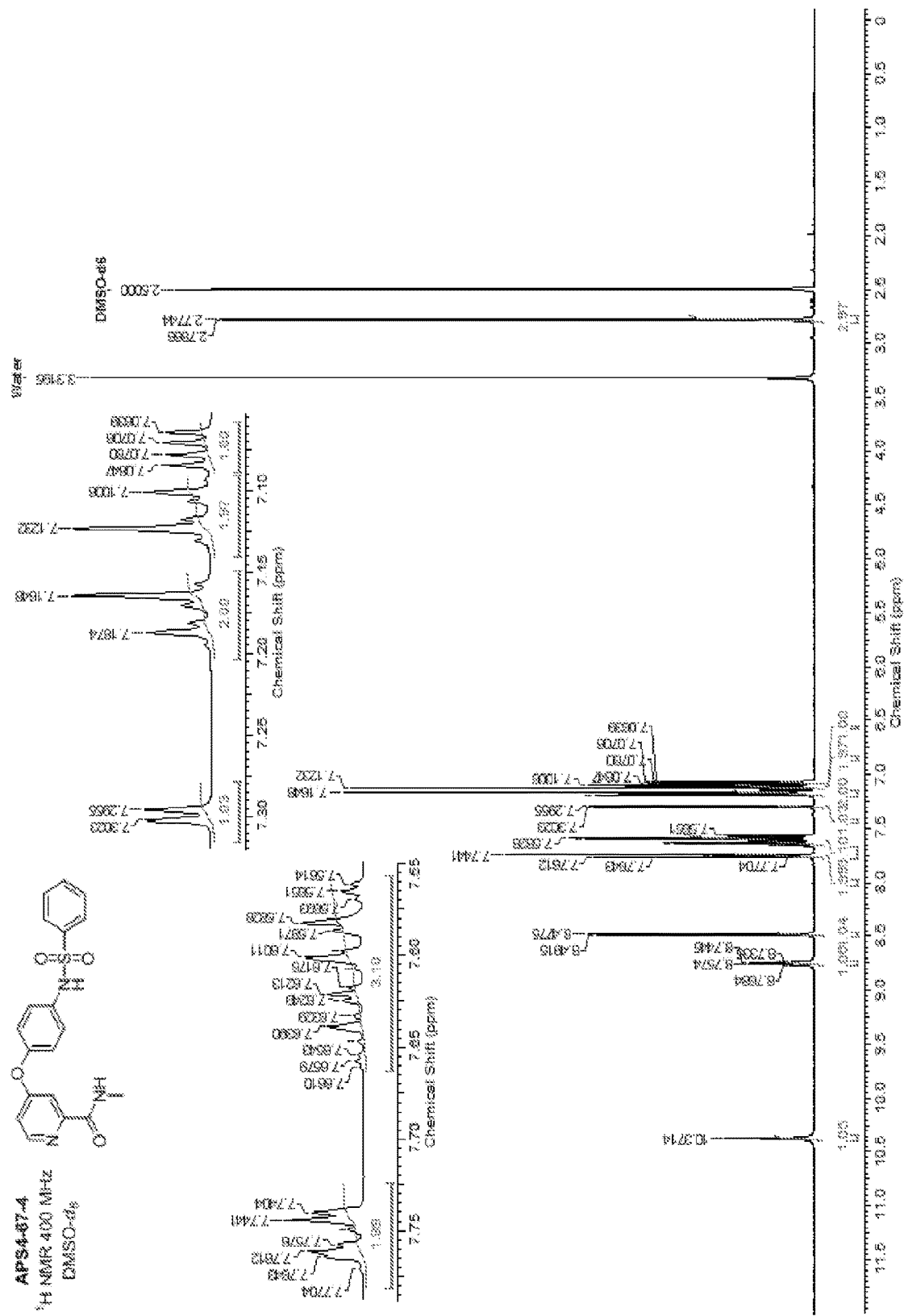
FIG. 40 shows $^1$H NMR spectra for compound APS4-67-4.

To a solution of HB/S1 (50.0 mg, 0.206 mmol) and CH$_2$Cl$_2$ (1 mL) was added benzene-1-sulfonyl chloride (32.0 μL, 0.251 mol; neat) and then pyridine (25.0 μL, 0.309 mmol). Obtained 58.1 mg (74%) of the title compound as an off-white solid: $^1$H NMR (400 MHz, DMSO-d$_6$) δ 10.37 (s, 1H), 8.75 (q, J=4.4 Hz, 1H), 8.48 (d, J=5.6 Hz, 1H), 7.72-7.78 (m, 2H), 7.55-7.67 (m, 3H), 7.30 (d, J=2.7 Hz, 1H), 7.15-7.20 (m, 2H), 7.09-7.14 (m, 2H), 7.07 (dd, J=5.6, 2.7 Hz, 1H), 2.78 (d, J=4.9 Hz, 2H); $^{13}$C NMR (100 MHz, DMSO-d$_6$) δ 165.6, 163.7, 152.5, 150.4, 149.6, 139.3, 135.3, 133.0, 129.3, 126.6, 122.5, 121.8, 114.1, 108.7, 26.0; LC-MS (ESI+) m/z: [M+H]$^+$ Calcd for C$_{19}$H$_{18}$N$_3$O$_4$S, 384.1; Found 384.2 (FIGS. 39-40).

Example 68

Preparation of N-Methyl-4-(4-(3-(trifluoromethyl) phenylsulfonamido) phenoxy)picolinamide (S1/L3/C2 (APS4-67-3))

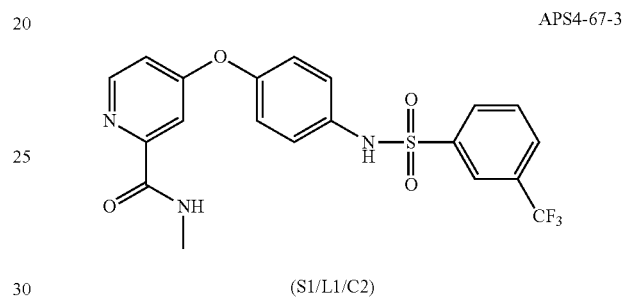

(S1/L1/C2)

To a solution of HB/S1 (50.0 mg, 0.206 mmol) and CH$_2$Cl$_2$ (1 mL) was added 3-(trifluoromethyl)benzene-1-sulfonyl chloride (40.0 μL, 0.250 mol; neat) and then pyridine (25.0 μL, 0.309 mmol). Obtained 37.4 mg (40%) of the title compound as an off-white solid: $^1$H NMR (400 MHz, DMSO-d$_6$) δ 10.51 (br s, 1H), 8.75 (br q, J=4.6 Hz, 1H), 8.48 (d, J=5.6 Hz, 1H), 7.96-8.08 (m, 3H), 7.81-7.88 (m, 1H), 7.32 (d, J=2.4 Hz, 1H), 7.11-7.21 (m, 4H), 7.06 (dd, J=5.6, 2.7 Hz, 1H), 2.78 (d, J=4.6 Hz, 3H); $^{19}$F NMR (376 MHz, DMSO-d$_6$) δ −61.1 (s, 3F); LC-MS (ESI+) m/z: [M+H]$^+$ Calcd for C$_{20}$H$_{17}$F$_3$N$_3$O$_4$S, 452.1; Found 452.2.

Example 69

Preparation of 4-(4-(4-Chloro-3-(trifluoromethyl) phenylsulfonamido) phenoxy)-N-methylpicolinamide (S1/L3/C3 (APS4-67-1))

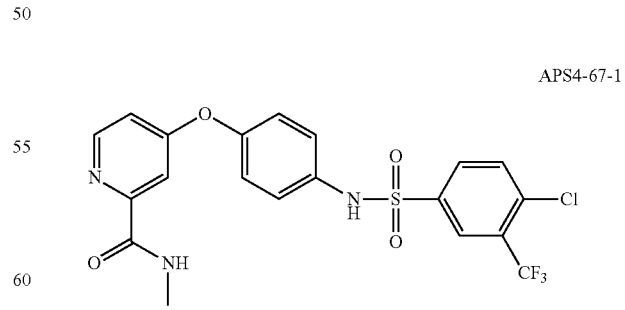

(S1/L3/C3)

Figure 41:
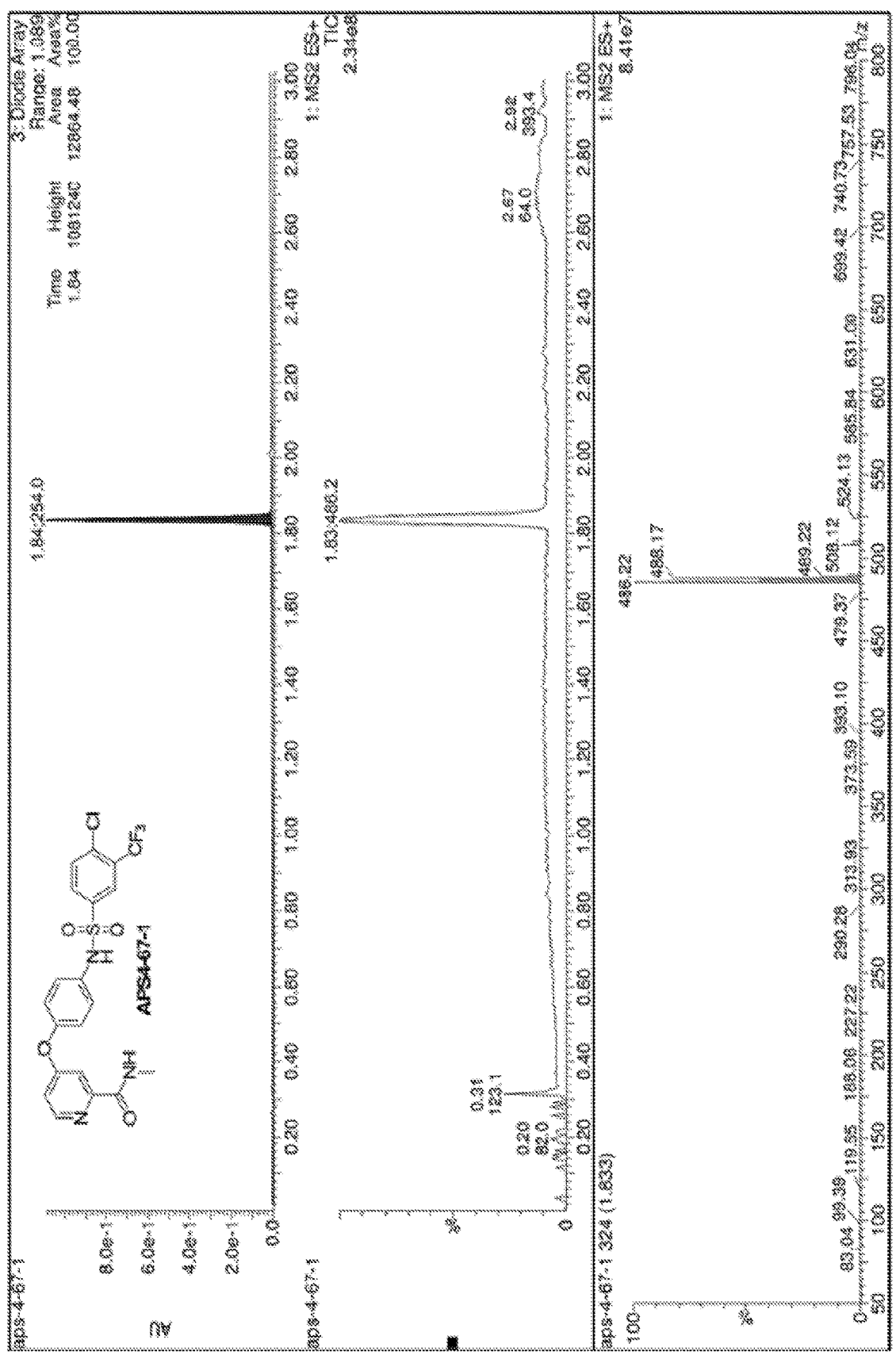
FIG. 41 shows LC-MS data for compound APS4-67-1.
Figure 42:
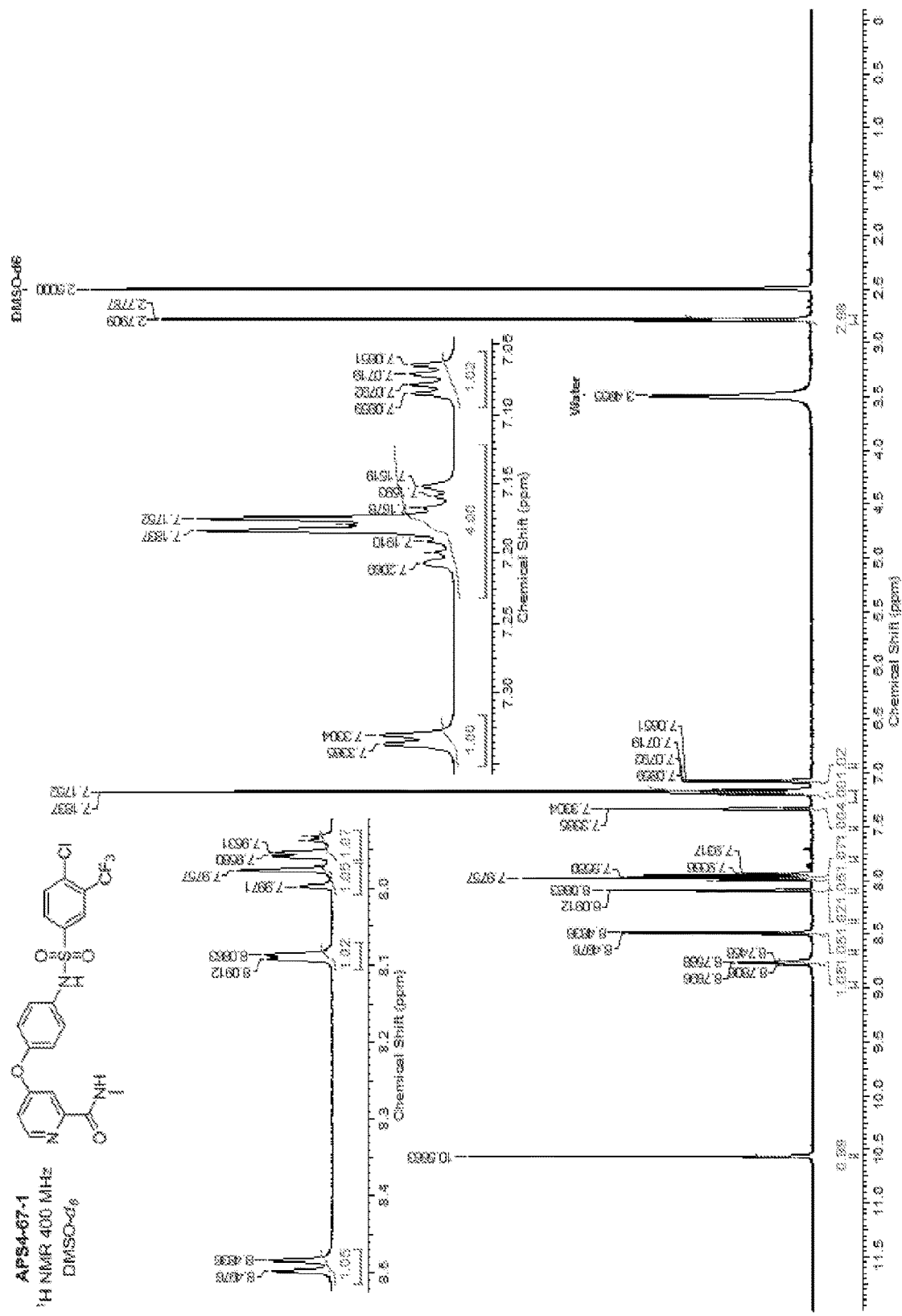
FIG. 42 shows $^1$H NMR spectra for compound APS4-67-1.

To a solution of HB/S1 (50.0 mg, 0.206 mmol) and CH$_2$Cl$_2$ (0.5 mL) was added 4-chloro-3-(trifluoromethyl) benzene-1-sulfonyl chloride (69.0 mg, 0.247 mmol; as a solution in 0.5 mL CH₂Cl₂) and then pyridine (25.0 μL, 0.309 mmol). Obtained 85.7 mg (86%) of the title compound as an off-white solid: $^1$H NMR (400 MHz, DMSO-d$_6$) δ 10.57 (s, 1H), 8.76 (br q, J=4.4 Hz, 1H), 8.49 (d, J=5.6 Hz, 1H), 8.09 (d, J=2.0 Hz, 1H), 7.97-8.01 (m, 1H), 7.92-7.97 (m, 1H), 7.33 (d, J=2.4 Hz, 1H), 7.14-7.22 (m, 4H), 7.08 (dd, J=5.6, 2.7 Hz, 1H), 2.78 (d, J=4.9 Hz, 3H); $^{19}$F NMR (376 MHz, DMSO-d$_6$) δ −61.5 (s, 3F); LC-MS (ESI+) m/z: [M+H]$^+$ Calcd for C$_{20}$H$_{16}$ClF$_3$N$_3$O$_4$S, 486.1; Found 486.2 (FIGS. 41-42).

Example 70

Preparation of 4-(4-(2-Fluoro-5-(trifluoromethyl)phenylsulfonamido) phenoxy)-N-methylpicolinamide (S1/L3/C4 (APS4-67-2))

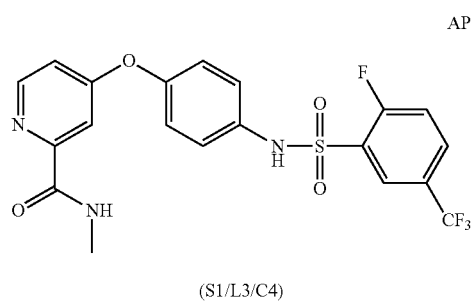

(S1/L3/C4)

Figure 43:
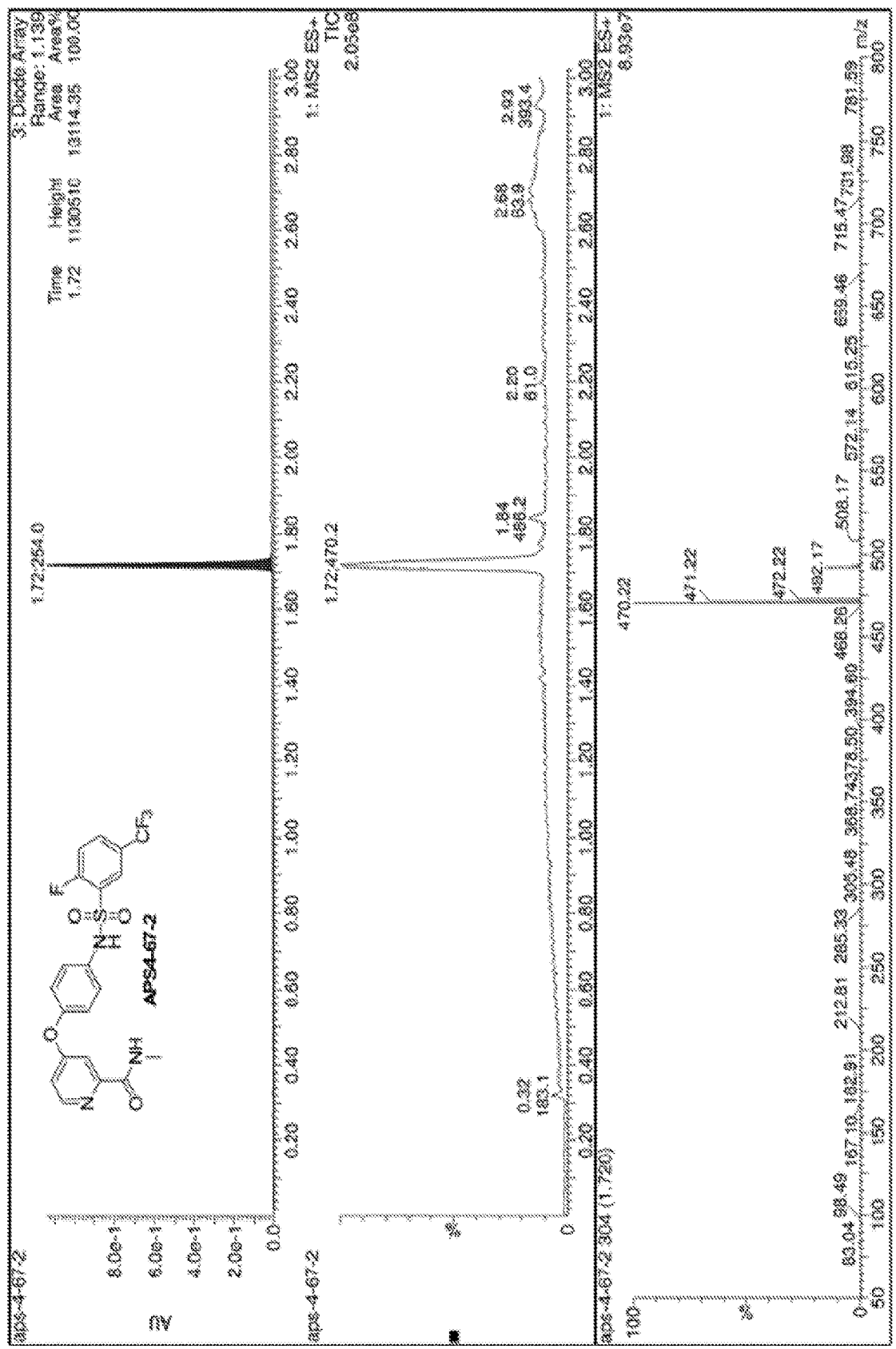
FIG. 43 shows LC-MS data for compound APS4-67-2.
Figure 44:
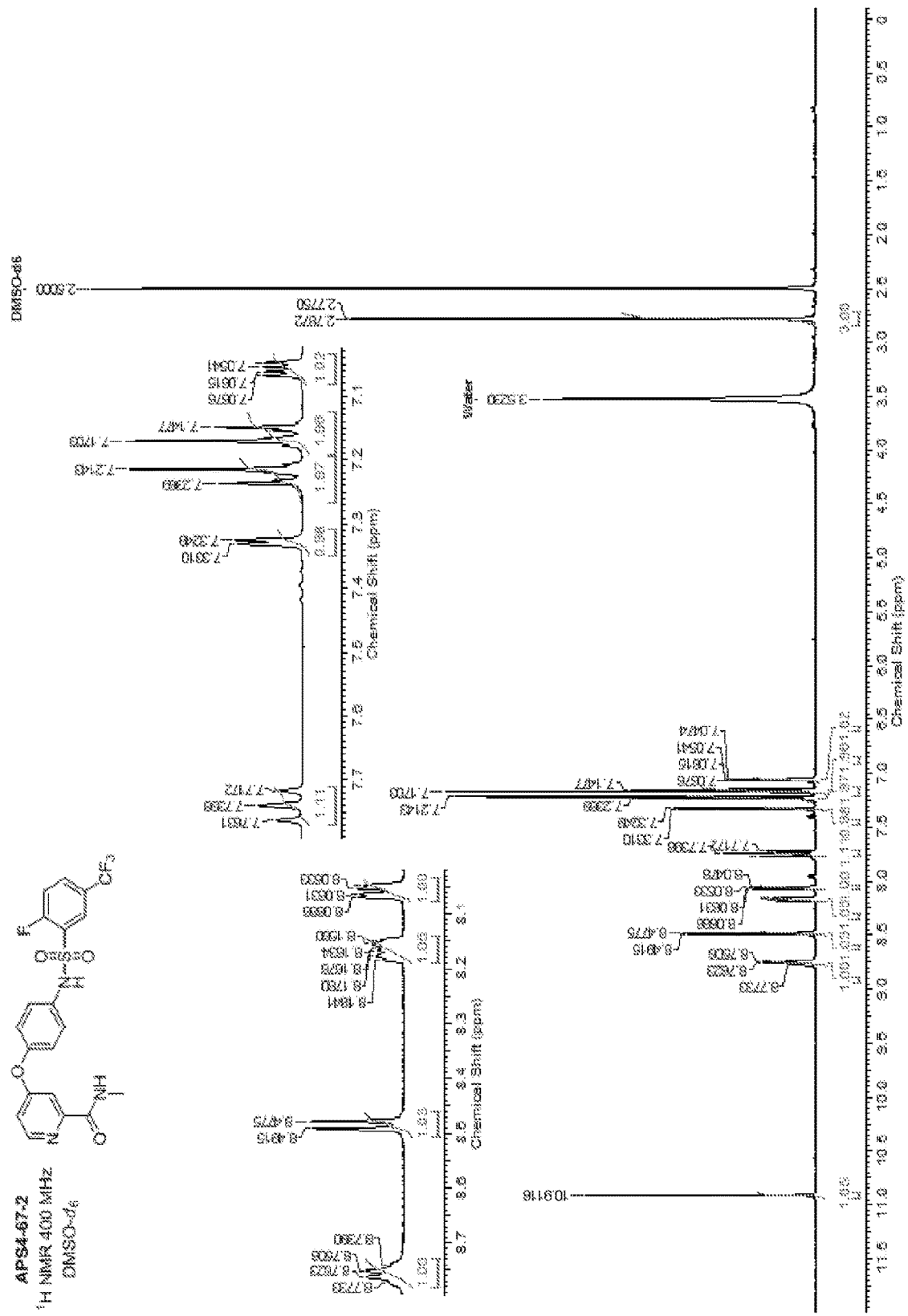
FIG. 44 shows $^1$H NMR spectra for compound APS4-67-2.

To a solution of HB/S1 (50.0 mg, 0.206 mmol) and CH₂Cl₂ (0.5 mL) was added 2-fluoro-5-(trifluoromethyl)benzene-1-sulfonyl chloride (65.0 mg, 0.248 mmol; as a solution in 0.5 mL CH₂Cl₂) and then pyridine (25.0 μL, 0.309 mmol). Obtained 54.6 mg (56%) of the title compound as an off-white solid: $^1$H NMR (400 MHz, DMSO-d$_6$) δ 10.91 (s, 1H), 8.76 (m, J=4.6 Hz, 1H), 8.48 (d, J=5.6 Hz, 1H), 8.14-8.20 (m, 1H), 8.06 (dd, J=6.1, 2.2 Hz, 1H), 7.74 (t, J=9.2 Hz, 1H), 7.33 (d, J=2.4 Hz, 1H), 7.20-7.25 (m, 2H), 7.13-7.19 (m, 2H), 7.06 (dd, J=5.5, 2.6 Hz, 1H), 2.78 (d, J=4.9 Hz, 3H); $^{19}$F NMR (376 MHz, DMSO-d$_6$) δ −60.4 (s, 3F), −102.8 (s, 1F); LC-MS (ESI+) m/z: [M+H]$^+$ Calcd for C$_{20}$H$_{16}$F$_4$N$_3$O$_4$S, 470.1; Found 470.2 (FIGS. 43-44).

Example 71

Preparation of 4-(3-Fluoro-4-(phenylsulfonamido)phenoxy)-N-methylpicolinamide (S2/L3/C1 (APS4-68-4))

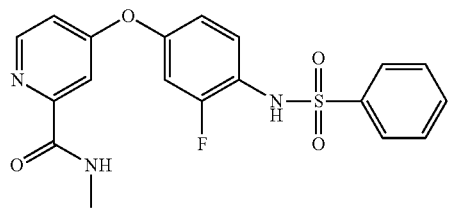

(S2/L3/C1)

Figure 45:
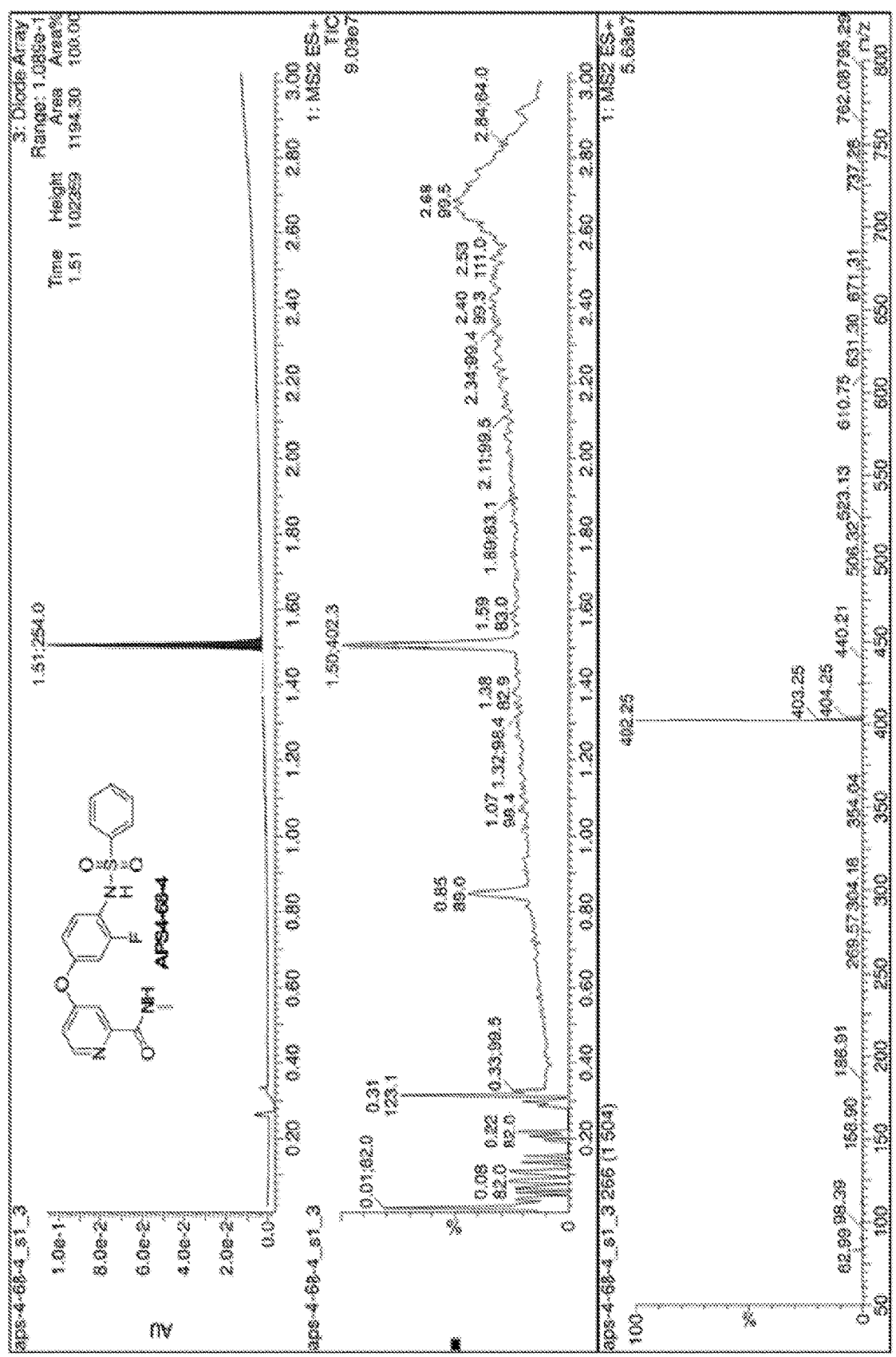
FIG. 45 shows LC-MS data for compound APS4-68-4.
Figure 46:
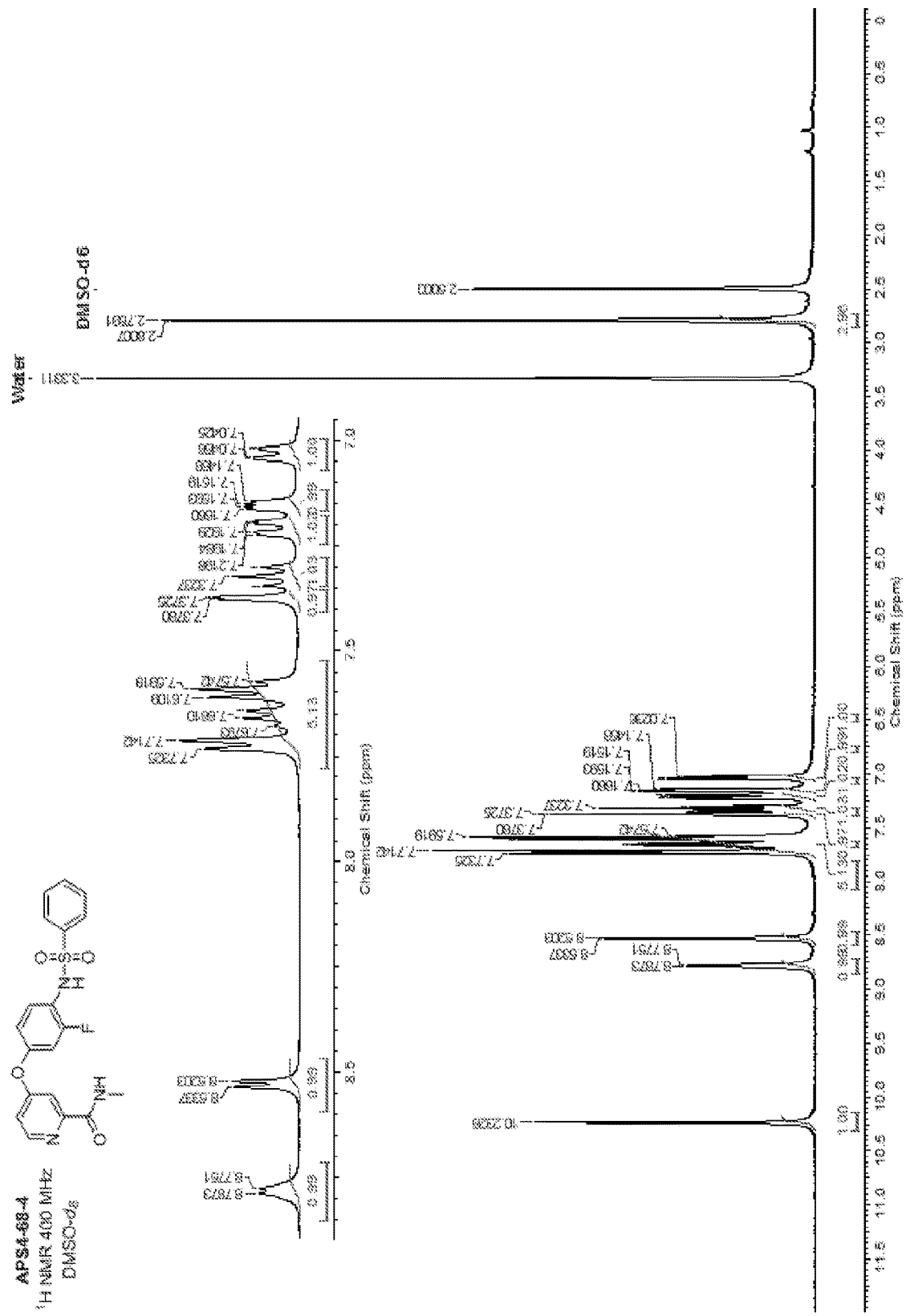
FIG. 46 shows $^1$H NMR spectra for compound APS4-68-4.

To a solution of HB/S2 (60.0 mg, 0.230 mmol) and CH₂Cl₂ (1 mL) was added benzene-1-sulfonyl chloride (35.0 μL, 0.274 mol; neat) and then pyridine (28.0 μL, 0.346 mmol). Obtained 44.5 mg (48%) of the title compound as a white solid: $^1$H NMR (400 MHz, DMSO-d$_6$) δ 10.23 (s, 1H), 8.78 (ap br d, J=4.9 Hz, 1H), 8.53 (d, J=5.4 Hz, 1H), 7.52-7.78 (m, 5H), 7.38 (d, J=2.2 Hz, 1H), 7.32 (t, J=8.9 Hz, 1H), 7.21 (dd, J=10.8, 2.2 Hz, 1H), 7.16 (dd, J=5.5, 2.6 Hz, 1H), 7.00-7.07 (m, 1H), 2.79 (d, J=4.9 Hz, 3H); $^{19}$F NMR (376 MHz, DMSO-d$_6$) δ −118.0 (s, 1F); LC-MS (ESI+) m/z: [M+H]$^+$ Calcd for C$_{19}$H$_{17}$FN$_3$O$_4$S, 402.1; Found 402.3 (FIGS. 45-46).

Example 72

Preparation of 4-(3-Fluoro-4-(3-(trifluoromethyl)phenylsulfonamido) phenoxy)-N-methylpicolinamide (S2/L3/C2 (APS4-68-3))

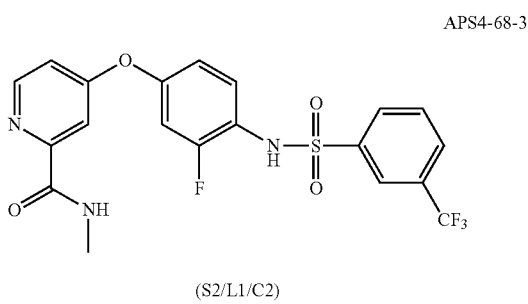 [SMILES: CNC(=O)c1cc(Oc2ccc(NS(=O)(=O)c3cccc(C(F)(F)F)c3)cc2)ccn1]

(S2/L1/C2)

Figure 47:
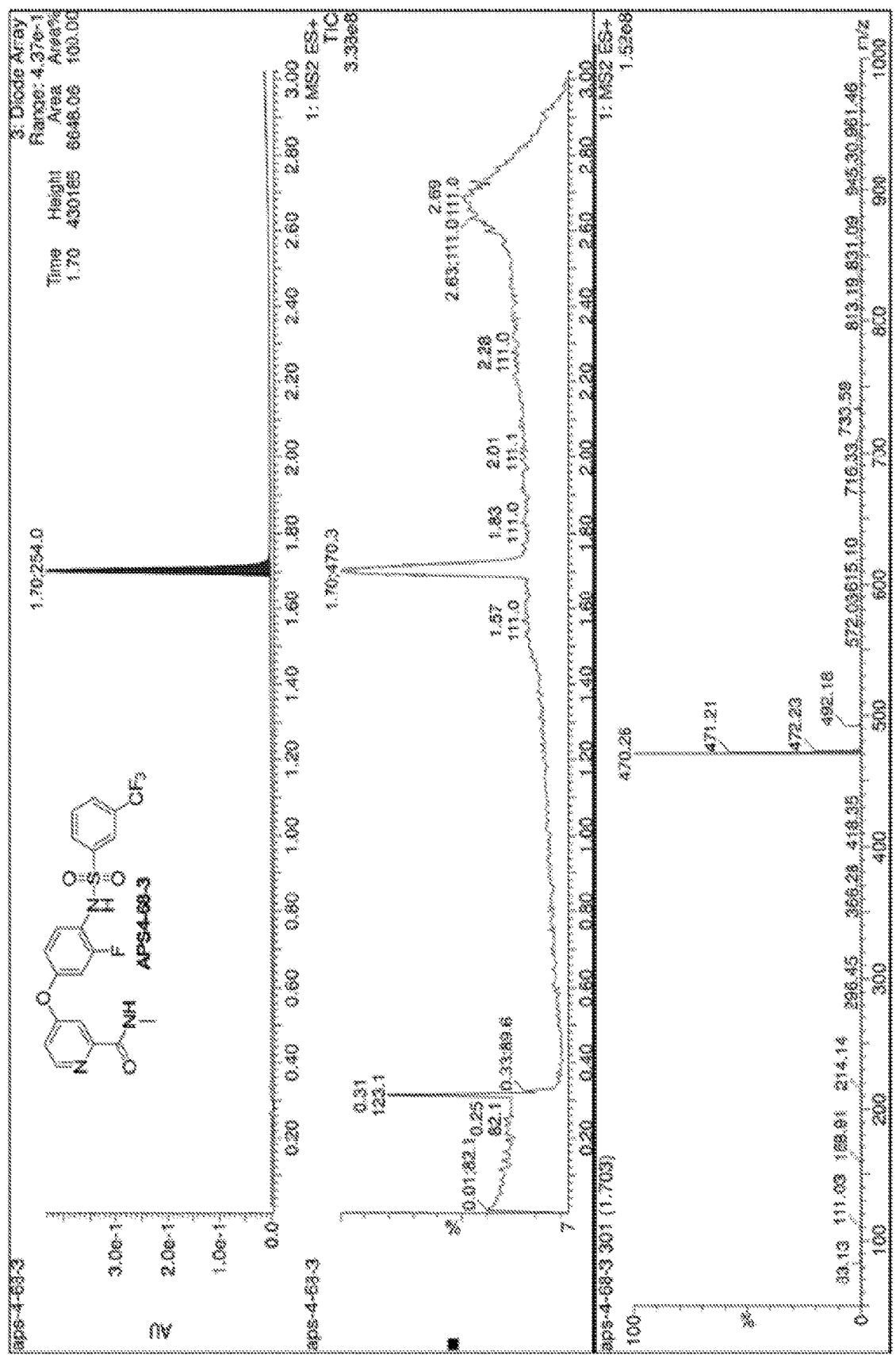
FIG. 47 shows LC-MS data for compound APS4-68-3.
Figure 48:
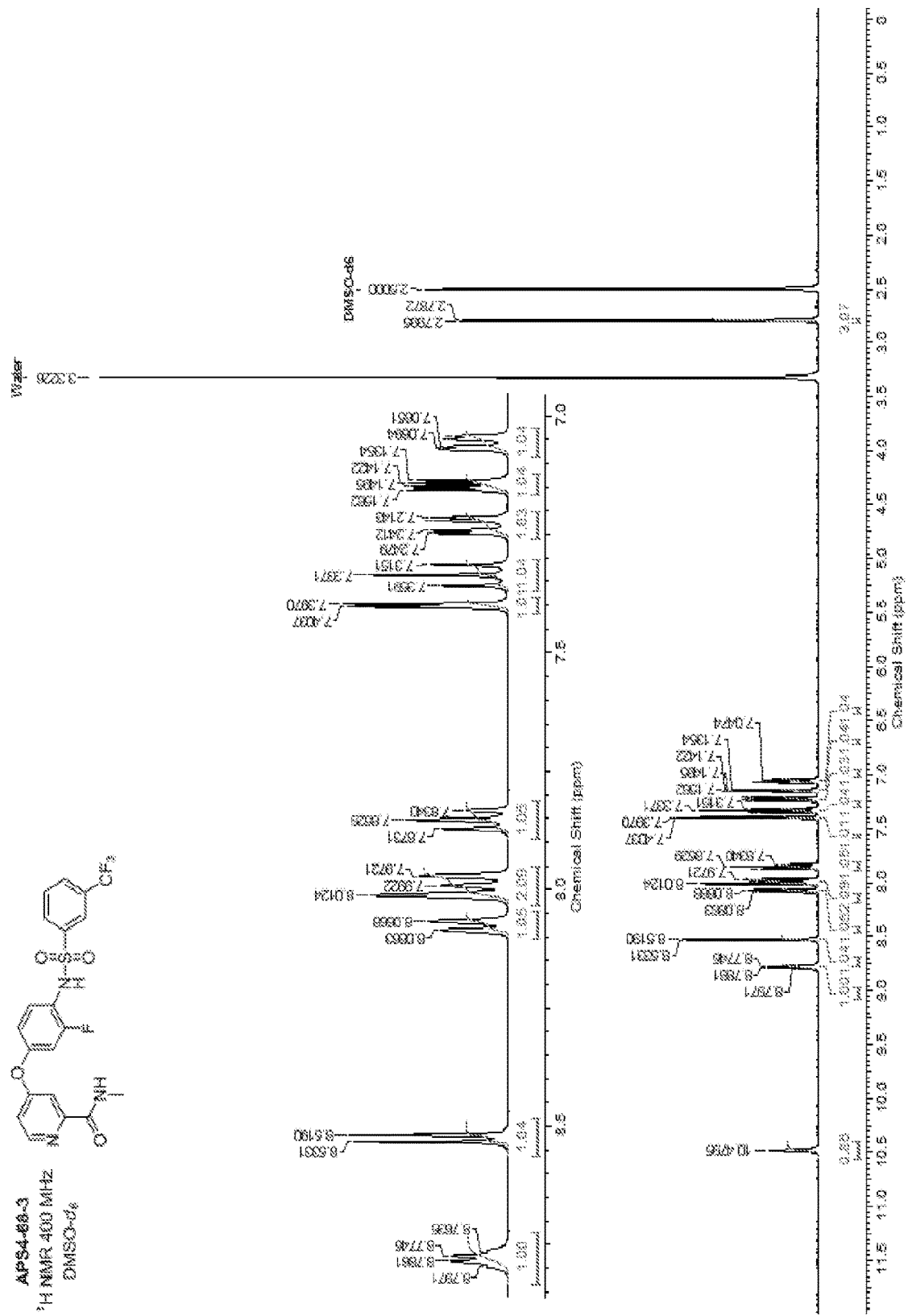
FIG. 48 shows $^1$H NMR spectra for compound APS4-68-3.

To a solution of HB/S2 (60.0 mg, 0.230 mmol) and CH₂Cl₂ (1 mL) was added 3-(trifluoromethyl)benzene-1-sulfonyl chloride (45.0 μL, 0.281 mol; neat) and then pyridine (28.0 μL, 0.346 mmol). Obtained 23.5 mg (22%) of the title compound as a white solid: $^1$H NMR (400 MHz, DMSO-d$_6$) δ 10.48 (br s, 1H), 8.78 (br q, J=4.4 Hz, 1H), 8.53 (d, J=5.6 Hz, 1H), 8.08 (d, J=7.8 Hz, 1H), 7.95-8.03 (m, 2H), 7.81-7.89 (m, 1H), 7.40 (d, J=2.7 Hz, 1H), 7.34 (t, J=8.8 Hz, 1H), 7.23 (dd, J=10.9, 2.6 Hz, 1H), 7.15 (dd, J=5.6, 2.7 Hz, 1H), 7.06 (dt, J=8.8, 1.3 Hz, 1H), 2.79 (d, J=4.9 Hz, 3H); $^{19}$F NMR (376 MHz, DMSO-d$_6$) δ −61.1 (s, 3F), −118.1 (s, 1F); LC-MS (ESI+) m/z: [M+H]$^+$ Calcd for C$_{20}$H$_{16}$F$_4$N$_3$O$_4$S, 470.1; Found 470.3 (FIGS. 47-48).

Example 73

Preparation of 4-(4-(4-Chloro-3-(trifluoromethyl)phenylsulfonamido)-3-fluorophenoxy)-N-methylpicolinamide (S2/L3/C3 (APS4-68-1))

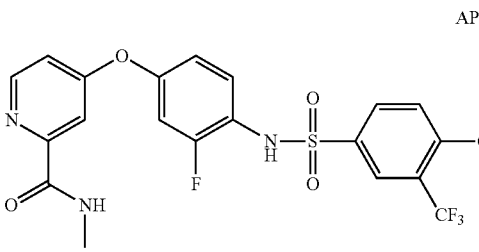

(S2/L3/C3)

Figure 49:
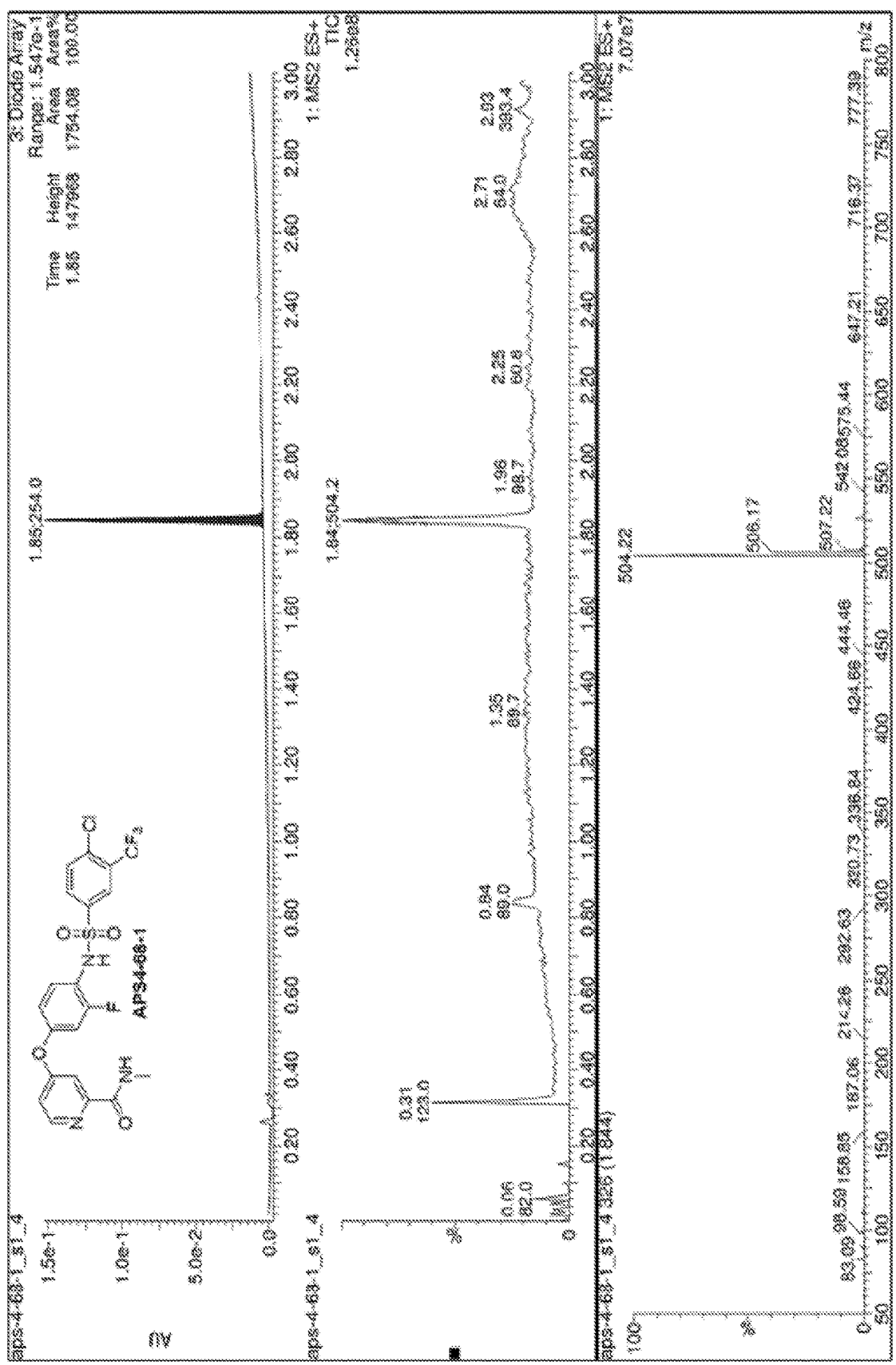
FIG. 49 shows LC-MS data for compound APS4-68-1.
Figure 50:
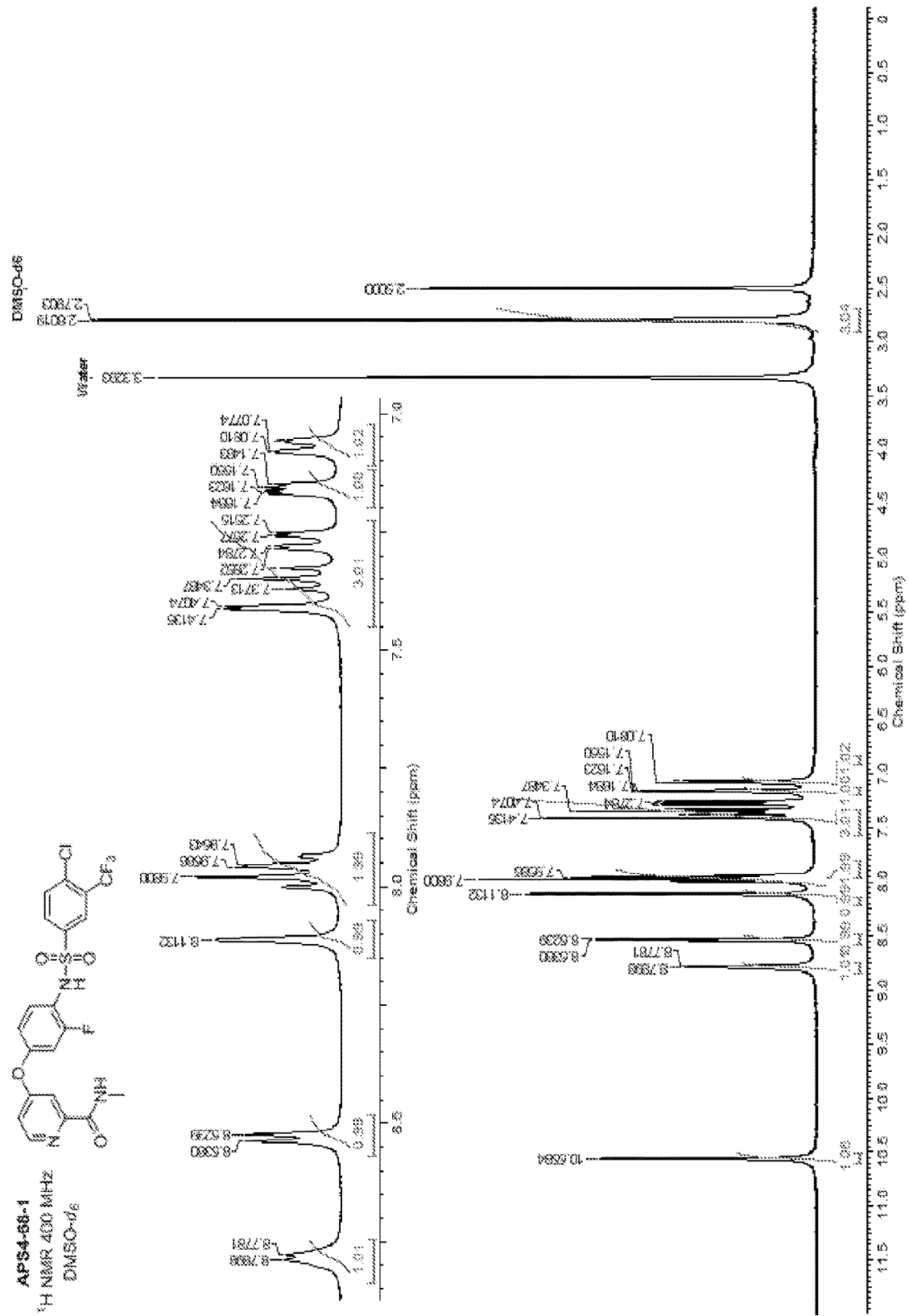
FIG. 50 shows $^1$H NMR spectra for compound APS4-68-1.

To a solution of HB/S2 (60.0 mg, 0.230 mmol) and CH$_2$Cl$_2$ (0.5 mL) was added 4-chloro-3-(trifluoromethyl) benzene-1-sulfonyl chloride (77.0 mg, 0.276 mmol; as a solution in 0.5 mL CH$_2$Cl$_2$) and then pyridine (28.0 µL, 0.346 mmol). Obtained 78.4 mg (68%) of the title compound as a white solid: $^1$H NMR (400 MHz, DMSO-d$_6$) δ 10.56 (s, 1H), 8.78 (br ap d, J=4.4 Hz, 1H), 8.53 (d, J=5.4 Hz, 1H), 8.11 (d, J=1.0 Hz, 1H), 7.89-8.04 (m, 2H), 7.41 (d, J=2.4 Hz, 1H), 7.35 (t, J=8.9 Hz, 1H), 7.27 (dd, J=10.9, 2.6 Hz, 1H), 7.16 (dd, J=5.5, 2.6 Hz, 1H), 7.07 (dd, J=8.7, 1.6 Hz, 1H), 2.80 (d, J=4.9 Hz, 3H); $^{19}$F NMR (376 MHz, DMSO-d$_6$) δ −61.5 (s, 3F), −118.0 (s, 1F); LC-MS (ESI+) m/z: [M+H]$^+$ Calcd for C$_{20}$H$_{15}$ClF$_4$N$_3$O$_4$S, 504.0; Found 504.2 (FIGS. 49-50).

Example 74

Preparation of 4-(3-Fluoro-4-(2-fluoro-5-(trifluoromethyl) phenylsulfonamido)phenoxy)-N-methyl-picolinamide (S2/L3/C4 (APS4-68-2))

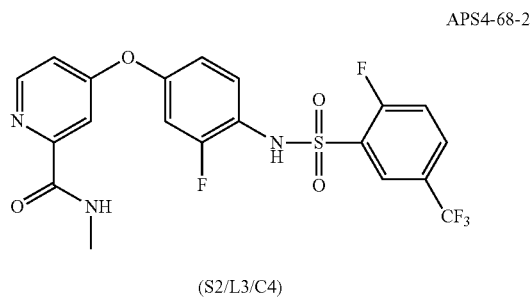 [SMILES: CNC(=O)c1cc(Oc2ccc(NS(=O)(=O)c3cc(C(F)(F)F)ccc3F)c(F)c2)ccn1]

APS4-68-2

(S2/L3/C4)

Figure 51:
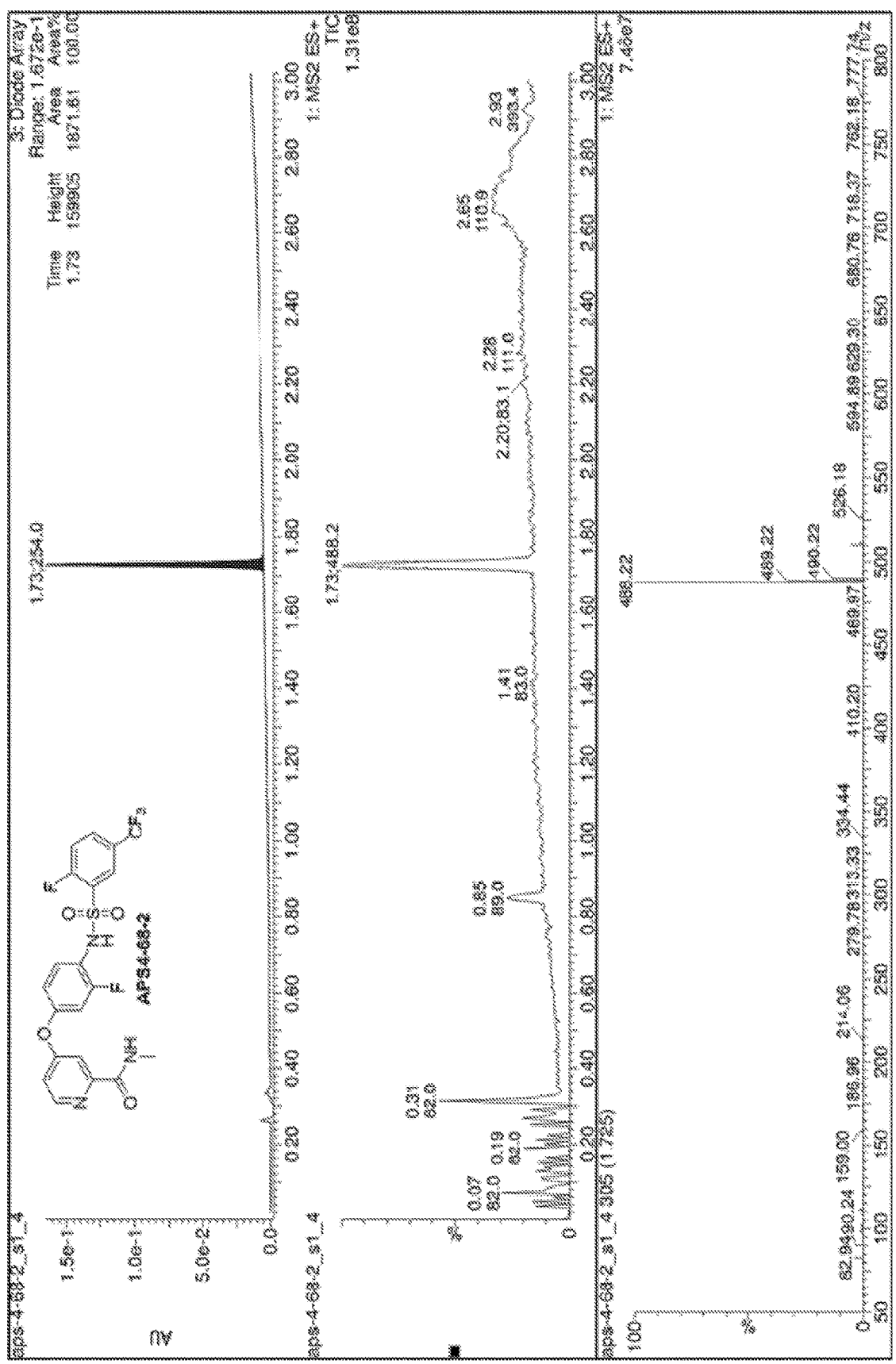
FIG. 51 shows LC-MS data for compound APS4-68-2.
Figure 52:
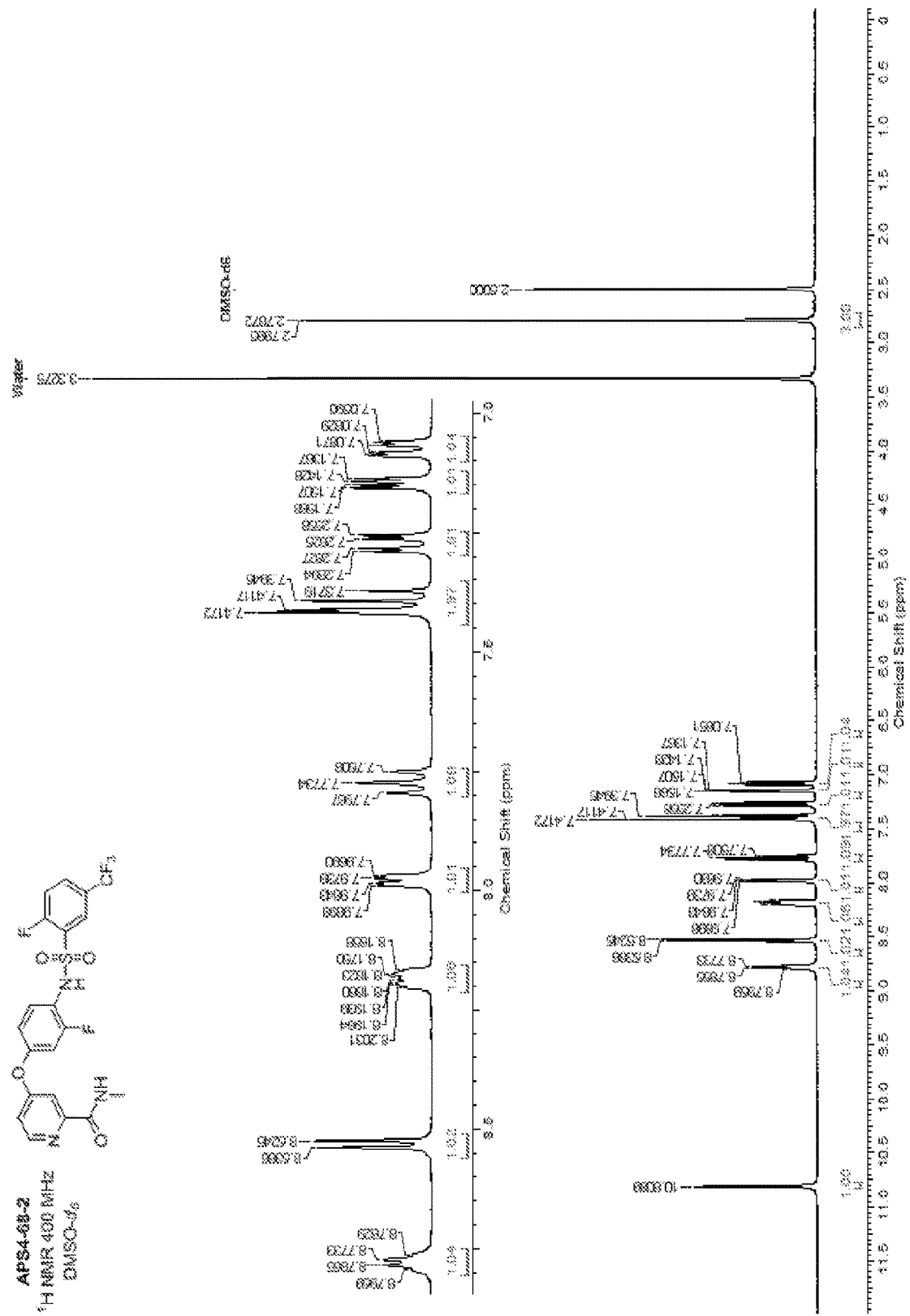
FIG. 52 shows $^1$H NMR spectra for compound APS4-68-2.

To a solution of HB/S2 (60.0 mg, 0.230 mmol) and CH$_2$Cl$_2$ (0.5 mL) was added 2-fluoro-5-(trifluoromethyl) benzene-1-sulfonyl chloride (72.5 mg, 0.276 mmol; as a solution in 0.5 mL CH$_2$Cl$_2$) and then pyridine (28.0 µL, 0.346 mmol). Obtained 78.4 mg (70%) of the title compound as a white solid: $^1$H NMR (400 MHz, DMSO-d$_6$) δ 10.81 (s, 1H), 8.78 (ap br d, J=4.9 Hz, 1H), 8.53 (d, J=5.4 Hz, 1H), 8.15-8.22 (m, 1H), 7.98 (dd, J=6.1, 2.0 Hz, 1H), 7.77 (t, J=9.2 Hz, 1H), 7.35-7.44 (m, 2H), 7.27 (dd, J=10.8, 2.7 Hz, 1H), 7.15 (dd, J=5.6, 2.4 Hz, 1H), 7.07 (ddd, J=8.7, 2.6, 1.1 Hz, 1H), 2.79 (d, J=4.9 Hz, 3H); $^{19}$F NMR (376 MHz, DMSO-d6) δ −60.4 (s, 3F), −102.6 (s, 1F), −117.9 (s, 1F); LC-MS (ESI+) m/z: [M+H]$^+$ Calcd for C$_{20}$H$_{15}$F$_5$N$_3$O$_4$S, 488.1; Found 488.2 (FIGS. 51-52).

Example 75

Materials and Methods

Fly Stocks

Kinase-mutated and balancer fly stocks were obtained from Bloomington *Drosophila* Stock Center (BDSC; Bloomington, Ind.). FM7a- or FM7c-balanced flies with mutated kinase genes on X chromosome were outcrossed with FM7a-Tb-RFP-balanced flies, and CyO- or SMS-balanced flies were rebalanced with CyO-Tb-RFP balancer (Lattao et al., "Tubby-Tagged Balancers for the *Drosophila* X and Second Chromosomes," Fly 5:369-370 (2011), which is hereby incorporated by reference in its entirety). Likewise, TM3- or MKRS-balanced flies were rebalanced with TM6B balancer. The active mutant form of dRet (dRet$^{M955T}$) carries M1007T mutation which corresponds to M918T mutation found in MEN type 2B patients (Vidal et al., "ZD6474 Suppresses Oncogenic RET Isoforms in a *Drosophila* Model for Type 2 Multiple Endocrine Neoplasia Syndromes and Papillary Thyroid Carcinoma," *Cancer Res.* 65:3538-3541 (2005), which is hereby incorporated by reference in its entirety). The ptc-gal4, UAS-GFP; UAS-dRet$^{M955T}$/SMS(tub-gal80)-TM6B transgenic flies were prepared according to standard protocols, and crossed with w$^−$ and kinase-mutant flies for drug screening and kinome genetic screening, respectively (FIGS. 62A-H). To validate the results of genetic screening, ten more alleles for the pro-targets were randomly picked and tested. Obtained results were essentially similar to the results for nine genes, confirming the integrity of the experimental design to determine pro-targets. Human orthologs of fly genes were predicted by DIOPT (www.flyrnai.org/cgi-bin/DRSC_orthologs.pl).

Fly Assays

FDA-approved drugs and sorafelogs were purchased from Selleck Chemicals (Houston, Tex.), LC Laboratories (Woburn, Mass.), and Tocris Bioscience (UK), or synthesized in-house. AD80 was synthesized as previously described (Dar et al., "Chemical Genetic Discovery of Targets and Anti-Targets for Cancer Polypharmacology," *Nature* 486: 80-84 (2012), which is hereby incorporated by reference in its entirety). All compounds were dissolved in DMSO and mixed with Semi-defined fly medium (BDSC) to make drug food (0.1% final DMSO concentration). About 100 ptc>dRet$^{M955T}$ embryos with or without kinase mutations were raised until adulthood on drug food for 15 days at 23° C. (genetic screening) or 13 days at 25° C. (drug screening and wing venation assay). The number of empty pupal cases (P in FIG. 53A) was divided by that of total pupal cases (A) to determine % viability.

Cell Migration and Wing Venation Assays

For in vivo cell migration assays, third-instar larvae were dissected to collect developing wing discs. After fixation with 4% paraformaldehyde in PBS, discs were whole-mounted and observed for dRet$^{M955T}$-expressing cells labeled with GFP under a confocal microscope. At least 20 wing discs were studied for each genotype or treatment. Phospho-Src was stained with anti-Src(pY418) antibody (Invitrogen). For wing venation assays, wing-specific 765-gal4 driver line was crossed with UAS-dRet$^{M955T}$ flies. More than 15 adult wings were scored for abnormal wing venation.

MTT Assays Using Cancer Lines

TT human MTC cells were cultured in RPMI1640 supplemented with 10% fetal bovine serum, 100 units/ml penicillin, and 0.1 mg/ml streptomycin mix at 37° C. Cells in 96-well plates were incubated with various doses of kinase inhibitors for 5 days, and cell viability was determined using Thiazolyl Blue Tetrazolium Bromide (MTT; SIGMA, St. Louis, Mo.) according to manufacturer's protocol.

Kinase Percent Inhibition Measurements

Figure 61:
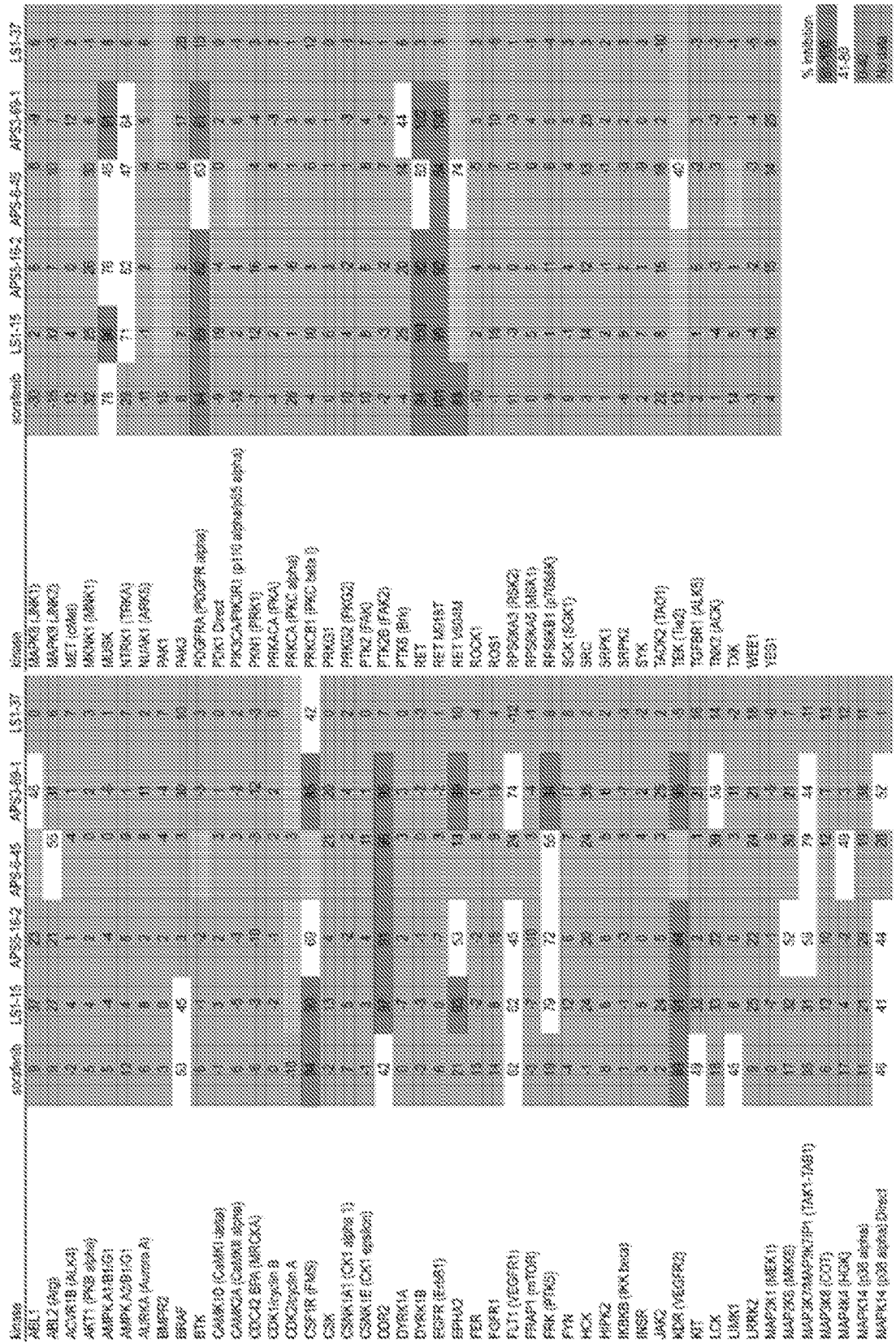
FIG. 61 is a table showing in vitro inhibition data for kinases. Percent inhibition of human kinase activities by sorafelogs. Red, greater than 80% inhibition. White, 41-80% inhibition. Blue, less than 40% inhibition. Grey, no useful data.
Figure 62:
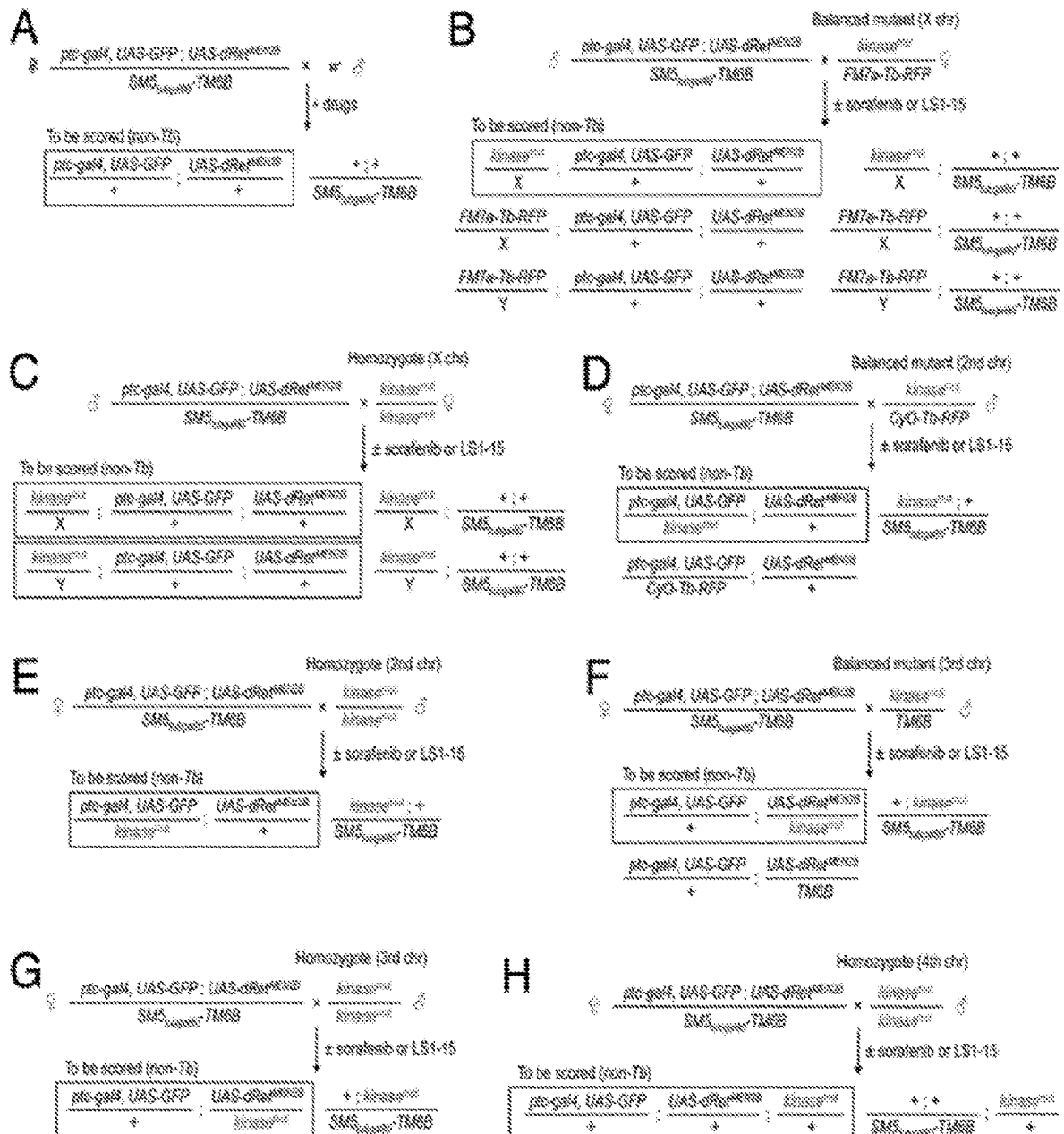
FIGS. 62A-H show determination of effects of inhibitors or heterozygosity of kinase genes in the *Drosophila* MTC model. In ptc-gal4, UAS-GFP; UAS-dRet$^{M955T}$/SMS(tub-gal80)-TM6B flies, tubulin promoter-driven gal80 inhibited gal4 activity to repress dRet$^{M955T}$ expression. For drug screening, they were crossed with w$^-$ flies to create non-Tb, oncogenic ptc-gal4, UAS-GFP; UAS-dRet$^{M955T}$ (ptc>dRet$^{M955T}$) flies that were morphologically distinguishable from Tb control flies at the pupal stage (FIG. 62A). Fly progenies were treated with or without drugs, and raised at 25° C. For genetic screening, ptc>dRet$^{M955T}$ flies were crossed with flies mutant for a kinase gene on either X (FIGS. 62B-C), 2nd (FIGS. 62D-E), 3rd (FIGS. 62F-G), or 4th (FIG. 62H) chromosomes, and their progenies were raised on fly food with or without drugs at 23° C. Mutant alleles in parent flies were either balanced with Tb allele (FIGS. 62B, 62D, and 62F), or homozygous (FIGS. 62C, 62G, and 62H).

The sorafelogs were assayed against a panel of purified human kinases (ThermoFisher) to measure percentage inhibition values and derive kinome profiles (FIG. 61). All compounds were screened at 1 µM, using two biological replicates to determine percent inhibition values. Detailed procedures for kinase reactions and assay formats are described at www.thermofisher.com/kinaseprofiling.

Kd Measurements

Kd values were determined by DiscoverX using a bead based competition assay (KINOMEscan). In brief, kinases were expressed on phage and immobilized on beads via active site-directed ligands. Test compounds were premixed with kinases and assayed for the ability to compete for immobilized ligands. Binding constants were calculated with a standard dose-response curve and the Hill equation, with Hill slope set to −1. The method has been used extensively to characterize kinase inhibitor-binding data (Davis et al., "Comprehensive Analysis of Kinase Inhibitor Selectivity," *Nat. Biotechnol.* 29:1046-51 (2011); Young et al., "Structure of the Kinase Domain of an Imatinib-Resistant Abl Mutant in Complex with the Aurora Kinase Inhibitor VX-680," *Cancer Res.* 66:1007-14 (2006), which are hereby incorporated by reference in their entirety). For each sorafelog-kinase pair, an 11-point series ranging from 30,000 to 0.5 nM, in 3-fold dilutions, were used to derive Kd values. Kd values and s.e.m. are the average of two biological replicates.

Computation: DFG-Out Modeling

Because sorafenib and other related kinase inhibitors are known type-II inhibitors that bind the DFG-out conformation, it was hypothesized that sorafelogs are also type-II kinase inhibits. To rationally design potent type-II inhibitors atomic structures of pro-targets and anti-targets in their DFG-out conformation were needed. While some pro-targets/anti-targets do not have known structures in the DFG-out conformation, homology modeling was used_to predict their structures. In particular, a DFGmodel was used that models a DFG-out conformation from the active DFG-in structure or sequence information alone (Ung et al., "DFG-model: Predicting Protein Kinase Structures in Inactive States for Structure-Based Discovery of Type-II Inhibitors," *ACS Chem. Biol.* 10:269-278 (2015), which is hereby incorporated by reference in its entirety).

Briefly, the sequence of the target kinases were aligned to a set of template kinase structure that represent a unique range of DFG-out conformations. DFGmodel then called on the automatic multi-template function of MODELLER (Sali et al., "Comparative Protein Modelling by Satisfaction of Spatial Restraints," *J. Mol. Biol.* 234:779-815 (1993), which is hereby incorporated by reference in its entirety) to generate homology models of the DFG-out conformation. Fifty initial models were built for each alignment and ranked according to the inhibitor-binding site volume calculated by POVME v2.0 (Durrant et al., "POVME 2.0: An Enhanced Tool for Determining Pocket Shape and Volume Characteristics," *J. Chem. Theory Comput.* 10:5047-5056 (2014), which is hereby incorporated by reference in its entirety), which was shown to be a good predictor of kinase-inhibitor binding for DFG-out models. For each kinase, 10 DFG-out models were selected based on their ability to discriminate of known type-II inhibitors from non-binders, thereby optimizing the model for protein-type II inhibitor complementarity.

Computation: Torsion Angle

The torsional energy of the urea linker to the N-substituents was calculated with Schrödinger's Maestro (Maestro, version 10.3, Schrödinger, LLC, New York, N.Y., 2015, which is hereby incorporated by reference in its entirety) using the molecular mechanics OPLS_2005 force field in aqueous solution. The torsion angles were scanned at two-degree intervals. The relative torsional energy was plotted against the torsional angles and compared to the corresponding torsional angles observed in the reference sorafenib x-ray structures.

Computation: DFG-Pocket

The average volume of the DFG-pocket of the top 10 DFG-out models generated by DFGmodel was calculated using POVME 2.0 (Durrant et al., "POVME 2.0: An Enhanced Tool for Determining Pocket Shape and Volume Characteristics," *J. Chem. Theory Comput.* 10:5047-5056 (2014), which is hereby incorporated by reference in its entirety).

Example 76

Sorafenib was Effective in a *Drosophila* MTC Model

The window between tumor inhibition and general toxicity, referred to as the therapeutic index, defines the effectiveness of clinical cancer drugs. Currently 31 kinase inhibitors are FDA approved for patient use. Most of these drugs show a narrow therapeutic index due to (i) the complexity of tumors coupled with (ii) the importance of maintaining proper cellular networks including those in normal tissues to minimize toxicity. Overall, the success rates of clinical trials for anti-cancer drugs have remained the lowest among drugs for major diseases, and the majority of failures are due to limited therapeutic index (Meanwell, N. A., "Improving Drug Candidates by Design: A Focus on Physicochemical Properties as a Means of Improving Compound Disposition and Safety," *Chem. Res. Toxicol.* 24:1420-1456 (2011); Hay et al., "Clinical Development Success Rates for Investigational Drugs," *Nat. Biotechnol.* 32:40-51 (2014), which are hereby incorporated by reference in their entirety). Emergent resistant to targeted therapies has often limited their effectiveness at increasing overall survival.

A transgenic *Drosophila* model for medullary thyroid cancer (MTC) was previously reported in which the patched (ptc) promoter directs expression of the M955T isoform of *Drosophila* Ret designed to model the human oncogenic isoform RET(M918T) (Dar et al., "Chemical Genetic Discovery of Targets and Anti-Targets for Cancer Polypharmacology," *Nature* 486:80-84 (2012); Mulligan, "RET Revisited: Expanding the Oncogenic Portfolio," *Nat. Rev. Cancer* 14:173-186 (2014), which are hereby incorporated by reference in their entirety). 100% of ptc>dRet$^{M955T}$ flies die before adulthood when cultured at 25° C., providing an efficient and quantitative "rescue-from-lethality" assay for candidate drugs (FIGS. 53A and 62A; (Dar et al., "Chemical Genetic Discovery of Targets and Anti-Targets for Cancer Polypharmacology," *Nature* 486:80-84 (2012), which is hereby incorporated by reference in its entirety)). This assay categorized molecules based on therapeutic index, where effective compounds must suppress oncogenic Ret-induced toxicity while not exhibiting toxic effects during normal fly development. Promising hits were then assessed for their ability to reduce Ret-mediated transformation.

Figure 54D:
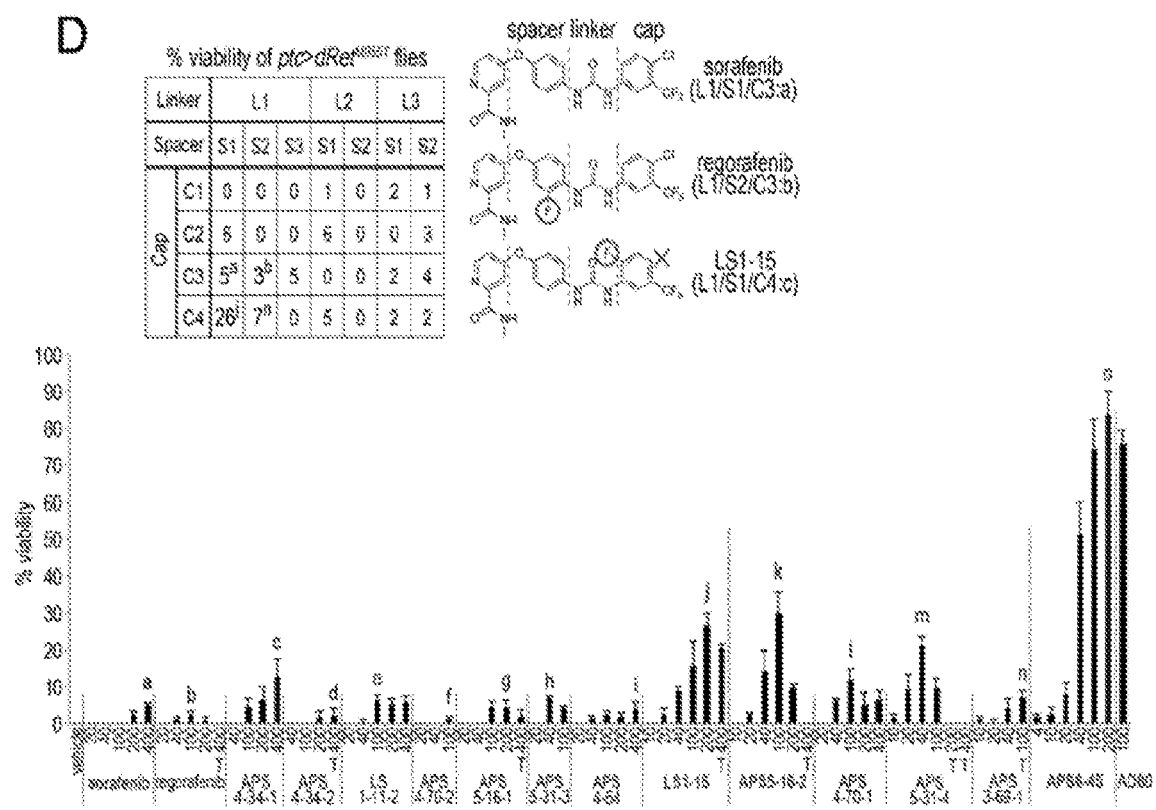

To select a drug to improve, a screen of clinical kinase inhibitors approved by the FDA for cancer therapy as of 2015 was performed. Drugs were mixed into fly media and thereby delivered orally. Of the 31 kinase inhibitors tested, sorafenib provided the strongest rescue-from-lethality of ptc>dRet$^{M955T}$ flies (FIG. 53B). Despite providing the strongest improvement of fly viability, however, sorafenib rescue was low (~5%) and the therapeutic window was small (only a 200-400 μM range in fly food; see FIG. 54D). This is consistent with reports from human patients: sorafenib displays marginal efficacy in treating liver and renal cell cancers as well as differentiated thyroid cancers, with severe side effects including diarrhea, pancreatic atrophy, and emergent skin tumors in treated patients (Hescot et al., "Pancreatic Atrophy—A New Late Toxic Effect of Sorafenib," *N. Engl. J. Med.* 369:1475-1476 (2013); Fu et al., "Inhibition of BET Bromodomains as a Therapeutic Strategy for Cancer Drug Discovery," *Oncotarget.* 6:5501-5516 (2015); Gharwan et al., "Kinase Inhibitors and Monoclonal Antibodies in Oncology: Clinical Implications," *Nat. Rev. Clin. Oncol.* 13:209-227 (2016), which are hereby incorporated by reference in their entirety). Of note, weak efficacy for the colorectal cancer drug regorafenib (Wilhelm et al., "Regorafenib (BAY 73-4506): A New Oral Multikinase Inhibitor of Angiogenic, Stromal and Oncogenic Receptor Tyrosine Kinases with Potent Preclinical of Antitumor Activity," *Int. J. Cancer* 129:245-255 (2011), which is hereby incorporated by reference in its entirety) a sorafenib analog that possesses an additional fluorine atom, was also found (FIG. 54D).

In addition to directing late lethality, the ptc>dRet$^{M955T}$ transgenes targeted dRet$^{M955T}$ expression to a stripe of cells at the midline of the developing wing disc epithelium; cells were visualized with an included UAS-GFP transgene. These ptc>dRet$^{M955T}$ cells underwent an epithelial-to-mesenchymal transition (EMT) and subsequent invasion beneath the wing epithelium, modeling early steps in cell transformation and metastasis (Vidal et al., "Csk-Deficient Boundary Cells are Eliminated from Normal *Drosophila* Epithelia by Exclusion, Migration, and Apoptosis," *Dev. Cell* 10:33-44 (2006); Rudrapatna et al., "A Jnk-Rho-Actin Remodeling Positive Feedback Network Directs Src-Driven Invasion," *Oncogene* 33(21):2801-2806 (2014), which are hereby incorporated by reference in their entirety). Sorafenib consistently suppressed both EMT and migration of dRet$^{M955T}$-expressing wing cells (FIG. 53C), demonstrating its ability to reduce aspects of transformation.

Example 77

Sorafelogs Demonstrate Striking Structure-Activity Relationships

Sorafenib binds to multiple kinases including RET, BRAF, and KDR/VEGFR (Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis," *Cancer Res.* 64:7099-7109 (2004), which is hereby incorporated by reference in its entirety). Crystal structures of sorafenib bound to these and other kinases revealed similar binding poses (FIG. 54A, left). Based on structural analysis, sorafenib was conceptually deconstructed into four subunits: (i) hinge binder that occupies the ATP-binding site of a target kinase (held constant in our studies), (ii) spacer, (iii) linker, and (iv) cap. The cap extends into the hydrophobic DFG-pocket, an element within the kinase domain that differs in composition and size between kinases (FIG. 54A; (Ung et al., "DFGmodel: Predicting Protein Kinase Structures in Inactive States for Structure-Based Discovery of Type-II Inhibitors," *ACS Chem. Biol.* 10:269-278 (2015), which is hereby incorporated by reference in its entirety)).

As part of the chemical modifier approach, sorafenib analogs ("sorafelogs") were developed to be used for SAR analysis in the ptc>dRet$^{M955T}$ model (FIG. 54B). The sorafelog series included molecules with varied linkers (L1-L6), spacers (S1-S4), or combinations in the context of four different caps (C1-C4; FIG. 54C). For initial series, approximately 100 sorafelogs were synthesized; the activity of these compounds was assessed based on rescue of ptc>dRet$^{M955T}$ animals (FIGS. 54D and 58A). Several general features emerged from this analysis. For example in the context of the cap test group ($C_1$-$C_4$), linkers L4, L5, and L6, and spacer S4 were ineffective (0% rescue, grey in FIG. 54C); the amide (L2) and the sulfonamide (L3) linkers showed weak activity. Overall, the urea (L1) proved most effective with variations at the cap position (FIG. 54D).

From initial series, the sorafelog LS1-15, a compound with the linker-spacer-cap structure of L1/S1/C4:j was identified as the most effective in rescuing lethality of ptc>dRet$^{M955T}$ animals (FIGS. 54C and 54D). LS1-15 was significantly more effective than sorafenib (L1/S1/C3:a). Additionally, both sorafenib and LS1-15 were more effective than their spacer S2 counterparts regorafenib (L1/S2/C3:b) and APS-3-69-1 (L1/S2/C4:n), respectively. Overall, sorafelogs containing spacer S2 demonstrated an increased toxicity relative to analogous compounds possessing spacer S1 (FIG. 63).

Figure 63:
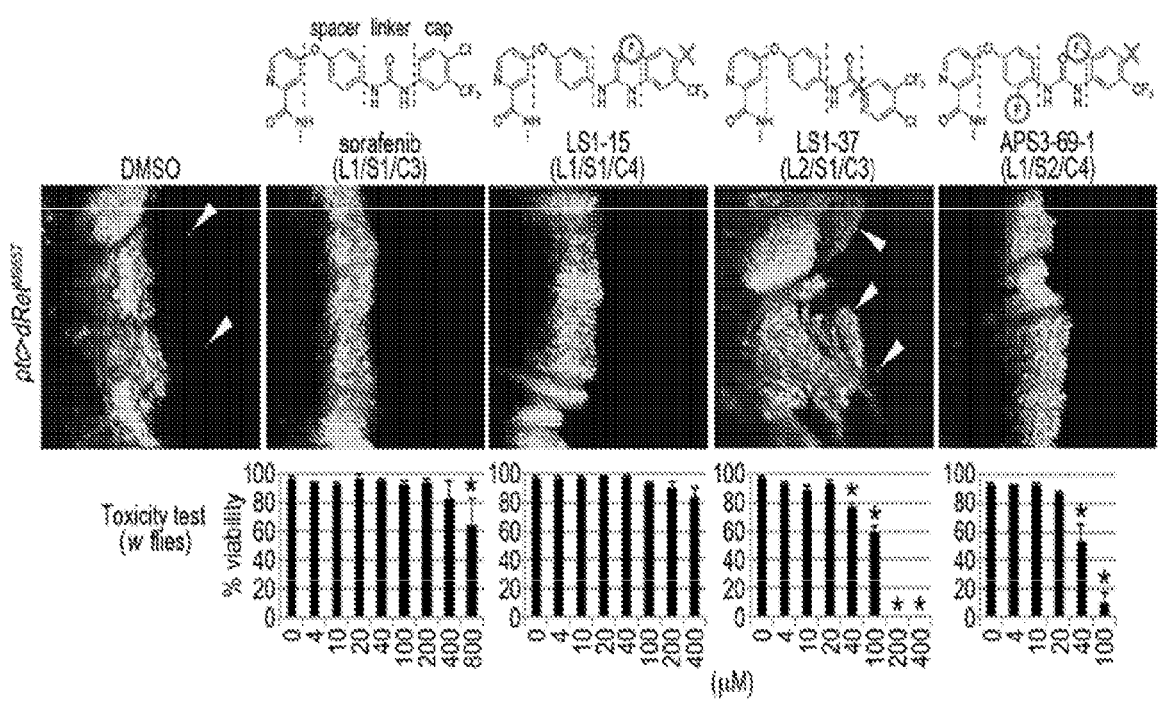
FIG. 63 shows distinct effects of sorafelogs on cell migration. Effects of sorafelogs (top) on cell migration in wing discs (middle) and whole-body toxicity in non-oncogenic w$^-$ flies (bottom). Circles and crosses, modified portion as compared with sorafenib. Arrowheads, dRet$^{M955T}$-expressing transformed cells migrating away from the ptc domain (apical views). Asterisks, p<0.05 in Student's t-test as compared with no-drug control.

Similar to sorafenib, LS1-15 and APS3-69-1 also strongly suppressed ptc>dRet$^{M955T}$-mediated EMT and invasion (FIG. 63). In contrast, LS1-37 (L2/S1/C3) worsened cell migration indicating that it activated the dRet$^{M955T}$ transformation network. Further, LS1-37 proved toxic even when fed to control, non-transformed flies, indicated whole body toxicity (FIG. 63). Together, these studies allowed to define the most useful spacer-linker-cap structure for suppressing Ret-mediated transformation.

Example 78

Computer-Guided Determination of Favorable Compound Structures

The sorafelogs provided quantitative SAR data regarding whole animal therapeutic index in the fly. In particular, it was noted that subtle structural changes in the cap group of sorafelogs led to marked differences in rescue from Ret-driven lethality. To better understand observed SAR, the physical features of these cap structures in silico were explored, looking for correlations between structure and whole animal function. Several cap properties did not significantly correlate with efficacy including partial charge distribution, pKa, and molecular dipole. Moreover, free energy calculations in models of compound docking against key pro-targets also did not strongly correlate with sorafelog efficacy.

Figure 64:
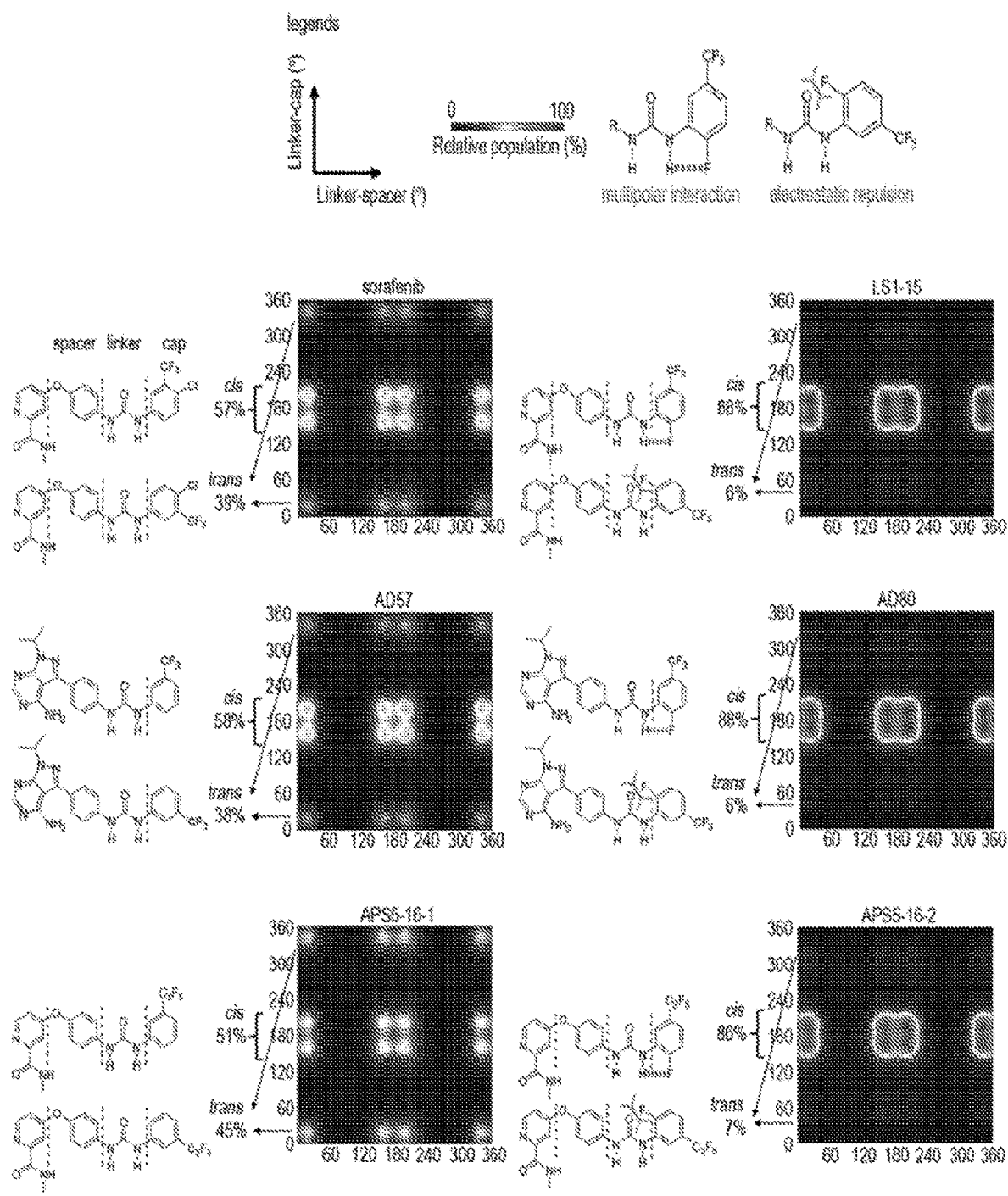
FIG. 64 shows results of computing physicochemical features for sorafelogs. Rotational energy of the torsional angles of linker/cap and linker/spacer is converted into relative conformational population of the compounds, represented in a heatmap. Since most sorafelogs do not have a substituent on the spacer region, linker>spacer was symmetric at 180°. Sorafenib, APS5-16-1, and AD57 have two predominant conformational populations, the cis- and the trans-conformers, likely due to the rotation of the linker/cap. Conversely, LS1-15, APS5-16-2, and AD80 strongly favor the cis- over the trans-conformation, likely due to the multipolar interaction between the urea amide hydrogen and fluorine (broken line), and strong electrostatic repulsion between the fluorine and the urea carbonyl oxygen in the trans-conformation (arcs).

A significant correlation between efficacy and the torsional angle of the N-substituted linker (urea)-cap was observed (FIG. 64). Exchanging (i) a chlorine atom at the cap's 4 position (sorafenib) for (ii) a fluorine atom at the cap's 2 position (LS1-15) significantly shifted LS1-15's preferred conformation in the unbound state relative to sorafenib. Of note, this preferred LS1-15 conformation closely matched the bound-state conformation of sorafenib reported for kinase co-crystal structures (FIGS. 54A and 64). LS1-15's preferred conformational likely resulted from (i) repulsive interactions between the 2-position fluorine in the cap with the urea oxygen and (ii) favorable multipolar interactions between the 2-position fluorine with the urea hydrogen. These interactions are lacking in both sorafenib and regorafenib. That is, constraining LS1-15's unbound-state conformation to 'pre-match' its optimal kinase binding conformation correlated with a strong improvement in whole-animal efficacy.

However, conformational dynamics and physical features alone were limited in providing guidelines for further improving lead compounds. For example, APS4-54 and APS4-35-1 displayed poor whole animal activity relative to LS1-15 despite similarly constrained torsion angle dynamics (FIG. 58A). It was postulated that a better understanding of the full palate of optimal therapeutic targets would help to further improve upon sorafenib and LS1-15.

Example 79

Identifying Pro-Targets and Anti-Targets for LS1-15 and Sorafenib

To increase the efficacy of the lead molecules, a genetic approach was used to identify kinases that, when reduced throughout the developing fly, altered the ability of LS1-15 or sorafenib to suppress ptc>dRet$^{M955T}$ lethality. Using temperature to control GAL4 driver activity, the viability of ptc>dRet$^{M955T}$ flies to ~50% was calibrated in the presence of LS1-15. This sensitized assay was used to screen for dominant 'pro(prospective)-targets' and 'anti-targets', genes that when heterozygous increased or decreased drug efficacy, respectively (FIGS. 54B, 55A, and 62B-H). Pro-targets served as positive modifiers of sorafenib efficacy. Anti-targets served as negative modifiers within tumor networks that, when inhibited, can reduce a drug's efficacy or promote a drug's whole body toxicity.

For example, LS1-15 rescued ptc>dRet$^{M955T}$ to 50% viability; removing one active allele of Lk6 (ptc>dRet$^{M955T}$, Lk6$^{-/+}$) led to 0% animal survival to adulthood (FIG. 55B). This defined Lk6 as an anti-target of LS1-15. Lk6 is the fly ortholog of mammalian MKNK1, an emerging cancer target (e.g., Joshi et al., "Mnk Kinase Pathway: Cellular Functions and Biological Outcomes," *World J. Biol. Chem.* 5:321-333 (2014); Teo et al., "An Integrated Approach for Discovery of Highly Potent and Selective Mnk Inhibitors: Screening, Synthesis and SAR Analysis," *Eur. J. Med. Chem.* 103:539-550 (2015); Basnet et al., "Identification of a Highly Conserved Allosteric Binding Site on Mnk1 and Mnk2," *Mol. Pharmacol.* 88:935-948 (2015), which are hereby incorporated by reference in their entirety); the present application suggests that MKNK1 may prove a poor therapeutic target in at least some contexts. In contrast, treating genotypically ptc>dRet$^{M955T}$, phl$^{-/+}$ flies with LS1-15 led to 96% viability. Phl is the *Drosophila* ortholog of Raf, defining Raf as a pro-target of LS1-15 (FIGS. 55C, 60, and 65A).

Figure 65:
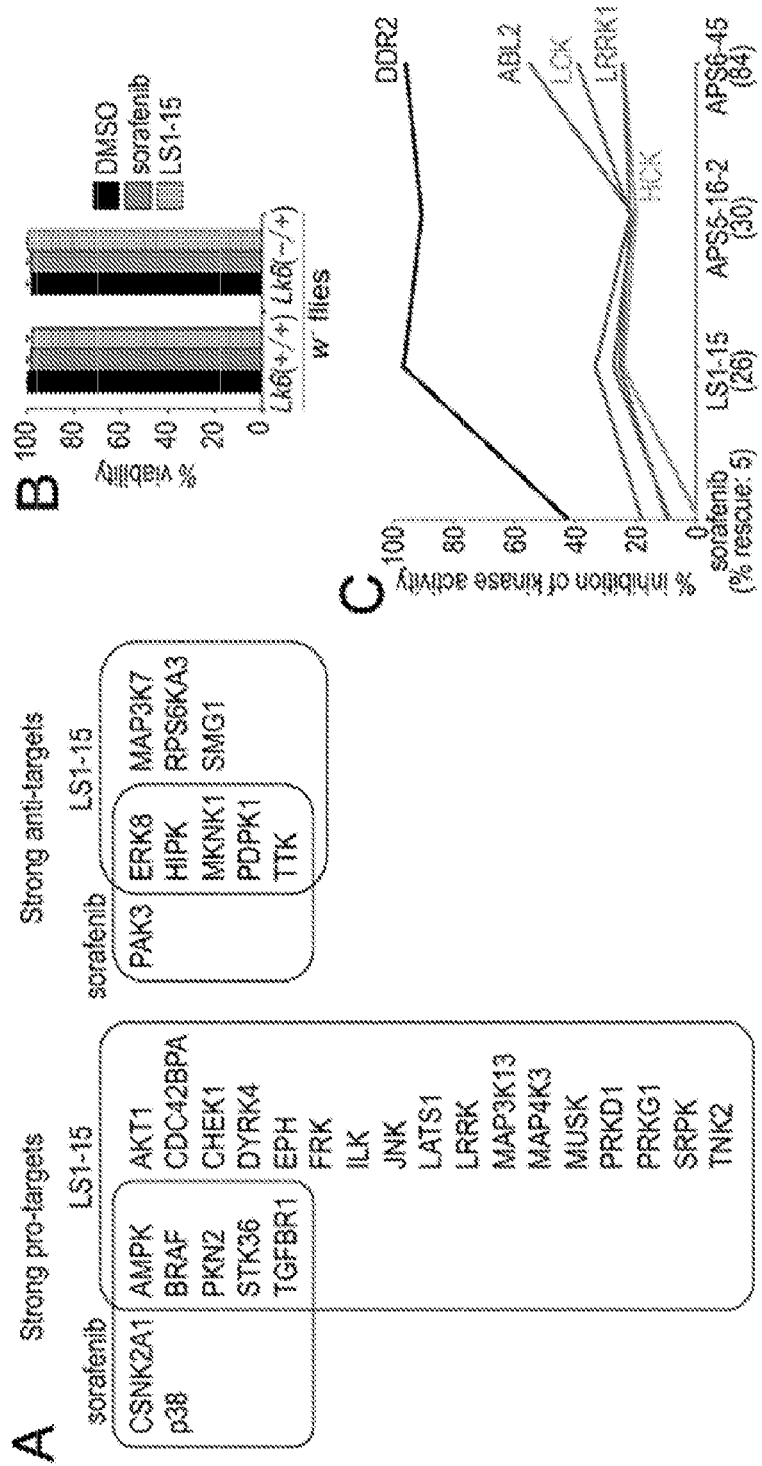
FIGS. 65A-C show shared and specific pro-/anti-targets.

206 genes were tested in the presence of LS1-15, covering more than 80% of the predicted *Drosophila* kinome. 22 strong pro-target genes for LS1-15 were identified, in which heterozygosity promoted significantly improved (>91%) viability (FIGS. 55B, 55C, 59, and 65A). To understand how LS1-15's functional network was different from sorafenib, a similar kinome screen was performed against sorafenib. Remarkably, 17 LS1-15-specific pro-targets failed to show a similar functional interaction with sorafenib (FIGS. 65A-C), indicating the two have significantly different cellular activities. In cell-free kinase inhibition assays, LS1-15 was found to inhibit at least two pro-targets, EPH and FRK (FIG. 61); nevertheless, this genetic modifier data indicate that LS1-15 would be still more effective with a further increase in EPH or FRK inhibition. 8 strong anti-targets for LS1-15 and 6 strong anti-targets for sorafenib were also identified, including Lk6 (FIGS. 55C and 65A). This indicates that reducing activity against Lk6/MKNK1 should lead to improved sorafelog efficacy. Interestingly, the *Drosophila* mTOR ortholog Tor was not identified as an anti-target. Tor was identified as an anti-target for AD57 previously (Dar et al., "Chemical Genetic Discovery of Targets and Anti-Targets for Cancer Polypharmacology," Nature 486:80-84 (2012), which is hereby incorporated by reference in its entirety), indicating that sorafelogs act on an overlapping but different network than AD57.

Example 80

Raf is Both a Pro-Target and an Anti-Target

In the course of these studies it was surprising to observe dual requirements for *Drosophila* Raf in the context of sorafenib and LS1-15: raf$^{-/+}$ acted as a pro-target at high drug dose but an anti-target at lower doses. Recent studies have demonstrated that first generation BRAF inhibitors can activate BRAF activity at low doses through "inhibitor-induced transactivation": drug-bound RAF protomers can stimulate the kinase activity of drug-free RAF protomers, leading to the activation of downstream MAPK activity (Poulikakos et al., "RAF Inhibitors Transactivate RAF Dimers and ERK Signalling in Cells with Wild-Type BRAF," Nature 464:427-430 (2010); Weeraratna, "RAF Around the Edges—The Paradox of BRAF Inhibitors," *N. Engl. J. Med.* 366:271-273 (2012), which are hereby incorporated by reference in their entirety). Higher drug doses were required to reduce the number of drug-free RAF protomers and, therefore, BRAF/MAPK activity.

Sorafenib was originally developed as a RAF inhibitor of relatively modest binding activity (Lyons et al., "Discovery of a Novel Raf kinase Inhibitor," *Endocr. Relat. Cancer* 8:219-225 (2001), which is hereby incorporated by reference in its entirety), raising the possibility that sorafenib and the sorafelogs direct a similar low dose activation/high dose inhibition in our *Drosophila* platform. Wing venation was used in the adult fly to explore the dose effects of sorafelogs on MAPK signaling activity in the context of a whole animal. Previous work has demonstrated that elevated Ras/MAPK pathway activity promotes ectopic wing venation during development (Karim et al., "Ectopic Expression of Activated Ras1 Induces Hyperplastic Growth and Increased cell Death in *Drosophila* Imaginal Tissues," Development 125:1-9 (1998), which is hereby incorporated by reference in its entirety), which was observed in the dRet$^{M955T}$ flies in which dRet$^{M955T}$ was driven by the wing disc-specific driver 765-gal4 (FIG. 56A).

Feeding control larvae low dose (10 μM) sorafenib or LS1-15 stimulated significant excess wing vein material (FIGS. 56A and 56B). These results indicated that low dose treatment of sorafenib or LS1-15 directed significant activation of Ras/MAPK activity. Consistent with this view, co-feeding low dose LS1-15 with the MEK inhibitor trametinib, a potent Ras pathway inhibitor that acts downstream of RAF (Slack et al., "The Ras-Erk-ETS-Signaling Pathway Is a Drug Target for Longevity," Cell 162:72-83 (2015), which is hereby incorporated by reference in its entirety) strongly suppressed ectopic wing venation (FIGS. 56A and 56B). In contrast, higher concentrations of sorafenib or LS1-15 that successfully rescued ptc>dRet$^{M955T}$ viability did not promote ectopic wing venation (FIGS. 56A and 56B).

Overall, results with sorafenib and LS1-15 were consistent with the inhibitor-induced transactivation model: a bell-shaped dose curve was identified in which moderate doses of sorafenib or LS1-15 led to increased wing venation in control animals at a dose that failed to rescue ptc>dRet$^{M955T}$ adults, while higher doses that rescued ptc>dRet$^{M955T}$ adults did not yield ectopic wing veins (FIG. 56B). These results also suggested the interesting possibility that the sorafelogs would have a broader therapeutic window if RAF kinases were removed as targets. That is, that RAF can act as an anti-target as well as a pro-target, a possibility that was tested.

Example 81

Developing the Novel Inhibitors APS5-16-2 and APS6-45

In vitro binding assays showed significant binding of sorafenib and LS1-15 to human BRAF (FIG. 56C). Based on wing venation results, the research was focused on reducing sorafelog activity against Raf kinases by focusing on their cap size.

Homology model of the key target RET in the DFG-out conformation indicated that it has a kinase cleft that included an allosteric DFG-pocket of approximately 163 Å$^3$. In contrast, analysis of experimentally determined structures and homology model of BRAF indicated that its allosteric DFG-pocket was significantly smaller, an estimated 136 Å$^3$ (FIG. 56D). It was therefore reasoned that activity against Raf kinases would be highly sensitive to modifications on the cap group.

The research was then focused on the —CF$_3$ at the 5-position in the cap, an approach that was substantiated by key trends found within sorafelog SAR. Removing a single fluorine atom (APS4-54:i) or all fluorine atoms (APS4-35-1) from the —CF$_3$ of LS1-15 resulted in reduced rescue of ptc>dRet$^{M955T}$ viability (FIGS. 54D and 58A). Removal of the 2-fluoro group in LS1-15 also reduced survival (LS1-11-2:e, FIGS. 54D and 58A). That is, reducing the —CF$_3$ group reduced sorafelog efficacy, emphasizing the importance of retaining the —CF$_3$ to constrain rotation of the overall cap group as described above (FIG. 64). The effects of enlarging this group were then tested.

Extending LS1-15's —CF$_3$ cap group by substituting with a —C$_2$F$_5$ or -isoC$_3$F$_7$ generated the compounds APS5-16-2 and APS6-45. Calculations predicted that these substitutions at the caps' 5-position would cause steric clash with RAF's DFG-pocket (FIGS. 56B and 56D). Indeed cell-free in vitro studies indicated that in comparison to sorafenib and LS1-15 both APS5-16-2 and APS6-45 showed significantly reduced BRAF binding while retaining RET inhibition (FIG. 56C). In vivo, both APS5-16-2 and APS6-45 failed to promote ectopic wing venation in 765>dRet$^{M955T}$ flies (FIG. 56B). This data indicates that neither activated Ras pathway activity at any dose tested, presumably reflecting their inability to bind to and activate Raf.

Most importantly, oral administration of APS5-16-2 and especially APS6-45 strongly increased overall ptc>dRet$^{M955T}$ survival beyond LS1-15 at optimal doses (FIGS. 54D and 58A). APS6-45 rescued ptc>dRet$^{M955T}$ flies to a remarkable 84% overall viability FIGS. 54D and 58A). This level of rescue is higher than all previously tested compounds, including previously reported optimized compound AD80, which itself displayed exceptional polypharmacological properties (Dar et al., "Chemical Genetic Discovery of Targets and Anti-Targets for Cancer Polypharmacology," *Nature* 486:80-84 (2012), which is hereby incorporated by reference in its entirety). Further, APS6-45's optimal dose range was shifted to lower doses compared to sorafenib or LS1-15 (FIGS. 54D and 58B). Interestingly, APS6-45 showed lower activity against wild type or oncogenic RET in vitro compared to sorafenib or sorafelogs described here (FIG. 56C), emphasizing the importance of its overall activity against cellular networks.

Example 82

APS6-45 Inhibits Ras Pathway Activity Through Multiple Means

Activation of Ras-MAPK signaling by targeting expression of either dRas$^{G12V}$ or dRet$^{M955T}$ to the developing eye epithelium leads to aspects of transformation, generating a 'rough eye' phenotype (Huang et al., "A Misexpression Screen Identifies Genes that can Modulate RAS1 Pathway Signaling in *Drosophila* Melanogaster," *Genetics* 156:1219-1230 (2000); Read et al., "A *Drosophila* Model of Multiple Endocrine Neoplasia type 2," *Genetics* 171:1057-1081 (2005), which are hereby incorporated by reference in their entirety). By dissecting open dying (vehicle-treated) ptc>dRet$^{M955T}$ pupae, a rough eye phenotype was observed in the anterior-most region of the eye (FIG. 57D), consistent with expression of ptc within the anterior eye field (Shyamala et al., "A Positive Role for Patched-Smoothened Signaling in Promoting Cell Proliferation During Normal Head Development in *Drosophila*," *Development* 129:1839-1847 (2002), which is hereby incorporated by reference in its entirety). APS6-45 strongly suppressed this anterior rough eye phenotype both in pupae and in rescued adults; other sorafelogs as well as AD80 did not (FIG. 57D). These results further indicate that APS6-45 inhibits Ras signaling at an especially high level, with minimal whole animal toxicity.

Finally, improvements in efficacy of APS5-16-2 and APS6-45 likely reflect changes in other pro-targets and anti-targets as well. For example, the MKNK1 ortholog Lk6 proved an especially strong anti-target of both sorafenib and LS1-15 (FIGS. 55B and 55C). Previous work has linked Lk6 to suppression of Ras pathway activity (Huang et al., "A Misexpression Screen Identifies Genes that can Modulate RAS1 Pathway Signaling in *Drosophila* Melanogaster," *Genetics* 156:1219-1230 (2000), which is hereby incorporated by reference in its entirety). Consistent with this view, 765>dRet$^{M955T}$, Lk6$^{-/+}$ flies showed enhanced wing venation and poor wing structure compared to 765>dRet$^{M955T}$ wings; these wing defects were suppressed by the Ras pathway inhibitor trametinib (FIGS. 57A and 57B).

Analysis of experimentally determined structures and homology modeling of MKNK1 indicated that its allosteric DFG-pocket was also smaller than RET, an estimated 150 Å$^3$ (FIG. 56D). Indeed, while APS6-45 exhibited only a small decrease in in vitro MKNK1 binding relative to sorafenib, APS5-16-2 exhibited significantly reduced MKNK1 binding (FIG. 56C). In vivo data matched these calculated activities. Reducing Lk6 (765>dRet$^{M955T}$, Lk6$^{-/+}$) reversed suppression of 765>dRet$^{M955T}$ cell migration by sorafenib or LS1-15 (FIG. 57C), consistent with Lk6 acting as an anti-target to both compounds. In contrast, efficacy of APS5-16-2 and APS6-45 were not affected by reduced Lk6 (FIG. 57C), consistent with their lower binding to MKNK1.

Taken together, these results suggest that reducing compound activity against MKNK1 may potentiate inhibition of Raf-MAPK signaling. Overall, it was concluded that sorafenib and sorafelogs such as LS1-15 can be improved by (i) constraining rotation of the cap group and (ii) extending the —CF$_3$ group to reduce binding to RAF and, potentially, other anti-targets such as MKNK1.

Example 83

In Vivo Efficacy of the Novel TCI APS6-45

Figure 66:
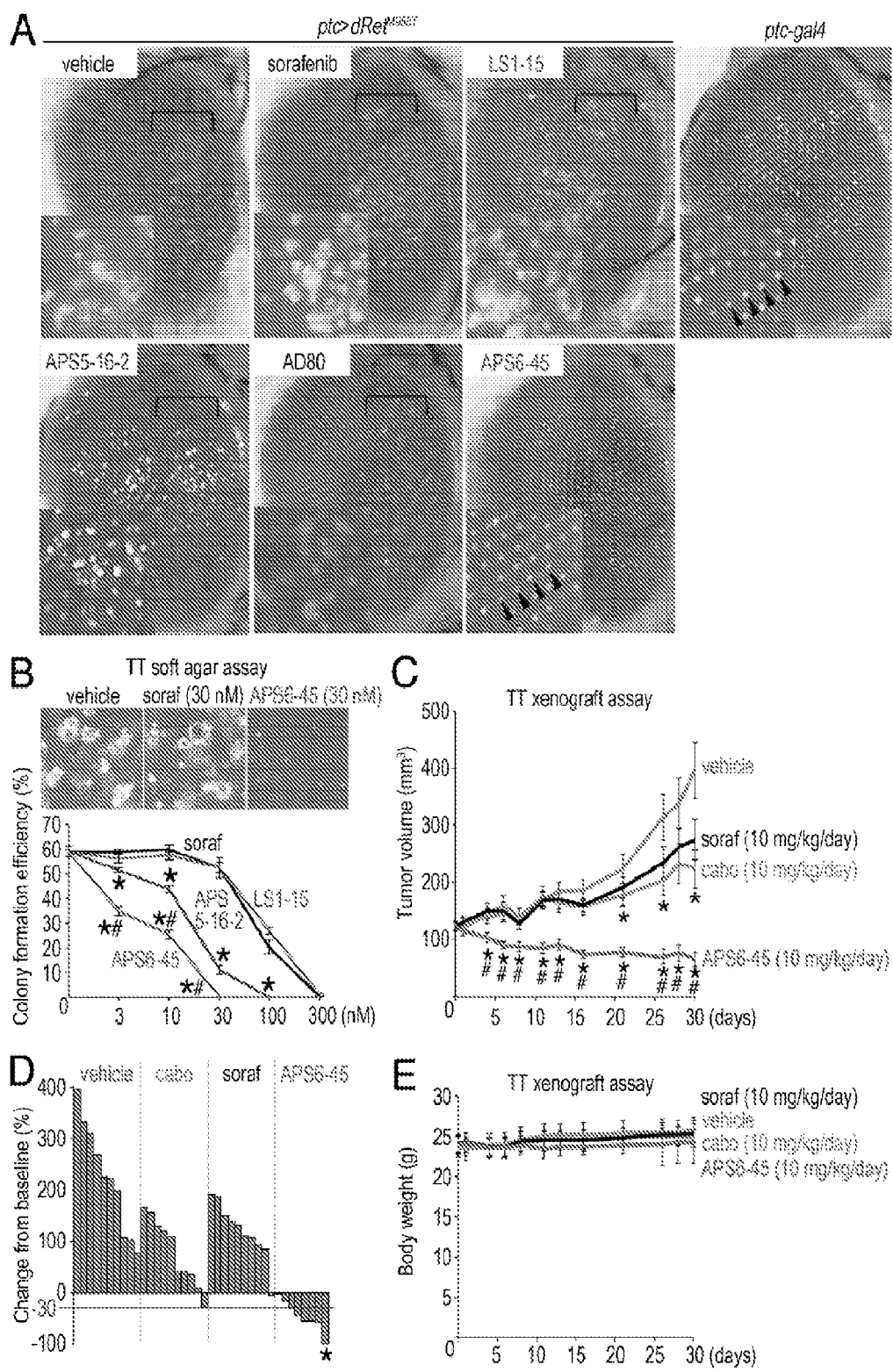
FIGS. 66A-E show the in vivo efficacy of APS6-45.

The effects of compounds on a fly rough eye phenotype were evaluated. ptc>dRet$^{M955T}$ exhibited a transformation-like phenotype including disarray of the ommatidial field in the anterior of the adult eye. APS6-45 strongly rescued the rough eye phenotype, leading to smoothly arrayed ommatidia similar to ptc-gal4 controls. Vehicle-treated control flies were dissected from pupal cases as they did not survive until adulthood. Drug concentrations: sorafenib (400 µM), LS1-15 (200 µM), APS5-16-2 (100 µM), APS6-45 (100 µM), and AD80 (100 µM) (FIG. 66A). Suppression of MTC colony formation by APS5-16-2 and APS6-45 is illustrated in FIG. 66B. TT human MTC cells were assayed for colony forming activity in a soft agar assay in the presence of TCIs. Representative morphology of colonies at three weeks is shown in FIG. 66B (top panels). Arrowheads (FIG. 66B) are examples of growing colonies. Imaged with ×40. Effect of TCIs on colony formation efficiency is shown in FIG. 66B (bottom). Colony numbers at three weeks were divided by the number of seeded cells to determine colony formation efficiency. 150-200 cells were scored in each experiment. Error bars, standard errors in triplicate. Asterisks, p<0.05 in Student's t-test as compared with sorafenib (soraf). Pounds, p<0.05 in Student's t-test as compared with APS5-16-2.

Figure 67:
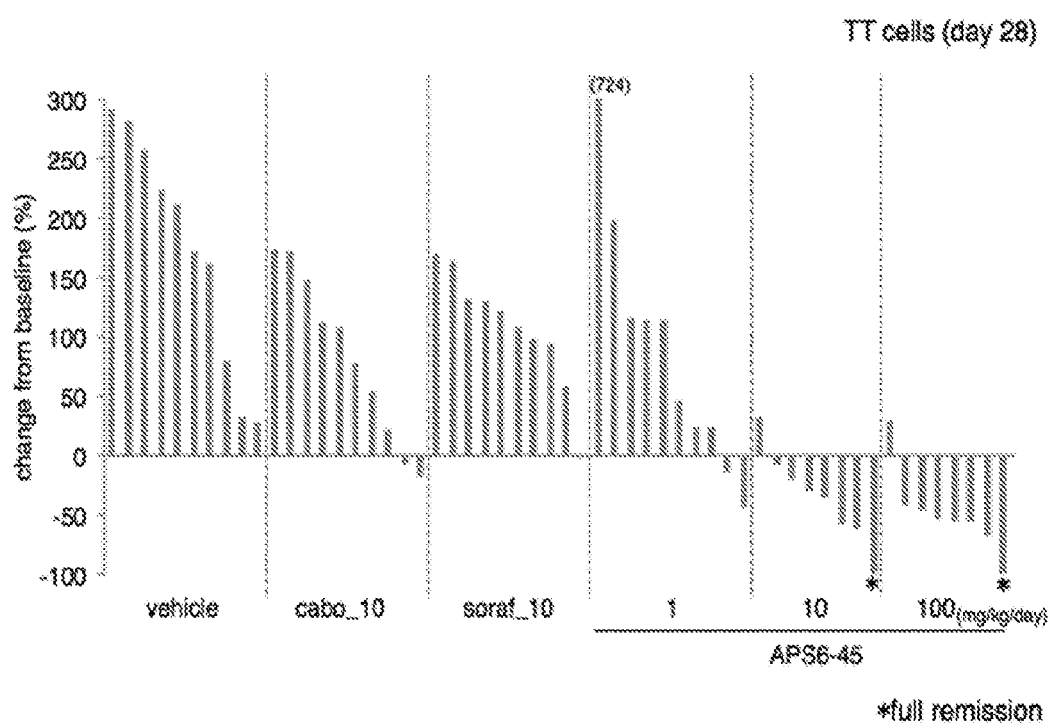
FIG. 67 shows dosing experiments of APS6-45 in mice. Forty female nude mice were implanted subcutaneously with TT cells. When tumor volume achieved ~120 mm$^3$, mice were randomly grouped into four arms, and each arm was dosed p.o. five days per week with vehicle (Cremophor EL/ethanol (1:1) diluted 4-fold with water) or 10 mg/kg/day of cabozantinib (LC Laboratories), sorafenib (LC Laboratories), or APS6-45.

FIGS. 66C-E illustrate the effectiveness of the oral administration of APS6-45 to mice with xenografts. Suppression of TT cell growth in vivo by APS6-45. Dosing (10 mg/kg/day each) was started on day 0 after establishing TT cell tumors (~120 mm³) subcutaneously in nude mice. Error bars, standard errors (n=10). Cabo, cabozantinib; soraf, sorafenib. Asterisks indicate p<0.05 in Student's t-test as compared with vehicle control; pound signs indicate p<0.05 in Student's t-test as compared with sorafenib and cabozantinib (FIG. 66C). FIG. 66D and FIG. 67 illustrate Waterfall plots showing percent changes in tumor volume on day 30 relative to pretreatment baselines. Each bar represents a single animal. The line indicates 30% tumor size reduction from baseline, the minimal decrease representing partial response defined by Response Evaluation Criteria in Solid Tumors (RECIST) (Eisenhauer et al., "New Response Evaluation Criteria in Solid Tumours: Revised RECIST Guideline," Eur. J. Cancer. 45:228-247 (2009) which is hereby incorporated by reference in its entirety). Asterisk, complete response. Two mice were lost during the course of the experiment due to unknown causes. Administration of APS6-45 had no effect on mouse body weight as illustrated in FIG. 66E (same legend as FIG. 66C).

Example 84

Dosing Experiments in Mice

All mouse experiments were carried out according to guidelines set forth by American Association for Accreditation of Laboratory Animal Science (AAALAC) or the Office for Laboratory and Animal Welfare (OLAW) division of the National Institute of Health (NIH).

Toleration assays for APS6-45 were performed by Washington Biotechnology (Baltimore, Md.). Briefly, five female athymic nude mice (5-6 weeks) were administered with increasing oral doses of APS6-45 starting at 0.1 mg/kg/day and observed for 2 days for signs of clinical distress such as weight loss, discharges, and morbidity. Dose was gradually escalated up to 160 mg/kg/day, and no such signs were observed.

Phamacokinetics assays for APS6-45 were performed by Medicilon Preclinical Research (Shanghai, China). 20 mg/kg of APS6-45 was dosed orally to male ICR mice (5-6 weeks of age), and its plasma concentrations were determined at 0.25, 0.5, 1, 2, 4, 8, 10, and 24 hours post dosing. No treatment-related clinical signs were observed following dosing.

Xenograft assays were also performed by Washington Biotechnology. 40 female nude mice (5-6 weeks) were implanted subcutaneously with TT cells. When tumor volume achieved ~120 mm³, mice were randomly grouped into four arms, and each arm was dosed p.o. five days per week with vehicle (Cremophor EL/ethanol (1:1) diluted 4-fold with water) or 10 mg/kg/day of cabozantinib (LC Laboratories), sorafenib (LC Laboratories), or APS6-45. These doses were expected to give clinically relevant AUCs and maximum plasma concentrations of each drug (Bentzien et al., "In Vitro and In Vivo Activity of Cabozantinib (XL184), an Inhibitor of RET, MET, and VEGFR2, in a Model of Medullary Thyroid Cancer," Thyroid. 23:1569-1577 (2013); Clark et al., "Safety and Pharmacokinetics of the Dual Action Raf Kinase and Vascular Endothelial Growth Factor Receptor Inhibitor, BAY 43-9006, In patients with Advanced, Refractory solid Tumors," Clin Cancer Res. 11:5472-5480 (2005); Kurzrock et al., "Activity of XL184 (Cabozantinib), an Oral Tyrosine Kinase Inhibitor, in Patients With Medullary Thyroid Cancer," J. Clin. Oncol. 29:2660-2666 (2011); Lacy et al., "Clinical Pharmacokinetics and Pharmacodynamics of Cabozantinib," Clin. Pharmacokinet. 56:477-491 (2017); Minami et al., "Phase I and Pharmacokinetic Study of Sorafenib, an Oral Multikinase Inhibitor, in Japanese Patients with Advanced Refractory Solid Tumors.," Cancer Sci. 99:1492-1498 (2008); Strumberg et al., "A Clinical Phase II Study with Sorafenib in Patients with Progressive Hormone-Refractory Prostate Cancer: A Study of the CESAR Central European Society for Anticancer Drug Research-EWIV," Br. J. Cancer 97:1480-1485 (2007); Zarrinkar et al., "A Quantitative Analysis of Kinase Inhibitor Selectivity," Nature Biotechnol. 26:127-132 (2009) which are hereby incorporated by reference in their entirety). Statistical analyses were performed using PRISM (GraphPad Software, Inc.; La Jolla, Calif.).

Example 85

Testing of Analogs in Ptc>dRETM955T Flies

Figure 68:
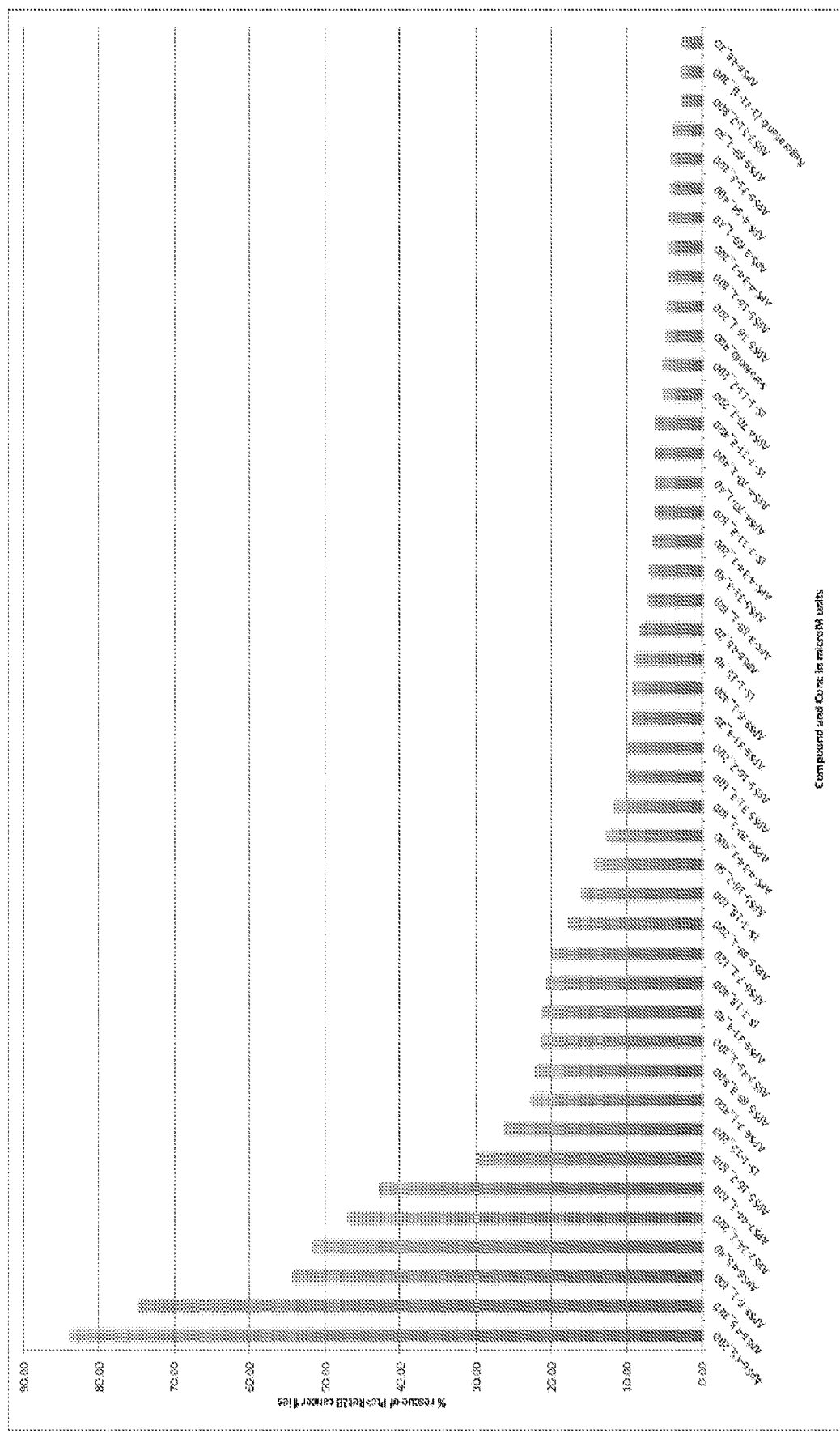
FIG. 68 is a rescue plot showing the testing of analogs in ptc>dRETM955T flies.

The two clinically approved kinase inhibitors sorafenib and regorafenib (also labeled 1-31-1) promoted less than 5% rescue at optimal doses. Compound names and concentration units, in microM, are labeled across the x axis. In this assay using ptc>dRet$^{M955T}$ flies, the patched (ptc) promoter drives an oncogenic mutant isoform of Drosophila Ret (dRet$^{M955T}$) in several tissues, directing lethality prior to emergence as adults. Larvae consume candidate drugs. Drug efficacy (Y-axis) is quantified by dividing the number of rescued adults (A) by the number of total pupae (P) (FIG. 68).

Example 86

Discussion

The work described herein demonstrates a platform that combines Drosophila genetics with medicinal and computational chemistry to develop polypharmacological drugs in a rational, stepwise manner. Research was focused on the FDA approved kinase inhibitor sorafenib as a clinically important cancer therapeutic that nonetheless has demonstrated significant contraindications in the clinics (see, e.g., Hescot et al., "Pancreatic Atrophy—A New Late Toxic Effect of Sorafenib," *N. Engl. J. Med.* 369:1475-1476 (2013); Hesselink et al., "Therapy of Endocrine Disease: Response and Toxicity of Small-Molecule Tyrosine Kinase Inhibitors in Patients with Thyroid Carcinoma: A Systematic Review and Meta-Analysis," *Eur. J. Endocrinol.* 172:R215-25 (2015); Zhang et al., "Meta-Analysis of Dermatological Toxicities Associated with Sorafenib," *Clin. Exp. Dermatol.* 36:344-350 (2011), which are hereby incorporated by reference in their entirety).

The present application demonstrates two steps in which sorafenib was improved. In the first step, whole animal structure/activity relationship studies identified the importance of constraining intra-chemical rotation, yielding sorafelogs that are locked into a more optimal conformation in the animal. In the second step, key pro-targets and especially anti-targets for sorafelogs were identified in the context of the whole animal. For example, evidence was found that activity against RAF kinases limited the level at which sorafelogs could be improved. Based on homology modeling of the allosteric pocket in the DFG-out conformation (FIG. 56D), a modification of the cap structure was expanded; the result was loss of activity against RAF kinases and compounds with higher efficacy than cabozantinib and vandetanib, drugs that are currently approved for MTC.

Importantly, sorafelog efficacy did not simply track with activity against RET. For example, APS6-45 showed the strongest efficacy but weakest RET binding (FIG. 56C). In vivo genetic screens indicated that other pro-targets and anti-targets also contributed to an overall network effect by the sorafelogs. In vitro assays showed a progressive inhibition of pro-targets DDR2, ABL2, LCK, LRRK1, and HCK by sorafelogs with distinct rescue effects (FIG. 65C). These results are consistent with previous reports that these pro-targets regulate proliferation and invasion of cancer cells (Montero et al., "Inhibition of SRC Family Kinases and Receptor Tyrosine Kinases by Dasatinib: Possible Combinations in Solid Tumors," *Clin. Cancer Res.* 17:5546-5552 (2011); Greuber et al., "Role of ABL Family Kinases in Cancer: from Leukaemia to Solid Tumours," *Nat. Rev. Cancer* 13:559-571 (2013); Rammal et al., "Discoidin Domain Receptors: Potential Actors and Targets in Cancer," *Front. Pharmacol.* 7:55 (2016), which are hereby incorporated by reference in their entirety). Also of note, reducing the anti-target MKNK1 led to an increase in Ras pathway activity. MKNK1 phosphorylates eIF-4E in both flies and mammals (Joshi et al., "Mnk Kinase Pathway: Cellular Functions and Biological Outcomes," *World J. Biol. Chem.* 5:321-333 (2014); Arquier et al., "*Drosophila* Lk6 Kinase Controls Phosphorylation of Eukaryotic Translation Initiation Factor 4E and Promotes Normal Growth and Development," *Curr. Biol.* 15:19-23 (2005), which are hereby incorporated by reference in their entirety). Previously it was shown that the eIF-4E activator mTOR can also act as an anti-target through Ras pathway activation (Dar et al., "Chemical Genetic Discovery of Targets and Anti-Targets for Cancer Polypharmacology," *Nature* 486:80-84 (2012); Dibble et al., "Regulation of mTORC1 by PI3K Signaling," *Trends Cell Biol.* 25:545-555 (2015), which are hereby incorporated by reference in their entirety). Together, this data suggests that MKNK1, mTOR, eIF-4E, and its translational targets constitute an 'anti-target pathway' in RET-dependent cancers.

In recent years, an important development in cancer therapeutics has been the move towards precision therapeutics in which the focus is a single target. The present application provides an alternative, complementary approach, an efficient, inexpensive platform for generating polypharmacological drugs that are optimized for cellular networks both within the tumor and in the context of the whole body. This approach may prove useful in drug development strategies for other diseases such as neural and cardiovascular diseases, where systemic or chronic treatment requires accounting for whole body networks, and where drug discovery can prove difficult and expensive.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound of formula (I) having the following structure:

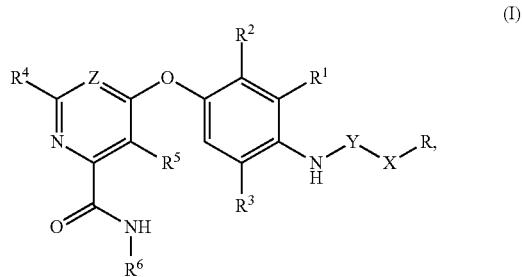

(I)

or a stereoisomer, pharmaceutically acceptable salt, oxide, or solvate thereof, wherein R is selected from the group consisting of $C_{1-6}$ alkyl, $C_{1-6}$ alkoxy, —N($C_{1-6}$ alkyl)$_2$, $C_{3-6}$ cycloalkyl, aryl, heteroaryl, and heterocyclyl, wherein $C_{1-6}$ alkyl, $C_{3-6}$ cycloalkyl, aryl, heteroaryl, and heterocyclyl can be optionally substituted n times with $R^{13}$;

$R^1$ is H;

$R^2$ is H;

or $R^1$ and $R^2$ combine with the phenyl ring to which they are attached to form

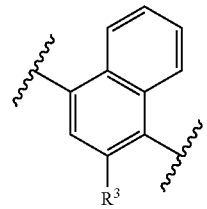

(a naphthyl group);

$R^3$ is H or halogen;

$R^4$ is H, halogen, or $C_1$-$C_6$ alkyl;

$R^5$ is H, halogen, or $C_1$-$C_6$ alkyl;

$R^6$ is $C_1$-$C_6$ alkyl;
X is optional and, if present, is NH;
Y is

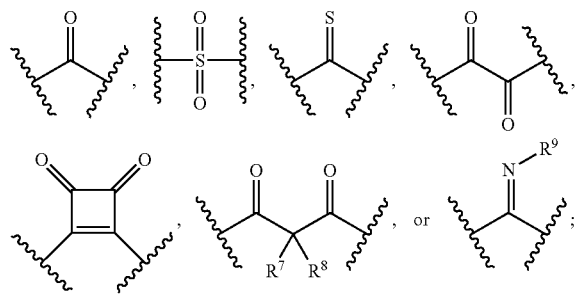

Z is $C(R^{12})$ or N;
$R^7$ is H or Me;
$R^8$ is H or Me;
or $R^7$ and $R^8$ are taken together with the carbon atom to which they are attached to form

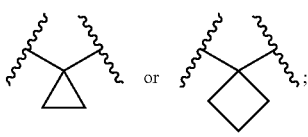 [SMILES: *C1(*)CC1 ; *C1(*)CCC1]

$R^9$ is H, $C_{1-6}$ alkyl, $C_{3-6}$ cycloalkyl, allyl, —CN, or

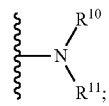

$R^{10}$ is H, $C_{1-6}$ alkyl, or $C_{3-6}$ cycloalkyl;
$R^{11}$ is H, $C_{1-6}$ alkyl, or $C_{3-6}$ cycloalkyl;
$R^{12}$ is H, halogen, or $C_1$-$C_6$ alkyl;
$R^{13}$ is selected independently at each occurrence thereof from the group consisting of H, halogen, $C_1$-$C_6$ alkyl, $CH_2F$, $CHF_2$, $CClF_2$, $CBrF_2$, $ClF_2$, $CF_3$, $C_2F_5$, $C_3F_7$, $C_4F_9$, $OCF_3$ and heterocyclyl; and
n is 1 to 5;
with the proviso that when
i) $R^1$ is H, $R^2$ is H, $R^3$ is H, $R^4$ is H, $R^5$ is H, $R^6$ is $CH_3$, Z is CH, X is NH, and Y is

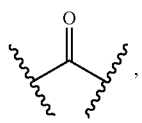

R cannot be

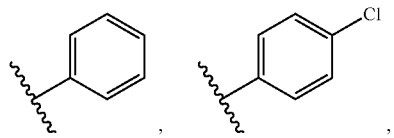

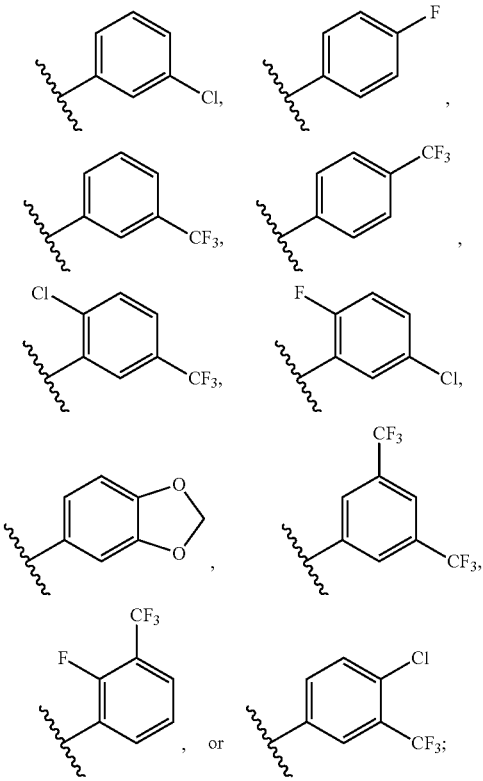

ii) $R^1$ is H, $R^2$ is H, $R^3$ is H, $R^4$ is H, $R^5$ is H, $R^6$ is $CH_3$, Z is CH, X is absent, and Y is

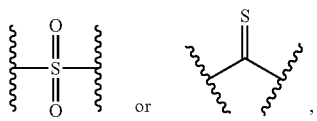

R cannot be

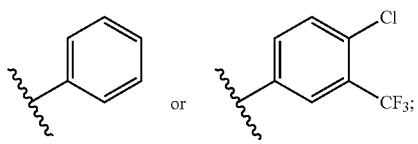 [SMILES: *c1ccccc1 ; *c1ccc(Cl)c(C(F)(F)F)c1]

iii) $R^1$ is H, $R^2$ is H, $R^3$ is H, $R^4$ is H, $R^5$ is H, $R^6$ is $CH_3$, Z is CH, Y is

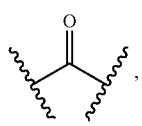

and n is 2, R cannot be

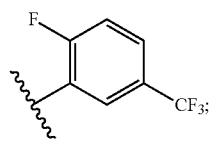 [SMILES: *c1cc(C(F)(F)F)ccc1F]

iv) $R^1$ is H, $R^2$ is H, $R^3$ is F, $R^4$ is H, $R^5$ is H, $R^6$ is $CH_3$, Z is CH, X is NH, Y is

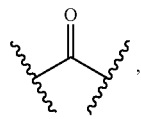

and n is 2, R cannot be

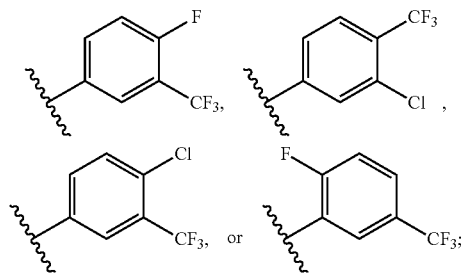

v) $R^1$ is H, $R^2$ is H, $R^3$ is H, $R^4$ is H, $R^5$ is H, $R^6$ is $CH_3$, Z is CH, X is absent, and Y is

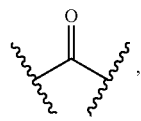

R cannot be

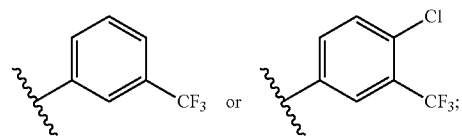 [SMILES: *c1cccc(C(F)(F)F)c1 ; *c1ccc(Cl)c(C(F)(F)F)c1]

and vi) $R^1$ is H, $R^2$ is H, $R^3$ is H, $R^4$ is H, $R^5$ is H, $R^6$ is $CH_3$, Z is CH, X is NH, and Y is

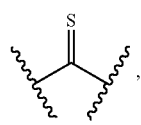

R cannot be

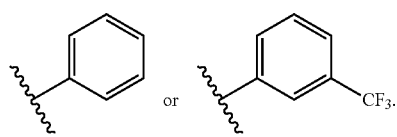 [SMILES: *c1ccccc1 ; *c1cccc(C(F)(F)F)c1]

2. The compound according to claim 1, wherein R is

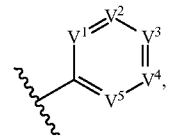

wherein
$V^1$ is $C(R^{14})$ or N;
$V^2$ is CH or N;
$V^3$ is $C(R^{15})$ or N;
$V^4$ is $C(R^{16})$ or N;
$V^5$ is CH or N;
$R^{14}$ is H or halogen;
$R^{15}$ is H or halogen;
$R^{16}$ is $C_1$-$C_6$ alkyl substituted from 2 to 13 times with halogen; and
wherein only one of $V^1$-$V^5$ is N.

3. The compound according to claim 2, wherein $R^{16}$ is $C_1$-$C_6$ alkyl substituted from 2 to 13 times with fluorine.

4. The compound according to claim 2, wherein $R^{16}$ is selected from the group consisting of $CH_2F$, $CHF_2$, $CClF_2$, $CBrF_2$, $ClF_2$, $CF_3$, $C_2F_5$, $C_3F_7$, and $C_4F_9$.

5. The compound according to claim 2, wherein $R^{14}$ is F.

6. The compound according to claim 1, wherein $R^3$ is F.

7. The compound according to claim 1, wherein
X is NH and
Y is

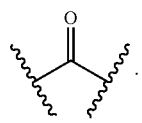

8. The compound of claim 1, wherein the compound is selected from the group consisting of

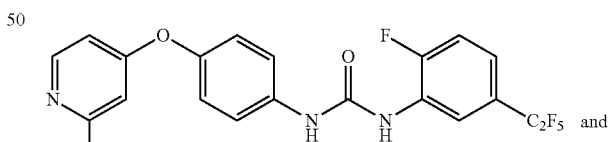

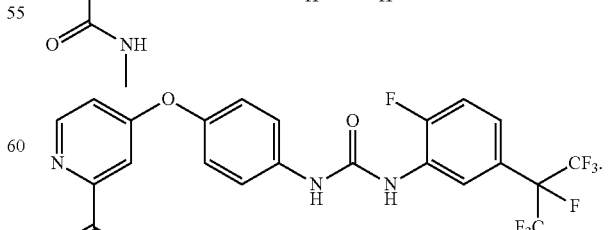

9. The compound of claim 1, wherein the compound is selected from the group consisting of
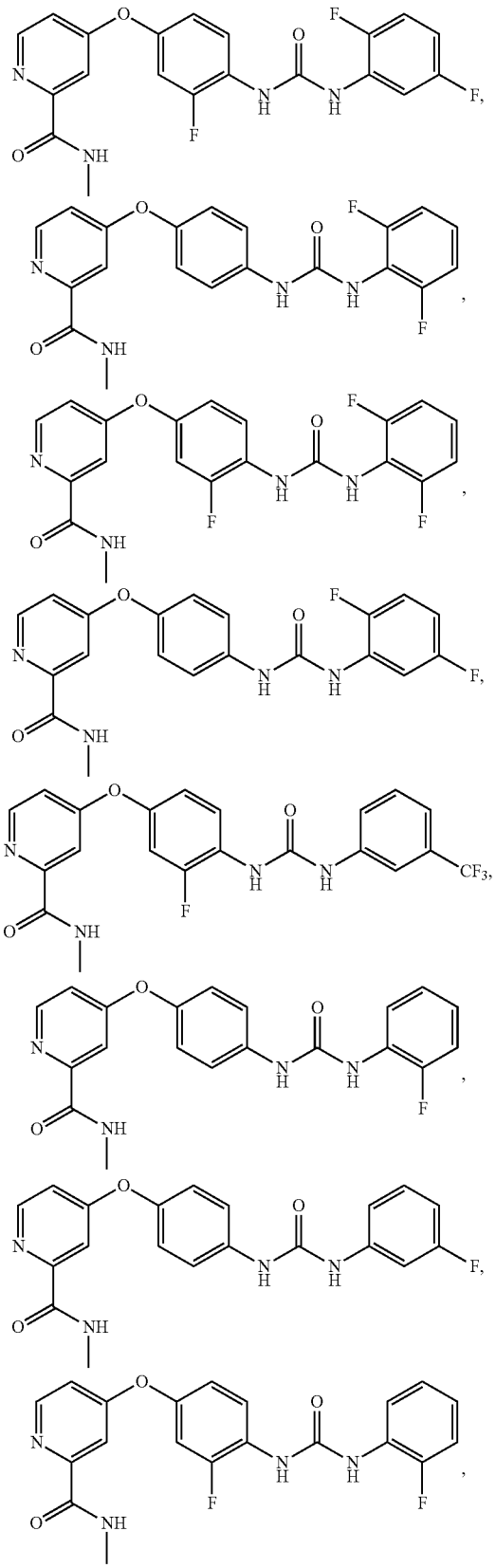
-continued
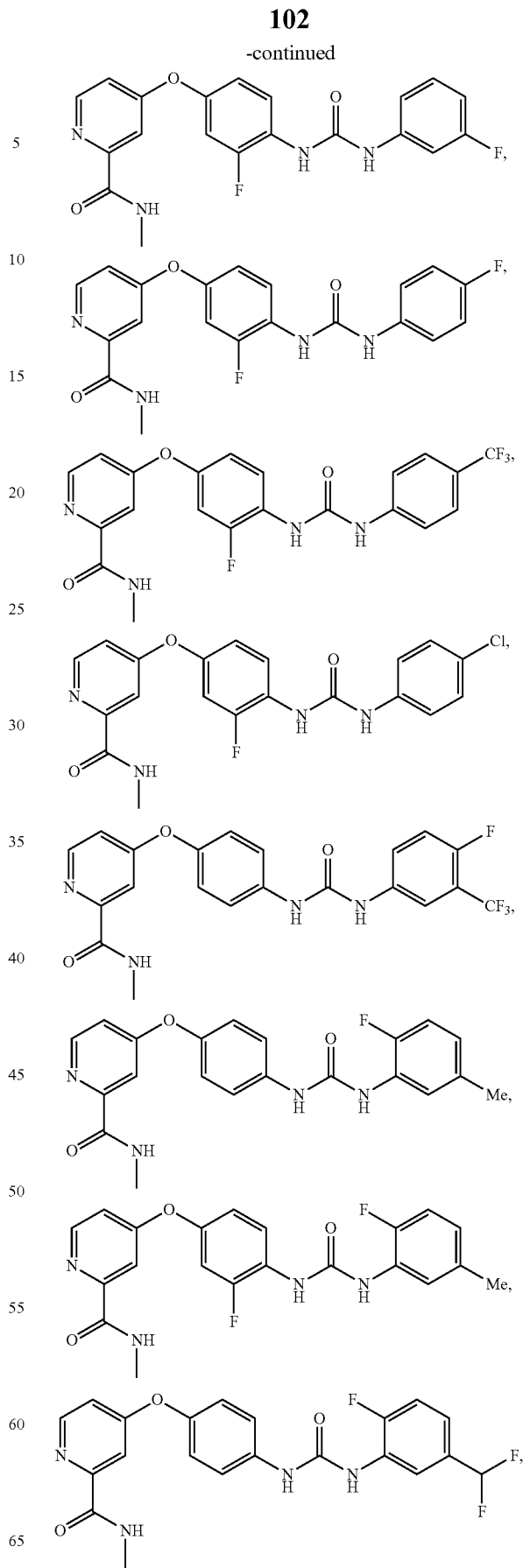

103
-continued
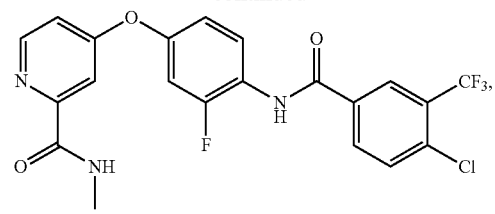
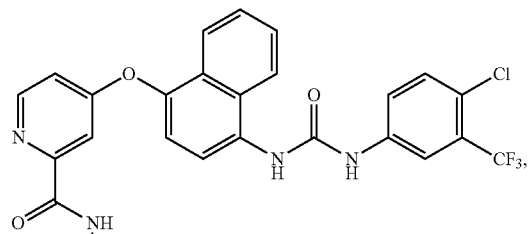
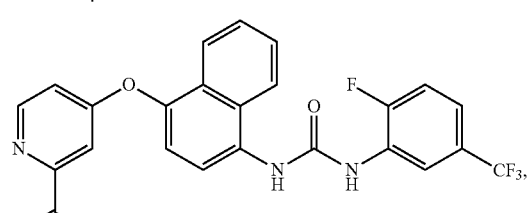
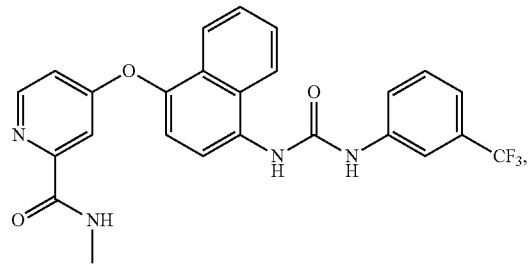
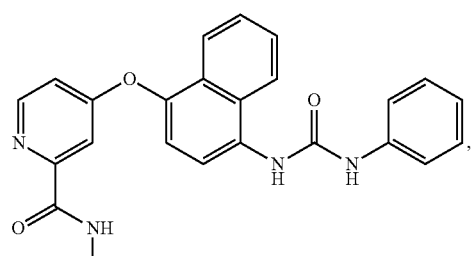
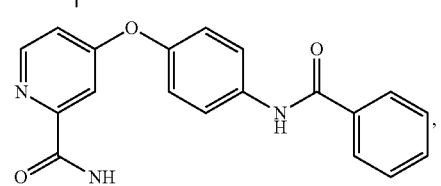
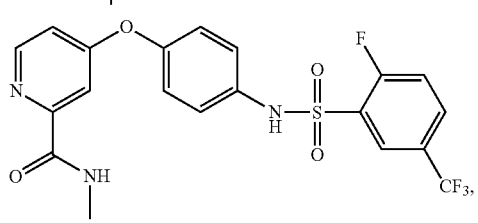
104
-continued
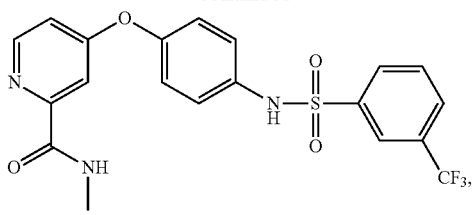
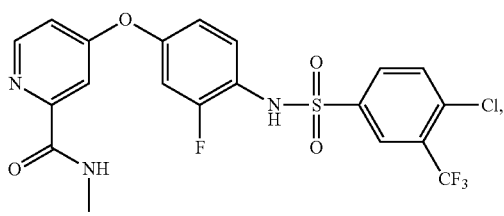
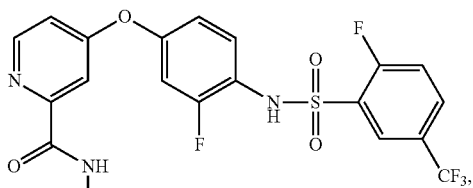
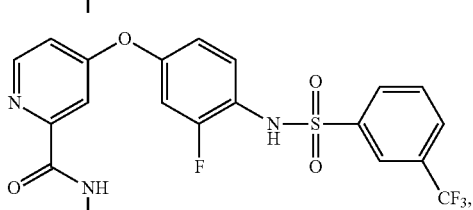
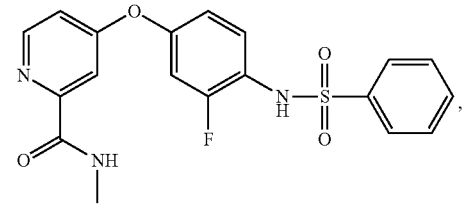
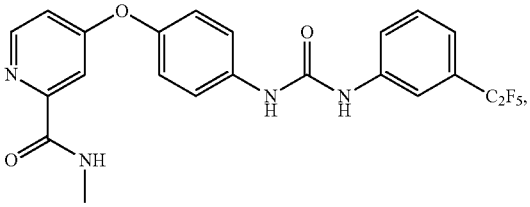
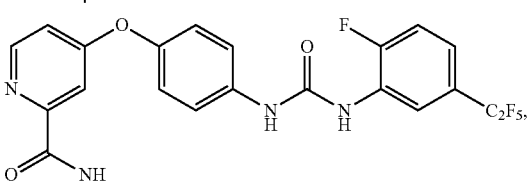
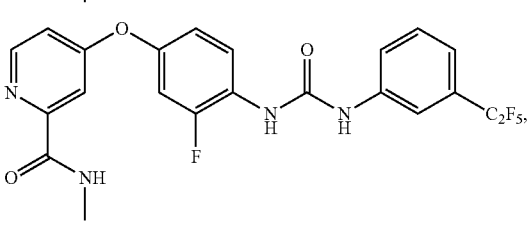

-continued
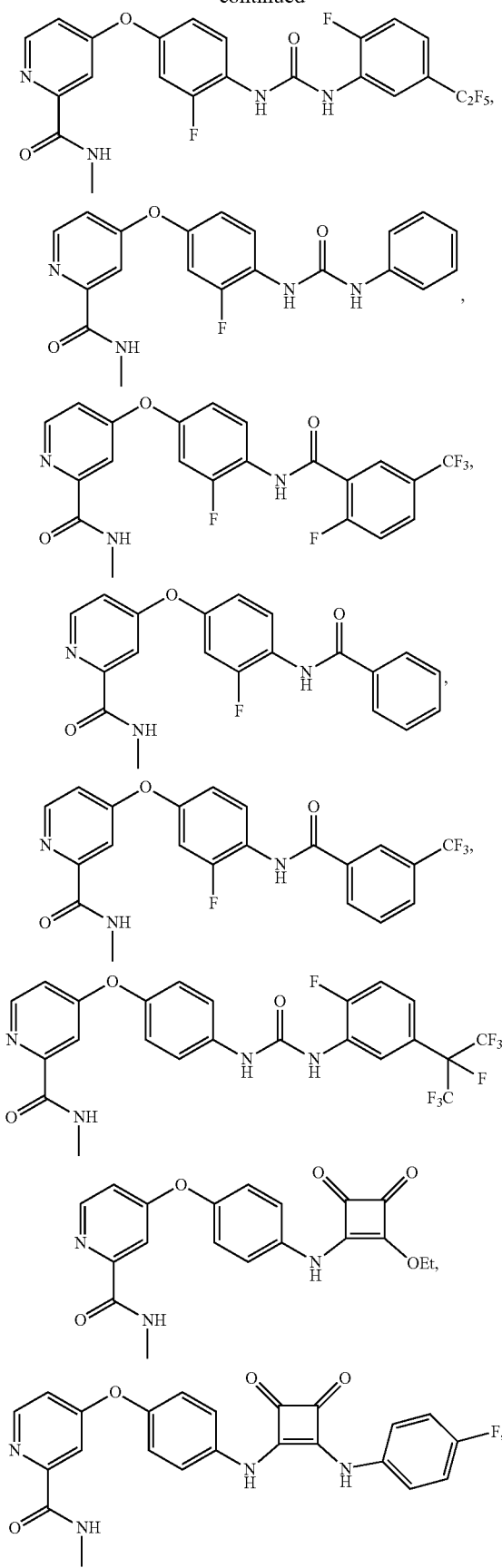
-continued
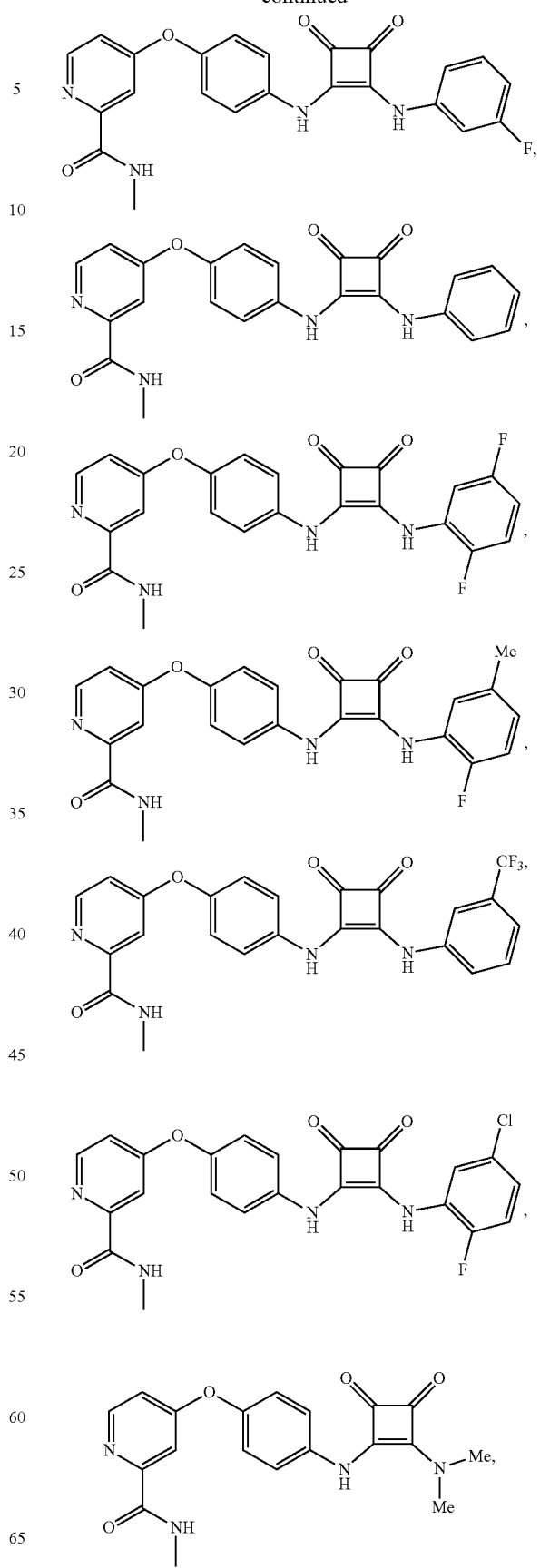

107
-continued
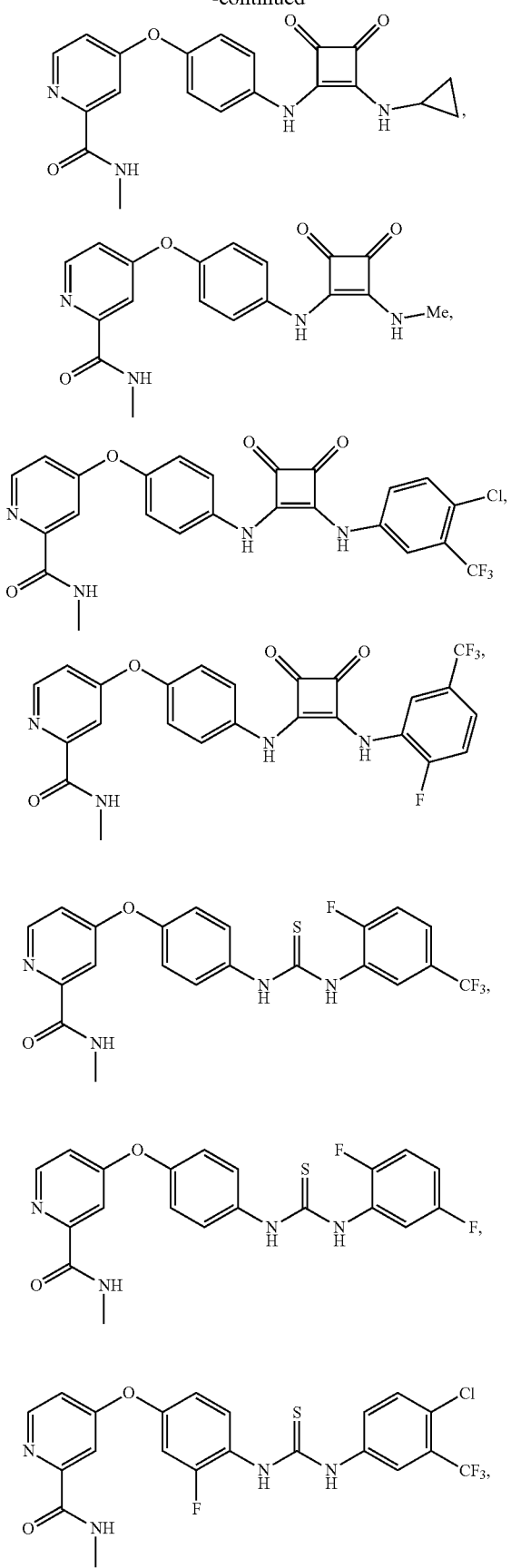
108
-continued
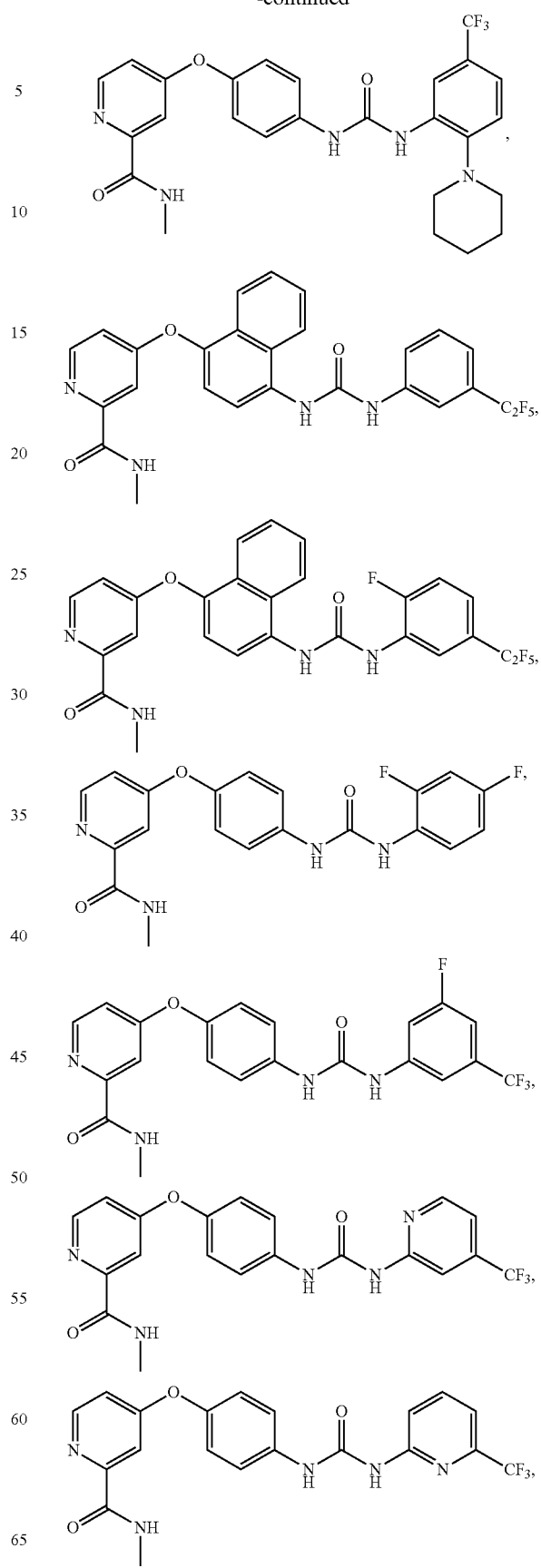

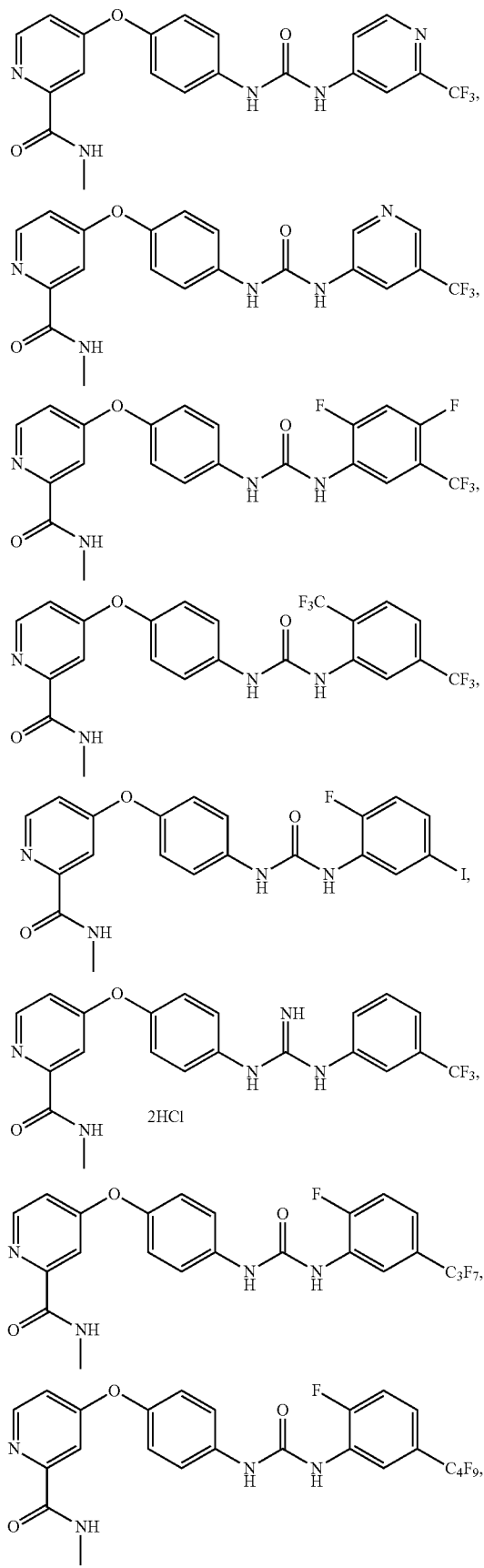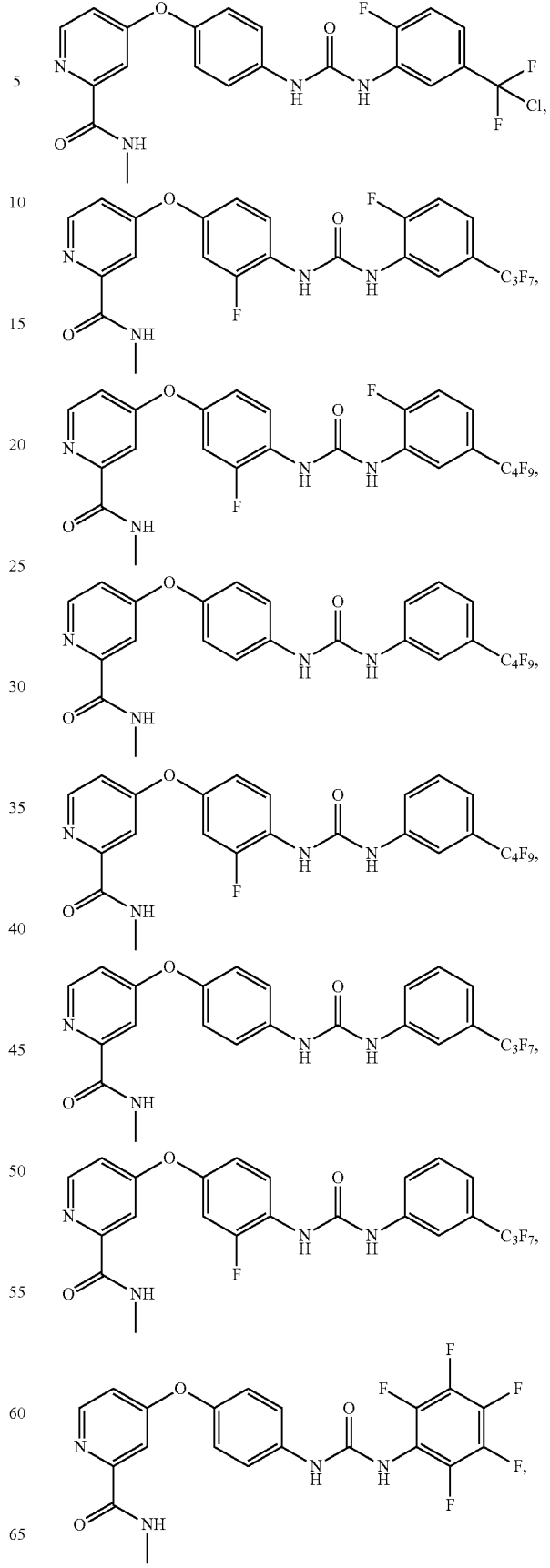

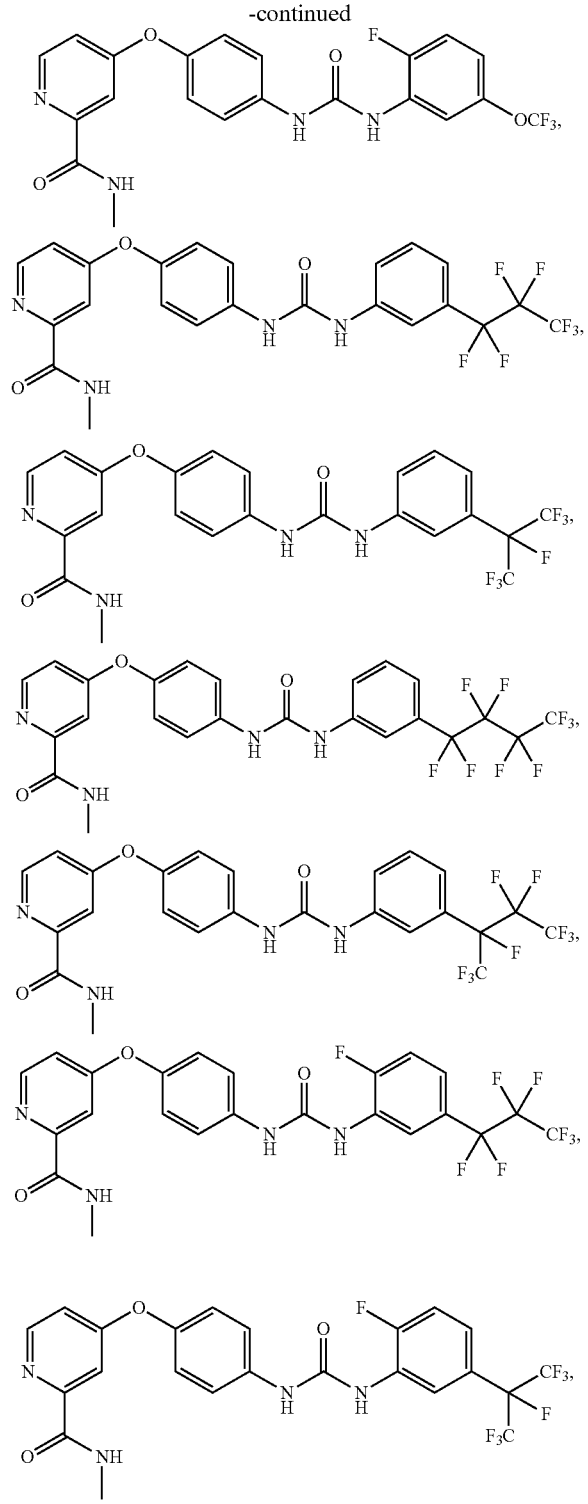
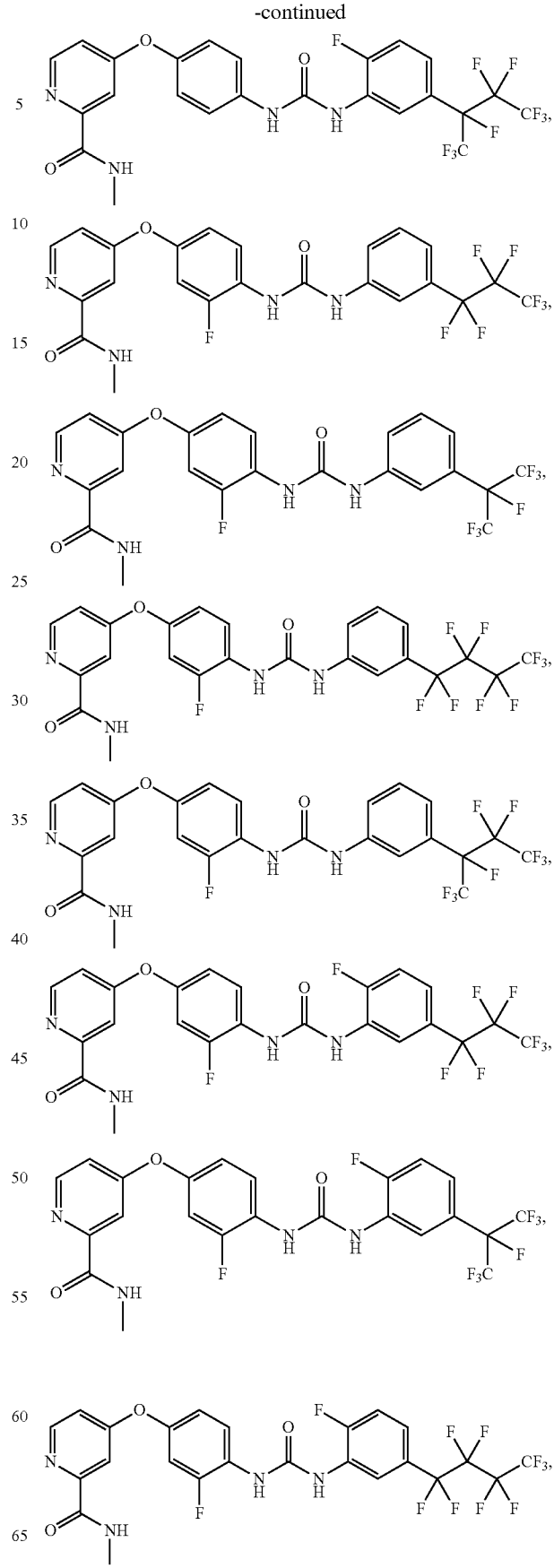

10. A composition comprising the compound according to claim 1 and a carrier.

11. The composition according to claim 10, wherein the carrier is a pharmaceutically-acceptable carrier.

12. A method of treating cancer in a subject, said method comprising:
administering to a subject a compound of formula (I) having the following structure:

(I)

or a stereoisomer, pharmaceutically acceptable salt, oxide, or solvate thereof, wherein R is selected from the group consisting of $C_{1-6}$ alkyl, $C_{1-6}$ alkoxy, $—N(C_{1-6}alkyl)_2$, $C_{3-6}$ cycloalkyl, aryl, heteroaryl, and heterocyclyl, wherein $C_{1-6}$ alkyl, $C_{3-6}$ cycloalkyl, aryl, heteroaryl, and heterocyclyl can be optionally substituted n times with $R^{13}$;

$R^1$ is H;

$R^2$ is H;

or $R^1$ and $R^2$ combine with the phenyl ring to which they are attached to form (a naphthyl group);

$R^3$ is H or halogen;

$R^4$ is H, halogen, or $C_1$-$C_6$ alkyl;

$R^5$ is H, halogen, or $C_1$-$C_6$ alkyl;

$R^6$ is $C_1$-$C_6$ alkyl;

X is optional and, if present, is NH;

Y is

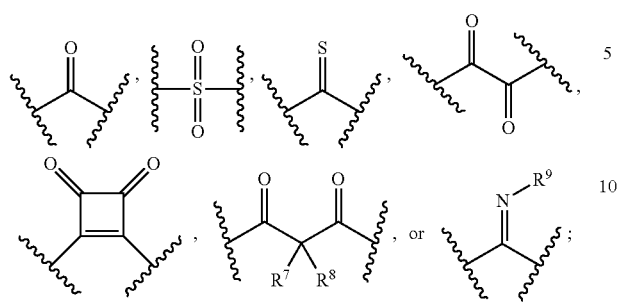

Z is C(R$^{12}$) or N;
R$^7$ is H or Me;
R$^8$ is H or Me;
or R$^7$ and R$^8$ are taken together with the carbon atom to which they are attached to form

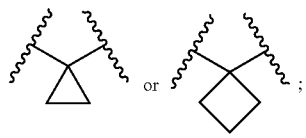 [SMILES: *C1(*)CC1 ; *C1(*)CCC1]

R$^9$ is H, C$_{1-6}$ alkyl, C$_{3-6}$ cycloalkyl, allyl, —CN, or

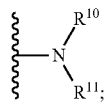

R$^{10}$ is H, C$_{1-6}$ alkyl, or C$_{3-6}$ cycloalkyl;
R$^{11}$ is H, C$_{1-6}$ alkyl, or C$_{3-6}$ cycloalkyl;
R$^{12}$ is H, halogen, or C$_1$-C$_6$ alkyl;
R$^{13}$ is selected independently at each occurrence thereof from the group consisting of H, halogen, C$_1$-C$_6$ alkyl, CH$_2$F, CHF$_2$, CClF$_2$, CBrF$_2$, ClF$_2$, CF$_3$, C$_2$F$_5$, C$_3$F$_7$, C$_4$F$_9$, OCF$_3$ and heterocyclyl; and
n is 1 to 5;
with the proviso that when
i) R$^1$ is H, R$^2$ is H, R$^3$ is H, R$^4$ is H, R$^5$ is H, R$^6$ is CH$_3$, Z is CH, X is NH, and Y is

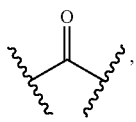 [SMILES: *C(*)=O]

R cannot be

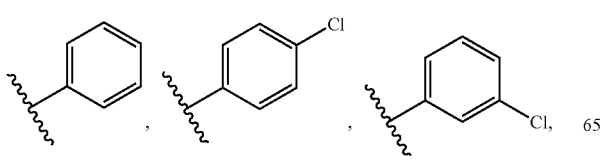

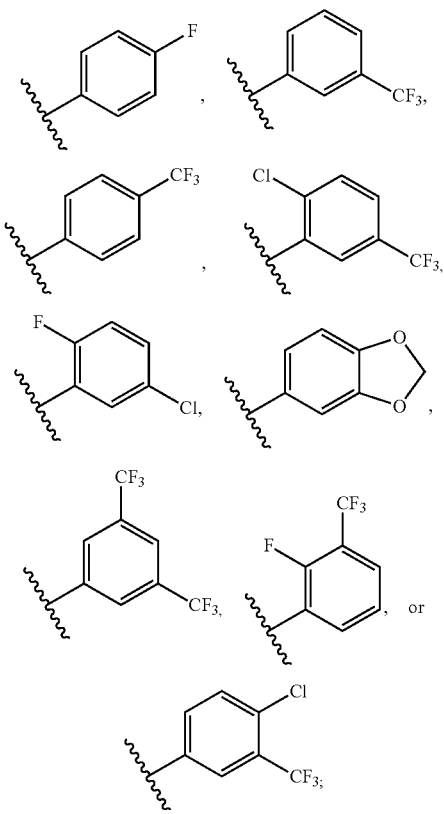

ii) R$^1$ is H, R$^2$ is H, R$^3$ is H, R$^4$ is H, R$^5$ is H, R$^6$ is CH$_3$, Z is CH, X is absent, and Y is

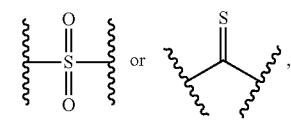

R cannot be

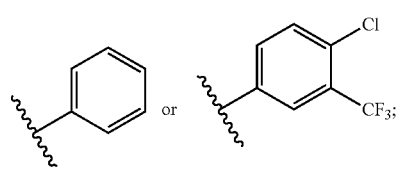 [SMILES: *c1ccccc1 ; *c1ccc(Cl)c(C(F)(F)F)c1]

iii) R$^1$ is H, R$^2$ is H, R$^3$ is H, R$^4$ is H, R$^5$ is H, R$^6$ is CH$_3$, Z is CH, Y is

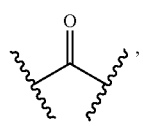

and n is 2, R cannot be

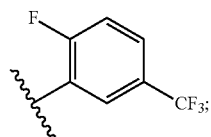 [SMILES: *c1cc(C(F)(F)F)ccc1F]

iv) R¹ is H, R² is H, R³ is F, R⁴ is H, R⁵ is H, R⁶ is CH₃, Z is CH, X is NH, Y is

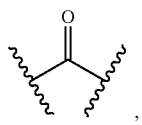

and n is 2, R cannot be

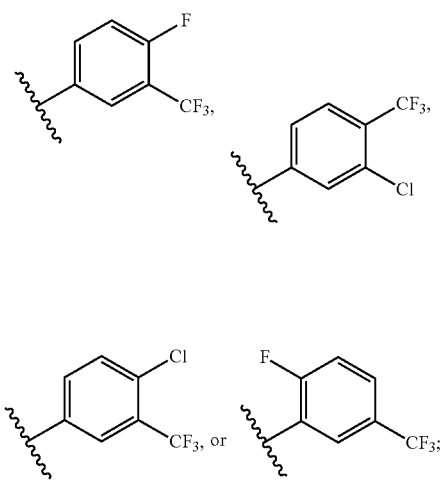

v) R¹ is H, R² is H, R³ is H, R⁴ is H, R⁵ is H, R⁶ is CH₃, Z is CH, X is absent, and Y is

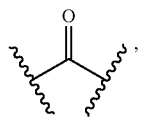

R cannot be

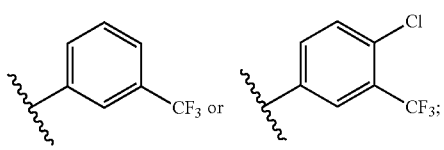 [SMILES: *c1cccc(C(F)(F)F)c1 ; *c1ccc(Cl)c(C(F)(F)F)c1]

and vi) R¹ is H, R² is H, R³ is H, R⁴ is H, R⁵ is H, R⁶ is CH₃, Z is CH, X is NH, and Y is

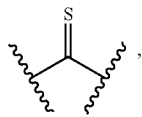

R cannot be

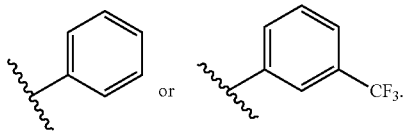 [SMILES: *c1ccccc1 ; *c1cccc(C(F)(F)F)c1]

13. The method according to claim 12, wherein the compound of formula (I) is selected from the group consisting of:

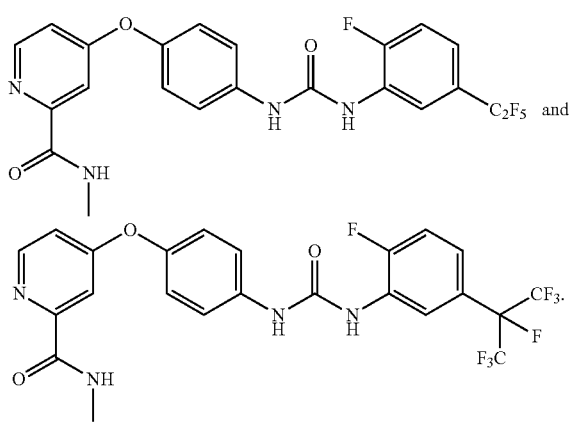

14. The method according to claim 12, wherein the compound of formula (I) is selected from the group consisting of:

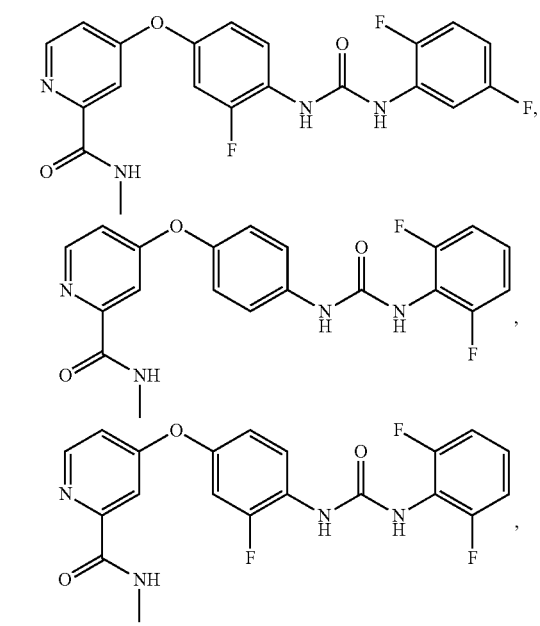

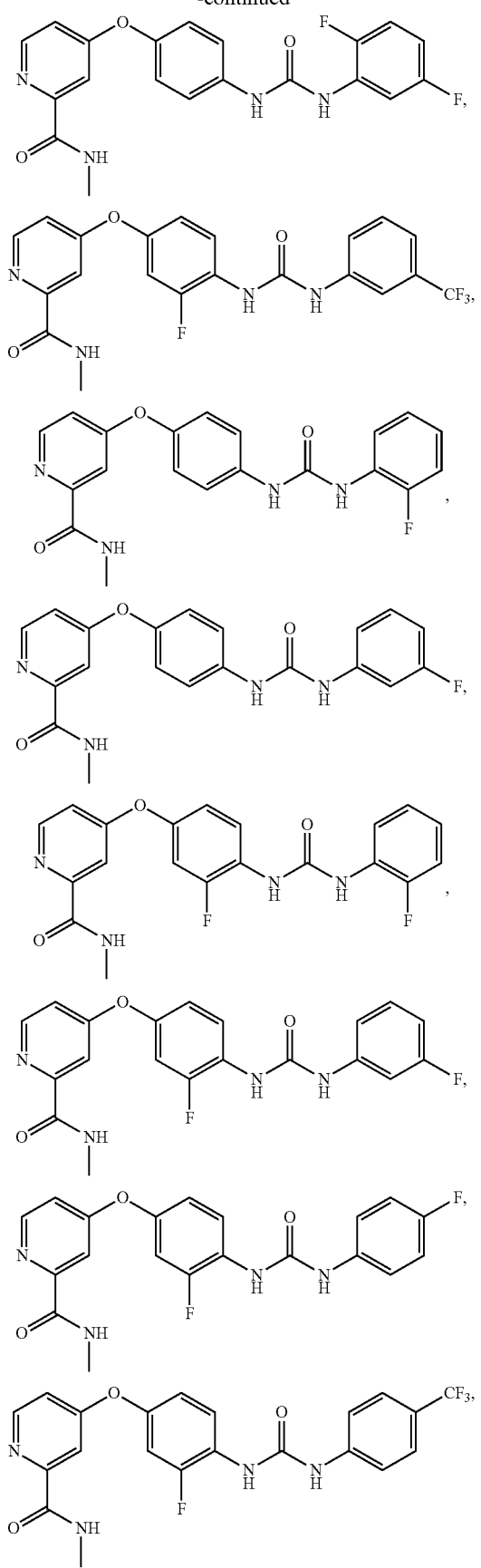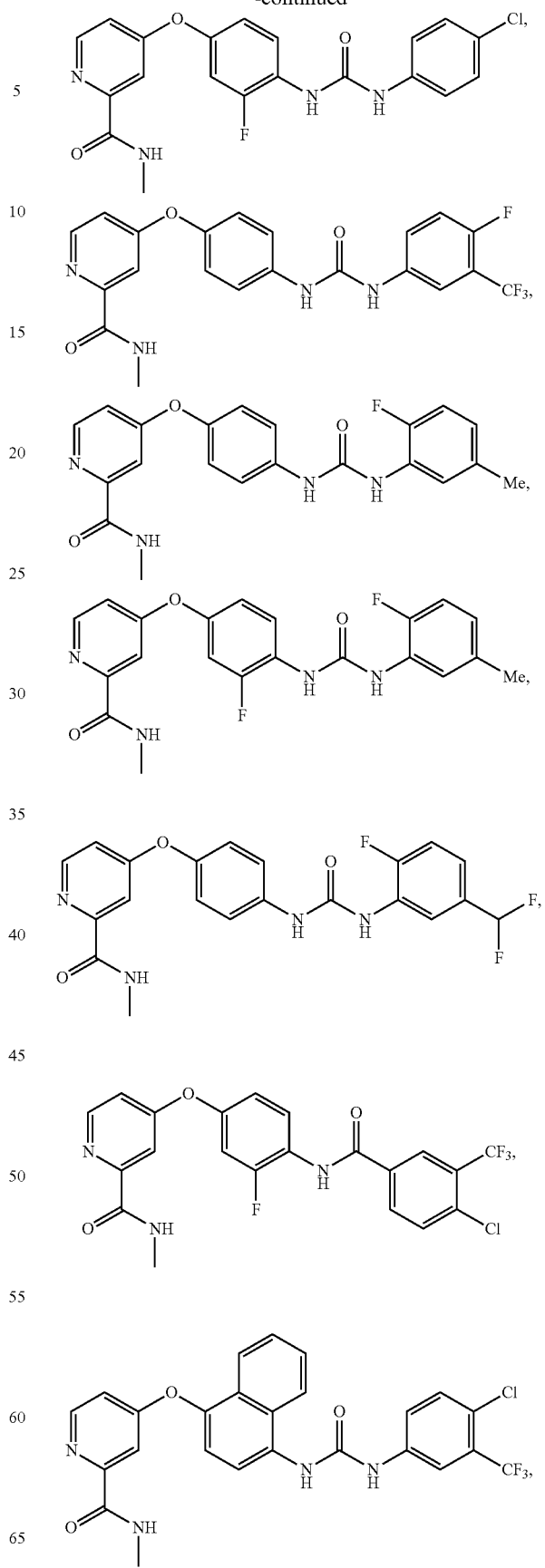

121
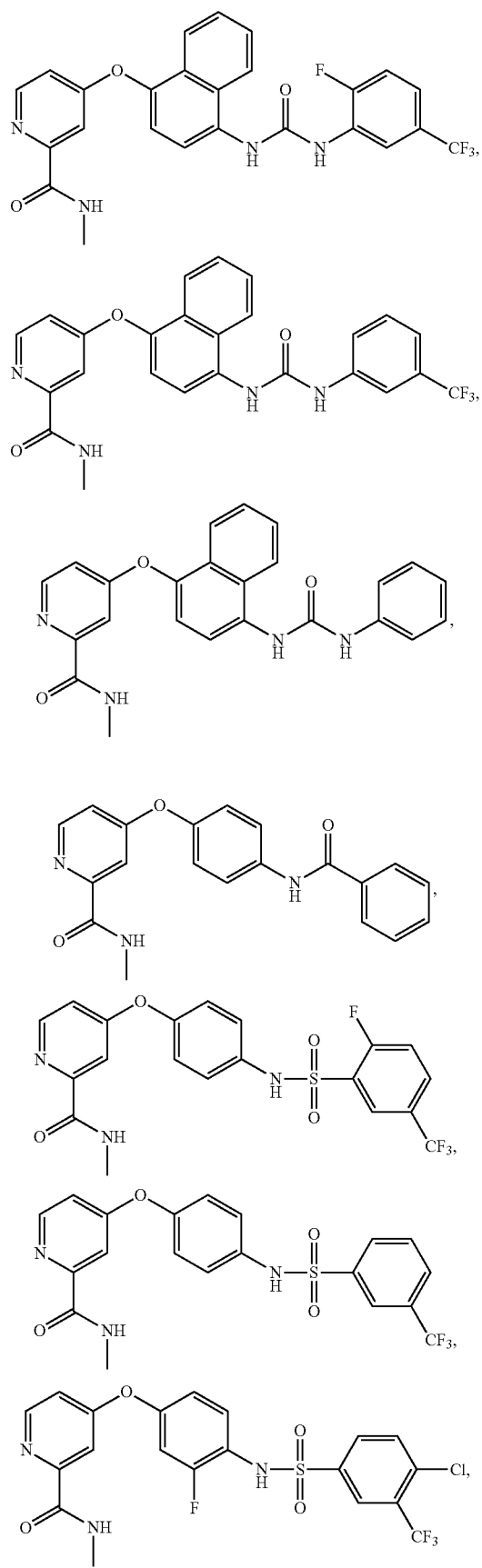
122
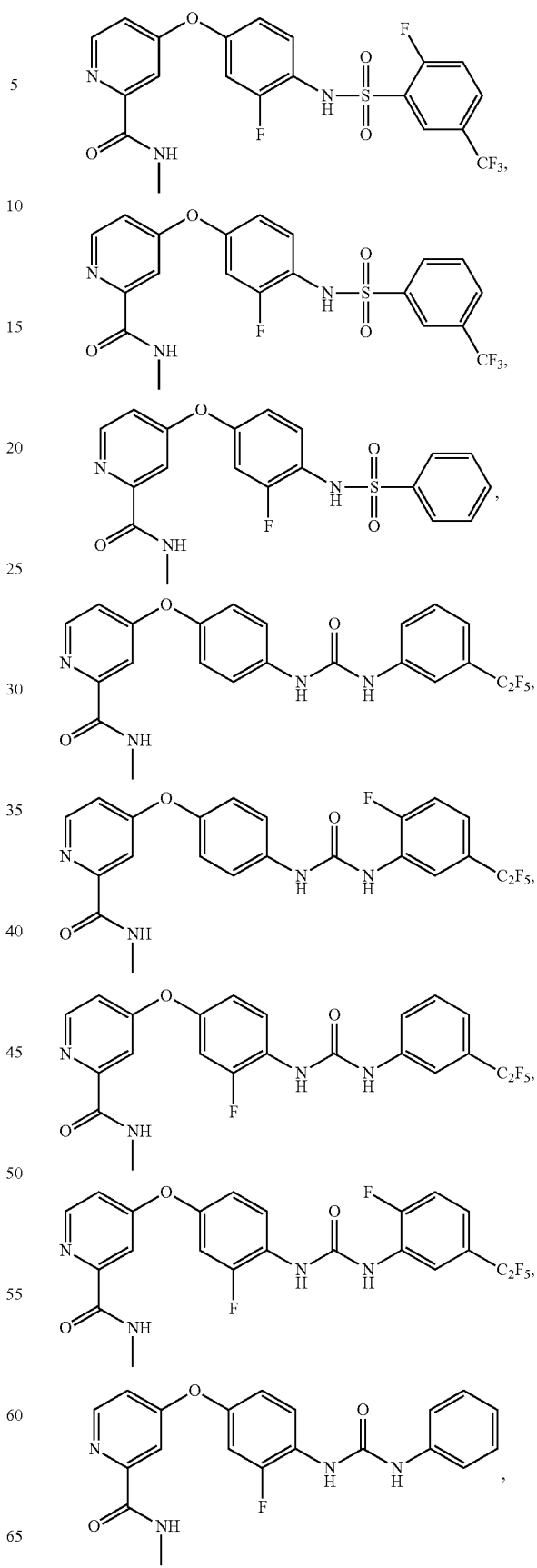

123
-continued
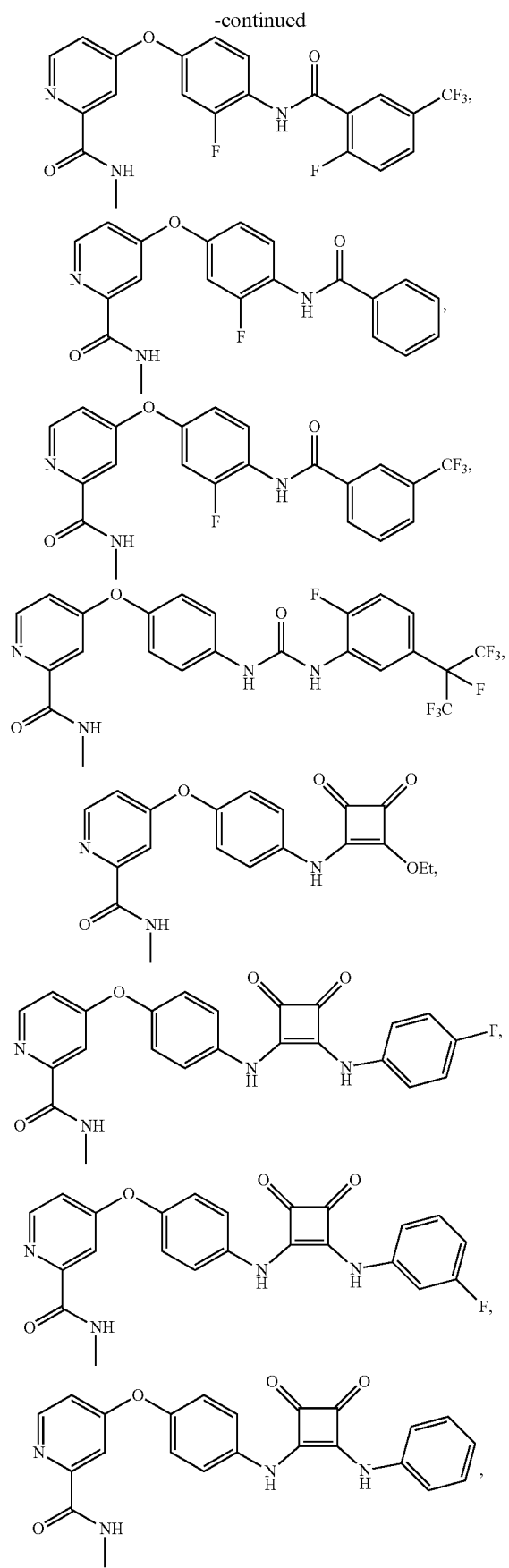
124
-continued
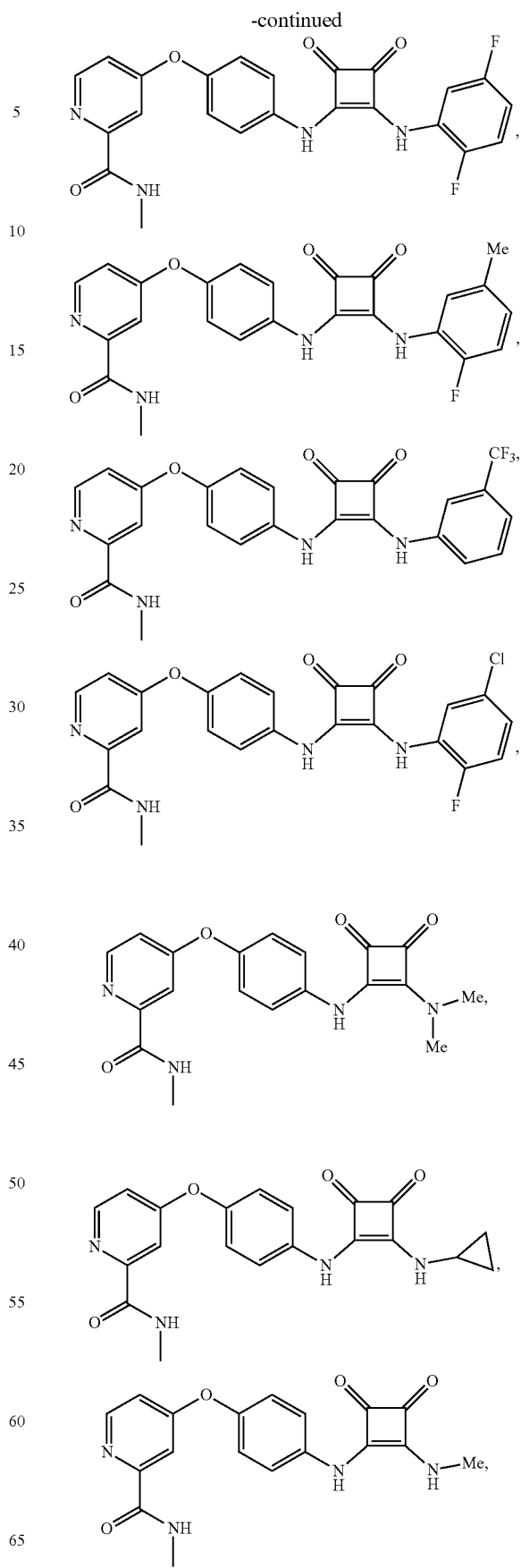

125
-continued
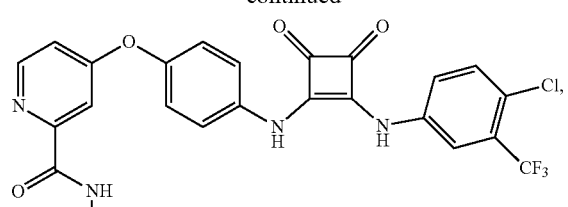
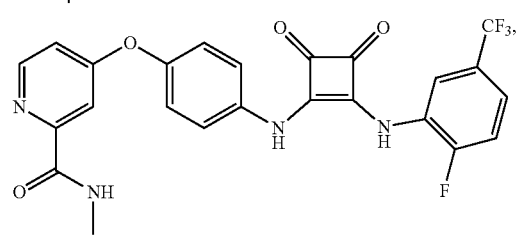
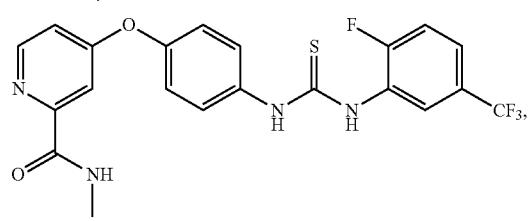
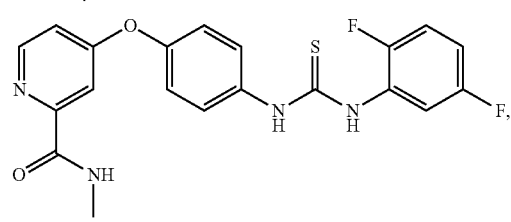
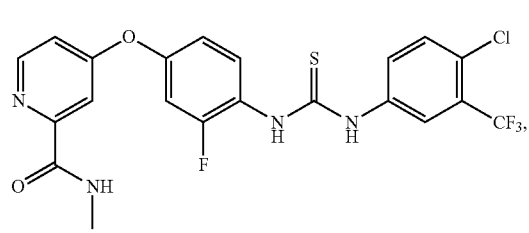
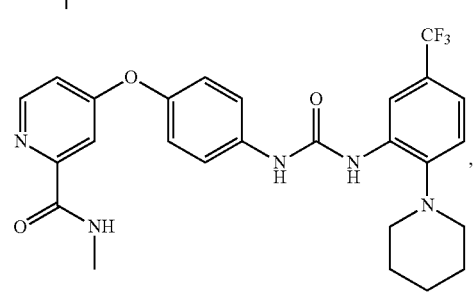
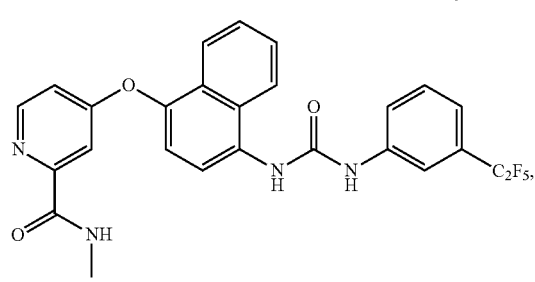
126
-continued
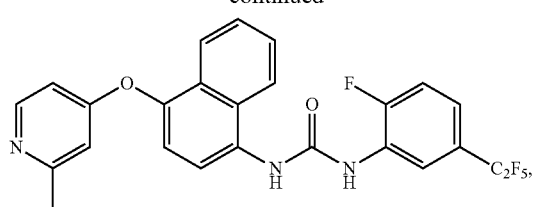
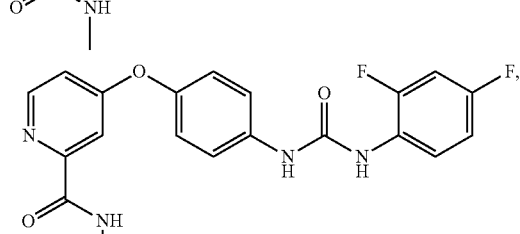
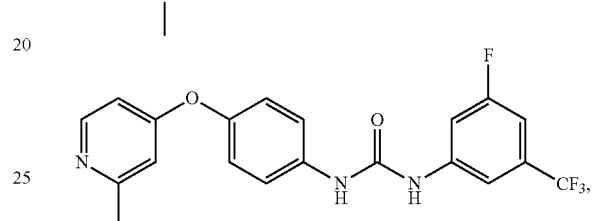
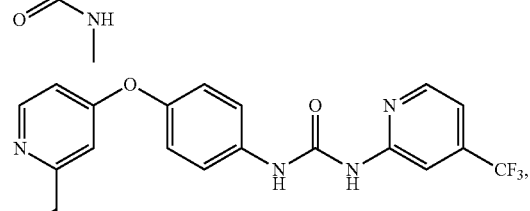
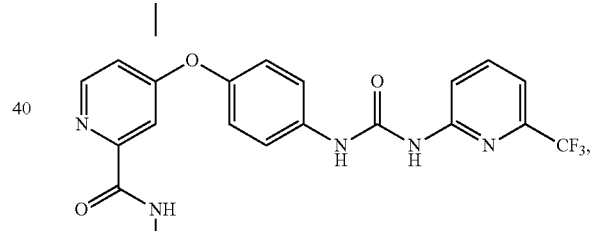
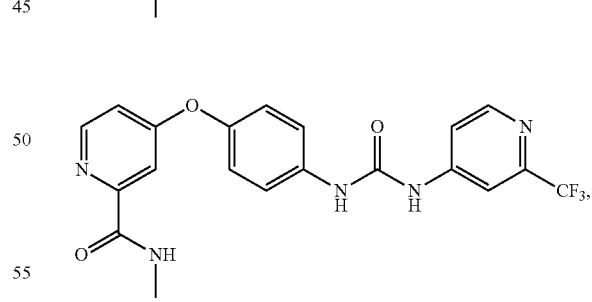
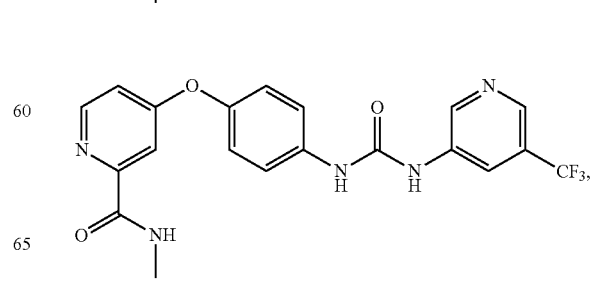

127
-continued
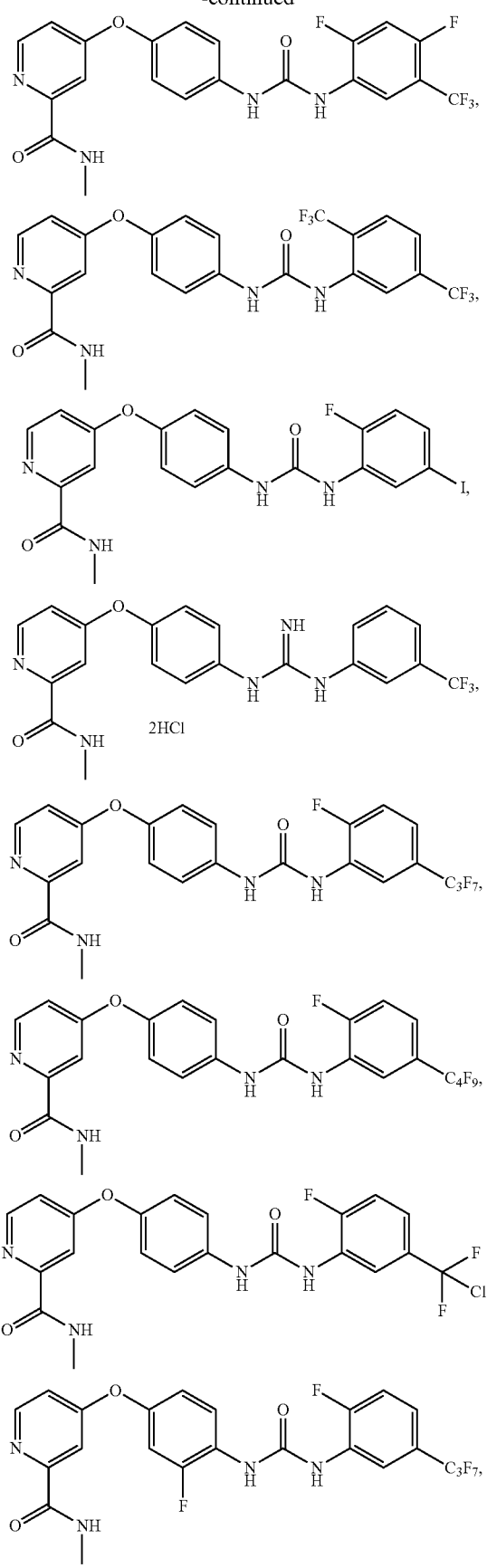
128
-continued
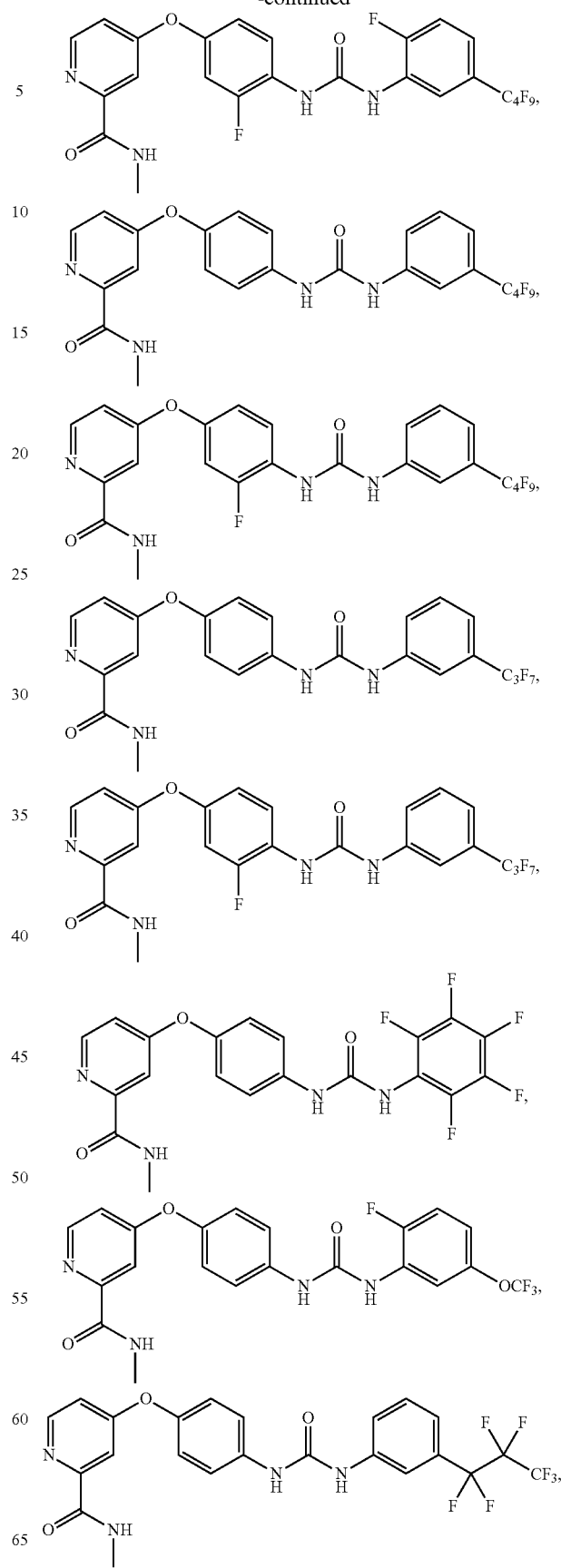

-continued
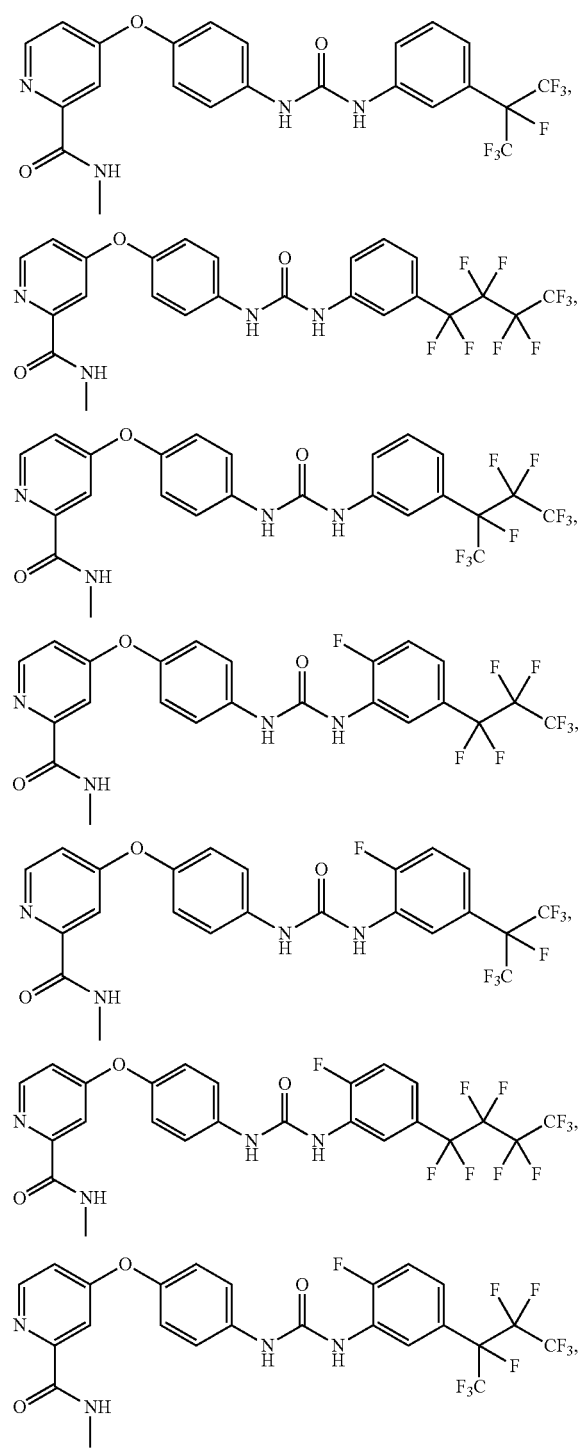
-continued
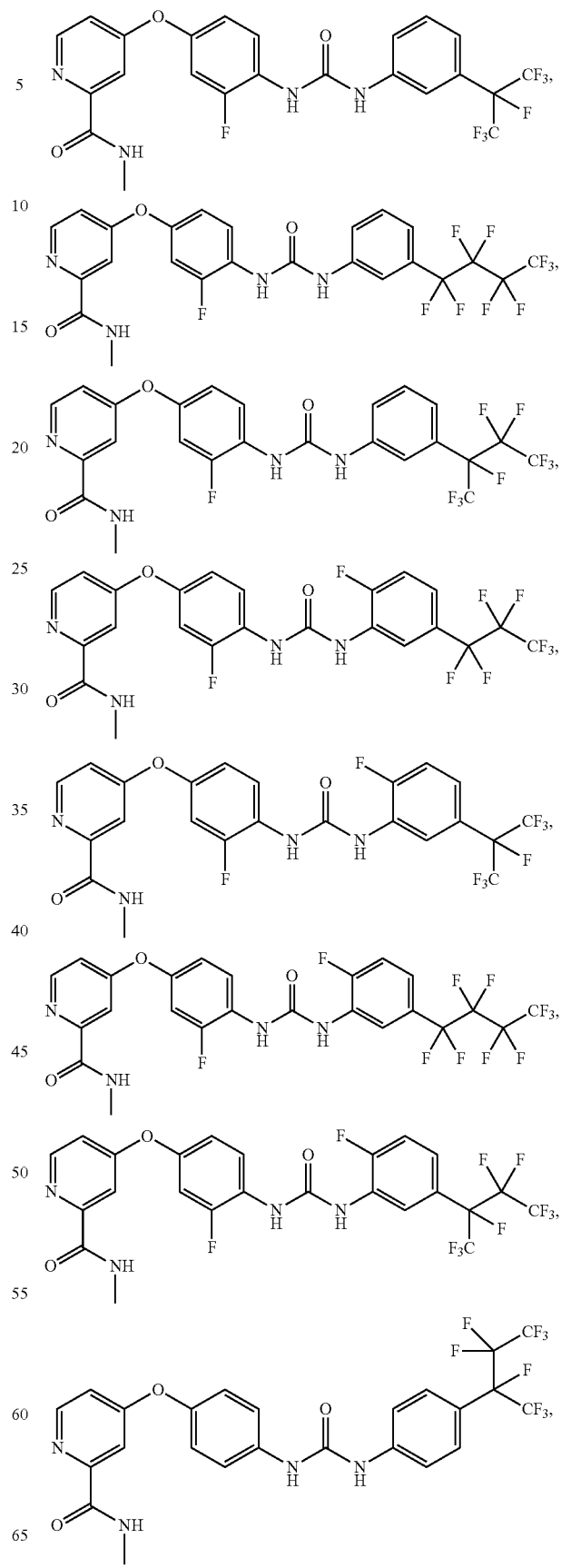

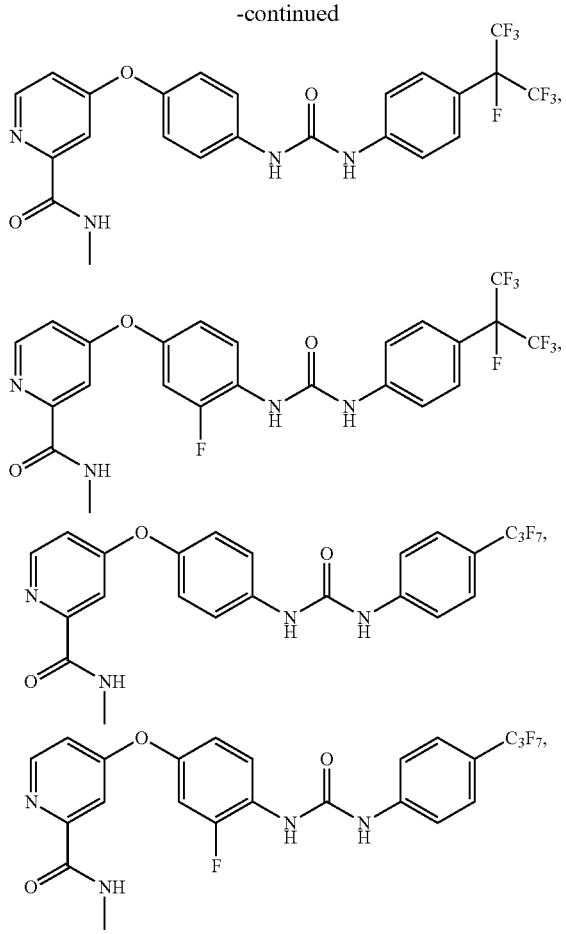

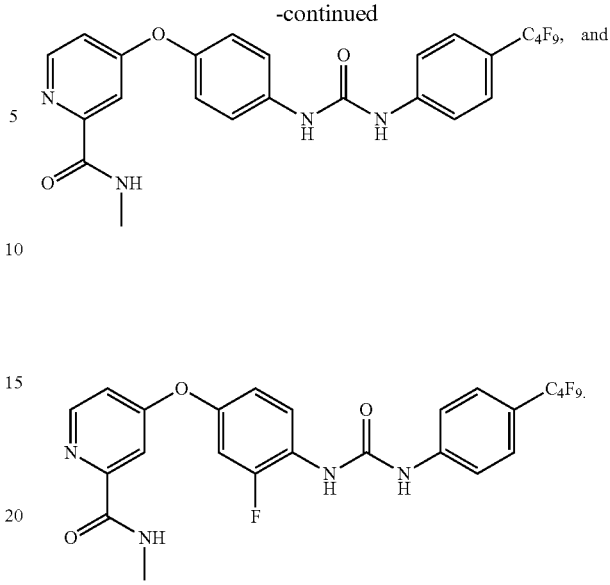

15. The method according to claim 12, wherein said administering is carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes.

16. The method according to claim 12, wherein the subject is a mammal.

17. The method according to claim 12, wherein the subject is a mammal.

* * * * *

UNITED STATES PATENT AND TRADEMARK OFFICE
CERTIFICATE OF CORRECTION

PATENT NO. : 10,519,113 B2
APPLICATION NO. : 16/325218
DATED : December 31, 2019
INVENTOR(S) : Dar et al.

Page 1 of 1

It is certified that error appears in the above-identified patent and that said Letters Patent is hereby corrected as shown below:

In Claim 17, at Column 132, Line 34, delete "12" and insert --16--; and
At Column 132, Line 35, delete "mammal" and insert --human--.

Signed and Sealed this
First Day of December, 2020

Andrei Iancu
*Director of the United States Patent and Trademark Office*